US011103508B2

(12) United States Patent
Augelli-Szafran et al.

(10) Patent No.: US 11,103,508 B2
(45) Date of Patent: Aug. 31, 2021

(54) SUBSTITUTED QUINAZOLINE SULFONAMIDES AS THIOREDOXIN INTERACTING PROTEIN (TXNIP) INHIBITORS

(71) Applicants: SOUTHERN RESEARCH INSTITUTE, Birmingham, AL (US); THE UAB RESEARCH FOUNDATION, Birmingham, AL (US)

(72) Inventors: Corinne E. Augelli-Szafran, Homewood, AL (US); Omar Moukha-Chafiq, Birmingham, AL (US); Mark J. Suto, Homewood, AL (US); Anath Shalev, Mountain Brook, AL (US); Lance Thielen, Lenexa, KS (US); Junqin Chen, Vestavia Hills, AL (US); Gu Jing, Vestavia Hills, AL (US)

(73) Assignees: SOUTHERN RESEARCH INSTITUTE, Birmingham, AL (US); THE UAB RESEARCH FOUNDATION, Birmingham, AL (US)

( * ) Notice: Subject to any disclaimer, the term of this patent is extended or adjusted under 35 U.S.C. 154(b) by 0 days.

(21) Appl. No.: 16/470,074

(22) PCT Filed: Oct. 31, 2018

(86) PCT No.: PCT/US2018/058356
§ 371 (c)(1),
(2) Date: Jun. 14, 2019

(87) PCT Pub. No.: WO2019/089693
PCT Pub. Date: May 9, 2019

(65) Prior Publication Data
US 2020/0038402 A1  Feb. 6, 2020

Related U.S. Application Data

(60) Provisional application No. 62/579,594, filed on Oct. 31, 2017.

(51) Int. Cl.
*A61K 31/517* (2006.01)
*A61P 1/16* (2006.01)
*A61P 3/06* (2006.01)
*A61P 3/10* (2006.01)
*A61K 31/5377* (2006.01)

(52) U.S. Cl.
CPC ........ *A61K 31/517* (2013.01); *A61K 31/5377* (2013.01); *A61P 1/16* (2018.01); *A61P 3/06* (2018.01); *A61P 3/10* (2018.01)

(58) Field of Classification Search
CPC ..... A61K 31/517; A61K 31/5377; A61P 1/16; A61P 3/06; A61P 3/10
See application file for complete search history.

(56) References Cited

U.S. PATENT DOCUMENTS

2013/0012489 A1* 1/2013 Mederski ................ A61P 35/04
514/210.18

FOREIGN PATENT DOCUMENTS

| WO | 2004/111014 A1 | 12/2004 |
| WO | 2007/058989 A2 | 5/2007 |
| WO | 2011/113512 A1 | 9/2011 |
| WO | 2018/021977 A1 | 2/2018 |

OTHER PUBLICATIONS

International Search Report and Written Opinion issued in Application No. PCT/US2018/058356 dated Mar. 7, 2019.
Naif Mahammad Alhawiti et al., "TXNIP in Metabolic Regulation: Physiological Role and Therapeutic Outlook", Current Drug Targets, vol. 18, No. 9, Jun. 2, 2017, pp. 1095-1103.
Wen-Jun Su et al., "Antidiabetic drug glyburide modulates depressive-like behavior comorbid with insulin resistance", Journal of Neuroinflammation, vol. 14, No. 210, Oct. 30, 2017, 12 pages.
G. Xu et al., "Preventing Cell Loss and Diabetes Wth Calcium Channel Blockers", Diabetes, vol. 61, Apr. 2012, pp. 848-856.
Office Action issued in Canadian Patent Application No. 3,049,259 dated Sep. 6, 2019, 6 pages.
Examination report No. 1 issued in Australian Patent Application No. 2018357933 dated Jul. 2, 2019, 3 pages.
Office Action issued in Canadian Patent Application No. 3,049,259 dated Apr. 28, 2020, 3 pages.
International Preliminary Report on Patentability issued in PCT/US2018/058356 dated May 14, 2020, 12 pages.

* cited by examiner

*Primary Examiner* — Timothy R Rozof
(74) *Attorney, Agent, or Firm* — Kilpatrick Townsend & Stockton LLP

(57) ABSTRACT

In one aspect, compounds and compositions that inhibit TXNIP expression and/or that lower hepatic glucose production and methods of identifying, making, and using same are disclosed. The disclosed compounds and compositions can be useful for disorders associated with elevated TXNIP and/or elevated glucagon levels such as, for example, diabetes and associated disorders. Further provided are methods for treating hyperlipidemia or fatty liver disease, optionally associated with elevated TXNIP and/or elevated glucagon levels.

39 Claims, 3 Drawing Sheets
Specification includes a Sequence Listing.

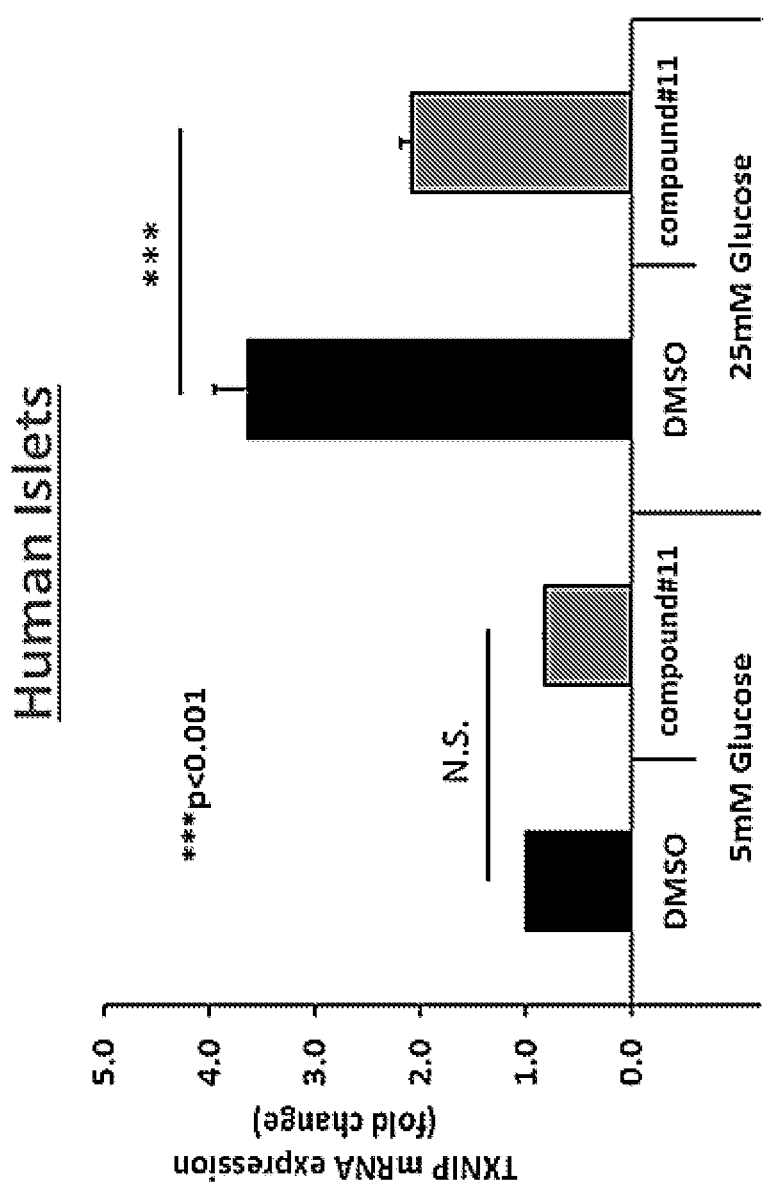
FIG. 1: Compound #11 Inhibits TXNIP Expression Under High Glucose Conditions

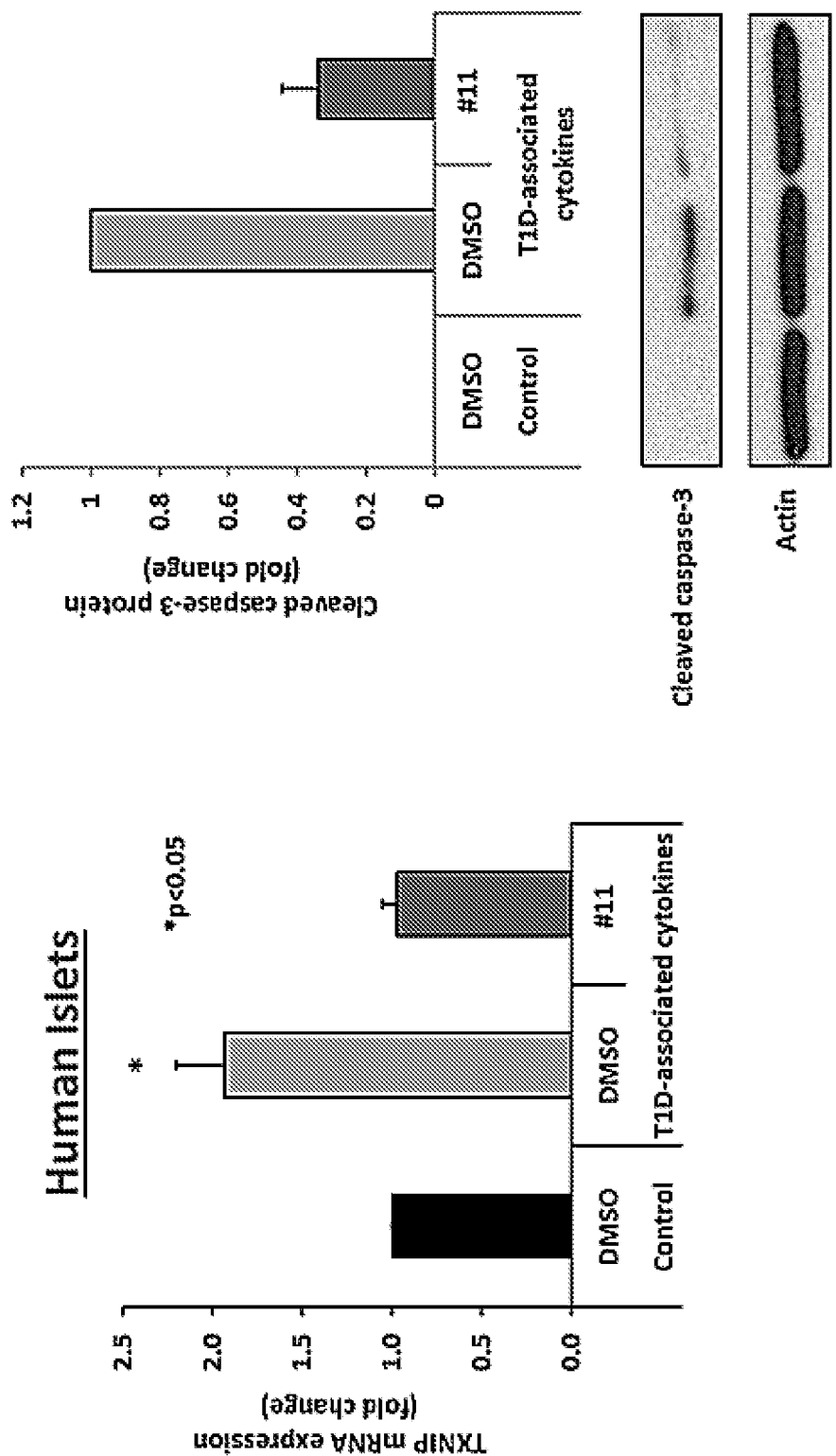
FIG. 2: Compound #11 Protects Against Cytokine-Induced Beta Cell Death

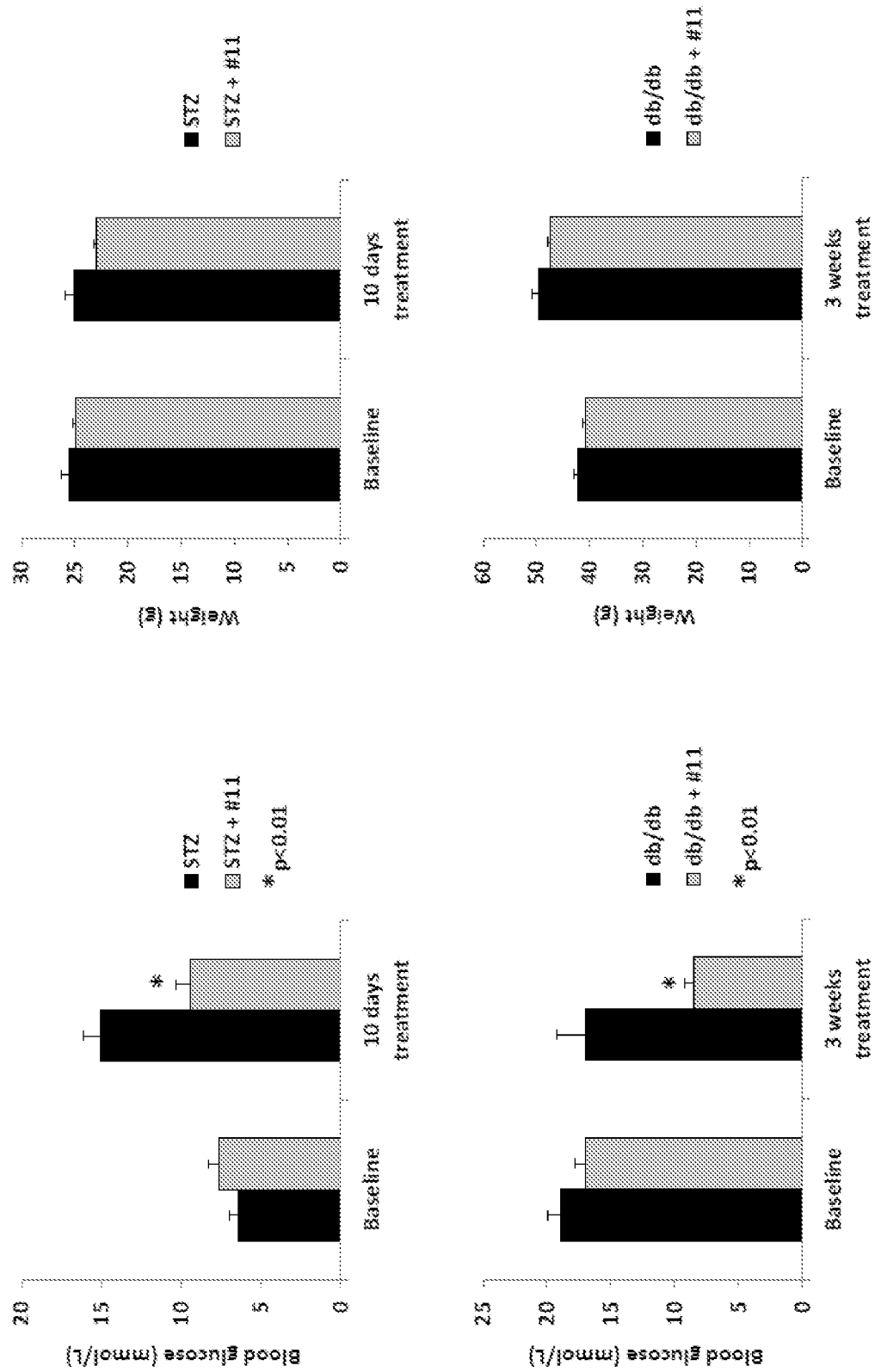
FIG. 3: Compound #11 Protects Against Diabetes

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<223> OTHER INFORMATION: Synthetic construct

<400> SEQUENCE: 1
cgagtcaaag ccgtcaggat                                      20

<210> SEQ ID NO 2
<211> LENGTH: 24
<212> TYPE: DNA
<213> ORGANISM: Artificial sequence
<220> FEATURE:
<223> OTHER INFORMATION: Synthetic construct

<400> SEQUENCE: 2
ttcatagcgc aagtagtcca aggt                                 24

<210> SEQ ID NO 3
<211> LENGTH: 21
<212> TYPE: DNA
<213> ORGANISM: Artificial sequence
<220> FEATURE:
<223> OTHER INFORMATION: Synthetic construct
```

```
<400> SEQUENCE: 3
agtccctgcc ctttgtacac a                                    21

<210> SEQ ID NO 4
<211> LENGTH: 21
<212> TYPE: DNA
<213> ORGANISM: Artificial sequence
<220> FEATURE:
<223> OTHER INFORMATION: Synthetic construct

<400> SEQUENCE: 4
gatccgaggg cctcactaaa c                                    21
```

SUBSTITUTED QUINAZOLINE SULFONAMIDES AS THIOREDOXIN INTERACTING PROTEIN (TXNIP) INHIBITORS

CROSS-REFERENCE TO PRIORITY APPLICATION

This application claims priority to U.S. Provisional Application No. 62/579,594, filed Oct. 31, 2017, which is incorporated by reference herein in its entirety.

STATEMENT REGARDING FEDERALLY FUNDED RESEARCH

This invention was made with government support under grant number UC4DK 104204 awarded by the National Institutes of Health. The government has certain rights in the invention.

REFERENCE TO SEQUENCE LISTING

The official copy of the sequence listing is submitted electronically via EFS-Web as an ASCII formatted sequence listing in a file named 035979_1110651_Seqlist.txt, created on Oct. 29, 2018, having a size of 4.00 kb and filed concurrently with the specification. The sequence listing contained in this ASCII formatted document is part of the specification and is herein incorporated by reference in its entirety.

BACKGROUND

Pancreatic β-cell dysfunction and death play a central role in the development and progression of diabetes and can be caused by multiple stressors including glucotoxicity, (gluco-)lipotoxicity, and cytokine toxicity (Poitout and Robertson (2002) *Endocrinology* 143: 339-342; Eizirik and Mandrup-Poulsen (2001) *Diabetologia* 44: 2115-2133). Glucotoxicity induced by chronic exposure of β-cells to high levels of glucose promotes β-cell apoptosis and, combined with the elevated glucagon levels associated with diabetes (Unger and Orci (1975) *Lancet* 1: 14-16), results in a vicious cycle with further worsening of the hyperglycemia (Poitout and Robertson (2002) *Endocrinology* 143: 339-342). It was previously shown that thioredoxin-interacting protein (TXNIP), a ubiquitously expressed cellular redox regulator (Nishiyama et al. (1999) *J. Biol. Chem.* 274: 21645-21650), is the top glucose-induced gene in a human islet gene expression microarray study (Shalev et al. (2002) *Endocrinology* 143:3695-98.) and that TXNIP is a crucial mediator of glucotoxicity-induced β-cell apoptosis (Chen et al. (2008) *Diabetes* 57: 938-44). It was further shown that β-cell TXNIP transcription is upregulated by glucose and its expression is increased in diabetes (Minn et al. (2005) *Endocrinology* 146:2397-2405.) Also, TXNIP-induced β-cell death is mediated by the intrinsic/mitochondrial death pathway (Chen et al. (2010) *Diabetes* 59: 440-447). Further, elevated TXNIP levels also contribute to β-cell dysfunction by inducing microRNA expression (miR-204), which in turn targets the insulin transcription factor MafA and thereby inhibits insulin production (Xu et al. (2013) *Nat. Med.* 19: 1141-1146). Conversely, TXNIP deficiency led to an increase in functional β-cell mass and protected against diabetes in mouse models of type 1 (T1D) and type 2 (T2D) diabetes (Chen et al. (2008) *FASEB J.* 22: 3581-3594). In addition, TXNIP deletion has been associated with reduced hepatic glucose production and beneficial effects in extrapancreatic tissues such as kidney, retina and the cardiovascular system in the context of diabetes. Despite the detrimental effects elevated TXNIP plays in diabetes and its associated disorders, prior to the present disclosure there was no known effective way to specifically block TXNIP expression.

SUMMARY

In accordance with the purpose(s) of the invention, as embodied and broadly described herein, the invention, in one aspect, relates to compositions and methods for use in the prevention and treatment of disorders associated with elevated TXNIP and/or elevated glucagon levels, such as, for example, diabetes and associated disorders (e.g., Type 1 diabetes, Type 2 diabetes, gestational diabetes, impaired glucose control, impaired glucose tolerance or pre-diabetes, insulin resistance, hyperlipidemia, non-alcoholic fatty liver disease, complications of diabetes, including diabetes-related nephropathy, neuropathy, retinopathy, cardiomyopathy, and cardiovascular disease, as well as pancreatic β-cell loss or pancreatic islet dysfunction, including dysregulation of insulin and/or glucagon production or secretion) or other disorders associated with endoplasmic reticulum stress and/or oxidative stress of the cell. Additionally, the compositions and methods are useful in preparing islets for transplantation and/or for treating a transplant recipient.

Disclosed is a method for treating a disorder associated with elevated TXNIP or elevated glucagon in a mammal, the method comprising the step of administering to the mammal a therapeutically effective amount of at least one compound having a structure represented by a formula selected from:

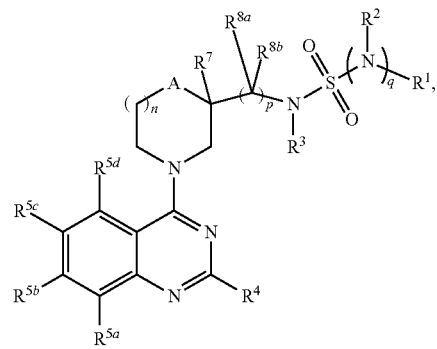

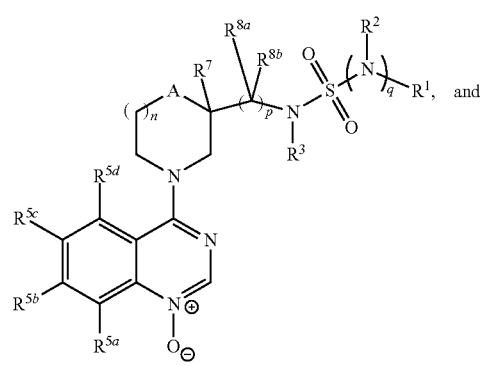

and

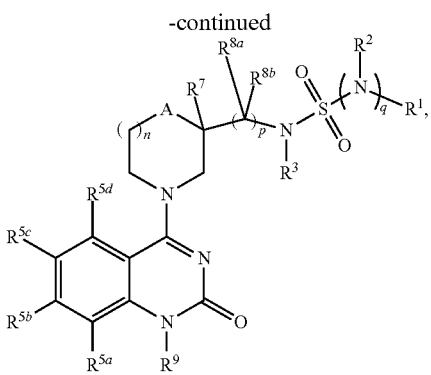

wherein n is 0, 1, or 2; wherein p is 0, 1, 2, 3, or 4; wherein q is 0 or 1; wherein $R^1$ is —$NH_2$, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl) (C1-C4 alkoxy), —(C1-C4 alkyl)$CO_2H$, or $Cy^1$; wherein $Cy^1$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^2$ is hydrogen or C1-C4 alkyl, or wherein each of $R^1$ and $R^2$ are covalently bonded together and, together with the intermediate atoms, comprise a 3- to 6-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^3$ is hydrogen or C1-C4 alkyl, or wherein each of $R^1$ and $R^3$ are covalently bonded together and, together with the intermediate atoms, comprise a 5- to 7-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^4$ is hydrogen, halogen, —$NH_2$, —OH, C1-C4 alkyl, C1-C4 alkoxy, C1-C4 alkylamino, (C1-C4)(C1-C4) dialkylamino, or $Cy^2$; wherein $Cy^2$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein each of $R^{5a}$, $R^{5b}$, $R^{5c}$, and $R^{5d}$ is independently hydrogen, halogen, —$NH_2$, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —$CO_2$(C1-C4 alkyl), —$CO_2H$, —$CO_2NH_2$, —NHC(O)$Cy^3$, —NHC(O)(C1-C4 alkyl), or $Cy^3$; wherein $Cy^3$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein A is O, $NR^{6a}$, or $CHR^{6b}$; wherein $R^{6a}$ is hydrogen or C1-C4 alkyl; and wherein $R^{6b}$ is hydrogen, C1-C4 alkyl, C1-C4 haloalkyl, C1-C4 alkoxy, C1-C4 alkylamino, (C1-C4)(C1-C4) dialkylamino, or —$CO_2H$; wherein $R^7$ is hydrogen, halogen, —OH, C1-C4 alkyl, C1-C4 haloalkyl, or C1-C4 alkoxy; wherein each occurrence of $R^{8a}$ and $R^{8b}$, when present, is independently hydrogen, C1-C4 alkyl, C1-C4 haloalkyl, phenyl, or —$CO_2H$; or wherein p is 1 and each of $R^{8a}$ and $R^{8b}$ together comprise =O; and wherein $R^9$ is hydrogen, C1-C4 alkyl, or $Cy^4$, wherein $Cy^4$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino, or a pharmaceutically acceptable salt thereof.

Also disclosed is a method for inhibiting TXNIP expression or lowering glucagon levels in a mammal, the method comprising the step of administering to the mammal an effective amount of at least one compound having a structure represented by a formula selected from:

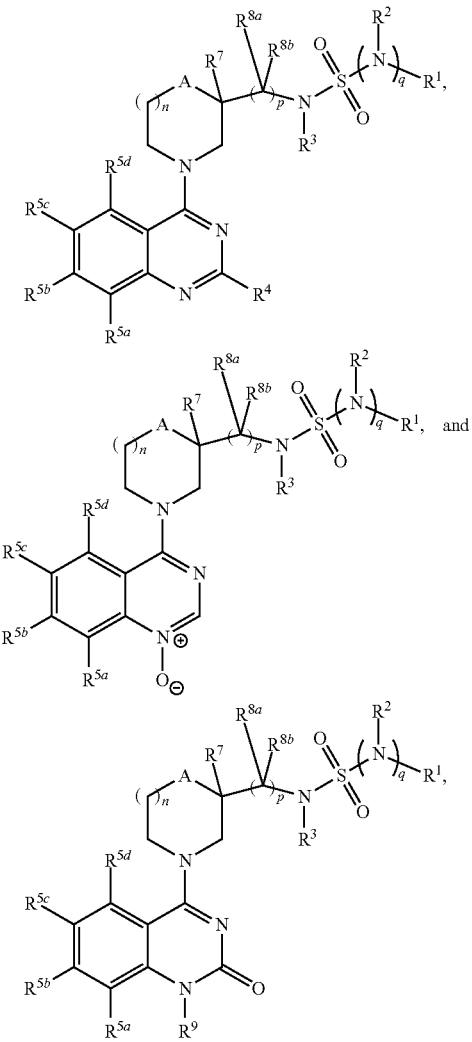

wherein n is 0, 1, or 2; wherein p is 0, 1, 2, 3, or 4; wherein q is 0 or 1; wherein $R^1$ is —$NH_2$, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl) (C1-C4 alkoxy), —(C1-C4 alkyl)$CO_2H$, or $Cy^1$; wherein $Cy^1$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^2$ is hydrogen or C1-C4 alkyl, or wherein each of $R^1$ and $R^2$ are covalently bonded together and, together with the intermediate atoms, comprise a 3- to 6-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein R$^3$ is hydrogen or C1-C4 alkyl, or wherein each of R$^1$ and R$^3$ are covalently bonded together and, together with the intermediate atoms, comprise a 5- to 7-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein R$^4$ is hydrogen, halogen, —NH$_2$, —OH, C1-C4 alkyl, C1-C4 alkoxy, C1-C4 alkylamino, (C1-C4)(C1-C4) dialkylamino, or Cy$^2$; wherein Cy$^2$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein each of R$^{5a}$, R$^{5b}$, R$^{5c}$, and R$^{5d}$ is independently hydrogen, halogen, —NH$_2$, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —CO$_2$(C1-C4 alkyl), —CO$_2$H, —CO$_2$NH$_2$, —NHC(O)Cy$^3$, —NHC(O)(C1-C4 alkyl), or Cy$^3$; wherein Cy$^3$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein A is O, NR$^{6a}$, or CHR$^{6b}$; wherein R$^{6a}$ is hydrogen or C1-C4 alkyl; and wherein R$^{6b}$ is hydrogen, C1-C4 alkyl, C1-C4 haloalkyl, C1-C4 alkoxy, C1-C4 alkylamino, (C1-C4)(C1-C4) dialkylamino, or —CO$_2$H; wherein R$^7$ is hydrogen, halogen, —OH, C1-C4 alkyl, C1-C4 haloalkyl, or C1-C4 alkoxy; wherein each occurrence of R$^{8a}$ and R$^{8b}$, when present, is independently hydrogen, C1-C4 alkyl, C1-C4 haloalkyl, phenyl, or —CO$_2$H; or wherein p is 1 and each of R$^{9a}$ and R$^{8b}$ together comprise =O; and wherein R$^9$ is hydrogen, C1-C4 alkyl, or Cy$^4$, wherein Cy$^4$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino, or a pharmaceutically acceptable salt thereof.

Also disclosed herein are pharmaceutical compositions comprising a pharmaceutically acceptable carrier and a therapeutically effective amount of at least one compound having a structure represented by a formula:

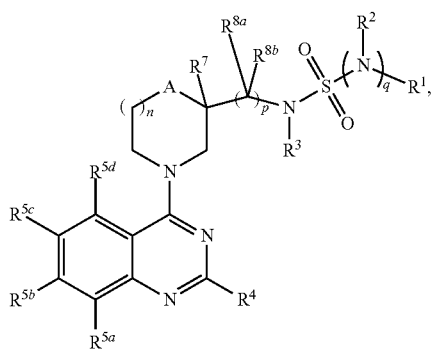

wherein n is 0, 1, or 2; wherein p is 1, 2, 3, or 4; wherein q is 0 or 1; wherein R$^1$ is —NH$_2$, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)CO$_2$H, or Cy$^1$; wherein Cy$^1$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein R$^2$ is hydrogen or C1-C4 alkyl, or wherein each of R$^1$ and R$^2$ are covalently bonded together and, together with the intermediate atoms, comprise a 3- to 6-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein R$^3$ is hydrogen or C1-C4 alkyl, or wherein each of R$^1$ and R$^3$ are covalently bonded together and, together with the intermediate atoms, comprise a 5- to 7-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein R$^4$ is hydrogen, halogen, —NH$_2$, —OH, C1-C4 alkyl, C1-C4 alkoxy, C1-C4 alkylamino, (C1-C4)(C1-C4) dialkylamino, or Cy$^2$; wherein Cy$^2$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein each of R$^{5a}$, R$^{5b}$, R$^{5c}$, and R$^{5d}$ is independently hydrogen, halogen, —NH$_2$, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —CO$_2$(C1-C4 alkyl), —CO$_2$H, —CO$_2$NH$_2$, —NHC(O)Cy$^3$, —NHC(O)(C1-C4 alkyl), or Cy$^3$; wherein Cy$^3$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein A is O, NR$^{6a}$, or CHR$^{6b}$; wherein R$^{6a}$ is hydrogen or C1-C4 alkyl; and wherein R$^{6b}$ is hydrogen, C1-C4 alkyl, C1-C4 haloalkyl, C1-C4 alkoxy, C1-C4 alkylamino, (C1-C4)(C1-C4) dialkylamino, or —CO$_2$H; wherein R$^7$ is hydrogen, halogen, —OH, C1-C4 alkyl, C1-C4 haloalkyl, or C1-C4 alkoxy; wherein each occurrence of R$^{8a}$ and R$^{8b}$, when present, is independently hydrogen, C1-C4 alkyl, C1-C4 haloalkyl, phenyl, or —CO$_2$H; or wherein p is 1 and each of R$^{8a}$ and R$^{8b}$ together comprise =O; and wherein R$^9$ is hydrogen, C1-C4 alkyl, or Cy$^4$, wherein Cy$^4$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino, or a pharmaceutically acceptable salt thereof.

Also disclosed are pharmaceutical compositions comprising a pharmaceutically acceptable carrier and a therapeutically effective amount of at least one compound having a structure represented by a formula:

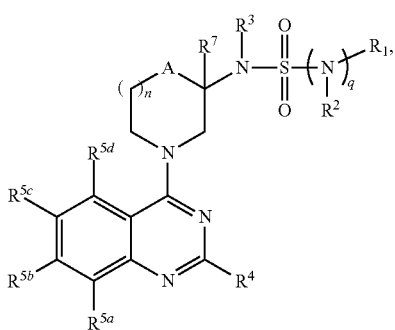

wherein n is 0, 1, or 2; wherein q is 0 or 1; wherein $R^1$ is —$NH_2$, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)$CO_2H$, or $Cy^1$; wherein $Cy^1$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^2$ is hydrogen or C1-C4 alkyl, or wherein each of $R^1$ and $R^2$ are covalently bonded together and, together with the intermediate atoms, comprise a 3- to 6-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^3$ is hydrogen or C1-C4 alkyl, or wherein each of $R^1$ and $R^3$ are covalently bonded together and, together with the intermediate atoms, comprise a 5- to 7-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^4$ is hydrogen, halogen, —$NH_2$, —OH, C1-C4 alkyl, C1-C4 alkoxy, C1-C4 alkylamino, (C1-C4)(C1-C4) dialkylamino, or $Cy^2$; wherein $Cy^2$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein each of $R^{5a}$, $R^{5b}$, and $R^{5d}$ is independently hydrogen, halogen, —$NH_2$, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —$CO_2$(C1-C4 alkyl), —$CO_2H$, —$CO_2NH_2$, —NHC(O)$Cy^3$, —NHC(O)(C1-C4 alkyl), or $Cy^3$; wherein $Cy^3$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^{5c}$ is hydrogen, halogen, —$NH_2$, —OH, —CN, C1-C4 alkyl, C1-C4 haloalkyl, C1-C4 alkoxy, C1-C4 haloalkoxy, C1-C4 alkylamino, (C1-C4)(C1-C4) dialkylamino, —$CO_2$(C1-C4 alkyl), —$CO_2H$, —$CO_2NH_2$, —NHC(O)$Cy^3$, —NHC(O)(C1-C4 alkyl), or aryl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein A is O, $NR^{6a}$, or $CHR^{6b}$; wherein $R^{6a}$ is hydrogen or C1-C4 alkyl; and wherein $R^{6b}$ is hydrogen, C1-C4 alkyl, C1-C4 haloalkyl, C1-C4 alkoxy, C1-C4 alkylamino, (C1-C4)(C1-C4) dialkylamino, or —$CO_2H$; wherein $R^7$ is hydrogen, halogen, —OH, C1-C4 alkyl, C1-C4 haloalkyl, or C1-C4 alkoxy; provided that when $R^{5b}$ is morpholinyl and $R^1$ is thiophenyl or thiazolyl, then q is 1 and at least one of $R^{5a}$, $R^{5c}$, and $R^{5d}$ is not hydrogen, or a pharmaceutically acceptable salt thereof.

Also disclosed are pharmaceutical compositions comprising a pharmaceutically acceptable carrier and a therapeutically effective amount of at least one compound having a structure represented by a formula selected from:

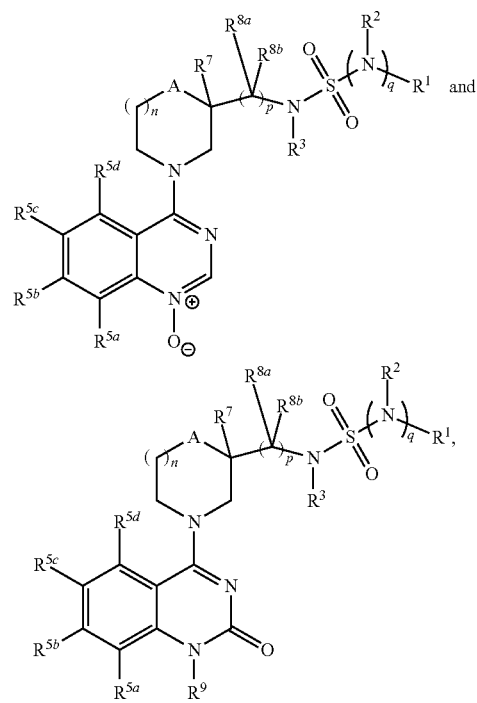

wherein n is 0, 1, or 2; wherein p is 0, 1, 2, 3, or 4; wherein q is 0 or 1; wherein $R^1$ is —$NH_2$, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)$CO_2H$, or $Cy^1$; wherein $Cy^1$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^2$ is hydrogen or C1-C4 alkyl, or wherein each of $R^1$ and $R^2$ are covalently bonded together and, together with the intermediate atoms, comprise a 3- to 6-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^3$ is hydrogen or C1-C4 alkyl, or wherein each of $R^1$ and $R^3$ are covalently bonded together and, together with the intermediate atoms, comprise a 5- to 7-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^4$ is hydrogen, halogen, —$NH_2$, —OH, C1-C4 alkyl, C1-C4 alkoxy, C1-C4 alkylamino, (C1-C4)(C1-C4) dialkylamino, or $Cy^2$; wherein $Cy^2$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein each of $R^{5a}$, $R^{5b}$, $R^{5c}$, and $R^{5d}$ is independently hydrogen, halogen, —NH$_2$, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —CO$_2$(C1-C4 alkyl), —CO$_2$H, —CO$_2$NH$_2$, —NHC(O)Cy$^3$, —NHC(O)(C1-C4 alkyl), or Cy$^3$; wherein Cy$^3$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein A is O, NR$^{6a}$, or CHR$^{6b}$; wherein R$^{6a}$ is hydrogen or C1-C4 alkyl; and wherein R$^{6b}$ is hydrogen, C1-C4 alkyl, C1-C4 haloalkyl, C1-C4 alkoxy, C1-C4 alkylamino, (C1-C4)(C1-C4) dialkylamino, or —CO$_2$H; wherein R$^7$ is hydrogen, halogen, —OH, C1-C4 alkyl, C1-C4 haloalkyl, or C1-C4 alkoxy; wherein each occurrence of $R^{8a}$ and $R^{8b}$, when present, is independently hydrogen, C1-C4 alkyl, C1-C4 haloalkyl, phenyl, or —CO$_2$H; or wherein p is 1 and each of $R^{8a}$ and $R^{8b}$ together comprise =O; and wherein R$^9$ is hydrogen, C1-C4 alkyl, or Cy$^4$, wherein Cy$^4$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino, or a pharmaceutically acceptable salt thereof.

Also disclosed are compounds having a structure represented by a formula:

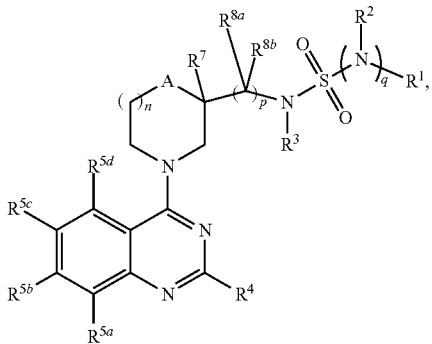

wherein n is 0, 1, or 2; wherein p is 1, 2, 3, or 4; wherein q is 0 or 1; wherein R$^1$ is —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)CO$_2$H, or Cy$^1$; wherein Cy$^1$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein R$^2$ is hydrogen or C1-C4 alkyl, or wherein each of R$^1$ and R$^2$ are covalently bonded together and, together with the intermediate atoms, comprise a 3- to 6-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein R$^3$ is hydrogen or C1-C4 alkyl, or wherein each of R$^1$ and R$^3$ are covalently bonded together and, together with the intermediate atoms, comprise a 5- to 7-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein R$^4$ is hydrogen, halogen, —NH$_2$, —OH, C1-C4 alkyl, C1-C4 alkoxy, C1-C4 alkylamino, (C1-C4)(C1-C4) dialkylamino, or Cy$^2$; wherein Cy$^2$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein each of $R^{5a}$, $R^{5b}$, $R^{5c}$, and $R^{5d}$ is independently hydrogen, halogen, —NH$_2$, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —CO$_2$(C1-C4 alkyl), —CO$_2$H, —CO$_2$NH$_2$, —NHC(O)Cy$^3$, —NHC(O)(C1-C4 alkyl), or Cy$^3$; wherein Cy$^3$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein A is O, NR$^{6a}$, or CHR$^{6b}$; wherein R$^{6a}$ is hydrogen or C1-C4 alkyl; and wherein R$^{6b}$ is hydrogen, C1-C4 alkyl, C1-C4 haloalkyl, C1-C4 alkoxy, C1-C4 alkylamino, (C1-C4)(C1-C4) dialkylamino, or —CO$_2$H; wherein R$^7$ is hydrogen, halogen, —OH, C1-C4 alkyl, C1-C4 haloalkyl, or C1-C4 alkoxy; and wherein each occurrence of $R^{8a}$ and $R^{8b}$, when present, is independently hydrogen, C1-C4 alkyl, C1-C4 haloalkyl, phenyl, or —CO$_2$H; or wherein p is 1 and each of $R^{8a}$ and $R^{8b}$ together comprise =O; provided that when R$^1$ is methyl and each of R$^3$ and R$^4$ is hydrogen then each of $R^{5a}$, $R^{5b}$, $R^{5c}$, and $R^{5d}$ is independently hydrogen, fluorine, —NH$_2$, —OH, C1-C4 alkyl, C1-C4 alkoxy, C1-C4 alkylamino, (C1-C4)(C1-C4) dialkylamino, or Cy$^3$, and provided that when n is 1, p is 1, q is 0, A is CHR$^{6b}$, and R$^1$ is methyl, then at least two of R$^4$, $R^{5a}$, $R^{5b}$, $R^{5c}$, and $R^{5d}$ are not hydrogen, or a pharmaceutically acceptable salt thereof.

Also disclosed are compounds having a structure represented by a formula:

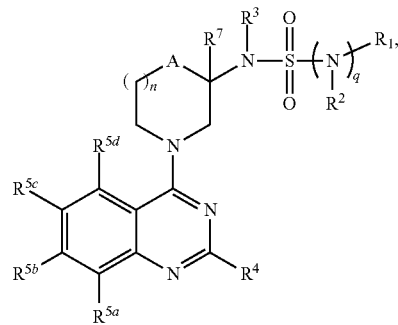

wherein n is 0, 1, or 2; wherein q is 0 or 1; wherein R$^1$ is —NH$_2$, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)CO$_2$H, or Cy$^1$; wherein Cy$^1$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein R$^2$ is hydrogen or C1-C4 alkyl, or wherein each of R$^1$ and R$^2$ are covalently bonded together and, together with the intermediate atoms, comprise a 3- to 6-membered heterocycloalkyl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein R³ is hydrogen or C1-C4 alkyl, or wherein each of R¹ and R³ are covalently bonded together and, together with the intermediate atoms, comprise a 5- to 7-membered heterocycloalkyl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein R⁴ is hydrogen, halogen, —NH₂, —OH, C1-C4 alkyl, C1-C4 alkoxy, C1-C4 alkylamino, (C1-C4)(C1-C4) dialkylamino, or Cy²; wherein Cy², when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein each of R$^{5a}$, R$^{5b}$, and R$^{5d}$ is independently hydrogen, halogen, —NH₂, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —CO₂(C1-C4 alkyl), —CO₂H, —CO₂NH₂, —NHC(O)Cy³, —NHC(O)(C1-C4 alkyl), or Cy³; wherein Cy³, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein R⁵ is hydrogen, halogen, —CN, —NH₂, —OH, C1-C4 alkyl, C1-C4 haloalkyl, C1-C4 alkoxy, C1-C4 haloalkoxy, C1-C4 alkylamino, (C1-C4)(C1-C4) dialkylamino, —CO₂(C1-C4 alkyl), —CO₂H, —CO₂NH₂, —NHC(O)Cy³, —NHC(O)(C1-C4 alkyl), or aryl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein A is O, NR$^{6a}$, or CHR$^{6b}$; wherein R$^{6a}$ is hydrogen or C1-C4 alkyl; wherein R$^{6b}$ is hydrogen, C1-C4 alkyl, C1-C4 haloalkyl, C1-C4 alkoxy, C1-C4 alkylamino, (C1-C4)(C1-C4) dialkylamino, or —CO₂H; and wherein R⁷ is hydrogen, halogen, —OH, C1-C4 alkyl, C1-C4 haloalkyl, or C1-C4 alkoxy; provided that when R$^{5b}$ is morpholinyl and R¹ is thiophenyl or thiazolyl, then q is 1 and at least one of R$^{5a}$, R$^{5c}$, and R$^{5d}$ is not hydrogen; provided that when q is 0 then Cy¹ is not aryl; and provided that at least one of R$^{5a}$R$^{5b}$, R$^{5c}$, and R$^{5d}$ is not hydrogen, or a pharmaceutically acceptable salt thereof.

Also disclosed are compounds having a structure represented by a formula selected from:

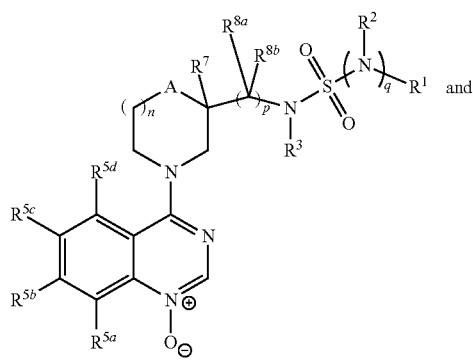

and

-continued

[structure]

wherein n is 0, 1, or 2; wherein p is 0, 1, 2, 3, or 4; wherein q is 0 or 1; wherein R¹ is —NH₂, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)CO₂H, or Cy¹; wherein Cy¹, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein R² is hydrogen or C1-C4 alkyl, or wherein each of R¹ and R² are covalently bonded together and, together with the intermediate atoms, comprise a 3- to 6-membered heterocycloalkyl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein R³ is hydrogen or C1-C4 alkyl, or wherein each of R¹ and R³ are covalently bonded together and, together with the intermediate atoms, comprise a 5- to 7-membered heterocycloalkyl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein R⁴ is hydrogen, halogen, —NH₂, —OH, C1-C4 alkyl, C1-C4 alkoxy, C1-C4 alkylamino, (C1-C4)(C1-C4) dialkylamino, or Cy²; wherein Cy², when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein each of R$^{5a}$, R$^{5b}$, R$^{5c}$, and R$^{5d}$ is independently hydrogen, halogen, —NH₂, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —CO₂(C1-C4 alkyl), —CO₂H, —CO₂NH₂, —NHC(O)Cy³, —NHC(O)(C1-C4 alkyl), or Cy³; wherein Cy³, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein A is O, NR$^{6a}$, or CHR$^{6b}$; wherein R$^{6a}$ is hydrogen or C1-C4 alkyl; and wherein R$^{6b}$ is hydrogen, C1-C4 alkyl, C1-C4 haloalkyl, C1-C4 alkoxy, C1-C4 alkylamino, (C1-C4)(C1-C4) dialkylamino, or —CO₂H; wherein R⁷ is hydrogen, halogen, —OH, C1-C4 alkyl, C1-C4 haloalkyl, or C1-C4 alkoxy; wherein each occurrence of R$^{8a}$ and R$^{8b}$, when present, is independently hydrogen, C1-C4 alkyl, C1-C4 haloalkyl, phenyl, or —CO₂H; or wherein p is 1 and each of R$^{8a}$ and R$^{8b}$ together comprise =O; and wherein R⁹ is hydrogen, C1-C4 alkyl, or Cy⁴, wherein Cy⁴, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino, or a pharmaceutically acceptable salt thereof.

Further disclosed are methods for treating a disorder associated with elevated TXNIP or elevated glucagon in a mammal, comprising administering to the mammal a therapeutically effective amount of at least one pharmaceutical composition or compound as described herein. Also disclosed are methods of lowering hepatic glucose production in a mammal in need thereof, comprising administering to the mammal a therapeutically effective amount of at least one pharmaceutical composition or compound as described herein.

Also provided are compositions and methods for use in the prevention and treatment of hyperlipidemia and/or fatty liver disease (e.g., nonalcoholic fatty liver disease) in a mammal, optionally in the absence of elevated TXNIP or in the absence of diabetes or diabetes related disorders. The disclosed methods include administering to the mammal a therapeutically effective amount of at least one pharmaceutical composition or compound as described herein.

Also disclosed are methods of identifying an inhibitor of glucose-induced TXNIP expression comprising culturing cells stably transfected with an exogenous TXNIP promoter in a first culture medium containing a low level of glucose; culturing a first subset of the cells of step (a) in a second culture medium containing a high level of glucose; culturing a second subset of the cells of step (a) in a third culture medium containing a high level of glucose and an agent to be tested; and comparing the level of TXNIP promoter activity in the first subset of cells with the level of TXNIP expression in the second subset of cells, wherein a lower level of TXNIP promoter activity in the second subset of cells as compared to the first subset of cells indicates the agent is an inhibitor of glucose-induced TXNIP expression. Optionally, the method can further comprise determining the identified inhibitor of glucose-induced TXNIP expression is a selective inhibitor of TXNIP expression and not a general transcriptional inhibitor comprising contacting a cell comprising a first and second exogenous promoter with the identified inhibitor of glucose-induced TXNIP expression, wherein the first exogenous promoter is a TXNIP promoter and the second exogenous promoter promotes expression of a non-TXNIP gene; and detecting the level of promoter activity of the TXNIP and the non-TXNIP gene, wherein detecting a reduction in the level of TXNIP promoter-driven gene expression without reduction in the level of non-TXNIP promoter-driven gene expression as compared to a control cell without contact with the inhibitor of glucose-induced TXNIP determines that the identified inhibitor of glucose-induced TXNIP expression is not a general inhibitor of transcription.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

FIG. 1 shows the effect of compound #11 (Table 1) on inhibition of TXNIP expression in primary human pancreatic islets under high glucose conditions, as compared to control (DMSO treated) islets.

FIG. 2 shows that compound #11 inhibits Type 1 diabetes associated inflammatory cytokine-induced β-cell death in primary cultures of human islets.

FIG. 3 shows the results of oral administration of compound #11a (day 5-15) in two different models of diabetes. The upper left panel shows significantly lower blood glucose levels in compound-treated wild-type mice previously treated with multiple low-dose streptozotocin (STZ) (day 1-5) to induce diabetes as compared to STZ-treated wild-type mice that did not receive compound #11a. The upper right panel shows no detrimental effect of compound #11a on the body weight of the STZ treated mice as compared to control STZ treated mice. The lower left panel shows significantly lower blood glucose levels in obese diabetic db/db mice (as a model of Type 2 diabetes) treated with compound #11a as compared to untreated db/db mice. Similar to the STZ treated mice, compound #11a had no significant effect on body weight of the db/db mice as shown in the lower right panel.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated+10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half maximal (50%) inhibitory concentration (IC) of a substance.

As used herein, "$EC_{50}$," is intended to refer to the concentration of a substance (e.g., a compound or a drug) that is required for 50% agonism of a biological process, or component of a process, including a protein, subunit, organelle, ribonucleoprotein, etc. In one aspect, an $EC_{50}$ can refer to the concentration of a substance that is required for 50% agonism in vivo, as further defined elsewhere herein. In a further aspect, $EC_{50}$ refers to the concentration of agonist that provokes a response halfway between the baseline and maximum response.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage forms can comprise inventive a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, terms such as "elevated," "increased," "reduced," and decreased" are generally considered relative to a control or normal state. For example, "a disorder associated with elevated TXNIP" refers to a disease or condition marked by an increase as compared to the normal or non-diseased state. However, when terms such as "reduce" or "decrease" are used herein relative to treatment, in which they refer to normalizing the level or amount toward the control or normal state and may include a partial or complete normalization.

A disorder associated with elevated TXNIP and/or glucagon includes, for example, "diabetes and associated disorders" (e.g., Type 1 diabetes, Type 2 diabetes, gestational diabetes, impaired glucose tolerance or pre-diabetes, insulin resistance, hyperlipidemia, non-alcoholic fatty liver disease, complications of diabetes, including diabetes-related nephropathy, neuropathy, retinopathy, cardiomyopathy, and cardiovascular disease as well as pancreatic β-cell loss or pancreatic islet dysfunction, including dysregulation of insulin and/or glucagon production or secretion) or other disorders associated with endoplasmic reticulum stress and/or oxidative stress of the cell (including endogenous, ex vivo, or transplanted pancreatic islets). As used herein, hyperlipidemia and fatty liver disease, for example, may or may not be associated with diabetes or elevated TXNIP.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14$^{th}$ edition), the Physicians' Desk Reference (64$^{th}$ edition), and The Pharmacological Basis of Therapeutics (12$^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the it clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —NH$_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein. A specific example of amino is —NH$_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$A)$_a$-, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multicyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxy" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SRO-$; $-(CH_2)_{0-4}SC(O)R$; $-(CH_2)_{0-4}C(O)NR^\circ_2$; $-C(S)NR^\circ_2$; $-C(S)SRO$; $-(CH_2)_{0-4}OC(O)NR^\circ 2$; $-C(O)N(OR)R^\circ$; $-C(O)C(O)R^\circ$; $-C(O)CH_2C(O)R$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R$; $-N(R^\circ)S(O)_2NR^\circ_2$; $-N(R^\circ)S(O)_2R$; $-N(OR)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C1-4$ straight or branched alkylene)O$-N(R^\circ)_2$; or $-(C_{1-4}$ straight or branched alkylene)C(O)O$-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)C(O)OR$^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Greene's Protective Groups in Organic Synthesis," P. G. M. Wuts, Wiley, 2014).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

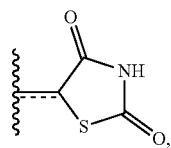

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R, R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radio-actively labeled forms, isomers, solvates and combinations thereof. The "combinations" mentioned in this context are refer to derivatives falling within at least two of the groups: pharmaceutically acceptable salts, prodrugs, deuterated forms, radio-actively labeled forms, isomers, and solvates. Examples of radio-actively labeled forms include compounds labeled with tritium, phosphorous-32, iodine-129, carbon-11, fluorine-18, and the like.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, 13C, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

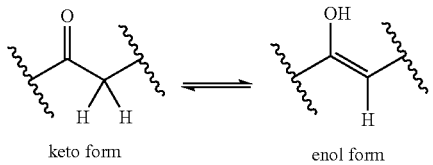

keto form      enol form

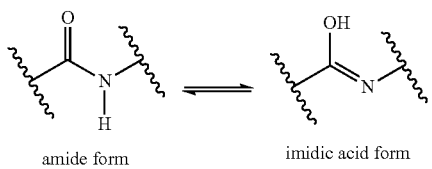

amide form      imidic acid form

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

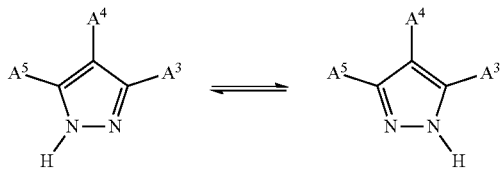

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

which is understood to be equivalent to a formula:

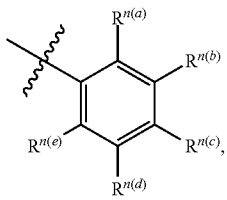

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^n(a)$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Strem Chemicals (Newburyport, Mass.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C—F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. METHODS OF TREATING OR PREVENTING A DISORDER ASSOCIATED WITH ELEVATED TXNIP OR GLUCAGON

In various aspects, the compounds and compositions disclosed herein are useful for treating, preventing, ameliorating, controlling or reducing the risk of a variety of disorders associated with elevated TXNIP expression and/or elevated glucagon levels, including, for example, diabetes or diabetes related disorders. Thus, in one aspect, disclosed are methods of treating or preventing a disorder associated with elevated TXNIP in a subject, the method comprising the step of administering to the subject an effective amount of at least one disclosed compound or a pharmaceutically acceptable salt thereof. Without meaning to be limited by theory, an effective amount of the at least one compound or pharmaceutically acceptable salt thereof may work by one or more mechanisms, for example, by directly or indirectly inhibiting TXNIP expression and signalingand/or by reducing circulating glucagon levels. Optionally, the compo unds or compositions as disclosed herein do not block calcium channels. The clinical outcome optionally includes improved blood glucose control, lower hepatic glucose production, lower serum glucagon levels, and/or signs of higher insulin production as compared to the absence of at least one compound or pharmaceutically acceptable salt thereof.

In one aspect, disclosed are methods for treating or preventing a disorder associated with elevated TXNIP or elevated glucagon levels in a mammal, the method comprising the step of administering to the mammal a therapeutically effective amount of at least one compound having a structure represented by a formula selected from:

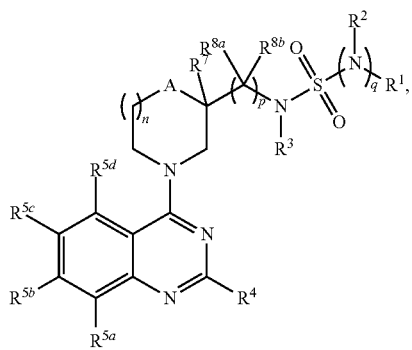

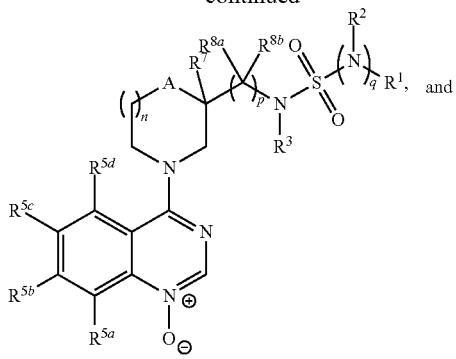

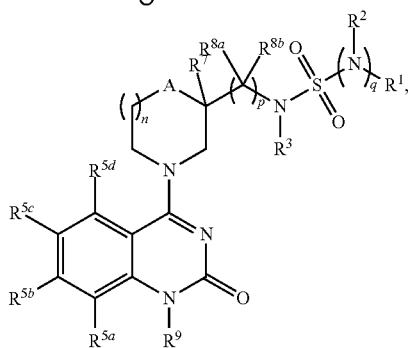

wherein n is 0, 1, or 2; wherein p is 0, 1, 2, 3, or 4; wherein q is 0 or 1; wherein $R^1$ is —$NH_2$, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)$CO_2H$, or $Cy^1$; wherein $Cy^1$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^2$ is hydrogen or C1-C4 alkyl, or wherein each of $R^1$ and $R^2$ are covalently bonded together and, together with the intermediate atoms, comprise a 3- to 6-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^3$ is hydrogen or C1-C4 alkyl, or wherein each of $R^1$ and $R^3$ are covalently bonded together and, together with the intermediate atoms, comprise a 5- to 7-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^4$ is hydrogen, halogen, —$NH_2$, —OH, C1-C4 alkyl, C1-C4 alkoxy, C1-C4 alkylamino, (C1-C4)(C1-C4) dialkylamino, or $Cy^2$; wherein $Cy^2$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein each of $R^{5a}$, $R^{5b}$, $R^{5c}$, and $R^{5d}$ is independently hydrogen, halogen, —$NH_2$, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —$CO_2$(C1-C4 alkyl), —$CO_2H$, —$CO_2NH_2$, —NHC(O)$Cy^3$, —NHC(O)(C1-C4 alkyl), or $Cy^3$; wherein $Cy^3$, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein A is O, NR$^{6a}$, or CHR$^{6b}$; wherein R$^{6a}$ is hydrogen or C1-C4 alkyl; and wherein R$^{6b}$ is hydrogen, C1-C4 alkyl, C1-C4 haloalkyl, C1-C4 alkoxy, C1-C4 alkylamino, (C1-C4)(C1-C4) dialkylamino, or —CO₂H; wherein R$^7$ is hydrogen, halogen, —OH, C1-C4 alkyl, C1-C4 haloalkyl, or C1-C4 alkoxy; wherein each occurrence of R$^{8a}$ and R$^{8b}$, when present, is independently hydrogen, C1-C4 alkyl, C1-C4 haloalkyl, phenyl, or —CO₂H; or wherein p is 1 and each of R$^{8a}$ and R$^{8b}$ together comprise =O; and wherein R$^9$ is hydrogen, C1-C4 alkyl, or Cy$^4$, wherein Cy$^4$, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino, or a pharmaceutically acceptable salt thereof.

Also disclosed are methods for treating or preventing a disorder associated with elevated TXNIP and/or glucagon in a mammal, the method comprising the step of administering to the mammal a therapeutically effective amount of at least one compound having a structure represented by a formula:

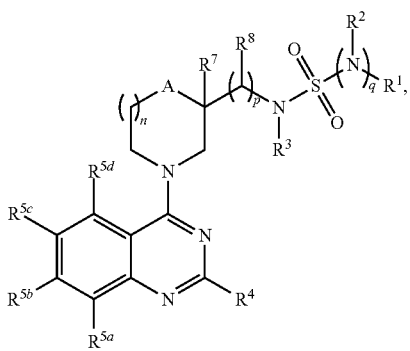

wherein n is 0, 1, or 2; wherein each of p and q is independently 0 or 1; wherein R$^1$ is —NH₂, —OH, C1-C4 alkyl, C1-C4 haloalkyl, C1-C4 alkoxy, C1-C4 alkylamino, (C1-C4)(C1-C4) dialkylamino, or Cy$^1$; wherein Cy$^1$, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein R$^2$ is hydrogen or C1-C4 alkyl, or wherein each of R$^1$ and R$^2$ are covalently bonded together and, together with the intermediate atoms, comprise a 3- to 6-membered heterocycloalkyl substituted with 0, 1, 2, or 3 groups independently selected from halogen, —NH₂, —OH, C1-C4 alkyl, C1-C4 haloalkyl, C1-C4 alkoxy, C1-C4 alkylamino, (C1-C4)(C1-C4) dialkylamino; wherein R$^3$ is hydrogen or C1-C4 alkyl; wherein R$^4$ is hydrogen, halogen, —NH₂, —OH, C1-C4 alkyl, C1-C4 alkoxy, C1-C4 alkylamino, (C1-C4)(C1-C4) dialkylamino, or Cy$^2$; wherein Cy$^2$, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein each of R$^{5a}$, R$^{5b}$, R$^{5c}$ and R$^{5d}$ is independently hydrogen, halogen, —NH₂, —CN, —OH, C1-C4 alkyl, C1-C4 haloalkyl, C1-C4 alkoxy, C1-C4 alkylamino, (C1-C4)(C1-C4) dialkylamino, —CO₂(C1-C4 alkyl), —CO₂H, —CO₂NH₂, —NHC(O)Cy$^3$, —NHC(O)(C1-C4 alkyl), or Cy$^3$; wherein Cy$^3$, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein A is O, NR$^{6a}$ or CHR$^{6b}$; wherein R$^{6a}$ is hydrogen or C1-C4 alkyl; and wherein R$^{6b}$ is hydrogen, C1-C4 alkyl, C1-C4 haloalkyl, C1-C4 alkoxy, C1-C4 alkylamino, or (C1-C4)(C1-C4) dialkylamino; wherein R$^7$ is hydrogen, halogen, —OH, C1-C4 alkyl, C1-C4 haloalkyl, or C1-C4 alkoxy; wherein R$^8$ is hydrogen, C1-C4 alkyl, or C1-C4 haloalkyl, or a pharmaceutically acceptable salt thereof.

In a further aspect, the disorder associated with elevated TXNIP and/or glucagon is a disorder affecting regulation of hepatic glucose production. In a still further aspect, the disorder associated with elevated TXNIP and/or glucagon is diabetes or a diabetes related disorder. In yet a further aspect, the diabetes is selected from Type I diabetes, Type II diabetes, and gestational diabetes. In an even further aspect, the diabetes is Type I diabetes. In a still further aspect, the diabetes is Type II diabetes. In yet a further aspect, the diabetes is gestational diabetes.

In various aspects, the disclosed compounds can be used in combination with one or more other drugs in the treatment, prevention, control, amelioration, or reduction of risk of disorders associated with elevated TXNIP and/or elevated glucagon levels for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly. Accordingly, the pharmaceutical compositions include those that contain one or more other active ingredients, in addition to a compound of the present invention.

In a further aspect, the compound exhibits inhibition of TXNIP expression or function and/or lowers glucagon levels. In a further aspect, the compound exhibits inhibition of TXNIP expression or function and/or lowers glucagon levels with an IC$_{50}$ of from about 0.001 μM to about 25 μM. In a still further aspect, the compound exhibits inhibition of TXNIP expression or function and/or lowers glucagon levels with an IC$_{50}$ of from about 0.001 μM to about 15 μM. In yet a further aspect, the compound exhibits inhibition of TXNIP expression or function and/or lowers glucagon levels with an IC$_{50}$ of from about 0.001 μM to about 10 μM. In an even further aspect, the compound exhibits inhibition of TXNIP expression or function and/or lowers glucagon with an IC$_{50}$ of from about 0.001 μM to about 5 μM. In a still further aspect, the compound exhibits inhibition of TXNIP expression or function and/or lowers glucagon levels with an IC$_{50}$ of from about 0.001 μM to about 1 μM. In yet a further aspect, the compound exhibits inhibition of TXNIP expression or function and/or lowers glucagon with an IC$_{50}$ of from about 0.001 μM to about 0.5 μM. In an even further aspect, the compound exhibits inhibition of TXNIP expression or function and/or lowers glucagon with an $IC_{50}$ of from about 0.001 µM to about 0.1 µM. In a still further aspect, the compound exhibits inhibition of TXNIP expression or function and/or lowers glucagon levels with an $IC_{50}$ of from about 0.001 µM to about 0.05 µM. In yet a further aspect, the compound exhibits inhibition of TXNIP expression or function and/or lowers glucagon levels with an $IC_{50}$ of from about 0.001 µM to about 0.01 µM. In an even further aspect, the compound exhibits inhibition of TXNIP expression or function and/or lowers glucagon levels with an $IC_{50}$ of from about 0.001 µM to about 0.005 µM. In a still further aspect, the compound exhibits inhibition of TXNIP expression or function and/or lowers glucagon levels with an $IC_{50}$ of from about 0.005 µM to about 25 µM. In yet a further aspect, the compound exhibits inhibition of TXNIP expression or function and/or lowers glucagon levels with an $IC_{50}$ of from about 0.01 µM to about 25 µM. In an even further aspect, the compound exhibits inhibition of TXNIP expression or function and/or lowers glucagon levels with an $IC_{50}$ of from about 0.05 µM to about 25 µM. In a still further aspect, the compound exhibits inhibition of TXNIP expression or function and/or lowers glucagon levels with a $IC_{50}$ of from about 0.1 µM to about 25 µM. In yet a further aspect, the compound exhibits inhibition of TXNIP expression or function and/or lowers glucagon levels with an $IC_{50}$ of from about 0.5 µM to about 25 µM. In an even further aspect, the compound exhibits inhibition of TXNIP expression or function and/or lowers glucagon levels with an $IC_{50}$ of from about 1 µM to about 25 µM. In a still further aspect, the compound exhibits inhibition of TXNIP expression or function and/or lowers glucagon levels with an $IC_{50}$ of from about 5 µM to about 25 µM. In yet a further aspect, the compound exhibits inhibition of TXNIP expression or function and/or lowers glucagon levels with an $IC_{50}$ of from about 10 µM to about 25 µM. In an even further aspect, the compound exhibits inhibition of TXNIP expression or function and/or lowers glucagon levels with a $IC_{50}$ of from about 15 µM to about 25 µM.

In a further aspect, the subject is a mammal. In a still further aspect, the mammal is a human.

In a further aspect, the subject has been diagnosed with a need for treatment of the disorder associated with elevated TXNIP and/or glucagon prior to the administering step. In a still further aspect, the subject is at risk for developing the disorder prior to the administering step.

In a further aspect, the effective amount is a therapeutically effective amount. In a still further aspect, the effective amount is a prophylactically effective amount.

In a further aspect, the method further comprises identifying a subject at risk for developing the disorder prior to the administering step.

In a further aspect, the method further comprises the step of identifying a subject in need of treatment of a disorder associated with elevated TXNIP and/or glucagon.

C. METHODS OF TREATING OR PREVENTING HYPERLIPEDMIA OR FATTY LIVER DISEASE

Described herein are methods for preventing or treating hyperlipidemia and/or fatty liver disease (e.g., nonalcoholic fatty liver disease) in a subject. The methods comprise administering to the subject an effective amount of at least one disclosed compound, or a pharmaceutically acceptable salt thereof. The hyperlipidemia and/or fatty liver disease is optionally in the presence or absence of elevated TXNIP or in the presence or absence of diabetes or other diabetes related disorders. Without meaning to be limited by theory, the disclosed compounds or pharmaceutical salts are effective in treating hyperlipidemia or fatty liver disease even without an apparent need for reduction of TXNIP. The disclosed methods include administering to the mammal a therapeutically effective amount of at least one pharmaceutical composition or compound as described herein.

The disclosed compounds can be used in combination with one or more other drugs in the treatment, prevention, control, amelioration, or reduction of risk of hyperlipidemia and/or fatty liver disease, where the combination of the drugs together are safer or more effective than either drug alone. Such other drug(s) can be administered, by a route and in an amount commonly used therefor, contemporaneously or sequentially with a disclosed compound, as described above.

In a further aspect, the subject is a mammal. In a still further aspect, the mammal is a human.

In a further aspect, the subject has been diagnosed with a need for treatment of hyperlipidemia and/or fatty liver disease prior to the administering step. In a still further aspect, the subject is at risk for developing hyperlipidemia and/or fatty liver disease prior to the administering step.

In a further aspect, the effective amount is a therapeutically effective amount. In a still further aspect, the effective amount is a prophylactically effective amount.

In a further aspect, the method further comprises identifying a subject at risk for developing hyperlipidemia and/or fatty liver disease prior to the administering step.

D. METHODS OF INHIBITING TXNIP EXPRESSION OR FUNCTION OR LOWERING HEPATIC GLUCOSE PRODUCTION IN A SUBJECT

In various aspects, disclosed are methods of inhibiting TXNIP expression or function or lowering hepatic glucose production in a subject, the method comprising the step of administering to the subject an effective amount of at least one disclosed compound, or a pharmaceutically acceptable salt thereof. The method of inhibiting TXNIP expression or function or lowering hepatic glucose production (e.g., by reducing glucagon levels) is optionally selected from the group consisting of diabetes, diabetes related disorders, hyperlipidemia, and fatty liver disease.

In one aspect, disclosed are methods for inhibiting TXNIP expression or function and/or lowering hepatic glucose production in a mammal, the method comprising the step of administering to the mammal an effective amount of at least one compound having a structure represented by a formula selected from:

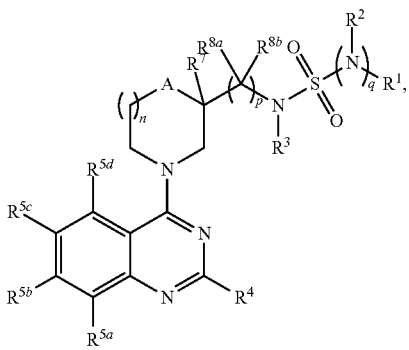

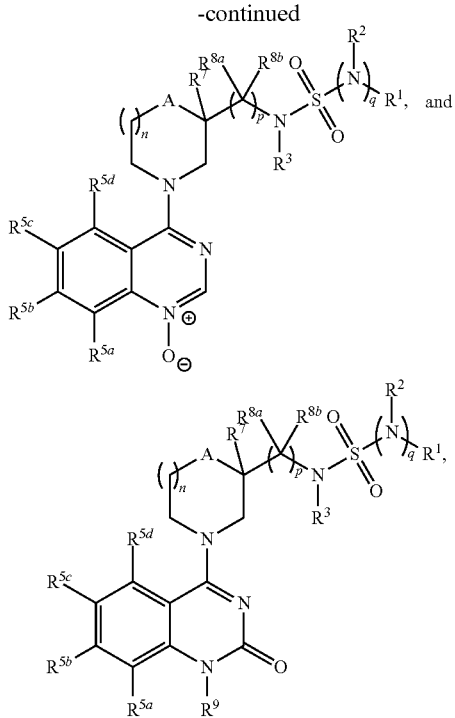

wherein n is 0, 1, or 2; wherein p is 0, 1, 2, 3, or 4; wherein q is 0 or 1; wherein $R^1$ is —$NH_2$, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)$CO_2H$, or $Cy^1$; wherein $Cy^1$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^2$ is hydrogen or C1-C4 alkyl, or wherein each of $R^1$ and $R^2$ are covalently bonded together and, together with the intermediate atoms, comprise a 3- to 6-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^3$ is hydrogen or C1-C4 alkyl, or wherein each of $R^1$ and $R^3$ are covalently bonded together and, together with the intermediate atoms, comprise a 5- to 7-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^4$ is hydrogen, halogen, —$NH_2$, —OH, C1-C4 alkyl, C1-C4 alkoxy, C1-C4 alkylamino, (C1-C4)(C1-C4) dialkylamino, or $Cy^2$; wherein $Cy^2$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein each of $R^{5a}$, $R^{5b}$, $R^{5c}$, and $R^{5d}$ is independently hydrogen, halogen, —$NH_2$, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —$CO_2$(C1-C4 alkyl), —$CO_2H$, —$CO_2NH_2$, —NHC(O)$Cy^3$, —NHC(O)(C1-C4 alkyl), or $Cy^3$; wherein $Cy^3$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein A is O, $NR^{6a}$, or $CHR^{6b}$; wherein $R^{6a}$ is hydrogen or C1-C4 alkyl; and wherein $R^{6b}$ is hydrogen, C1-C4 alkyl, C1-C4 haloalkyl, C1-C4 alkoxy, C1-C4 alkylamino, (C1-C4)(C1-C4) dialkylamino, or —$CO_2H$; wherein $R^7$ is hydrogen, halogen, —OH, C1-C4 alkyl, C1-C4 haloalkyl, or C1-C4 alkoxy; wherein each occurrence of $R^{8a}$ and $R^{8b}$, when present, is independently hydrogen, C1-C4 alkyl, C1-C4 haloalkyl, phenyl, or —$CO_2H$; or wherein p is 1 and each of $R^{8a}$ and $R^{8b}$ together comprise =O; and wherein $R^9$ is hydrogen, C1-C4 alkyl, or $Cy^4$, wherein $Cy^4$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino, or a pharmaceutically acceptable salt thereof.

Also disclosed are methods for inhibiting TXNIP expression and/or lowering hepatic glucose production in a mammal, the method comprising the step of administering to the mammal an effective amount of at least one compound having a structure represented by a formula:

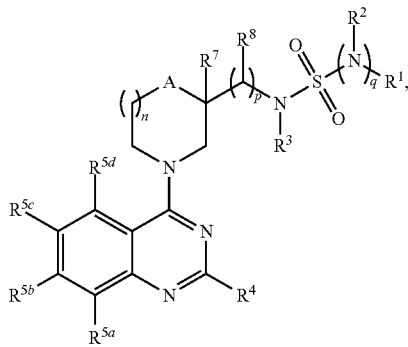

wherein n is 0, 1, or 2; wherein each of p and q is independently 0 or 1; wherein $R^1$ is —$NH_2$, —OH, C1-C4 alkyl, C1-C4 haloalkyl, C1-C4 alkoxy, C1-C4 alkylamino, (C1-C4)(C1-C4) dialkylamino, or $Cy^1$; wherein $Cy^1$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^2$ is hydrogen or C1-C4 alkyl, or wherein each of $R^1$ and $R^2$ are covalently bonded together and, together with the intermediate atoms, comprise a 3- to 6-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, (C1-C4)(C1-C4) dialkylamino; wherein $R^3$ is hydrogen or C1-C4 alkyl; wherein $R^4$ is hydrogen, halogen, —$NH_2$, —OH, C1-C4 alkyl, C1-C4 alkoxy, C1-C4 alkylamino, (C1-C4)(C1-C4) dialkylamino, or $Cy^2$; wherein $Cy^2$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein each of $R^{5a}$, $R^{5b}$, $R^{5c}$, and $R^{5d}$ is independently hydrogen, halogen, —$NH_2$, —CN, —OH, C1-C4 alkyl, C1-C4 haloalkyl, C1-C4 alkoxy, C1-C4 alkylamino, (C1-C4)(C1-C4) dialkylamino, —$CO_2$(C1-C4 alkyl), —$CO_2H$, —$CO_2NH_2$, —NHC(O)Cy$^3$, —NHC(O)(C1-C4 alkyl), or Cy$^3$; wherein Cy$^3$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein A is O, NR$^{6a}$, or CHR$^{6b}$; wherein R$^{6a}$ is hydrogen or C1-C4 alkyl; and wherein R$^{6b}$ is hydrogen, C1-C4 alkyl, C1-C4 haloalkyl, C1-C4 alkoxy, C1-C4 alkylamino, or (C1-C4)(C1-C4) dialkylamino; wherein R$^7$ is hydrogen, halogen, —OH, C1-C4 alkyl, C1-C4 haloalkyl, or C1-C4 alkoxy; wherein R$^8$ is hydrogen, C1-C4 alkyl, or C1-C4 haloalkyl, or a pharmaceutically acceptable salt thereof.

In a further aspect, inhibiting TXNIP expression and/or lowering hepatic glucose production in the mammal treats diabetes in the mammal.

In a further aspect, the subject has been diagnosed with a disorder associated with elevated TXNIP and/or glucagon prior to the administering step. In a still further aspect, the subject has been diagnosed with diabetes prior to the administering step. In yet a further aspect, the method further comprises the step of identifying a subject in need of treatment of a disorder of hepatic glucose regulation dysfunction. In an even further aspect, the method further comprises the step of identifying a subject in need of treatment of diabetes.

In a further aspect, the subject has been diagnosed with a need for inhibition of TXNIP and/or lowering hepatic glucose production prior to the administering step. In a still further aspect, the subject has been diagnosed with a need for treatment of a disorder associated with elevated TXNIP and/or glucagon prior to the administering step. In yet a further aspect, the method further comprises the step of identifying a subject in need of treatment.

In a further aspect, the disorder associated with elevated TXNIP and/or glucagon is a disorder of hepatic glucose regulation dysfunction. In a still further aspect, the disorder is diabetes. In yet a further aspect, the diabetes is selected from Type I diabetes, Type II diabetes, gestational diabetes, or pre-diabetes/impaired glucose tolerance or a diabetes related disorder. In an even further aspect, the diabetes is Type I diabetes. In a still further aspect, the diabetes is Type II diabetes. In yet a further aspect, the diabetes is gestational diabetes or pre-diabetes/impaired glucose tolerance.

In a further aspect, the compound exhibits inhibition of TXNIP and/or lowers glucagon levels with an IC$_{50}$ of from about 0.001 µM to about 25 µM. In a still further aspect, the compound exhibits inhibition of TXNIP and/or lowers glucagon with an IC$_{50}$ of from about 0.001 µM to about 15 µM. In yet a further aspect, the compound exhibits inhibition of TXNIP and/or lowers glucagon levels with an IC$_{50}$ of from about 0.001 µM to about 10 µM. In an even further aspect, the compound exhibits inhibition of TXNIP and/or lowers glucagon levels with an IC$_{50}$ of from about 0.001 µM to about 5 µM. In a still further aspect, the compound exhibits inhibition of TXNIP and/or lowers glucagon levels with an IC$_{50}$ of from about 0.001 µM to about 1 µM. In yet a further aspect, the compound exhibits inhibition of TXNIP and/or lowers glucagon levels with an IC$_{50}$ of from about 0.001 µM to about 0.5 µM. In an even further aspect, the compound exhibits inhibition of TXNIP and/or lowers glucagon levels with an IC$_{50}$ of from about 0.001 µM to about 0.1 µM. In a still further aspect, the compound exhibits inhibition of TXNIP and/or lowers glucagon levels with an IC$_{50}$ of from about 0.001 µM to about 0.05 µM. In yet a further aspect, the compound exhibits inhibition of TXNIP and/or lowers glucagon levels with an IC$_{50}$ of from about 0.001 µM to about 0.01 µM. In an even further aspect, the compound exhibits inhibition of TXNIP and/or lowers glucagon levels with an IC$_{50}$ of from about 0.001 µM to about 0.005 µM. In a still further aspect, the compound exhibits inhibition of TXNIP and/or lowers glucagon levels with an IC$_{50}$ of from about 0.005 µM to about 25 µM. In yet a further aspect, the compound exhibits inhibition of TXNIP and/or lowers glucagon levels with an IC$_{50}$ of from about 0.01 µM to about 25 µM. In an even further aspect, the compound exhibits inhibition of TXNIP and/or lowers glucagon levels with an IC$_{50}$ of from about 0.05 µM to about 25 µM. In a still further aspect, the compound exhibits inhibition of TXNIP and/or lowers glucagon levels with an IC$_{50}$ of from about 0.1 µM to about 25 µM. In yet a further aspect, the compound exhibits inhibition of TXNIP and/or lowers glucagon levels with an IC$_{50}$ of from about 0.5 µM to about 25 µM. In an even further aspect, the compound exhibits inhibition of TXNIP and/or lowers glucagon levels with an IC$_{50}$ of from about 1 µM to about 25 µM. In a still further aspect, the compound exhibits inhibition of TXNIP and/or lowers glucagon levels with an IC$_{50}$ of from about 5 µM to about 25 µM. In yet a further aspect, the compound exhibits inhibition of TXNIP and/or lowers glucagon levels with an IC$_{50}$ of from about 10 µM to about 25 µM. In an even further aspect, the compound exhibits inhibition of TXNIP and/or lowers glucagon levels with an IC$_{50}$ of from about 15 µM to about 25 µM.

In a further aspect, the subject is a mammal. In a still further aspect, the mammal is a human.

In a further aspect, the effective amount is a therapeutically effective amount. In a still further aspect, the effective amount is a prophylactically effective amount.

E. METHODS OF IDENTIFYING AN INHIBITOR OF GLUCOSE-INDUCED TXNIP Expression

Provided herein is a method of identifying an inhibitor of glucose-induced TXNIP expression. The method includes culturing cells stably transfected with an exogenous TXNIP promoter (e.g., a human TXNIP promoter) in a first culture medium containing a low level of glucose; then culturing a first subset of the cells in a second culture medium containing a high level of glucose and a second subset of the cells in a third culture medium containing a high level of glucose and an agent to be tested; and comparing the level of TXNIP promoter activity in the first subset of cells with the level of TXNIP promoter activity in the second subset of cells. A lower level of TXNIP promoter activity in the second subset of cells as compared to the first subset of cells indicates the agent is an inhibitor of glucose-induced TXNIP expression.

In the method of identifying an inhibitor of glucose-induced TXNIP expression, culturing in a high level of glucose or a low level of glucose refers to the levels higher or lower than the optimal level of glucose for culture of the specific cell type. For example, the optimal glucose level for culturing INS-1 cells is about 11.1 mM. Thus a low level of glucose is less than 11.1 (e.g., 3-10 mM, 5-7 mM, or more specifically about 5 mM), and a high level of glucose is higher than 11.1 (e.g., 12-30 mM, 15-25 mM, or, more specifically, about 25 mM).

Optionally, the method further includes determining the identified inhibitor of glucose-induced TXNIP expression is a selective inhibitor of TXNIP expression rather than a general transcriptional inhibitor by testing its effects on the promoter of a non-TXNIP gene (e.g., a CMV promoter) and/or treating a cell co-transfected with a first and second exogenous promoter with the identified inhibitor of glucose-induced TXNIP expression, wherein the first exogenous promoter is a TXNIP promoter and the second exogenous promoter promotes expression of a control non-TXNIP gene (e.g., a pRLTK promoter), and detecting the level of promoter activity of the TXNIP and the non-TXNIP gene. Detecting a reduction in the level of the TXNIP promoter activity without reduction in the level of the non-TXNIP gene control promoter as compared to a control cell without contact with the inhibitor of glucose-induced TXNIP determines that the identified inhibitor of glucose-induced TXNIP expression is not a general transcriptional inhibitor.

Optionally, the method further comprises screening the inhibitor of glucose-induced TXNIP by contacting a primary culture of cells (e.g., isolated islets or cardiomyocytes) with the agent in the presence of low and high glucose and/or by administering the inhibitor to a subject with diabetes.

F. PHARMACEUTICAL COMPOSITIONS

In one aspect, disclosed are pharmaceutical compositions comprising a disclosed compound, or a pharmaceutically acceptable salt thereof and a pharmaceutically acceptable carrier.

In one aspect, disclosed are pharmaceutical compositions comprising a pharmaceutically acceptable carrier and a therapeutically effective amount of at least one compound having a structure represented by a formula:

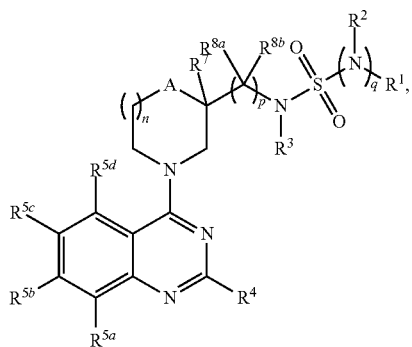

wherein n is 0, 1, or 2; wherein p is 1, 2, 3, or 4; wherein q is 0 or 1; wherein $R^1$ is —$NH_2$, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)$CO_2H$, or $Cy^1$; wherein $Cy^1$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^2$ is hydrogen or C1-C4 alkyl, or wherein each of $R^1$ and $R^2$ are covalently bonded together and, together with the intermediate atoms, comprise a 3- to 6-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^3$ is hydrogen or C1-C4 alkyl, or wherein each of $R^1$ and $R^3$ are covalently bonded together and, together with the intermediate atoms, comprise a 5- to 7-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^4$ is hydrogen, halogen, —$NH_2$, —OH, C1-C4 alkyl, C1-C4 alkoxy, C1-C4 alkylamino, (C1-C4)(C1-C4) dialkylamino, or $Cy^2$; wherein $Cy^2$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein each of $R^{5a}$, $R^{5b}$, $R^{5c}$, and $R^{5d}$ is independently hydrogen, halogen, —$NH_2$, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —$CO_2$(C1-C4 alkyl), —$CO_2H$, —$CO_2NH_2$, —NHC(O)$Cy^3$, —NHC(O)(C1-C4 alkyl), or $Cy^3$; wherein $Cy^3$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein A is O, $NR^{6a}$, or $CHR^{6b}$; wherein $R^{6a}$ is hydrogen or C1-C4 alkyl; and wherein $R^{6b}$ is hydrogen, C1-C4 alkyl, C1-C4 haloalkyl, C1-C4 alkoxy, C1-C4 alkylamino, (C1-C4)(C1-C4) dialkylamino, or —$CO_2H$; wherein $R^7$ is hydrogen, halogen, —OH, C1-C4 alkyl, C1-C4 haloalkyl, or C1-C4 alkoxy; wherein each occurrence of $R^{8a}$ and $R^{8b}$, when present, is independently hydrogen, C1-C4 alkyl, C1-C4 haloalkyl, phenyl, or —$CO_2H$; or wherein p is 1 and each of $R^{8a}$ and $R^{8b}$ together comprise =O; and wherein $R^9$ is hydrogen, C1-C4 alkyl, or $Cy^4$, wherein $Cy^4$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino, or a pharmaceutically salt thereof.

In one aspect, disclosed are pharmaceutical compositions comprising a pharmaceutically acceptable carrier and a therapeutically effective amount of at least one compound having a structure represented by a formula:

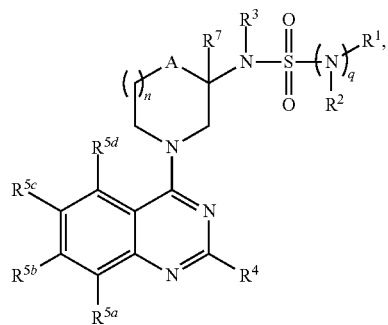

wherein n is 0, 1, or 2; wherein q is 0 or 1; wherein $R^1$ is —$NH_2$, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)$CO_2H$, or $Cy^1$; wherein $Cy^1$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^2$ is hydrogen or C1-C4 alkyl, or wherein each of $R^1$ and $R^2$ are covalently bonded together and, together with the intermediate atoms, comprise a 3- to 6-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein R$^3$ is hydrogen or C1-C4 alkyl, or wherein each of R$^1$ and R$^3$ are covalently bonded together and, together with the intermediate atoms, comprise a 5- to 7-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein R$^4$ is hydrogen, halogen, —NH$_2$, —OH, C1-C4 alkyl, C1-C4 alkoxy, C1-C4 alkylamino, (C1-C4)(C1-C4) dialkylamino, or Cy$^2$; wherein Cy$^2$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein each of R$^{5a}$, R$^{5b}$, and R$^{5d}$ is independently hydrogen, halogen, —NH$_2$, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —CO$_2$(C1-C4 alkyl), —CO$_2$H, —CO$_2$NH$_2$, —NHC(O)Cy$^3$, —NHC(O)(C1-C4 alkyl), or Cy$^3$; wherein Cy$^3$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein R$^{5c}$ is hydrogen, halogen, —NH$_2$, —OH, —CN, C1-C4 alkyl, C1-C4 haloalkyl, C1-C4 alkoxy, C1-C4 haloalkoxy, C1-C4 alkylamino, (C1-C4)(C1-C4) dialkylamino, —CO$_2$(C1-C4 alkyl), —CO$_2$H, —CO$_2$NH$_2$, —NHC(O)Cy$^3$, —NHC(O)(C1-C4 alkyl), or aryl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein A is O, NR$^{6a}$, or CHR$^{6b}$; wherein R$^{6a}$ is hydrogen or C1-C4 alkyl; and wherein R$^{6b}$ is hydrogen, C1-C4 alkyl, C1-C4 haloalkyl, C1-C4 alkoxy, C1-C4 alkylamino, (C1-C4)(C1-C4) dialkylamino, or —CO$_2$H; wherein R$^7$ is hydrogen, halogen, —OH, C1-C4 alkyl, C1-C4 haloalkyl, or C1-C4 alkoxy; provided that when R$^{5b}$ is morpholinyl and R$^1$ is thiophenyl or thiazolyl, then q is 1 and at least one of R$^{5a}$, R$^{5c}$, and R$^{5d}$ is not hydrogen, or a pharmaceutically acceptable salt thereof.

Also disclosed are pharmaceutical compositions comprising a pharmaceutically acceptable carrier and a therapeutically effective amount of at least one compound having a structure represented by a formula selected from:

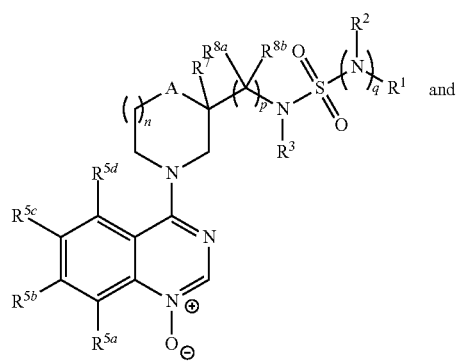

and

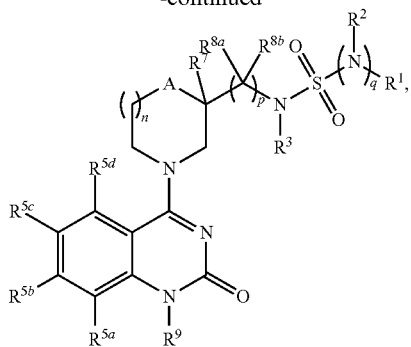

wherein n is 0, 1, or 2; wherein p is 0, 1, 2, 3, or 4; wherein q is 0 or 1; wherein R$^1$ is —NH$_2$, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)CO$_2$H, or Cy$^1$; wherein Cy$^1$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein R$^2$ is hydrogen or C1-C4 alkyl, or wherein each of R$^1$ and R$^2$ are covalently bonded together and, together with the intermediate atoms, comprise a 3- to 6-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein R$^3$ is hydrogen or C1-C4 alkyl, or wherein each of R$^1$ and R$^3$ are covalently bonded together and, together with the intermediate atoms, comprise a 5- to 7-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein R$^4$ is hydrogen, halogen, —NH$_2$, —OH, C1-C4 alkyl, C1-C4 alkoxy, C1-C4 alkylamino, (C1-C4)(C1-C4) dialkylamino, or Cy$^2$; wherein Cy$^2$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein each of R$^{5a}$, R$^{5b}$, R$^{5c}$, and R$^{5d}$ is independently hydrogen, halogen, —NH$_2$, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —CO$_2$(C1-C4 alkyl), —CO$_2$H, —CO$_2$NH$_2$, —NHC(O)Cy$^3$, —NHC(O)(C1-C4 alkyl), or Cy$^3$; wherein Cy$^3$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein A is O, NR$^{6a}$, or CHR$^{6b}$; wherein R$^{6a}$ is hydrogen or C1-C4 alkyl; and wherein R$^{6b}$ is hydrogen, C1-C4 alkyl, C1-C4 haloalkyl, C1-C4 alkoxy, C1-C4 alkylamino, (C1-C4)(C1-C4) dialkylamino, or —CO$_2$H; wherein R$^7$ is hydrogen, halogen, —OH, C1-C4 alkyl, C1-C4 haloalkyl, or C1-C4 alkoxy; wherein each occurrence of R$^{8a}$ and R$^{8b}$, when present, is independently hydrogen, C1-C4 alkyl, C1-C4 haloalkyl, phenyl, or —CO$_2$H; or wherein p is 1 and each of R$^{8a}$ and R$^{8b}$ together comprise =O; and wherein R$^9$ is hydrogen, C1-C4 alkyl, or Cy$^4$, wherein Cy$^4$, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino, or a pharmaceutically acceptable salt thereof.

Also disclosed are pharmaceutical compositions comprising a pharmaceutically acceptable carrier and a therapeutically effective amount of at least one compound having a structure represented by a formula:

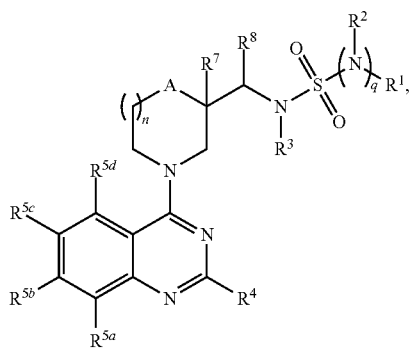

wherein n is 0, 1, or 2; wherein q is 0 or 1; wherein $R^1$ is —NH₂, —OH, C1-C4 alkyl, C1-C4 haloalkyl, C1-C4 alkoxy, C1-C4 alkylamino, (C1-C4)(C1-C4) dialkylamino, or $Cy^1$; wherein $Cy^1$, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein $R^2$ is hydrogen or C1-C4 alkyl, or wherein each of $R^1$ and $R^2$ are covalently bonded together and, together with the intermediate atoms, comprise a 3- to 6-membered heterocycloalkyl substituted with 0, 1, 2, or 3 groups independently selected from halogen, —NH₂, —OH, C1-C4 alkyl, C1-C4 haloalkyl, C1-C4 alkoxy, C1-C4 alkylamino, (C1-C4)(C1-C4) dialkylamino; wherein $R^3$ is hydrogen or C1-C4 alkyl; wherein $R^4$ is hydrogen, halogen, —NH₂, —OH, C1-C4 alkyl, C1-C4 alkoxy, C1-C4 alkylamino, (C1-C4)(C1-C4) dialkylamino, or $Cy^2$; wherein $Cy^2$, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein each of $R^{5a}$, $R^{5b}$, $R^{5c}$, and $R^{5d}$ is independently hydrogen, halogen, —NH₂, —CN, —OH, C1-C4 alkyl, C1-C4 haloalkyl, C1-C4 alkoxy, C1-C4 alkylamino, (C1-C4)(C1-C4) dialkylamino, —CO₂(C1-C4 alkyl), —CO₂H, —CO₂NH₂, —NHC(O)$Cy^3$, —NHC(O)(C1-C4 alkyl), or $Cy^3$; wherein $Cy^3$, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein A is O, $NR^{6a}$, or $CHR^{6b}$; wherein $R^{6a}$ is hydrogen or C1-C4 alkyl; and wherein $R^{6b}$ is hydrogen, C1-C4 alkyl, C1-C4 haloalkyl, C1-C4 alkoxy, C1-C4 alkylamino, or (C1-C4)(C1-C4) dialkylamino; wherein $R^7$ is hydrogen, halogen, —OH, C1-C4 alkyl, C1-C4 haloalkyl, or C1-C4 alkoxy; wherein $R^8$ is hydrogen, C1-C4 alkyl, or C1-C4 haloalkyl, or a pharmaceutically acceptable salt thereof.

In one aspect, disclosed are pharmaceutical compositions comprising pharmaceutically acceptable carrier and a therapeutically effective amount of at least one compound having a structure represented by a formula:

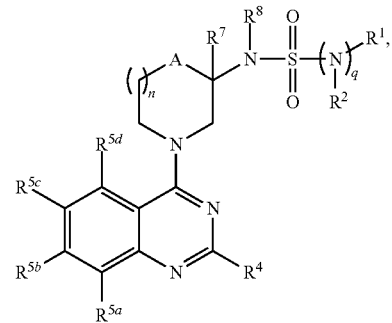

wherein n is 0, 1, or 2; wherein q is 0 or 1; wherein $R^1$ is —NH₂, —OH, C1-C4 alkyl, C1-C4 haloalkyl, C1-C4 alkoxy, C1-C4 alkylamino, (C1-C4)(C1-C4) dialkylamino, or $Cy^1$; wherein $Cy^1$, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein $R^2$ is hydrogen or C1-C4 alkyl, or wherein each of $R^1$ and $R^2$ are covalently bonded together and, together with the intermediate atoms, comprise a 3- to 6-membered heterocycloalkyl substituted with 0, 1, 2, or 3 groups independently selected from halogen, —NH₂, —OH, C1-C4 alkyl, C1-C4 haloalkyl, C1-C4 alkoxy, C1-C4 alkylamino, (C1-C4)(C1-C4) dialkylamino; wherein $R^3$ is hydrogen or C1-C4 alkyl; wherein $R^4$ is hydrogen, halogen, —NH₂, —OH, C1-C4 alkyl, C1-C4 alkoxy, C1-C4 alkylamino, (C1-C4)(C1-C4) dialkylamino, or $Cy^2$; wherein $Cy^2$, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein each of $R^{5a}$, $R^{5b}$, and $R^{5d}$ is independently hydrogen, halogen, —NH₂, —CN, —OH, C1-C4 alkyl, C1-C4 haloalkyl, C1-C4 alkoxy, C1-C4 alkylamino, (C1-C4)(C1-C4) dialkylamino, —CO₂(C1-C4 alkyl), —CO₂H, —CO₂NH₂, —NHC(O)$Cy^3$, —NHC(O)(C1-C4 alkyl), or $Cy^3$; and $R^{5c}$ is hydrogen, halogen, —CN, —NH₂, —OH, C1-C4 alkyl, C1-C4 haloalkyl, C1-C4 alkoxy, C1-C4 alkylamino, (C1-C4)(C1-C4) dialkylamino, —CO₂(C1-C4 alkyl), —CO₂H, —CO₂NH₂, —NHC(O)$Cy^3$, —NHC(O)(C1-C4 alkyl), or aryl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein A is O, $NR^{6a}$, or $CHR^{6b}$; wherein $R^{6a}$ is hydrogen or C1-C4 alkyl; and wherein $R^{6b}$ is hydrogen, C1-C4 alkyl, C1-C4 haloalkyl, C1-C4 alkoxy, C1-C4 alkylamino, or (C1-C4)(C1-C4) dialkylamino; wherein $R^7$ is hydrogen, halogen, —OH, C1-C4 alkyl, C1-C4 haloalkyl, or C1-C4 alkoxy, or a pharmaceutically acceptable salt thereof.

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, Pa. 1990.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, an effective amount is a therapeutically effective amount. In a still further aspect, an effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is used to treat a disorder associated with TXNIP activity such as, for example, a disorder associated with elevated TXNIP (e.g., diabetes).

In a further aspect, the pharmaceutical composition is used to treat a disorder of hepatic glucose regulation dysfunction. In a still further aspect, the disorder associated with elevated TXNIP is diabetes. In yet a further aspect, the diabetes is Type I diabetes, Type II diabetes, or gestational diabetes. In an even further aspect, the diabetes is Type I diabetes. In a still further aspect, the diabetes is Type II diabetes. In yet a further aspect, the diabetes is gestational diabetes.

It is understood that the disclosed compositions can be prepared from the disclosed compounds. It is also understood that the disclosed compositions can be employed in the disclosed methods of using.

G. COMPOUNDS

In one aspect, disclosed are compounds useful in treating or preventing a disorder associated with TXNIP activity such as, for example, disorders associated with elevated TXNIP and/or elevated glucagon levels (e.g., diabetes). In a further aspect, the disclosed compounds exhibit modulation of TXNIP activity. In a still further aspect, the disclosed compounds exhibit inhibition of TXNIP activity.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compound having a structure represented by a formula:

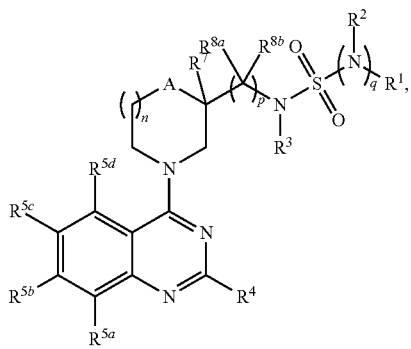

wherein n is 0, 1, or 2; wherein p is 1, 2, 3, or 4; wherein q is 0 or 1; wherein $R^1$ is —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)$CO_2$H, or $Cy^1$; wherein $Cy^1$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^2$ is hydrogen or C1-C4 alkyl, or wherein each of $R^1$ and $R^2$ are covalently bonded together and, together with the intermediate atoms, comprise a 3- to 6-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^3$ is hydrogen or C1-C4 alkyl, or wherein each of $R^1$ and $R^3$ are covalently bonded together and, together with the intermediate atoms, comprise a 5- to 7-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^4$ is hydrogen, halogen, —$NH_2$, —OH, C1-C4 alkyl, C1-C4 alkoxy, C1-C4 alkylamino, (C1-C4)(C1-C4) dialkylamino, or $Cy^2$; wherein $Cy^2$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein each of $R^{5a}$, $R^{5b}$, $R^{5c}$, and $R^{5d}$ is independently hydrogen, halogen, —$NH_2$, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —$CO_2$(C1-C4 alkyl), —$CO_2$H, —$CO_2NH_2$, —NHC(O)$Cy^3$, —NHC(O)(C1-C4 alkyl), or $Cy^3$; wherein $Cy^3$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein A is O, $NR^{6a}$, or $CHR^{6b}$; wherein $R^{6a}$ is hydrogen or C1-C4 alkyl; and wherein $R^{6b}$ is hydrogen, C1-C4 alkyl, C1-C4 haloalkyl, C1-C4 alkoxy, C1-C4 alkylamino, (C1-C4)(C1-C4) dialkylamino, or —$CO_2$H; wherein $R^7$ is hydrogen, halogen, —OH, C1-C4 alkyl, C1-C4 haloalkyl, or C1-C4 alkoxy; and wherein each occurrence of $R^{8a}$ and $R^{8b}$, when present, is independently hydrogen, C1-C4 alkyl, C1-C4 haloalkyl, phenyl, or —CO$_2$H; or wherein p is 1 and each of $R^{8a}$ and $R^{8b}$ together comprise =O; provided that when $R^1$ is methyl and each of $R^3$ and $R^4$ is hydrogen then each of $R^{5a}$, $R^{5b}$, $R^{5c}$, and $R^{5d}$ is independently hydrogen, fluorine, —NH$_2$, —OH, C1-C4 alkyl, C1-C4 alkoxy, C1-C4 alkylamino, (C1-C4)(C1-C4) dialkylamino, or Cy$^3$, and provided that when n is 1, p is 0, A is CHR$^{6b}$, and $R^1$ is methyl, then at least two of $R^4$, $R^{5a}$, $R^{5b}$, $R^{5c}$, and $R^{5d}$ are not hydrogen, or a pharmaceutically acceptable salt thereof.

In another aspect, disclosed are compounds having a structure represented by a formula:

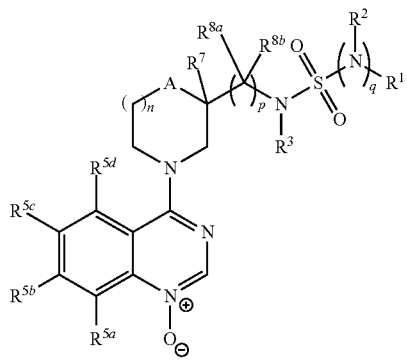

wherein n is 0, 1, or 2; wherein p is 0, 1, 2, 3, or 4; wherein q is 0 or 1; wherein $R^1$ is —NH$_2$, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)CO$_2$H, or Cy$^1$; wherein Cy$^1$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein $R^2$ is hydrogen or C1-C4 alkyl, or wherein each of $R^1$ and $R^2$ are covalently bonded together and, together with the intermediate atoms, comprise a 3- to 6-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein $R^3$ is hydrogen or C1-C4 alkyl, or wherein each of $R^1$ and $R^3$ are covalently bonded together and, together with the intermediate atoms, comprise a 5- to 7-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein $R^4$ is hydrogen, halogen, —NH$_2$, —OH, C1-C4 alkyl, C1-C4 alkoxy, C1-C4 alkylamino, (C1-C4)(C1-C4) dialkylamino, or Cy$^2$; wherein Cy$^2$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein each of $R^{5a}$, $R^{5b}$, $R^{5c}$, and $R^{5d}$ is independently hydrogen, halogen, —NH$_2$, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —CO$_2$(C1-C4 alkyl), —CO$_2$H, —CO$_2$NH$_2$, —NHC(O)Cy$^3$, —NHC(O)(C1-C4 alkyl), or Cy$^3$; wherein Cy$^3$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein A is O, NR$^{6a}$, or CHR$^{6b}$; wherein R$^{6a}$ is hydrogen or C1-C4 alkyl; and wherein R$^{6b}$ is hydrogen, C1-C4 alkyl, C1-C4 haloalkyl, C1-C4 alkoxy, C1-C4 alkylamino, (C1-C4)(C1-C4) dialkylamino, or —CO$_2$H; wherein $R^7$ is hydrogen, halogen, —OH, C1-C4 alkyl, C1-C4 haloalkyl, or C1-C4 alkoxy; and wherein each occurrence of $R^{8a}$ and $R^{8b}$, when present, is independently hydrogen, C1-C4 alkyl, C1-C4 haloalkyl, phenyl, or —CO$_2$H; or wherein p is 1 and each of $R^{8a}$ and $R^{8b}$ together comprise =O.

In a further aspect, disclosed are compounds having a structure represented by a formula:

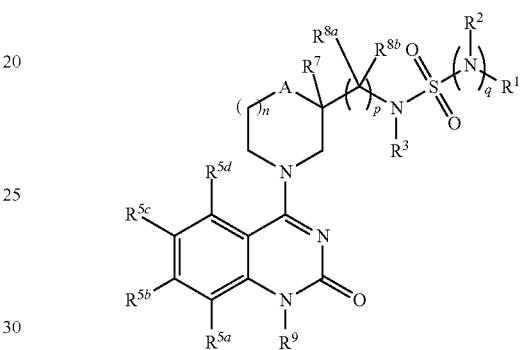

wherein n is 0, 1, or 2; wherein p is 0, 1, 2, 3, or 4; wherein q is 0 or 1; wherein $R^1$ is —NH$_2$, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)CO$_2$H, or Cy$^1$; wherein Cy$^1$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein $R^2$ is hydrogen or C1-C4 alkyl, or wherein each of $R^1$ and $R^2$ are covalently bonded together and, together with the intermediate atoms, comprise a 3- to 6-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein $R^3$ is hydrogen or C1-C4 alkyl, or wherein each of $R^1$ and $R^3$ are covalently bonded together and, together with the intermediate atoms, comprise a 5- to 7-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein $R^4$ is hydrogen, halogen, —NH$_2$, —OH, C1-C4 alkyl, C1-C4 alkoxy, C1-C4 alkylamino, (C1-C4)(C1-C4) dialkylamino, or Cy$^2$; wherein Cy$^2$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino; wherein each of $R^{5a}$, $R^{5b}$, $R^{5c}$, and $R^{5d}$ is independently hydrogen, halogen, —NH$_2$, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —CO$_2$(C1-C4 alkyl), —CO$_2$H, —CO$_2$NH$_2$, —NHC(O)Cy$^3$, —NHC(O)(C1-C4 alkyl), or Cy³; wherein Cy³, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein A is O, NR⁶ᵃ, or CHR⁶ᵇ; wherein R⁶ᵃ is hydrogen or C1-C4 alkyl; and wherein R⁶ᵇ is hydrogen, C1-C4 alkyl, C1-C4 haloalkyl, C1-C4 alkoxy, C1-C4 alkylamino, (C1-C4)(C1-C4) dialkylamino, or —CO₂H; wherein R⁷ is hydrogen, halogen, —OH, C1-C4 alkyl, C1-C4 haloalkyl, or C1-C4 alkoxy; wherein each occurrence of R⁸ᵃ and R⁸ᵇ, when present, is independently hydrogen, C1-C4 alkyl, C1-C4 haloalkyl, phenyl, or —CO₂H; or wherein p is 1 and each of R⁸ᵃ and R⁸ᵇ together comprise =O; and wherein R⁹ is hydrogen, C1-C4 alkyl, or Cy⁴, wherein Cy⁴, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino, or a pharmaceutically acceptable salt thereof.

In a further aspect, disclosed are compounds having a structure represented by a formula:

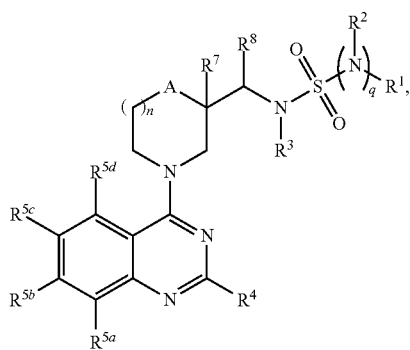

wherein n is 0, 1, or 2; wherein q is 0 or 1; wherein R¹ is —OH, C1-C4 alkyl, C1-C4 haloalkyl, C1-C4 alkoxy, C1-C4 alkylamino, (C1-C4)(C1-C4) dialkylamino, or Cy¹; wherein Cy¹, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein R² is hydrogen or C1-C4 alkyl, or wherein each of R¹ and R² are covalently bonded together and, together with the intermediate atoms, comprise a 3- to 6-membered heterocycloalkyl substituted with 0, 1, 2, or 3 groups independently selected from halogen, —NH₂, —OH, C1-C4 alkyl, C1-C4 haloalkyl, C1-C4 alkoxy, C1-C4 alkylamino, (C1-C4)(C1-C4) dialkylamino; wherein R³ is hydrogen or C1-C4 alkyl; wherein R⁴ is hydrogen, halogen, —NH₂, —OH, C1-C4 alkyl, C1-C4 alkoxy, C1-C4 alkylamino, (C1-C4)(C1-C4) dialkylamino, or Cy²; wherein Cy², when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein each of R⁵ᵃ, R⁵ᵇ, R⁵ᶜ, and R⁵ᵈ is independently hydrogen, halogen, —NH₂, —CN, —OH, C1-C4 alkyl, C1-C4 haloalkyl, C1-C4 alkoxy, C1-C4 alkylamino, (C1-C4)(C1-C4) dialkylamino, —CO₂(C1-C4 alkyl), —CO₂H, —CO₂NH₂, —NHC(O)Cy³, —NHC(O)(C1-C4 alkyl), or Cy³; wherein Cy³, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein A is O, NR⁶ᵃ, or CHR⁶ᵇ; wherein R⁶ᵃ is hydrogen or C1-C4 alkyl; and wherein R⁶ᵇ is hydrogen, C1-C4 alkyl, C1-C4 haloalkyl, C1-C4 alkoxy, C1-C4 alkylamino, or (C1-C4)(C1-C4) dialkylamino; wherein R⁷ is hydrogen, halogen, —OH, C1-C4 alkyl, C1-C4 haloalkyl, or C1-C4 alkoxy; and wherein R⁸ is hydrogen, C1-C4 alkyl, or C1-C4 haloalkyl; with the proviso that when R¹ is methyl and each of R³ and R⁴ is hydrogen then each of R⁵ᵃ, R⁵ᵇ, R⁵ᶜ, and R⁵ᵈ is independently hydrogen, fluorine, —NH₂, —OH, C1-C4 alkyl, C1-C4 alkoxy, C1-C4 alkylamino, (C1-C4)(C1-C4) dialkylamino, or Cy³, or a pharmaceutically acceptable salt thereof.

In one aspect, disclosed are compounds having a structure represented by a formula:

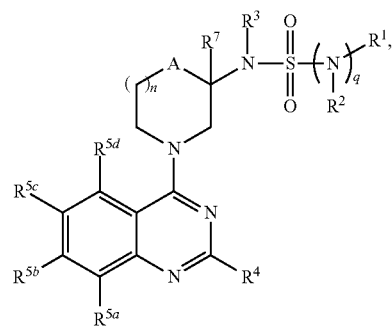

wherein n is 0, 1, or 2; wherein q is 0 or 1; wherein R¹ is —NH₂, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)CO₂H, or Cy¹; wherein Cy¹, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein R² is hydrogen or C1-C4 alkyl, or wherein each of R¹ and R² are covalently bonded together and, together with the intermediate atoms, comprise a 3- to 6-membered heterocycloalkyl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein R³ is hydrogen or C1-C4 alkyl, or wherein each of R¹ and R³ are covalently bonded together and, together with the intermediate atoms, comprise a 5- to 7-membered heterocycloalkyl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein R⁴ is hydrogen, halogen, —NH₂, —OH, C1-C4 alkyl, C1-C4 alkoxy, C1-C4 alkylamino, (C1-C4)(C1-C4) dialkylamino, or Cy²; wherein Cy², when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein each of R⁵ᵃ, R⁵ᵇ, and R⁵ᵈ is independently hydrogen, halogen, —NH₂, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —CO₂(C1-C4 alkyl), —CO₂H, —CO₂NH₂, —NHC(O)Cy³, —NHC(O)(C1-C4 alkyl), or Cy³; wherein Cy³, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein $R^5$ is hydrogen, halogen, —CN, —NH₂, —OH, C1-C4 alkyl, C1-C4 haloalkyl, C1-C4 alkoxy, C1-C4 haloalkoxy, C1-C4 alkylamino, (C1-C4)(C1-C4) dialkylamino, —CO₂(C1-C4 alkyl), —CO₂H, —CO₂NH₂, —NHC(O)Cy³, —NHC(O)(C1-C4 alkyl), or aryl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino; wherein A is O, $NR^{6a}$, or $CHR^{6b}$; wherein $R^{6a}$ is hydrogen or C1-C4 alkyl; wherein $R^{6b}$ is hydrogen, C1-C4 alkyl, C1-C4 haloalkyl, C1-C4 alkoxy, C1-C4 alkylamino, (C1-C4)(C1-C4) dialkylamino, or —CO₂H; and wherein $R^7$ is hydrogen, halogen, —OH, C1-C4 alkyl, C1-C4 haloalkyl, or C1-C4 alkoxy; provided that when $R^{5b}$ is morpholinyl and $R^1$ is thiophenyl or thiazolyl, then q is 1 and at least one of $R^{5a}$, $R^{5c}$, and $R^{5d}$ is not hydrogen; provided that when q is 0 then $Cy^1$ is not aryl; and provided that at least one of $R^{5a}R^{5b}$, $R^{5c}$, and $R^{5d}$ is not hydrogen, or a pharmaceutically acceptable salt thereof.

In a further aspect, the compound has a structure represented by a formula:

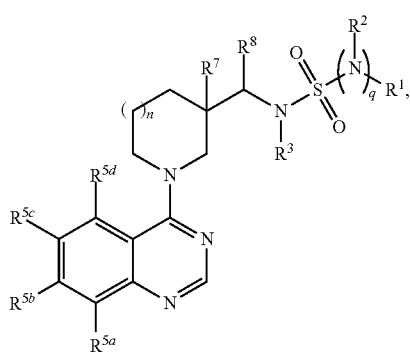

or a pharmaceutically acceptable salt thereof.

In a further aspect, the compound has a structure represented by a formula:

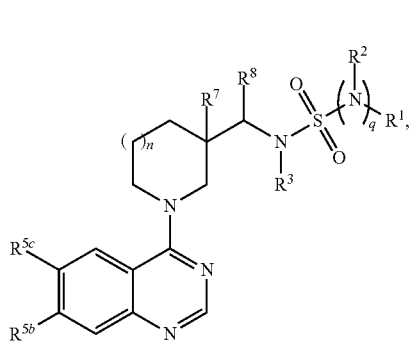

or a pharmaceutically acceptable salt thereof.

In a further aspect, the compound has a structure represented by a formula:

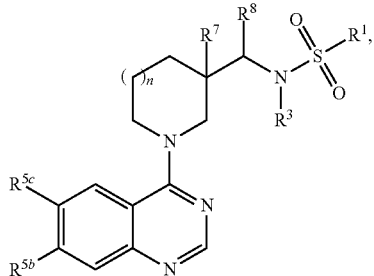

or a pharmaceutically acceptable salt thereof.

In a further aspect, the compound has a structure represented by a formula:

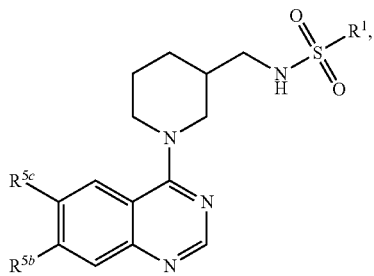

or a pharmaceutically acceptable salt thereof.

In a further aspect, the compound has a structure represented by a formula:

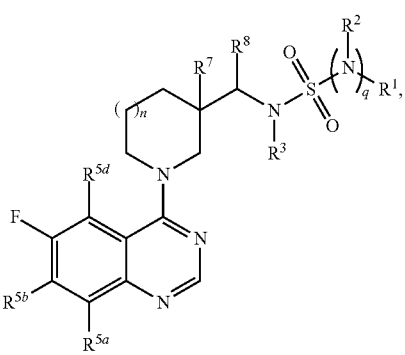

or a pharmaceutically acceptable salt thereof.

In a further aspect, the compound has a structure represented by a formula:

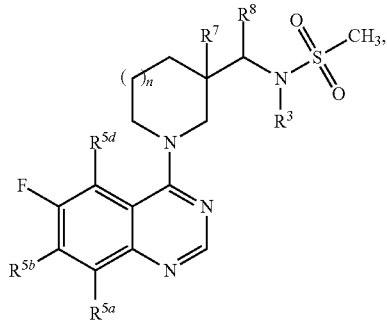

or a pharmaceutically acceptable salt thereof.

In a further aspect, the compound has a structure represented by a formula:

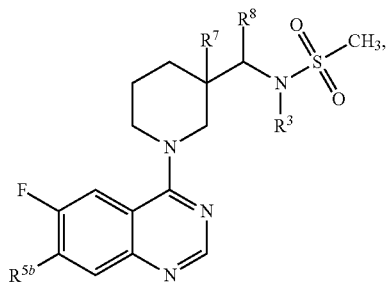

or a pharmaceutically acceptable salt thereof.

In a further aspect, the compound has a structure represented by a formula:

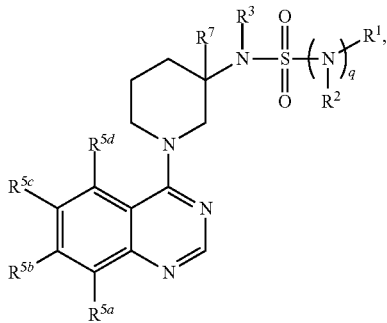

or a pharmaceutically acceptable salt thereof.

In a further aspect, the compound has a structure represented by a formula:

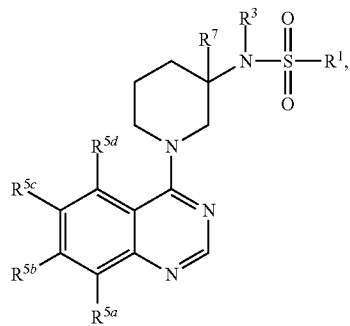

or a pharmaceutically acceptable salt thereof.

In a further aspect, the compound has a structure represented by a formula:

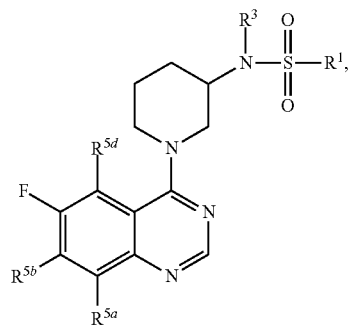

or a pharmaceutically acceptable salt thereof.

In a further aspect, the compound has a structure represented by a formula:

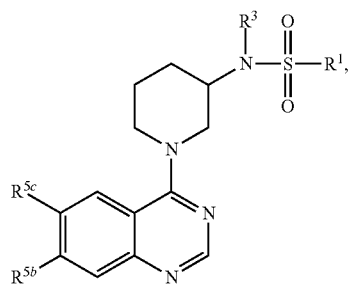

or a pharmaceutically acceptable salt thereof.

In a further aspect, the compound is not:

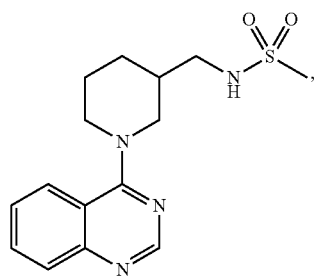

-continued
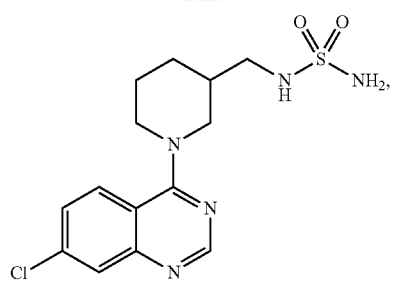
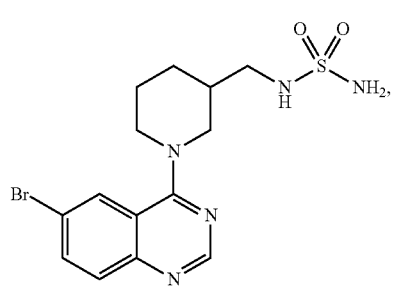
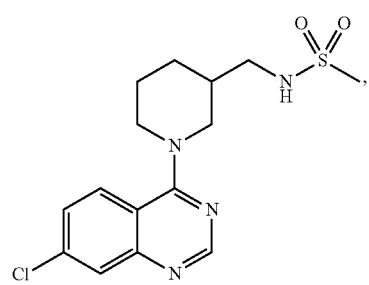
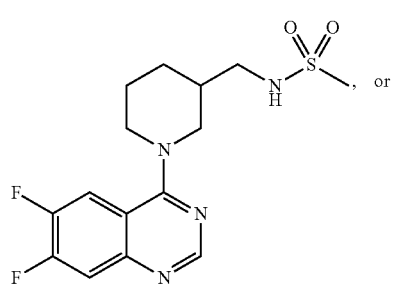, or
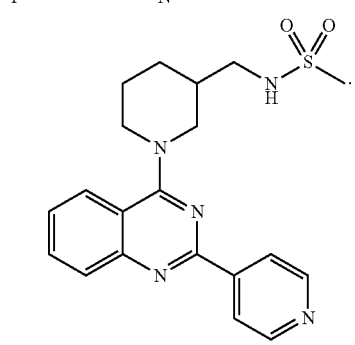
In a further aspect, the compound is not:
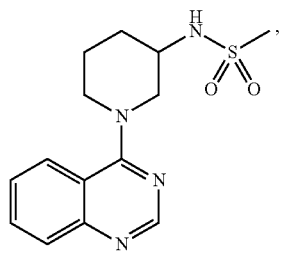
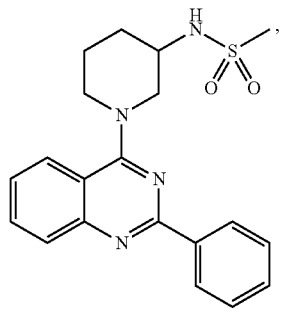
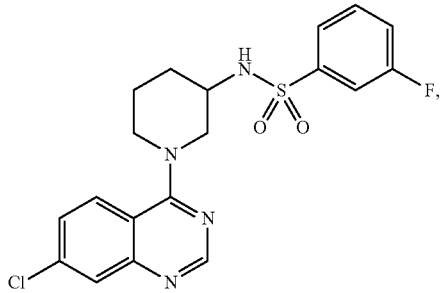
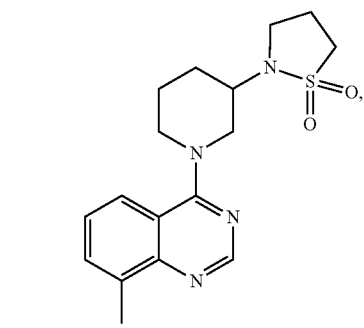
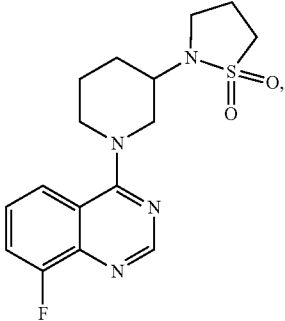

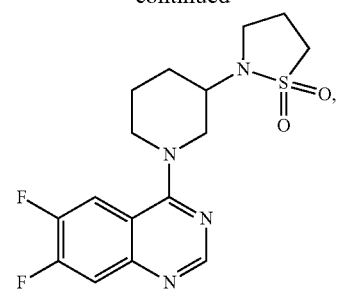
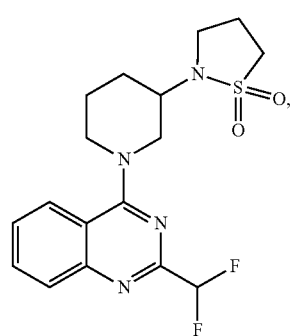
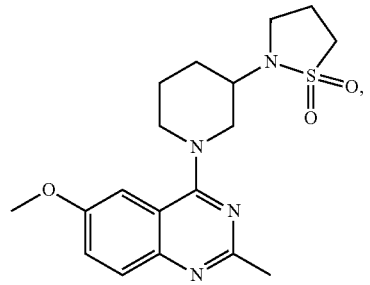
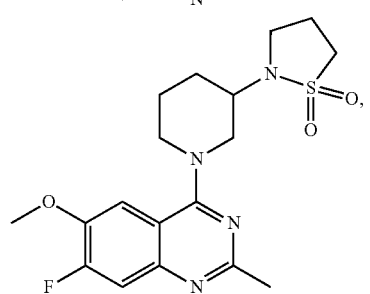
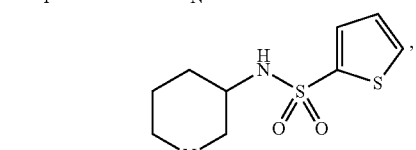
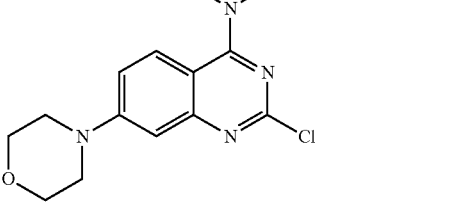
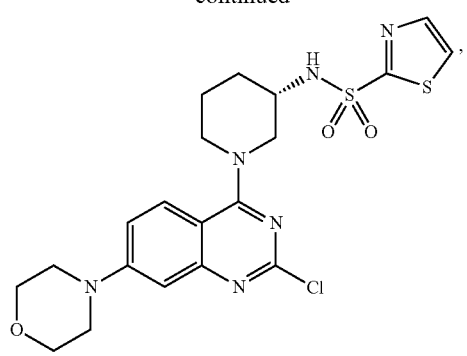
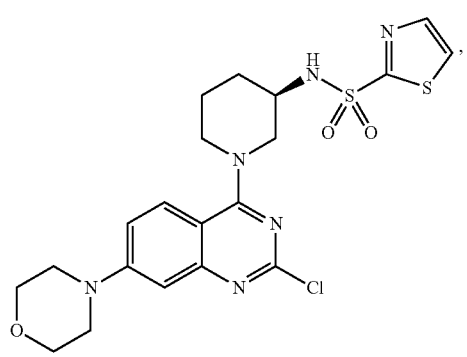
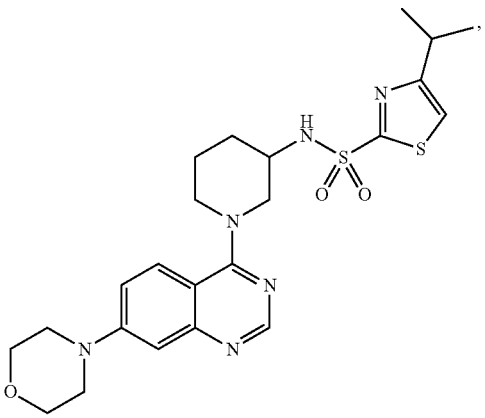
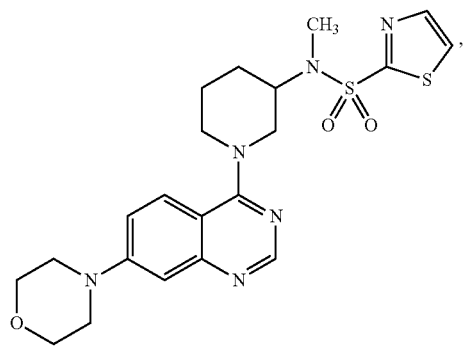

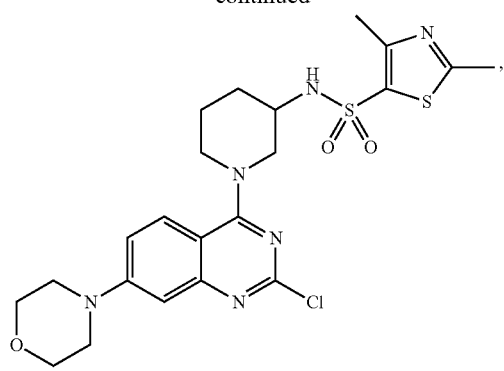
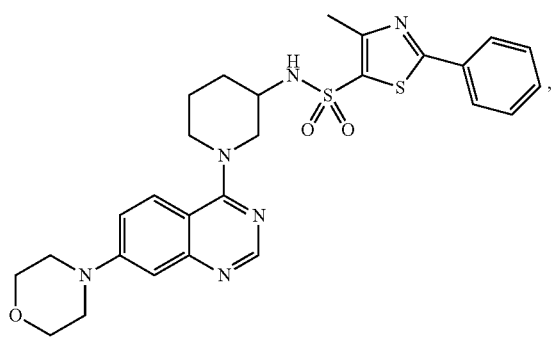
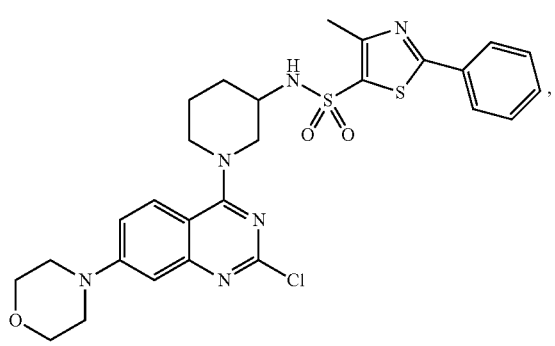
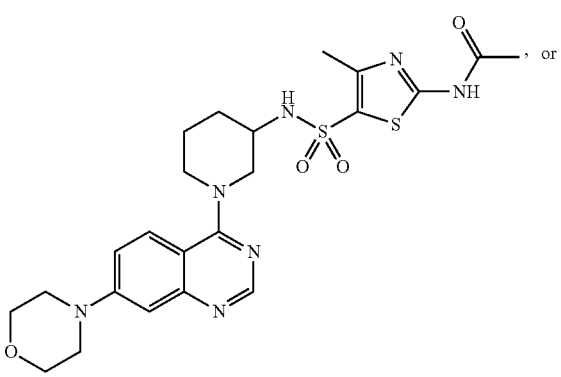
In a further aspect, the compound is not:
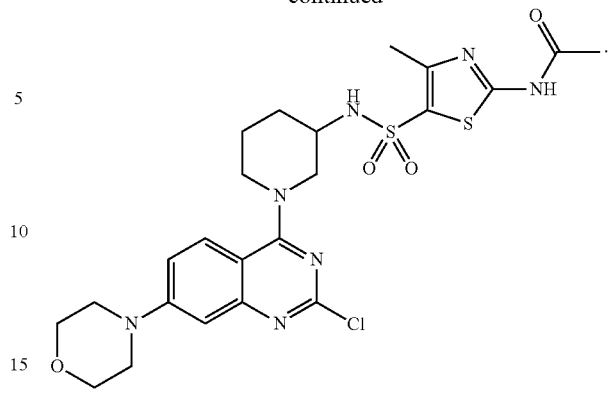
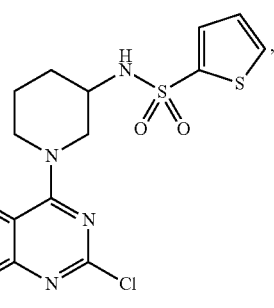
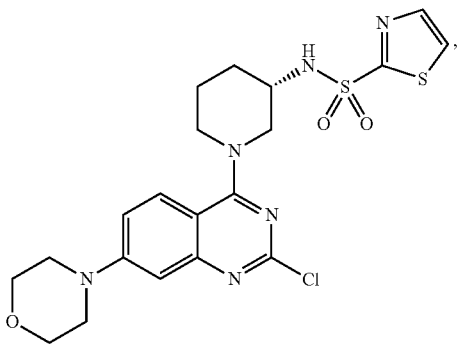
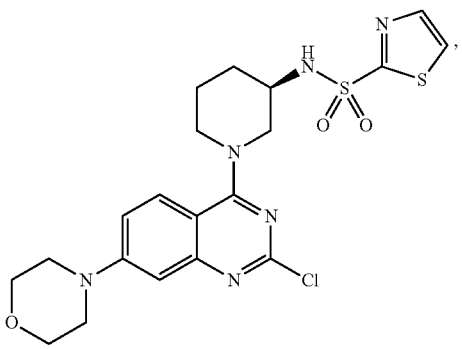

-continued
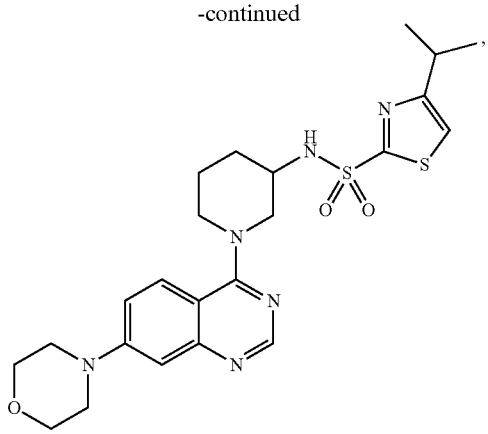
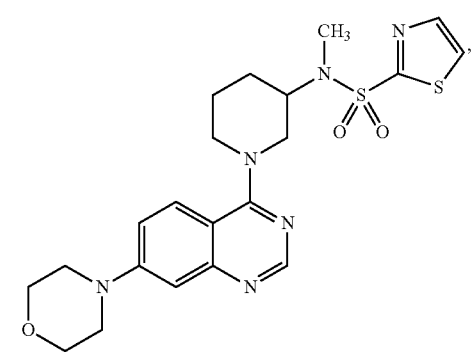
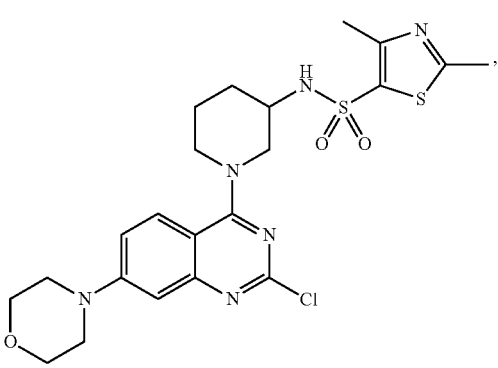
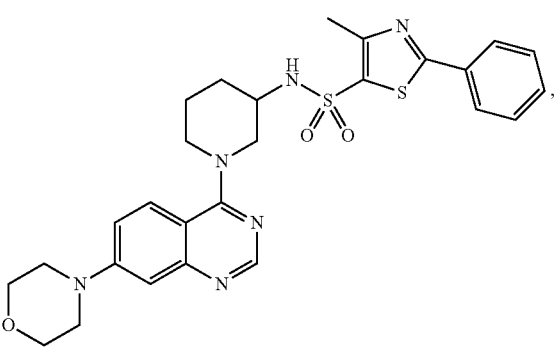
-continued
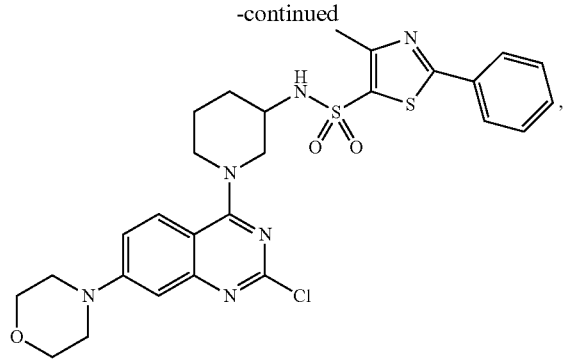
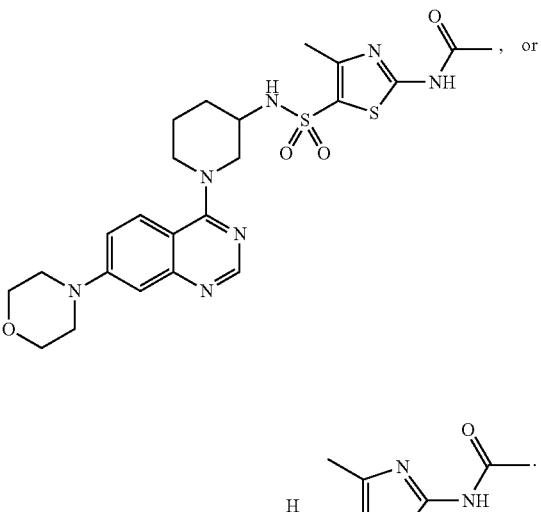
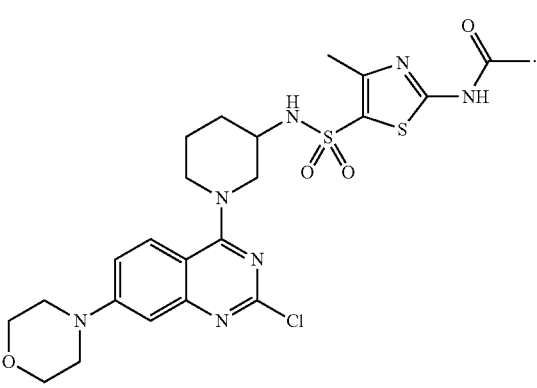 [SMILES: CC(=O)Nc1nc(C)c(S(=O)(=O)NC2CCCN(c3nc(Cl)nc4cc(N5CCOCC5)ccc34)C2)s1]
In a further aspect, the compound has a structure represented by a formula:
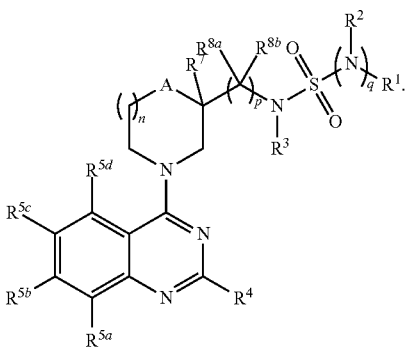

In a further aspect, the compound has a structure represented by a formula selected from:

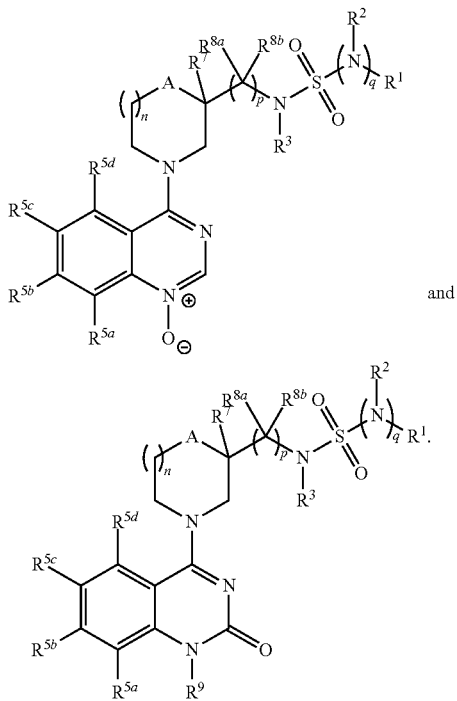

and

In a further aspect, p is 0 or 1; $R^1$ is —$NH_2$, —OH, C1-C4 alkyl, C1-C4 haloalkyl, C1-C4 alkoxy, C1-C4 alkylamino, (C1-C4)(C1-C4) dialkylamino, or $Cy^1$; each of $R^{5a}$, $R^{5b}$, $R^{5c}$, and $R^{5d}$ is independently hydrogen, halogen, —$NH_2$, —CN, —OH, C1-C4 alkyl, C1-C4 haloalkyl, C1-C4 alkoxy, C1-C4 alkylamino, (C1-C4)(C1-C4) dialkylamino, —$CO_2$(C1-C4 alkyl), —$CO_2H$, —$CO_2NH_2$, —NHC(O)$Cy^3$, —NHC(O)(C1-C4 alkyl), or $Cy^3$; and $R^{8a}$ is hydrogen and $R^{8b}$ is hydrogen, C1-C4 alkyl, or C1-C4 haloalkyl.

In a further aspect, p is 1; $R^1$ is —OH, C1-C4 alkyl, C1-C4 haloalkyl, C1-C4 alkoxy, C1-C4 alkylamino, (C1-C4)(C1-C4) dialkylamino, or $Cy^1$; each of $R^{5a}$, $R^{5b}$, $R^{5c}$, and $R^{5d}$ is independently hydrogen, halogen, —$NH_2$, —CN, —OH, C1-C4 alkyl, C1-C4 haloalkyl, C1-C4 alkoxy, C1-C4 alkylamino, (C1-C4)(C1-C4) dialkylamino, —$CO_2$(C1-C4 alkyl), —$CO_2H$, —$CO_2NH_2$, —NHC(O)$Cy^3$, —NHC(O)(C1-C4 alkyl), or $Cy^3$; and $R^{8a}$ is hydrogen and $R^{8b}$ is hydrogen, C1-C4 alkyl, or C1-C4 haloalkyl.

In a further aspect, $R^1$ is methyl and each of $R^3$ and $R^4$ is hydrogen then each of $R^{5a}$, $R^{5b}$, $R^{5c}$, and $R^{5d}$ is independently hydrogen, fluorine, —$NH_2$, —OH, C1-C4 alkyl, C1-C4 alkoxy, C1-C4 alkylamino, (C1-C4)(C1-C4) dialkylamino, or $Cy^3$. In a still further aspect, $R^1$ is methyl, each of $R^3$ and $R^4$ is hydrogen, and each of $R^{5a}$, $R^{5b}$, $R^{5c}$, and $R^{5d}$ is independently hydrogen, —$NH_2$, —OH, C1-C4 alkyl, C1-C4 alkoxy, C1-C4 alkylamino, (C1-C4)(C1-C4) dialkylamino, or $Cy^3$. In yet a further aspect, $R^1$ is methyl, each of $R^3$ and $R^4$ is hydrogen, and $R^{5b}$ is fluorine.

In one aspect, n is 0, 1, or 2. In a further aspect, n is 0 or 1. In a still further aspect, n is 1 or 2. In yet a further aspect, n is 0. In an even further aspect, n is 1. In a still further aspect, n is 2.

In a further aspect, q is 0 or 1. In a still further aspect, q is 0. In yet a further aspect, q is 1.

In one aspect, p is 0, 1, 2, 3, or 4. In a further aspect, p is 1, 2, 3, or 4. In a further aspect, p is 0 or 1. In a still further aspect, p is 0. In yet a further aspect, p is 1.

In a further aspect, each of p and q is independently 0 or 1. In a still further aspect, p is 0 and q is 1. In yet a further aspect, p is 1 and q is 0. In an even further aspect, p is 0 or 1 and q is 0. In a still further aspect, q is 0 or 1 and p is 0. In yet a further aspect, p is 0 or 1 and q is 1. In an even further aspect, q is 0 or 1 and p is 1. In a still further aspect, each of p and q is 0. In yet a further aspect, each of p and q is 1.

a. A Groups

In one aspect, A is O, $NR^{6a}$, or $CHR^{6b}$. In a further aspect, A is O or $NR^6$a. In a still further aspect, A is O or $CHR^{6b}$. In yet a further aspect, A is $NR^{6a}$ or $CHR^{6b}$. In an even further aspect, A is O. In a still further aspect, A is $NR^{6a}$. In yet a further aspect, A is $CHR^{6b}$. In an even further aspect, A is NH. In a still further aspect, A is $CH_2$.

b. $R^1$ Groups

In one aspect, $R^1$ is —$NH_2$, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)$CO_2H$, or $Cy^1$.

In one aspect, each of $R^1$ and $R^3$ are covalently bonded together and, together with the intermediate atoms, comprise a 5- to 7-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a further aspect, each of $R^1$ and $R^3$ are covalently bonded together and, together with the intermediate atoms, comprise a 5- to 7-membered heterocycloalkyl substituted with 0, 1, or 2 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, each of $R^1$ and $R^3$ are covalently bonded together and, together with the intermediate atoms, comprise a 5- to 7-membered heterocycloalkyl substituted with 0 or 1 group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In yet a further aspect, each of $R^1$ and $R^3$ are covalently bonded together and, together with the intermediate atoms, comprise a 5- to 7-membered heterocycloalkyl monosubstituted with a group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In an even further aspect, each of $R^1$ and $R^3$ are covalently bonded together and, together with the intermediate atoms, comprise an unsubstituted 5- to 7-membered heterocycloalkyl.

In one aspect, $R^1$ is —$NH_2$, —OH, C1-C4 alkyl, C1-C4 haloalkyl, C1-C4 alkoxy, C1-C4 alkylamino, (C1-C4)(C1-C4) dialkylamino, or $Cy^1$.

In one aspect, $R^1$ is —OH, C1-C4 alkyl, C1-C4 haloalkyl, C1-C4 alkoxy, C1-C4 alkylamino, (C1-C4)(C1-C4) dialkylamino, or $Cy^1$.

In a further aspect, $R^1$ is —$NH_2$, —OH, methyl, ethyl, n-propyl, i-propyl, —$CH_2F$, —$CH_2Cl$, —$CH_2CH_2F$, —$CH_2CH_2Cl$, —$CH_2CH_2CH_2F$, —$CH_2CH_2CH_2Cl$, —$CH(CH_3)CH_2F$, —$CH(CH_3)CH_2Cl$, —$OCH_3$, —$OCH_2CH_3$, —$OCH_2CH_2CH_3$, —$OCH(CH_3)CH_3$, —$CH_2OH$, —$CH_2CH_2OH$, —$CH_2CH_2CH_2OH$, —$CH(CH_3)CH_2OH$, —$NHCH_3$, —$NHCH_2CH_3$, —$NHCH_2CH_2CH_3$, —$NHCH(CH_3)CH_3$, —$N(CH_3)_2$, —$N(CH_2CH_3)_2$, —$N(CH_2CH_2CH_3)_2$, —$N(CH(CH_3)CH_3)_2$, —$N(CH_3)(CH_2CH_3)$, —$CH_2OCH_3$, —$CH_2CH_2OCH_3$, —$CH_2CH_2CH_2OCH_3$, —$CH_2CO_2H$, —$CH_2CH_2CO_2H$, —CH₂CH₂CH₂CO₂H, or Cy¹. In a still further aspect, R¹ is —NH₂, —OH, methyl, ethyl, —CH₂F, —CH₂Cl, —CH₂CH₂F, —CH₂CH₂Cl, —OCH₃, —OCH₂CH₃, —CH₂OH, —CH₂CH₂OH, —NHCH₃, —NHCH₂CH₃, —N(CH₃)₂, —N(CH₂CH₃)₂, —N(CH₃)(CH₂CH₃), —CH₂OCH₃, —CH₂CH₂OCH₃, —CH₂CO₂H, —CH₂CH₂CO₂H, or Cy¹. In yet a further aspect, R¹ is —NH₂, —OH, methyl, —CH₂F, —CH₂Cl, —OCH₃, —CH₂OH, —NHCH₃, —N(CH₃)₂, —CH₂OCH₃, —CH₂CO₂H, or Cy¹.

In a further aspect, R¹ is —NH₂, —OH, methyl, ethyl, n-propyl, i-propyl, —CH₂F, —CH₂Cl, —CH₂CH₂F, —CH₂CH₂Cl, —CH₂CH₂CH₂F, —CH₂CH₂CH₂Cl, —CH(CH₃)CH₂F, —CH(CH₃)CH₂Cl, —OCH₃, —OCH₂CH₃, —OCH₂CH₂CH₃, —OCH(CH₃)CH₃, —NHCH₃, —NHCH₂CH₃, —NHCH₂CH₂CH₃, —NHCH(CH₃)CH₃, —N(CH₃)₂, —N(CH₂CH₃)₂, —N(CH₂CH₂CH₃)₂, —N(CH(CH₃)CH₃)₂, —N(CH₃)(CH₂CH₃), or Cy¹. In a still further aspect, R¹ is —NH₂, —OH, methyl, ethyl, —CH₂F, —CH₂Cl, —CH₂CH₂F, —CH₂CH₂Cl, —OCH₃, —OCH₂CH₃, —NHCH₃, —NHCH₂CH₃, —N(CH₃)₂, —N(CH₂CH₃)₂, —N(CH₃)(CH₂CH₃), or Cy¹. In yet a further aspect, R¹ is —NH₂, —OH, methyl, —CH₂F, —CH₂Cl, —OCH₃, —NHCH₃, —N(CH₃)₂, or Cy¹.

In a further aspect, R¹ is —OH, methyl, ethyl, n-propyl, i-propyl, —CH₂F, —CH₂Cl, —CH₂CH₂F, —CH₂CH₂Cl, —CH₂CH₂CH₂F, —CH₂CH₂CH₂Cl, —CH(CH₃)CH₂F, —CH(CH₃)CH₂Cl, —OCH₃, —OCH₂CH₃, —OCH₂CH₂CH₃, —OCH(CH₃)CH₃, —NHCH₃, —NHCH₂CH₃, —NHCH₂CH₂CH₃, —NHCH(CH₃)CH₃, —N(CH₃)₂, —N(CH₂CH₃)₂, —N(CH₂CH₂CH₃)₂, —N(CH(CH₃)CH₃)₂, —N(CH₃)(CH₂CH₃), or Cy¹. In a still further aspect, R¹ is —OH, methyl, ethyl, —CH₂F, —CH₂Cl, —CH₂CH₂F, —CH₂CH₂Cl, —OCH₃, —OCH₂CH₃, —NHCH₃, —NHCH₂CH₃, —N(CH₃)₂, —N(CH₂CH₃)₂, —N(CH₃)(CH₂CH₃), or Cy¹. In yet a further aspect, R¹ is —OH, methyl, —CH₂F, —CH₂Cl, —OCH₃, —NHCH₃, —N(CH₃)₂, or Cy¹.

In a further aspect, R¹ is C1-C4 alkyl, C1-C4 haloalkyl, C1-C4 alkoxy, C1-C4 alkylamino, or (C1-C4)(C1-C4) dialkylamino, or Cy¹. In a still further aspect, R¹ is methyl, ethyl, n-propyl, i-propyl, —CH₂F, —CH₂Cl, —CH₂CH₂F, —CH₂CH₂Cl, —CH₂CH₂CH₂F, —CH₂CH₂CH₂Cl, —CH(CH₃)CH₂F, —CH(CH₃)CH₂Cl, —OCH₃, —OCH₂CH₃, —OCH₂CH₂CH₃, —OCH(CH₃)CH₃, —NHCH₃, —NHCH₂CH₃, —NHCH₂CH₂CH₃, —NHCH(CH₃)CH₃, —N(CH₃)₂, —N(CH₂CH₃)₂, —N(CH₂CH₂CH₃)₂, —N(CH(CH₃)CH₃)₂, —N(CH₃)(CH₂CH₃), or Cy¹. In yet a further aspect, R¹ is methyl, ethyl, —CH₂F, —CH₂Cl, —CH₂CH₂F, —CH₂CH₂Cl, —OCH₃, —OCH₂CH₃, —NHCH₃, —NHCH₂CH₃, —N(CH₃)₂, —N(CH₂CH₃)₂, —N(CH₃)(CH₂CH₃), or Cy¹. In an even further aspect, R¹ is methyl, —CH₂F, —CH₂Cl, —OCH₃, —NHCH₃, —N(CH₃)₂, or Cy¹.

In a further aspect, R¹ is —NH₂, —OH, C1-C4 alkyl, C1-C4 alkoxy, C1-C4 alkylamino, (C1-C4)(C1-C4) dialkylamino, or Cy¹. In a still further aspect, R¹ is —NH₂, —OH, methyl, ethyl, n-propyl, i-propyl, —OCH₃, —OCH₂CH₃, —OCH₂CH₂CH₃, —OCH(CH₃)CH₃, —NHCH₃, —NHCH₂CH₃, —NHCH₂CH₂CH₃, —NHCH(CH₃)CH₃, —N(CH₃)₂, —N(CH₂CH₃)₂, —N(CH₂CH₂CH₃)₂, —N(CH(CH₃)CH₃)₂, —N(CH₃)(CH₂CH₃), or Cy¹. In a still further aspect, R¹ is —NH₂, —OH, methyl, —OCH₃, —OCH₂CH₃, —NHCH₃, —NHCH₂CH₃, —N(CH₃)₂, —N(CH₂CH₃)₂, —N(CH₃)(CH₂CH₃), or Cy¹. In yet a further aspect, R¹ is —NH₂, —OH, methyl, —OCH₃, —NHCH₃, —N(CH₃)₂, or Cy¹.

In a further aspect, R¹ is —OH, C1-C4 alkyl, C1-C4 alkoxy, C1-C4 alkylamino, (C1-C4)(C1-C4) dialkylamino, or Cy¹. In a still further aspect, R¹ is —OH, methyl, ethyl, n-propyl, i-propyl, —OCH₃, —OCH₂CH₃, —OCH₂CH₂CH₃, —OCH(CH₃)CH₃, —NHCH₃, —NHCH₂CH₃, —NHCH₂CH₂CH₃, —NHCH(CH₃)CH₃, —N(CH₃)₂, —N(CH₂CH₃)₂, —N(CH₂CH₂CH₃)₂, —N(CH(CH₃)CH₃)₂, —N(CH₃)(CH₂CH₃), or Cy¹. In a still further aspect, R¹ is —OH, methyl, ethyl, —OCH₃, —OCH₂CH₃, —NHCH₃, —NHCH₂CH₃, —N(CH₃)₂, —N(CH₂CH₃)₂, —N(CH₃)(CH₂CH₃), or Cy¹. In yet a further aspect, R¹ is —OH, methyl, —OCH₃, —NHCH₃, —N(CH₃)₂, or Cy¹.

In a further aspect, R¹ is —NH₂, —OH, C1-C4 alkyl, C1-C4 alkoxy, or Cy¹. In a still further aspect, R¹ is —NH₂, —OH, methyl, ethyl, n-propyl, i-propyl, —OCH₃, —OCH₂CH₃, —OCH₂CH₂CH₃, —OCH(CH₃)CH₃, or Cy¹. In a still further aspect, R¹ is —NH₂, —OH, methyl, ethyl, —OCH₃, —OCH₂CH₃, or Cy¹. In yet a further aspect, R¹ is —NH₂, —OH, methyl, —OCH₃, or Cy¹.

In a further aspect, R¹ is —OH, C1-C4 alkyl, C1-C4 alkoxy, or Cy¹. In a still further aspect, R¹ is —OH, methyl, ethyl, n-propyl, i-propyl, —OCH₃, —OCH₂CH₃, —OCH₂CH₂CH₃, —OCH(CH₃)CH₃, or Cy¹. In a still further aspect, R¹ is —OH, methyl, ethyl, —OCH₃, —OCH₂CH₃, or Cy¹. In yet a further aspect, R¹ is —OH, methyl, —OCH₃, or Cy¹.

In a further aspect, R¹ is C1-C4 alkyl, C1-C4 haloalkyl, or C1-C4 alkoxy. In a still further aspect, R¹ is methyl, ethyl, n-propyl, i-propyl, —CH₂F, —CH₂Cl, —CH₂CH₂F, —CH₂CH₂Cl, —CH₂CH₂CH₂F, —CH₂CH₂CH₂Cl, —CH(CH₃)CH₂F, —CH(CH₃)CH₂Cl, —OCH₃, —OCH₂CH₃, —OCH₂CH₂CH₃, or —OCH(CH₃)CH₃. In yet a further aspect, R¹ is methyl, ethyl, —CH₂F, —CH₂Cl, —CH₂CH₂F, —CH₂CH₂Cl, —OCH₃, or —OCH₂CH₃. In yet a further aspect, R¹ is methyl, —CH₂F, —CH₂Cl, or —OCH₃.

In a further aspect, R¹ is Cy¹.

In a further aspect, R¹ is C1-C4 haloalkyl. In a still further aspect, R¹ is —CH₂F, —CH₂Cl, —CH₂CH₂F, —CH₂CH₂Cl, —CH₂CH₂CH₂F, —CH₂CH₂CH₂Cl, —CH(CH₃)CH₂F, or —CH(CH₃)CH₂Cl. In yet a further aspect, R¹ is —CH₂F, —CH₂Cl, —CH₂CH₂F, or —CH₂CH₂Cl. In yet a further aspect, R¹ is —CH₂F or —CH₂Cl.

In a further aspect, R¹ is C1-C4 alkyl. In a still further aspect, R¹ is methyl, ethyl, n-propyl, i-propyl, n-butyl, i-butyl, s-butyl, or t-butyl. In yet a further aspect, R¹ is methyl, ethyl, n-propyl, or i-propyl. In an even further aspect, R¹ is methyl or ethyl. In a still further aspect, R¹ is ethyl. In yet a further aspect, R¹ is methyl.

In a further aspect, each of R¹ and R³ are covalently bonded together and, together with the intermediate atoms, comprise a 5- to 6-membered heterocycloalkyl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino. In a still further aspect, R¹ and R³ are covalently bonded together and, together with the intermediate atoms, comprise a 5- to 6-membered heterocycloalkyl substituted with 0, 1, or 2 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino. In yet a further aspect, R¹ and R³ are covalently bonded together and, together with the intermediate atoms, comprise a 5- to 6-membered heterocycloalkyl substituted with 0 or 1 group selected from halogen, —NH₂, —OH, C1-C4 alkyl, C1-C4 haloalkyl, C1-C4 alkoxy, C1-C4 alkylamino, and (C1-C4)(C1-C4) dialkylamino. In an even further aspect, R¹ and R³ are covalently bonded together and, together with the intermediate atoms, comprise a 5- to 6-membered heterocycloalkyl monosubstituted with a group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, $R^1$ and $R^3$ are covalently bonded together and, together with the intermediate atoms, comprise an unsubstituted 5- to 6-membered heterocycloalkyl.

In a further aspect, each of $R^1$ and $R^3$ are covalently bonded together and, together with the intermediate atoms, comprise a 5-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, each of $R^1$ and $R^3$ are covalently bonded together and, together with the intermediate atoms, comprise a 6-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In yet a further aspect, each of $R^1$ and $R^3$ are covalently bonded together and, together with the intermediate atoms, comprise a 7-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino.

c. $R^2$ Groups

In one aspect, $R^2$ is hydrogen or C1-C4 alkyl, or wherein each of $R^1$ and $R^2$ are covalently bonded together and, together with the intermediate atoms, comprise a 3- to 6-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, (C1-C4)(C1-C4) dialkylamino.

In a further aspect, $R^2$ is hydrogen or C1-C4 alkyl. In a still further aspect, $R^2$ is hydrogen.

In a further aspect, $R^2$ is hydrogen, methyl, ethyl, isopropyl, n-propyl, isobutyl, n-butyl, s-butyl, or t-butyl. In a still further aspect, $R^2$ is hydrogen, methyl, ethyl, isopropyl, or n-propyl. In yet a further aspect, $R^2$ is hydrogen, methyl, or ethyl. In an even further aspect, $R^2$ is hydrogen or methyl. In a still further aspect, $R^2$ is hydrogen or ethyl.

In a further aspect, $R^2$ is methyl, ethyl, isopropyl, n-propyl, isobutyl, n-butyl, s-butyl, or t-butyl. In a still further aspect, $R^2$ is methyl, ethyl, isopropyl, or n-propyl. In yet a further aspect, $R^2$ is methyl, or ethyl. In an even further aspect, $R^2$ is methyl. In a still further aspect, $R^2$ is ethyl.

In a further aspect, each of $R^1$ and $R^2$ are covalently bonded together and, together with the intermediate atoms, comprise a 3- to 6-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, (C1-C4)(C1-C4) dialkylamino. In a still further aspect, each of $R^1$ and $R^2$ are covalently bonded together and, together with the intermediate atoms, comprise a 3- to 6-membered heterocycloalkyl substituted with 0, 1, or 2 groups independently selected from halogen, —NH$_2$, —OH, C1-C4 alkyl, C1-C4 haloalkyl, C1-C4 alkoxy, C1-C4 alkylamino, (C1-C4)(C1-C4) dialkylamino. In yet a further aspect, each of $R^1$ and $R^2$ are covalently bonded together and, together with the intermediate atoms, comprise a 3- to 6-membered heterocycloalkyl substituted with 0 or 1 group selected from halogen, —NH$_2$, —OH, C1-C4 alkyl, C1-C4 haloalkyl, C1-C4 alkoxy, C1-C4 alkylamino, (C1-C4)(C1-C4) dialkylamino. In an even further aspect, each of $R^1$ and $R^2$ are covalently bonded together and, together with the intermediate atoms, comprise a 3- to 6-membered heterocycloalkyl monosubstituted with a group selected from halogen, —NH$_2$, —OH, C1-C4 alkyl, C1-C4 haloalkyl, C1-C4 alkoxy, C1-C4 alkylamino, (C1-C4)(C1-C4) dialkylamino. In a still further aspect, each of $R^1$ and $R^2$ are covalently bonded together and, together with the intermediate atoms, comprise an unsubstituted 3- to 6-membered heterocycloalkyl.

In a further aspect, each of $R^1$ and $R^2$ are covalently bonded together and, together with the intermediate atoms, comprise a 3- to 5-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, (C1-C4)(C1-C4) dialkylamino. In a still further aspect, each of $R^1$ and $R^2$ are covalently bonded together and, together with the intermediate atoms, comprise a 3- to 4-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, (C1-C4)(C1-C4) dialkylamino. In yet a further aspect, each of $R^1$ and $R^2$ are covalently bonded together and, together with the intermediate atoms, comprise a 6-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, (C1-C4)(C1-C4) dialkylamino. In an even further aspect, each of $R^1$ and $R^2$ are covalently bonded together and, together with the intermediate atoms, comprise a 5-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, (C1-C4)(C1-C4) dialkylamino. In a still further aspect, each of $R^1$ and $R^2$ are covalently bonded together and, together with the intermediate atoms, comprise a 4-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, (C1-C4)(C1-C4) dialkylamino. In yet a further aspect, each of $R^1$ and $R^2$ are covalently bonded together and, together with the intermediate atoms, comprise a 3-membered heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, (C1-C4)(C1-C4) dialkylamino.

d. $R^3$ Groups

In one aspect, $R^3$ is hydrogen or C1-C4 alkyl. In a further aspect, $R^3$ is hydrogen.

In a further aspect, $R^3$ is hydrogen, methyl, ethyl, isopropyl, n-propyl, isobutyl, n-butyl, s-butyl, or t-butyl. In a still further aspect, $R^3$ is hydrogen, methyl, ethyl, isopropyl, or n-propyl. In yet a further aspect, $R^3$ is hydrogen, methyl, or ethyl. In an even further aspect, $R^3$ is hydrogen or methyl. In a still further aspect, $R^3$ is hydrogen or ethyl.

In a further aspect, $R^3$ is methyl, ethyl, isopropyl, n-propyl, isobutyl, n-butyl, s-butyl, or t-butyl. In a still further aspect, $R^3$ is methyl, ethyl, isopropyl, or n-propyl. In yet a further aspect, $R^3$ is methyl, or ethyl. In an even further aspect, $R^3$ is methyl. In a still further aspect, $R^3$ is ethyl.

e. $R^4$ Groups

In one aspect, $R^4$ is hydrogen, halogen, —NH$_2$, —OH, C1-C4 alkyl, C1-C4 alkoxy, C1-C4 alkylamino, (C1-C4)(C1-C4) dialkylamino, or $Cy^2$. In a further aspect, $R^4$ is hydrogen.

In a further aspect, $R^4$ is —F, —Cl, —NH$_2$, —OH, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH₂CH₂CH₂Cl, —CH(CH₃)CH₂F, —CH(CH₃)CH₂Cl, —OCH₃, —OCH₂CH₃, —OCH₂CH₂CH₃, —OCH(CH₃)CH₃, —NHCH₃, —NHCH₂CH₃, —NHCH₂CH₂CH₃, —NHCH(CH₃)CH₃, —N(CH₃)₂, —N(CH₂CH₃)₂, —N(CH₂CH₂CH₃)₂, —N(CH(CH₃)CH₃)₂, —N(CH₃)(CH₂CH₃), or Cy². In a still further aspect, R⁴ is —F, —Cl, —NH₂, —OH, methyl, ethyl, —CH₂F, —CH₂Cl, —CH₂CH₂F, —CH₂CH₂Cl, —OCH₃, —OCH₂CH₃, —NHCH₃, —NHCH₂CH₃, —N(CH₃)₂, —N(CH₂CH₃)₂, —N(CH₃)(CH₂CH₃), or Cy². In yet a further aspect, R⁴ is —F, —Cl, —NH₂, —OH, methyl, —CH₂F, —CH₂Cl, —OCH₃, —NHCH₃, —N(CH₃)₂, or Cy².

In a further aspect, R⁴ is C1-C4 alkyl, C1-C4 haloalkyl, C1-C4 alkoxy, C1-C4 alkylamino, or (C1-C4)(C1-C4) dialkylamino, or Cy². In a still further aspect, R⁴ is methyl, ethyl, n-propyl, i-propyl, —CH₂F, —CH₂Cl, —CH₂CH₂F, —CH₂CH₂Cl, —CH₂CH₂CH₂F, —CH₂CH₂CH₂Cl, —CH(CH₃)CH₂F, —CH(CH₃)CH₂Cl, —OCH₃, —OCH₂CH₃, —OCH₂CH₂CH₃, —OCH(CH₃)CH₃, —NHCH₃, —NHCH₂CH₃, —NHCH₂CH₂CH₃, —NHCH(CH₃)CH₃, —N(CH₃)₂, —N(CH₂CH₃)₂, —N(CH₂CH₂CH₃)₂, —N(CH(CH₃)CH₃)₂, —N(CH₃)(CH₂CH₃), or Cy². In yet a further aspect, R⁴ is methyl, ethyl, —CH₂F, —CH₂Cl, —CH₂CH₂F, —CH₂CH₂Cl, —OCH₃, —OCH₂CH₃, —NHCH₃, —NHCH₂CH₃, —N(CH₃)₂, —N(CH₂CH₃)₂, —N(CH₃)(CH₂CH₃), or Cy². In an even further aspect, R⁴ is methyl, —CH₂F, —CH₂Cl, —OCH₃, —NHCH₃, —N(CH₃)₂, or Cy².

In a further aspect, R⁴ is —F, —Cl, —NH₂, —OH, C1-C4 alkyl, C1-C4 alkoxy, C1-C4 alkylamino, (C1-C4)(C1-C4) dialkylamino, or Cy². In a still further aspect, R⁴ is —F, —Cl, —NH₂, —OH, methyl, ethyl, n-propyl, i-propyl, —OCH₃, —OCH₂CH₃, —OCH₂CH₂CH₃, —OCH(CH₃)CH₃, —NHCH₃, —NHCH₂CH₃, —NHCH₂CH₂CH₃, —NHCH(CH₃)CH₃, —N(CH₃)₂, —N(CH₂CH₃)₂, —N(CH₂CH₂CH₃)₂, —N(CH(CH₃)CH₃)₂, —N(CH₃)(CH₂CH₃), or Cy². In a still further aspect, R⁴ is —F, —Cl, —NH₂, —OH, methyl, ethyl, —OCH₃, —OCH₂CH₃, —NHCH₃, —NHCH₂CH₃, —N(CH₃)₂, —N(CH₂CH₃)₂, —N(CH₃)(CH₂CH₃), or Cy². In yet a further aspect, R⁴ is —F, —Cl, —NH₂, —OH, methyl, —OCH₃, —NHCH₃, —N(CH₃)₂, or Cy².

In a further aspect, R⁴ is —F, —Cl, —NH₂, —OH, C1-C4 alkyl, C1-C4 alkoxy, or Cy². In a still further aspect, R⁴ is —F, —Cl, —NH₂, —OH, methyl, ethyl, n-propyl, i-propyl, —OCH₃, —OCH₂CH₃, —OCH₂CH₂CH₃, —OCH(CH₃)CH₃, or Cy². In a still further aspect, R⁴ is —F, —Cl, —NH₂, —OH, methyl, ethyl, —OCH₃, —OCH₂CH₃, or Cy². In yet a further aspect, R⁴ is —F, —Cl, —NH₂, —OH, methyl, —OCH₃, or Cy².

In a further aspect, R⁴ is C1-C4 alkyl, C1-C4 haloalkyl, or C1-C4 alkoxy. In a still further aspect, R⁴ is methyl, ethyl, n-propyl, i-propyl, —CH₂F, —CH₂Cl, —CH₂CH₂F, —CH₂CH₂Cl, —CH₂CH₂CH₂F, —CH₂CH₂CH₂Cl, —CH(CH₃)CH₂F, —CH(CH₃)CH₂Cl, —OCH₃, —OCH₂CH₃, —OCH₂CH₂CH₃, or —OCH(CH₃)CH₃. In yet a further aspect, R⁴ is methyl, ethyl, —CH₂F, —CH₂Cl, —CH₂CH₂F, —CH₂CH₂Cl, —OCH₃, or —OCH₂CH₃. In yet a further aspect, R⁴ is methyl, —CH₂F, —CH₂Cl, or —OCH₃.

In a further aspect, R⁴ is Cy².

In a further aspect, R⁴ is C1-C4 haloalkyl. In a still further aspect, R⁴ is —CH₂F, —CH₂Cl, —CH₂CH₂F, —CH₂CH₂Cl, —CH₂CH₂CH₂F, —CH₂CH₂CH₂Cl, —CH(CH₃)CH₂F, or —CH(CH₃)CH₂Cl. In yet a further aspect, R⁴ is —CH₂F, —CH₂Cl, —CH₂CH₂F, or —CH₂CH₂Cl. In yet a further aspect, R⁴ is —CH₂F or —CH₂Cl.

In a further aspect, R⁴ is C1-C4 alkyl. In a still further aspect, R⁴ is methyl, ethyl, n-propyl, i-propyl, n-butyl, i-butyl, s-butyl, or t-butyl. In yet a further aspect, R⁴ is methyl, ethyl, n-propyl, or i-propyl. In an even further aspect, R⁴ is methyl or ethyl. In a still further aspect, R⁴ is ethyl. In yet a further aspect, R⁴ is methyl.

f. $R^{5A}$, $R^{5B}$, $R^{5C}$, and $R^{5D}$ Groups

In one aspect, each of $R^{5a}$, $R^{5b}$, $R^{5c}$, and $R^{5d}$ is independently hydrogen, halogen, —NH₂, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —CO₂ (C1-C4 alkyl), —CO₂H, —CO₂NH₂, —NHC(O)Cy³, —NHC(O)(C1-C4 alkyl), or Cy³.

In one aspect, each of $R^{5a}$, $R^{5b}$, $R^{5c}$, and $R^{5d}$ is independently hydrogen, halogen, —NH₂, —CN, —OH, C1-C4 alkyl, C1-C4 haloalkyl, C1-C4 alkoxy, C1-C4 alkylamino, (C1-C4)(C1-C4) dialkylamino, —CO₂(C1-C4 alkyl), —CO₂H, —CO₂NH₂, —NHC(O)Cy³, —NHC(O)(C1-C4 alkyl), or Cy³. In a further aspect, at least one of $R^{5a}$, $R^{5b}$ $R^{5c}$, and $R^{5d}$ is not hydrogen. In a still further aspect, one of $R^{5a}$, $R^{5b}$, $R^{5c}$, and $R^{5d}$ is hydrogen. In yet a further aspect, two of $R^{5a}$, $R^{5b}$, $R^{5c}$, and $R^{5d}$ is hydrogen. In an even further aspect, three of $R^{5a}$, $R^{5b}$, $R^{5c}$, and $R^{5d}$ are hydrogen.

In one aspect, each of $R^{5a}$, $R^{5b}$, and $R^{5d}$ is independently hydrogen, halogen, —NH₂, —CN, —OH, C1-C4 alkyl, C1-C4 haloalkyl, C1-C4 alkoxy, C1-C4 alkylamino, (C1-C4)(C1-C4) dialkylamino, —CO₂(C1-C4 alkyl), —CO₂H, —CO₂NH₂, —NHC(O)Cy³, —NHC(O)(C1-C4 alkyl), or Cy³; and R⁵ is hydrogen, halogen, —CN, —NH₂, —OH, C1-C4 alkyl, C1-C4 haloalkyl, C1-C4 alkoxy, C1-C4 alkylamino, (C1-C4)(C1-C4) dialkylamino, —CO₂(C1-C4 alkyl), —CO₂H, —CO₂NH₂, —NHC(O)Cy³, —NHC(O)(C1-C4 alkyl), or aryl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino.

In a further aspect, each of $R^{5a}$, $R^{5b}$, $R^{5c}$, and $R^{5d}$ is independently hydrogen, —F, —Cl, —NH₂, —CN, —OH, methyl, ethyl, n-propyl, i-propyl, —CH₂F, —CH₂Cl, —CH₂CH₂F, —CH₂CH₂Cl, —CH₂CH₂CH₂F, —CH₂CH₂CH₂Cl, —CH(CH₃)CH₂F, —CH(CH₃)CH₂Cl, —OCH₃, —OCH₂CH₃, —OCH₂CH₂CH₃, —OCH(CH₃)CH₃, —OCF₃, —OCH₂CF₃, —OCH₂CH₂CF₃, —OCH(CH₃)CF₃, —NHCH₃, —NHCH₂CH₃, —NHCH₂CH₂CH₃, —NHCH(CH₃)CH₃, —N(CH₃)₂, —N(CH₂CH₃)₂, —N(CH₂CH₂CH₃)₂, —N(CH(CH₃)CH₃)₂, —N(CH₃) (CH₂CH₃), —CO₂CH₃, —CO₂CH₂CH₃, —CO₂CH₂CH₂CH₃, —CO₂CH(CH₃)₂, —CO₂H, —CO₂NH₂, —NHC(O)Cy³, —NHC(O)CH₃, —NHC(O) CH₂CH₃, —NHC(O)CH₂CH₂CH₃, —NHC(O)CH(CH₃)₂, or Cy³. In a still further aspect, each of $R^{5a}$, $R^{5b}$, $R^{5c}$, and $R^{5d}$ is independently hydrogen, —F, —Cl, —NH₂, —CN, —OH, methyl, ethyl, —CH₂F, —CH₂Cl, —CH₂CH₂F, —CH₂CH₂Cl, —OCH₃, —OCH₂CH₃, —OCF₃, —OCH₂CF₃, —NHCH₃, —NHCH₂CH₃, —N(CH₃)₂, —N(CH₂CH₃)₂, —N(CH₃)(CH₂CH₃), —CO₂CH₃, —CO₂CH₂CH₃, —CO₂H, —CO₂NH₂, —NHC(O)Cy³, —NHC(O)CH₃, —NHC(O)CH₂CH₃, or Cy³. In yet a further aspect, each of $R^{5a}$, $R^{5b}$, $R^{5c}$, and $R^{5d}$ is independently hydrogen, —F, —Cl, —NH₂, —CN, —OH, methyl, —CH₂F, —CH₂Cl, —OCH₃, —OCF₃, —NHCH₃, —N(CH₃)₂, —CO₂CH₃, —CO₂H, —CO₂NH₂, —NHC(O) Cy³, —NHC(O)CH₃, or Cy³.

In a further aspect, each of $R^{5a}$, $R^{5b}$, $R^{5c}$, and $R^{5d}$ is independently hydrogen, —F, —Cl, —NH₂, —CN, —OH, methyl, ethyl, n-propyl, i-propyl, —CH₂F, —CH₂Cl, —CH₂CH₂F, —CH₂CH₂Cl, —CH₂CH₂CH₂F, —CH$_2$CH$_2$CH$_2$Cl, —CH(CH$_3$)CH$_2$F, —CH(CH$_3$)CH$_2$Cl, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CO$_2$CH$_3$, —CO$_2$CH$_2$CH$_3$, —CO$_2$CH$_2$CH$_2$CH$_3$, —CO$_2$CH(CH$_3$)$_2$, —CO$_2$H, —CO$_2$NH$_2$, —NHC(O)Cy$^3$, —NHC(O)CH$_3$, —NHC(O)CH$_2$CH$_3$, —NHC(O)CH$_2$CH$_2$CH$_3$, —NHC(O)CH(CH$_3$)$_2$, or Cy$^3$. In a still further aspect, each of R$^{5a}$, R$^{5b}$, R$^{5c}$, and R$^{5d}$ is independently hydrogen, —F, —Cl, —NH$_2$, —CN, —OH, methyl, ethyl, —CH$_2$F, —CH$_2$Cl, —CH$_2$CH$_2$F, —CH$_2$CH$_2$Cl, —OCH$_3$, —OCH$_2$CH$_3$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CO$_2$CH$_3$, —CO$_2$CH$_2$CH$_3$, —CO$_2$H, —CO$_2$NH$_2$, —NHC(O)Cy$^3$, —NHC(O)CH$_3$, —NHC(O)CH$_2$CH$_3$, or Cy$^3$. In yet a further aspect, each of R$^{5a}$R$^{5b}$, R$^{5c}$, and R$^{5d}$ is independently hydrogen, —F, —Cl, —NH$_2$, —CN, —OH, methyl, —CH$_2$F, —CH$_2$Cl, —OCH$_3$, —NHCH$_3$, —N(CH$_3$)$_2$, —CO$_2$CH$_3$, —CO$_2$H, —CO$_2$NH$_2$, —NHC(O)Cy$^3$, —NHC(O)CH$_3$, or Cy$^3$.

In a further aspect, each of R$^{5a}$, R$^{5b}$, R$^{5c}$, and R$^{5d}$ is independently hydrogen, C1-C4 alkyl, C1-C4 haloalkyl, C1-C4 alkoxy, C1-C4 alkylamino, or (C1-C4)(C1-C4) dialkylamino, —CO$_2$(C1-C4 alkyl), —CO$_2$H, —CO$_2$NH$_2$, —NHC(O)Cy$^3$, —NHC(O)(C1-C4 alkyl), or Cy$^3$. In a still further aspect, each of R$^{5a}$, R$^{5b}$, R$^{5c}$, and R$^{5d}$ is independently hydrogen, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CO$_2$CH$_3$, —CO$_2$CH$_2$CH$_3$, —CO$_2$CH$_2$CH$_2$CH$_3$, —CO$_2$CH(CH$_3$)$_2$, —CO$_2$H, —CO$_2$NH$_2$, —NHC(O)Cy$^3$, —NHC(O)CH$_3$, —NHC(O)CH$_2$CH$_3$, —NHC(O)CH$_2$CH$_2$CH$_3$, —NHC(O)CH(CH$_3$)$_2$, or Cy$^3$. In yet a further aspect, each of R$^{5a}$, R$^{5b}$, R$^{5c}$, and R$^{5d}$ is independently hydrogen, methyl, ethyl, —CH$_2$F, —CH$_2$Cl, —CH$_2$CH$_2$F, —CH$_2$CH$_2$Cl, —OCH$_3$, —OCH$_2$CH$_3$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CO$_2$CH$_3$, —CO$_2$CH$_2$CH$_3$, —CO$_2$H, —CO$_2$NH$_2$, —NHC(O)Cy$^3$, —NHC(O)CH$_2$CH$_3$, or Cy$^3$. In an even further aspect, each of R$^{5a}$, R$^{5b}$, R$^{5c}$, and R$^{5d}$ is independently hydrogen, methyl, —CH$_2$F, —CH$_2$Cl, —OCH$_3$, —NHCH$_3$, —N(CH$_3$)$_2$, —CO$_2$CH$_3$, —CO$_2$H, —CO$_2$NH$_2$, —NHC(O)Cy$^3$, —NHC(O)CH$_3$, or Cy$^3$.

In a further aspect, each of R$^{5a}$, R$^{5b}$, R$^{5c}$, and R$^{5d}$ is independently hydrogen, —F, —Cl, —NH$_2$, —CN, —OH, C1-C4 alkyl, C1-C4 alkoxy, C1-C4 alkylamino, (C1-C4)(C1-C4) dialkylamino, —CO$_2$(C1-C4 alkyl), —CO$_2$H, —CO$_2$NH$_2$, —NHC(O)Cy$^3$, —NHC(O)(C1-C4 alkyl), or Cy$^3$. In a still further aspect, each of R$^{5a}$, R$^{5b}$, R$^{5c}$, and R$^{5d}$ is independently hydrogen, —F, —Cl, —NH$_2$, —CN, —OH, methyl, ethyl, n-propyl, i-propyl, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CO$_2$CH$_3$, —CO$_2$CH$_2$CH$_3$, —CO$_2$CH$_2$CH$_2$CH$_3$, —CO$_2$CH(CH$_3$)$_2$, —CO$_2$H, —CO$_2$NH$_2$, —NHC(O)Cy$^3$, —NHC(O)CH$_3$, —NHC(O)CH$_2$CH$_3$, or Cy$^3$. In yet a further aspect, each of R$^{5a}$, R$^{5b}$, R$^{5c}$, and R$^{5d}$ is independently hydrogen, —F, —Cl, —NH$_2$, —CN, —OH, methyl, —OCH$_3$, —NHCH$_3$, —N(CH$_3$)$_2$, —CO$_2$CH$_3$, —CO$_2$H, —CO$_2$NH$_2$, —NHC(O)Cy$^3$, —NHC(O)CH$_3$, or Cy$^3$.

In a further aspect, each of R$^{5a}$, R$^{5b}$, R$^{5c}$, and R$^{5d}$ is independently hydrogen, —F, —Cl, —NH$_2$, —CN, —OH, C1-C4 alkyl, C1-C4 alkoxy, —CO$_2$(C1-C4 alkyl), —CO$_2$H, —CO$_2$NH$_2$, —NHC(O)Cy$^3$, —NHC(O)(C1-C4 alkyl), or Cy$^3$. In a still further aspect, each of R$^{5a}$, R$^{5b}$, R$^{5c}$, and R$^{5d}$ is independently hydrogen, —F, —Cl, —NH$_2$, —CN, —OH, methyl, ethyl, n-propyl, i-propyl, —OCH$_3$, —OCH$_2$CH$_3$, —OCH$_2$CH$_2$CH$_3$, —OCH(CH$_3$)CH$_3$, —CO$_2$CH$_3$, —CO$_2$CH$_2$CH$_3$, —CO$_2$CH$_2$CH$_2$CH$_3$, —CO$_2$CH(CH$_3$)$_2$, —CO$_2$H, —CO$_2$NH$_2$, —NHC(O)Cy$^3$, —NHC(O)CH$_3$, —NHC(O)CH$_2$CH$_3$, —NHC(O) CH$_2$CH$_2$CH$_3$, —NHC(O)CH(CH$_3$)$_2$, or Cy$^3$. In a still further aspect, each of R$^{5a}$, R$^{5b}$, R$^{5c}$, and R$^{5d}$ is independently hydrogen, —F, —Cl, —NH$_2$, —CN, —OH, methyl, ethyl, —OCH$_3$, —OCH$_2$CH$_3$, —CO$_2$CH$_3$, —CO$_2$CH$_2$CH$_3$, —CO$_2$H, —CO$_2$NH$_2$, —NHC(O)Cy$^3$, —NHC(O)CH$_3$, —NHC(O)CH$_2$CH$_3$, or Cy$^3$. In yet a further aspect, each of R$^{5a}$R$^{5b}$, R$^{5c}$, and R$^{5d}$ is independently hydrogen, —F, —Cl, —NH$_2$, —CN, —OH, methyl, —OCH$_3$, —CO$_2$CH$_3$, —CO$_2$H, —CO$_2$NH$_2$, —NHC(O)Cy$^3$, —NHC(O)CH$_3$, or Cy$^3$. In a still further aspect, each of R$^{5a}$, R$^{5b}$, R$^{5c}$, and R$^{5d}$ is independently hydrogen, —NH$_2$, —OH, C1-C4 alkyl, C1-C4 alkoxy, C1-C4 alkylamino, (C1-C4)(C1-C4) dialkylamino, or Cy$^3$.

In a further aspect, each of R$^{5a}$, R$^{5b}$, R$^{5c}$, and R$^{5d}$ is independently hydrogen, C1-C4 alkyl, C1-C4 haloalkyl, or C1-C4 alkoxy. In a still further aspect, each of R$^{5a}$, R$^{5b}$, R$^{5c}$, and R$^{5d}$ is independently hydrogen, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCH$_3$, —OCH$_2$CH$_3$, —OCH$_2$CH$_2$CH$_3$, or —OCH(CH$_3$)CH$_3$. In yet a further aspect, each of R$^{5a}$, R$^{5b}$, R$^{5c}$, and R$^{5d}$ is independently hydrogen, methyl, ethyl, —CH$_2$F, —CH$_2$Cl, —CH$_2$CH$_2$F, —CH$_2$CH$_2$Cl, —OCH$_3$, or —OCH$_2$CH$_3$. In yet a further aspect, each of R$^{5a}$R$^{5b}$, R$^{5c}$, and R$^{5d}$ is independently hydrogen, methyl, —CH$_2$F, —CH$_2$Cl, or —OCH$_3$.

In a further aspect, each of R$^{5a}$, R$^{5b}$, R$^{5c}$, and R$^{5d}$ is independently hydrogen or Cy$^3$.

In a further aspect, each of R$^{5a}$, R$^{5b}$, R$^{5c}$, and R$^{5d}$ is independently hydrogen, —CO$_2$(C1-C4 alkyl), —CO$_2$H, —CO$_2$NH$_2$, —NHC(O)Cy$^3$, or —NHC(O)(C1-C4 alkyl). In a still further aspect, each of R$^{5a}$, R$^{5b}$, R$^{5c}$, and R$^{5d}$ is independently hydrogen, —CO$_2$CH$_3$, —CO$_2$CH$_2$CH$_3$, —CO$_2$CH$_2$CH$_2$CH$_3$, —CO$_2$CH(CH$_3$)$_2$, —CO$_2$H, —CO$_2$NH$_2$, —NHC(O)Cy$^3$, —NHC(O)CH$_3$, —NHC(O)CH$_2$CH$_3$, —NHC(O)CH$_2$CH$_2$CH$_3$, or —NHC(O)CH(CH$_3$)$_2$. In yet a further aspect, each of R$^{5a}$, R$^{5b}$, R$^{5c}$, and R$^{5d}$ is independently hydrogen, —CO$_2$CH$_3$, —CO$_2$CH$_2$CH$_3$, —CO$_2$H, —CO$_2$NH$_2$, —NHC(O)Cy$^3$, —NHC(O)CH$_3$, or —NHC(O)CH$_2$CH$_3$. In an even further aspect, each of R$^{5a}$, R$^{5b}$, R$^{5c}$, and R$^{5d}$ is independently hydrogen, —CO$_2$CH$_3$, —CO$_2$H, —CO$_2$NH$_2$, —NHC(O)Cy$^3$, or —NHC(O)CH$_3$.

In a further aspect, each of R$^{5a}$, R$^{5b}$, R$^{5c}$, and R$^{5d}$ is independently hydrogen or C1-C4 haloalkyl. In a still further aspect, each of R$^{5a}$, R$^{5b}$, R$^{5c}$, and R$^{5d}$ is independently hydrogen, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, or —CH(CH$_3$)CH$_2$Cl. In yet a further aspect, each of R$^{5a}$, R$^{5b}$, R$^{5c}$, and R$^{5d}$ is independently hydrogen, —CH$_2$F, —CH$_2$Cl, —CH$_2$CH$_2$F, or —CH$_2$CH$_2$Cl. In yet a further aspect, each of R$^{5a}$, R$^{5b}$, R$^{5c}$, and R$^{5d}$ is independently hydrogen, —CH$_2$F or —CH$_2$Cl.

In a further aspect, each of R$^{5a}$, R$^{5b}$, R$^{5c}$, and R$^{5d}$ is independently hydrogen or C1-C4 alkyl. In a still further aspect, each of R$^{5a}$, R$^{5b}$, R$^{5c}$, and R$^{5d}$ is independently hydrogen, methyl, ethyl, n-propyl, i-propyl, n-butyl, i-butyl, s-butyl, or t-butyl. In yet a further aspect, each of R$^{5a}$, R$^{5b}$, R$^{5c}$, and R$^{5d}$ is independently hydrogen, methyl, ethyl, n-propyl, or i-propyl. In an even further aspect, each of R$^{5a}$, R$^{5b}$, R$^{5c}$, and R$^{5d}$ is independently hydrogen, methyl or ethyl. In a still further aspect, each of R$^{5a}$, R$^{5b}$, R$^{5c}$, and R$^{5d}$ is independently hydrogen or ethyl. In yet a further aspect, each of R$^{5a}$, R$^{5b}$, R$^{5c}$, and R$^{5d}$ is independently hydrogen or methyl.

In a further aspect, each of R$^{5a}$, R$^{5b}$, R$^{5c}$, and R$^{5d}$ is independently hydrogen, halogen, —NH$_2$, —CN, —OH, C1-C4 alkyl, C1-C4 alkoxy, C1-C4 alkylamino, or (C1-C4)(C1-C4) dialkylamino. In a further aspect, each of R$^{5a}$, R$^{5b}$, R$^{5c}$, and R$^{5d}$ is independently hydrogen, halogen, —NH$_2$, —OH, C1-C4 alkyl, C1-C4 alkoxy, C1-C4 alkylamino, or (C1-C4)(C1-C4) dialkylamino. In a further aspect, each of R$^{5a}$, R$^{5b}$, R$^{5c}$, and R$^{5d}$ is independently hydrogen, —F, —Cl, —NH$_2$, —CN, —OH, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, or —N(CH$_3$)(CH$_2$CH$_3$). In a still further aspect, each of R$^{5a}$, R$^{5b}$, R$^{5c}$, and R$^{5d}$ is independently hydrogen, —F, —Cl, —NH$_2$, —CN, —OH, methyl, ethyl, —CH$_2$F, —CH$_2$Cl, —CH$_2$CH$_2$F, —CH$_2$CH$_2$Cl, —OCH$_3$, —OCH$_2$CH$_3$, —NHCH$_3$, —NHCH$_2$CH$_3$, —N(CH$_3$)$_2$, —N(CH$_2$CH$_3$)$_2$, or —N(CH$_3$)(CH$_2$CH$_3$). In yet a further aspect, each of R$^{5a}$, R$^{5b}$, R$^{5c}$, and R$^{5d}$ is independently hydrogen, —F, —Cl, —NH$_2$, —CN, —OH, methyl, —CH$_2$F, —CH$_2$Cl, —OCH$_3$, —NHCH$_3$, or —N(CH$_3$)$_2$.

In a further aspect, each of R$^{5a}$, R$^{5b}$, and R$^{5d}$ is independently hydrogen, —F, —Cl, —NH$_2$, —CN, —OH, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), or Cy$^3$. In a still further aspect, each of R$^{5a}$, R$^{5b}$, and R$^{5d}$ is independently hydrogen, —F, —Cl, —NH$_2$, —CN, —OH, methyl, ethyl, —CH$_2$F, —CH$_2$Cl, —CH$_2$CH$_2$F, —CH$_2$CH$_2$Cl, —OCH$_3$, —OCH$_2$CH$_3$, —NHCH$_3$, —NHCH$_2$CH$_3$, —N(CH$_3$)$_2$, —N(CH$_2$CH$_3$)$_2$, —N(CH$_3$)(CH$_2$CH$_3$), or Cy$^3$. In yet a further aspect, each of R$^{5a}$, R$^{5b}$, and R$^{5d}$ is independently hydrogen, —F, —Cl, —NH$_2$, —CN, —OH, methyl, —CH$_2$F, —CH$_2$Cl, —OCH$_3$, —NHCH$_3$, —N(CH$_3$)$_2$, or Cy$^3$.

In a further aspect, each of R$^{5a}$, R$^{5b}$, and R$^{5d}$ is independently hydrogen, C1-C4 alkyl, C1-C4 haloalkyl, C1-C4 alkoxy, C1-C4 alkylamino, or (C1-C4)(C1-C4) dialkylamino, —CO$_2$(C1-C4 alkyl), —CO$_2$H, —CO$_2$NH$_2$, —NHC(O)Cy$^3$, —NHC(O)(C1-C4 alkyl), or Cy$^3$. In a still further aspect, each of R$^{5a}$, R$^{5b}$, and R$^{5d}$ is independently hydrogen, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —N(CH$_3$)(CH$_2$CH$_3$), —CO$_2$CH$_3$, —CO$_2$CH$_2$CH$_3$, —CO$_2$CH$_2$CH$_2$CH$_3$, —CO$_2$CH(CH$_3$)$_2$, —CO$_2$H, —CO$_2$NH$_2$, —NHC(O)Cy$^3$, —NHC(O)CH$_3$, —NHC(O)CH$_2$CH$_3$, —NHC(O)CH$_2$CH$_2$CH$_3$, —NHC(O)CH(CH$_3$)$_2$, or Cy$^3$. In yet a further aspect, each of R$^{5a}$, R$^{5b}$, and R$^{5d}$ is independently hydrogen, methyl, ethyl, —CH$_2$F, —CH$_2$Cl, —CH$_2$CH$_2$F, —CH$_2$CH$_2$Cl, —OCH$_3$, —OCH$_2$CH$_3$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CO$_2$CH$_3$, —CO$_2$CH$_2$CH$_3$, —CO$_2$H, —CO$_2$NH$_2$, —NHC(O)Cy$^3$, —NHC(O)CH$_3$, —NHC(O)CH$_2$CH$_3$, or Cy$^3$. In an even further aspect, each of R$^{5a}$, R$^{5b}$, and R$^{5d}$ is independently hydrogen, methyl, —CH$_2$F, —CH$_2$Cl, —OCH$_3$, —NHCH$_3$, —N(CH$_3$)$_2$, —CO$_2$CH$_3$, —CO$_2$H, —CO$_2$NH$_2$, —NHC(O)Cy$^3$, —NHC(O)CH$_3$, or Cy$^3$.

In a further aspect, each of R$^{5a}$, R$^{5b}$, and R$^{5d}$ is independently hydrogen, —F, —Cl, —NH$_2$, —CN, —OH, C1-C4 alkyl, C1-C4 alkoxy, C1-C4 alkylamino, (C1-C4)(C1-C4) dialkylamino, —CO$_2$(C1-C4 alkyl), —CO$_2$H, —CO$_2$NH$_2$, —NHC(O)Cy$^3$, —NHC(O)(C1-C4 alkyl), or Cy$^3$. In a still further aspect, each of R$^{5a}$, R$^{5b}$, and R$^{5d}$ is independently hydrogen, —F, —Cl, —NH$_2$, —CN, —OH, methyl, ethyl, n-propyl, i-propyl, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CO$_2$CH$_3$, —CO$_2$CH$_2$CH$_3$, —CO$_2$CH$_2$CH$_2$CH$_3$, —CO$_2$CH(CH$_3$)$_2$, —CO$_2$H, —CO$_2$NH$_2$, —NHC(O)Cy$^3$, —NHC(O)CH$_3$, —NHC(O)CH$_2$CH$_3$, —NHC(O)CH$_2$CH$_2$CH$_3$, —NHC(O)CH(CH$_3$)$_2$, or Cy$^3$. In a still further aspect, each of R$^{5a}$, R$^{5b}$, and R$^{5d}$ is independently hydrogen, —F, —Cl, —NH$_2$, —CN, —OH, methyl, ethyl, —OCH$_3$, —OCH$_2$CH$_3$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CO$_2$CH$_3$, —CO$_2$CH$_2$CH$_3$, —CO$_2$H, —CO$_2$NH$_2$, —NHC(O)Cy$^3$, —NHC(O)CH$_3$, —NHC(O)CH$_2$CH$_3$, or Cy$^3$. In yet a further aspect, each of R$^{5a}$, R$^{5b}$, and R$^{5d}$ is independently hydrogen, —F, —Cl, —NH$_2$, —CN, —OH, methyl, —OCH$_3$, —NHCH$_3$, —N(CH$_3$)$_2$, —CO$_2$CH$_3$, —CO$_2$H, —CO$_2$NH$_2$, —NHC(O)Cy$^3$, —NHC(O)CH$_3$, or Cy$^3$.

In a further aspect, each of R$^{5a}$, R$^{5b}$, and R$^{5d}$ is independently hydrogen, —F, —Cl, —NH$_2$, —CN, —OH, C1-C4 alkyl, C1-C4 alkoxy, —CO$_2$(C1-C4 alkyl), —CO$_2$H, —CO$_2$NH$_2$, —NHC(O)Cy$^3$, —NHC(O)(C1-C4 alkyl), or Cy$^3$. In a still further aspect, each of R$^{5a}$, R$^{5b}$, and R$^{5d}$ is independently hydrogen, —F, —Cl, —NH$_2$, —CN, —OH, methyl, ethyl, n-propyl, i-propyl, —OCH$_3$, —OCH$_2$CH$_3$, —OCH$_2$CH$_2$CH$_3$, —OCH(CH$_3$)CH$_3$, —CO$_2$CH$_3$, —CO$_2$CH$_2$CH$_3$, —CO$_2$CH$_2$CH$_2$CH$_3$, —CO$_2$CH(CH$_3$)$_2$, —CO$_2$H, —CO$_2$NH$_2$, —NHC(O)Cy$^3$, —NHC(O)CH$_3$, —NHC(O)CH$_2$CH$_3$, —NHC(O)CH$_2$CH$_2$CH$_3$, —NHC(O)CH(CH$_3$)$_2$, or Cy$^3$. In a still further aspect, each of R$^{5a}$, R$^{5b}$, and R$^{5d}$ is independently hydrogen, —F, —Cl, —NH$_2$, —CN, —OH, methyl, ethyl, —OCH$_3$, —OCH$_2$CH$_3$, —CO$_2$CH$_3$, —CO$_2$CH$_2$CH$_3$, —CO$_2$H, —CO$_2$NH$_2$, —NHC(O)Cy$^3$, —NHC(O)CH$_3$, —NHC(O)CH$_2$CH$_3$, or Cy$^3$. In yet a further aspect, each of R$^{5a}$R$^{5b}$, and R$^{5d}$ is independently hydrogen, —F, —Cl, —NH$_2$, —CN, —OH, methyl, —OCH$_3$, —CO$_2$CH$_3$, —CO$_2$H, —CO$_2$NH$_2$, —NHC(O)Cy$^3$, —NHC(O)CH$_3$, or Cy$^3$.

In a further aspect, each of $R^{5a}$, $R^{5b}$, and $R^{5d}$ is independently hydrogen, C1-C4 alkyl, C1-C4 haloalkyl, or C1-C4 alkoxy. In a still further aspect, each of $R^{5a}$, $R^{5b}$, and $R^{5d}$ is independently hydrogen, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCH$_3$, —OCH$_2$CH$_3$, —OCH$_2$CH$_2$CH$_3$, or —OCH(CH$_3$)CH$_3$. In yet a further aspect, each of $R^{5a}$, $R^{5b}$, and $R^{5d}$ is independently hydrogen, methyl, ethyl, —CH$_2$F, —CH$_2$Cl, —CH$_2$CH$_2$F, —CH$_2$CH$_2$Cl, —OCH$_3$, or —OCH$_2$CH$_3$. In yet a further aspect, each of $R^{5a}$, $R^{5b}$, and $R^{5d}$ is independently hydrogen, methyl, —CH$_2$F, —CH$_2$Cl, or —OCH$_3$.

In a further aspect, each of $R^{5a}$, $R^{5b}$, and $R^{5d}$ is independently hydrogen or Cy$^3$.

In a further aspect, each of $R^{5a}$, $R^{5b}$, and $R^{5d}$ is independently hydrogen, —CO$_2$(C1-C4 alkyl), —CO$_2$H, —CO$_2$NH$_2$, —NHC(O)Cy$^3$, or —NHC(O)(C1-C4 alkyl). In a still further aspect, each of $R^{5a}$, $R^{5b}$, and $R^{5d}$ is independently hydrogen, —CO$_2$CH$_3$, —CO$_2$CH$_2$CH$_3$, —CO$_2$CH$_2$CH$_2$CH$_3$, —CO$_2$CH(CH$_3$)$_2$, —CO$_2$H, —CO$_2$NH$_2$, —NHC(O)Cy$^3$, —NHC(O)CH$_3$, —NHC(O)CH$_2$CH$_3$, —NHC(O)CH$_2$CH$_2$CH$_3$, or —NHC(O)CH(CH$_3$)$_2$. In yet a further aspect, each of $R^{5a}$, $R^{5b}$, and $R^{5d}$ is independently hydrogen, —CO$_2$CH$_3$, —CO$_2$CH$_2$CH$_3$, —CO$_2$H, —CO$_2$NH$_2$, —NHC(O)Cy$^3$, —NHC(O)CH$_3$, or —NHC(O)CH$_2$CH$_3$. In an even further aspect, each of $R^{5a}$, $R^{5b}$, and $R^{5d}$ is independently hydrogen, —CO$_2$CH$_3$, —CO$_2$H, —CO$_2$NH$_2$, —NHC(O)Cy$^3$, or —NHC(O)CH$_3$.

In a further aspect, each of $R^{5a}$, $R^{5b}$, and $R^{5d}$ is independently hydrogen or C1-C4 haloalkyl. In a still further aspect, each of $R^{5a}$, $R^{5b}$, and $R^{5d}$ is independently hydrogen, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, or —CH(CH$_3$)CH$_2$Cl. In yet a further aspect, each of $R^{5a}$, $R^{5b}$, and $R^{5d}$ is independently hydrogen, —CH$_2$F, —CH$_2$Cl, —CH$_2$CH$_2$F, or —CH$_2$CH$_2$Cl. In yet a further aspect, each of $R^{5a}$, $R^{5b}$, and $R^{5d}$ is independently hydrogen, —CH$_2$F or —CH$_2$Cl.

In a further aspect, each of $R^{5a}$, $R^{5b}$, and $R^{5d}$ is independently hydrogen or C1-C4 alkyl. In a still further aspect, each of $R^{5a}$, $R^{5b}$, and $R^{5d}$ is independently hydrogen, methyl, ethyl, n-propyl, i-propyl, n-butyl, i-butyl, s-butyl, or t-butyl. In yet a further aspect, each of $R^{5a}$, $R^{5b}$, and $R^{5d}$ is independently hydrogen, methyl, ethyl, n-propyl, or i-propyl. In an even further aspect, each of $R^{5a}$, $R^{5b}$, and $R^{5d}$ is independently hydrogen, methyl or ethyl. In a still further aspect, each of $R^{5a}$, $R^{5b}$, and $R^{5d}$ is independently hydrogen or ethyl. In yet a further aspect, each of $R^{5a}$, $R^{5b}$, and $R^{5d}$ is independently hydrogen or methyl.

In a further aspect, each of $R^{5a}$, $R^{5b}$, and $R^{5d}$ is independently hydrogen, halogen, —NH$_2$, —CN, —OH, C1-C4 alkyl, C1-C4 alkoxy, C1-C4 alkylamino, or (C1-C4)(C1-C4) dialkylamino. In a further aspect, each of $R^{5a}$, $R^{5b}$, and $R^{5d}$ is independently hydrogen, —F, —Cl, —NH$_2$, —CN, —OH, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, or —N(CH$_3$)(CH$_2$CH$_3$). In a still further aspect, each of $R^{5a}$, $R^{5b}$, and $R^{5d}$ is independently hydrogen, —F, —Cl, —NH$_2$, —CN, —OH, methyl, ethyl, —CH$_2$F, —CH$_2$Cl, —CH$_2$CH$_2$F, —CH$_2$CH$_2$Cl, —OCH$_3$, —OCH$_2$CH$_3$, —NHCH$_3$, —NHCH$_2$CH$_3$, —N(CH$_3$)$_2$, —N(CH$_2$CH$_3$)$_2$, or —N(CH$_3$)(CH$_2$CH$_3$). In yet further aspect, each of $R^{5a}$, $R^{5b}$, and $R^{5d}$ is independently hydrogen, —F, —Cl, —NH$_2$, —CN, —OH, methyl, —CH$_2$F, —CH$_2$Cl, —OCH$_3$, —NHCH$_3$, or —N(CH$_3$)$_2$.

In a further aspect, $R^{5b}$ is fluorine.

In a further aspect, $R^{5c}$ is hydrogen, halogen, —NH$_2$, —CN, —OH, C1-C4 alkyl, C1-C4 alkoxy, C1-C4 alkylamino, or (C1-C4)(C1-C4) dialkylamino. In a further aspect, $R^{5c}$ is hydrogen, halogen, —NH$_2$, —OH, C1-C4 alkyl, C1-C4 alkoxy, C1-C4 alkylamino, or (C1-C4)(C1-C4) dialkylamino. In a still further aspect, $R^{5c}$ is hydrogen, halogen, —NH$_2$, —OH, -C1-C4 alkoxy, C1-C4 alkylamino, or (C1-C4)(C1-C4) dialkylamino. In a still further aspect, $R^{5c}$ is hydrogen, —F, —Cl, —NH$_2$, —OH, methyl, ethyl, n-propyl, i-propyl, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, or —N(CH$_3$)(CH$_2$CH$_3$). In a still further aspect, $R^{5c}$ is hydrogen, —F, —Cl, —NH$_2$, —CN, —OH, methyl, ethyl, —OCH$_3$, —OCH$_2$CH$_3$, —NHCH$_3$, —NHCH$_2$CH$_3$, —N(CH$_3$)$_2$, —N(CH$_2$CH$_3$)$_2$, or —N(CH$_3$)(CH$_2$CH$_3$). In yet a further aspect, $R^{5c}$ is hydrogen, —F, —Cl, —NH$_2$, —CN, —OH, methyl, —OCH$_3$, —NHCH$_3$, or —N(CH$_3$)$_2$.

In a further aspect, $R^{5c}$ is hydrogen, —F, —NH$_2$, —CN, —OH, C1-C4 alkyl, C1-C4 alkoxy, C1-C4 alkylamino, or (C1-C4)(C1-C4) dialkylamino. In a still further aspect, $R^{5c}$ is hydrogen, —F, —NH$_2$, —CN, —OH, methyl, ethyl, n-propyl, i-propyl, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, or —N(CH$_3$)(CH$_2$CH$_3$). In a still further aspect, $R^{5c}$ is hydrogen, —F, —NH$_2$, —CN, —OH, methyl, ethyl, —OCH$_3$, —OCH$_2$CH$_3$, —NHCH$_3$, —NHCH$_2$CH$_3$, —N(CH$_3$)$_2$, —N(CH$_2$CH$_3$)$_2$, or —N(CH$_3$)(CH$_2$CH$_3$). In yet a further aspect, $R^{5c}$ is hydrogen, —F, —NH$_2$, —CN, —OH, methyl, —OCH$_3$, —NHCH$_3$, or —N(CH$_3$)$_2$.

In a further aspect, $R^{5c}$ is halogen, —NH$_2$, —CN, —OH, C1-C4 alkyl, C1-C4 alkoxy, C1-C4 alkylamino, or (C1-C4)(C1-C4) dialkylamino. In a still further aspect, $R^{5c}$ is —F, —Cl, —NH$_2$, —CN, —OH, methyl, ethyl, n-propyl, i-propyl, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, or —N(CH$_3$)(CH$_2$CH$_3$). In a still further aspect, $R^{5c}$ is —F, —Cl, —NH$_2$, —CN, —OH, methyl, ethyl, —OCH$_3$, —OCH$_2$CH$_3$, —NHCH$_3$, —NHCH$_2$CH$_3$, —N(CH$_3$)$_2$, —N(CH$_2$CH$_3$)$_2$, or —N(CH$_3$)(CH$_2$CH$_3$). In yet a further aspect, $R^{5c}$ is —F, —Cl, —NH$_2$, —CN, —OH, methyl, —OCH$_3$, —NHCH$_3$, or —N(CH$_3$)$_2$.

In a further aspect, $R^{5c}$ is —F, —NH$_2$, —CN, —OH, C1-C4 alkyl, C1-C4 alkoxy, C1-C4 alkylamino, or (C1-C4)(C1-C4) dialkylamino. In a still further aspect, $R^{5c}$ is —F, —NH$_2$, —CN, —OH, methyl, ethyl, n-propyl, i-propyl, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, or —N(CH$_3$)(CH$_2$CH$_3$). In a still further aspect, $R^{5c}$ is —F, —NH$_2$, —CN, —OH, methyl, ethyl, —OCH$_3$, —OCH$_2$CH$_3$, —NHCH$_3$, —NHCH$_2$CH$_3$, —N(CH$_3$)$_2$, —N(CH$_2$CH$_3$)$_2$, or —N(CH$_3$)(CH$_2$CH$_3$). In yet a further aspect, $R^{5c}$ is —F, —NH$_2$, —CN, —OH, methyl, —OCH$_3$, —NHCH$_3$, or —N(CH$_3$)$_2$.

In a further aspect, $R^{5c}$ is hydrogen, halogen, —NH$_2$, —OH, —CN, C1-C4 alkyl, C1-C4 haloalkyl, C1-C4 alkoxy, C1-C4 haloalkoxy, C1-C4 alkylamino, (C1-C4)(C1-C4) dialkylamino, —CO$_2$(C1-C4 alkyl), —CO$_2$H, —CO$_2$NH$_2$, —NHC(O)Cy$^3$, —NHC(O)(C1-C4 alkyl), or aryl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino.

In a further aspect, $R^{5c}$ is fluorine.

g. $R^{6A}$ Groups

In one aspect, $R^{6a}$ is hydrogen or C1-C4 alkyl. In a further aspect, $R^{6a}$ is hydrogen.

In a further aspect, $R^{6a}$ is hydrogen, methyl, ethyl, isopropyl, n-propyl, isobutyl, n-butyl, s-butyl, or t-butyl. In a still further aspect, $R^{6a}$ is hydrogen, methyl, ethyl, isopropyl, or n-propyl. In yet a further aspect, $R^{6a}$ is hydrogen, methyl, or ethyl. In an even further aspect, $R^{6a}$ is hydrogen or methyl. In a still further aspect, $R^{6a}$ is hydrogen or ethyl.

In a further aspect, $R^{6a}$ is methyl, ethyl, isopropyl, n-propyl, isobutyl, n-butyl, s-butyl, or t-butyl. In a still further aspect, $R^{6a}$ is methyl, ethyl, isopropyl, or n-propyl. In yet a further aspect, $R^{6a}$ is methyl, or ethyl. In an even further aspect, $R^{6a}$ is methyl. In a still further aspect, $R^{6a}$ is ethyl.

h. $R^{6B}$ Groups

In one aspect, $R^{6b}$ is hydrogen, C1-C4 alkyl, C1-C4 haloalkyl, C1-C4 alkoxy, C1-C4 alkylamino, (C1-C4)(C1-C4) dialkylamino, or —CO$_2$H. In a further aspect, $R^{6b}$ is —CO$_2$H.

In one aspect, $R^{6b}$ is hydrogen, C1-C4 alkyl, C1-C4 haloalkyl, C1-C4 alkoxy, C1-C4 alkylamino, or (C1-C4)(C1-C4) dialkylamino. In a further aspect, $R^{6b}$ is hydrogen.

In a further aspect, $R^{6b}$ is hydrogen, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, or —N(CH$_3$)(CH$_2$CH$_3$). In a still further aspect, $R^{6b}$ is hydrogen, methyl, ethyl, —CH$_2$F, —CH$_2$Cl, —CH$_2$CH$_2$F, —CH$_2$CH$_2$Cl, —OCH$_3$, —OCH$_2$CH$_3$, —NHCH$_3$, —NHCH$_2$CH$_3$, —N(CH$_3$)$_2$, —N(CH$_2$CH$_3$)$_2$, or —N(CH$_3$)(CH$_2$CH$_3$). In yet a further aspect, $R^{6b}$ is hydrogen, methyl, —CH$_2$F, —CH$_2$Cl, —OCH$_3$, —NHCH$_3$, or —N(CH$_3$)$_2$.

In a further aspect, $R^{6b}$ is hydrogen, C1-C4 alkyl, C1-C4 alkoxy, C1-C4 alkylamino, or (C1-C4)(C1-C4) dialkylamino. In a still further aspect, $R^{6b}$ is hydrogen, methyl, ethyl, n-propyl, i-propyl, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, or —N(CH$_3$)(CH$_2$CH$_3$). In a still further aspect, $R^{6b}$ is hydrogen, methyl, ethyl, —OCH$_3$, —OCH$_2$CH$_3$, —NHCH$_3$, —NHCH$_2$CH$_3$, —N(CH$_3$)$_2$, —N(CH$_2$CH$_3$)$_2$, or —N(CH$_3$)(CH$_2$CH$_3$). In yet a further aspect, $R^{6b}$ is hydrogen, methyl, —OCH$_3$, —NHCH$_3$, or —N(CH$_3$)$_2$.

In a further aspect, $R^{6b}$ is hydrogen, C1-C4 alkyl, or C1-C4 alkoxy. In a still further aspect, $R^{6b}$ is hydrogen, methyl, ethyl, n-propyl, i-propyl, —OCH$_3$, —OCH$_2$CH$_3$, —OCH$_2$CH$_2$CH$_3$, or —OCH(CH$_3$)CH$_3$. In a still further aspect, $R^{6b}$ is hydrogen, methyl, ethyl, —OCH$_3$, or —OCH$_2$CH$_3$. In yet a further aspect, $R^{6b}$ is hydrogen, methyl, or —OCH$_3$.

In a further aspect, $R^{6b}$ is hydrogen, C1-C4 alkyl, C1-C4 haloalkyl, or C1-C4 alkoxy. In a still further aspect, $R^{6b}$ is hydrogen, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCH$_3$, —OCH$_2$CH$_3$, —OCH$_2$CH$_2$CH$_3$, or —OCH(CH$_3$)CH$_3$. In yet a further aspect, $R^{6b}$ is hydrogen, methyl, ethyl, —CH$_2$F, —CH$_2$Cl, —CH$_2$CH$_2$F, —CH$_2$CH$_2$Cl, —OCH$_3$, or —OCH$_2$CH$_3$. In yet a further aspect, $R^{6b}$ is hydrogen, methyl, —CH$_2$F, —CH$_2$Cl, or —OCH$_3$.

In a further aspect, $R^{6b}$ is C1-C4 alkyl. In a still further aspect, $R^{6b}$ is methyl, ethyl, n-propyl, i-propyl, n-butyl, i-butyl, s-butyl, or t-butyl. In yet a further aspect, $R^{6b}$ is methyl, ethyl, n-propyl, or i-propyl. In an even further aspect, $R^{6b}$ is methyl or ethyl. In a still further aspect, $R^{6b}$ is ethyl. In yet a further aspect, $R^{6b}$ is methyl.

i. $R^7$ Groups

In one aspect, $R^7$ is hydrogen, halogen, —OH, C1-C4 alkyl, C1-C4 haloalkyl, or C1-C4 alkoxy. In a further aspect, $R^7$ is hydrogen.

In a further aspect, $R^7$ is hydrogen, —F, —Cl, —OH, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCH$_3$, —OCH$_2$CH$_3$, —OCH$_2$CH$_2$CH$_3$, or —OCH(CH$_3$)CH$_3$. In a still further aspect, $R^7$ is hydrogen, —F, —Cl, —OH, methyl, ethyl, —CH$_2$F, —CH$_2$Cl, —CH$_2$CH$_2$F, —CH$_2$CH$_2$Cl, —OCH$_3$, or —OCH$_2$CH$_3$. In yet a further aspect, $R^7$ is hydrogen, —F, —Cl, —OH, methyl, —CH$_2$F, —CH$_2$Cl, or —OCH$_3$.

In a further aspect, $R^7$ is hydrogen, —F, —Cl, —OH, C1-C4 alkyl, or C1-C4 alkoxy. In a still further aspect, $R^7$ is hydrogen, —F, —Cl, —OH, methyl, ethyl, n-propyl, i-propyl, —OCH$_3$, —OCH$_2$CH$_3$, —OCH$_2$CH$_2$CH$_3$, or —OCH(CH$_3$)CH$_3$. In a still further aspect, $R^7$ is hydrogen, —F, —Cl, —OH, methyl, ethyl, —OCH$_3$, or —OCH$_2$CH$_3$. In yet a further aspect, $R^7$ is hydrogen, —F, —Cl, —OH, methyl, or —OCH$_3$.

In a further aspect, $R^7$ is hydrogen, C1-C4 alkyl, C1-C4 haloalkyl, or C1-C4 alkoxy. In a still further aspect, $R^7$ is hydrogen, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCH$_3$, —OCH$_2$CH$_3$, —OCH$_2$CH$_2$CH$_3$, or —OCH(CH$_3$)CH$_3$. In yet a further aspect, $R^7$ is hydrogen, methyl, ethyl, —CH$_2$F, —CH$_2$Cl, —CH$_2$CH$_2$F, —CH$_2$CH$_2$Cl, —OCH$_3$, or —OCH$_2$CH$_3$. In yet a further aspect, $R^7$ is hydrogen, methyl, —CH$_2$F, —CH$_2$Cl, or —OCH$_3$.

In a further aspect, $R^7$ is C1-C4 alkyl. In a still further aspect, $R^7$ is methyl, ethyl, n-propyl, i-propyl, n-butyl, i-butyl, s-butyl, or t-butyl. In yet a further aspect, $R^7$ is methyl, ethyl, n-propyl, or i-propyl. In an even further aspect, $R^7$ is methyl or ethyl. In a still further aspect, $R^7$ is ethyl. In yet a further aspect, $R^7$ is methyl.

j. $R^8$ Groups

In one aspect, $R^8$ is hydrogen, C1-C4 alkyl, or C1-C4 haloalkyl. In a further aspect, $R^8$ is hydrogen.

In a further aspect, $R^8$ is hydrogen, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, or —CH(CH$_3$)CH$_2$Cl. In a still further aspect, $R^8$ is hydrogen, methyl, ethyl, —CH$_2$F, —CH$_2$Cl, —CH$_2$CH$_2$F, or —CH$_2$CH$_2$Cl. In yet a further aspect, $R^8$ is hydrogen, methyl, —CH$_2$F, or —CH$_2$Cl.

In a further aspect, $R^8$ is hydrogen or C1-C4 alkyl. In a still further aspect, $R^8$ is hydrogen, methyl, ethyl, n-propyl, or i-propyl. In a still further aspect, $R^8$ is hydrogen, methyl, or ethyl. In yet a further aspect, $R^8$ is hydrogen or ethyl. In an even further aspect, $R^8$ is hydrogen or methyl.

In a further aspect, $R^8$ is hydrogen or C1-C4 haloalkyl. In a still further aspect, $R^8$ is hydrogen, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, or —CH(CH$_3$)CH$_2$Cl. In yet a further aspect, $R^8$ is hydrogen, —CH$_2$F, —CH$_2$Cl, —CH$_2$CH$_2$F, or —CH$_2$CH$_2$Cl. In yet a further aspect, $R^8$ is hydrogen, —CH$_2$F, or —CH$_2$Cl.

In a further aspect, $R^8$ is C1-C4 haloalkyl. In a still further aspect, $R^8$ is —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, or —CH(CH$_3$)CH$_2$Cl. In yet a further aspect, $R^8$ is —CH$_2$F, —CH$_2$Cl, —CH$_2$CH$_2$F, or —CH$_2$CH$_2$Cl. In yet a further aspect, $R^8$ is —CH$_2$F or —CH$_2$Cl.

In a further aspect, $R^8$ is C1-C4 alkyl. In a still further aspect, $R^8$ is methyl, ethyl, n-propyl, i-propyl, n-butyl, i-butyl, s-butyl, or t-butyl. In yet a further aspect, $R^8$ is methyl, ethyl, n-propyl, or i-propyl. In an even further aspect, $R^8$ is methyl or ethyl. In a still further aspect, $R^8$ is ethyl. In yet a further aspect, $R^8$ is methyl.

k. $R^{8A}$ and $R^{8B}$ Groups

In one aspect, each occurrence of $R^{8a}$ and $R^{8b}$, when present, is independently hydrogen, C1-C4 alkyl, C1-C4 haloalkyl, phenyl, or —CO$_2$H. In a further aspect, each of $R^{8a}$ and $R^{8b}$ together is =O. In a still further aspect, $R^{8a}$, when present, is hydrogen. In yet a further aspect, $R^{8b}$, when present, is hydrogen, C1-C4 alkyl, or C1-C4 haloalkyl.

In a further aspect, $R^{8a}$, when present, is C1-C4 alkyl. In a still further aspect, $R^{8a}$, when present, is methyl, ethyl, n-propyl, i-propyl, n-butyl, i-butyl, s-butyl, or t-butyl. In yet a further aspect, $R^{8a}$, when present, is methyl, ethyl, n-propyl, or i-propyl. In an even further aspect, $R^{8a}$, when present, is methyl or ethyl. In a still further aspect, $R^{8a}$, when present, is ethyl. In yet a further aspect, $R^{8a}$, when present, is methyl.

In a further aspect, $R^{8b}$, when present, is C1-C4 alkyl. In a still further aspect, $R^{8b}$, when present, is methyl, ethyl, n-propyl, i-propyl, n-butyl, i-butyl, s-butyl, or t-butyl. In yet a further aspect, $R^{8b}$, when present, is methyl, ethyl, n-propyl, or i-propyl. In an even further aspect, $R^{8b}$, when present, is methyl or ethyl. In a still further aspect, $R^{8b}$, when present, is ethyl. In yet a further aspect, $R^{8b}$, when present, is methyl.

In a further aspect, $R^{sa}$, when present, is C1-C4 haloalkyl. In a still further aspect, $R^{8a}$, when present, is —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, or —CH(CH$_3$)CH$_2$Cl. In yet a further aspect, $R^{8a}$, when present, is —CH$_2$F, —CH$_2$Cl, —CH$_2$CH$_2$F, or —CH$_2$CH$_2$Cl. In yet a further aspect, $R^{8a}$, when present, is —CH$_2$F or —CH$_2$Cl.

In a further aspect, $R^{8b}$, when present, is C1-C4 haloalkyl. In a still further aspect, $R^{8b}$, when present, is —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, or —CH(CH$_3$)CH$_2$Cl. In yet a further aspect, $R^{8b}$, when present, is —CH$_2$F, —CH$_2$Cl, —CH$_2$CH$_2$F, or —CH$_2$CH$_2$Cl. In yet a further aspect, $R^{8b}$, when present, is —CH$_2$F or —CH$_2$Cl.

In a further aspect, $R^{sa}$ is phenyl. Optionally, $R^{sa}$ is phenyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, $R^{8a}$, when present, is phenyl substituted with 0, 1, or 2 groups independently selected from halogen, —NH$_2$, —OH, C1-C4 alkyl, C1-C4 haloalkyl, C1-C4 alkoxy, C1-C4 alkylamino, and (C1-C4) (C1-C4) dialkylamino. In yet a further aspect, $R^{8a}$, when present, is phenyl substituted with 0 or 1 group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In an even further aspect, $R^{8a}$, when present, is phenyl monosubstituted with a group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, $R^{8a}$, when present, is unsubstituted phenyl.

In a further aspect, $R^{8b}$ is phenyl. Optionally, $R^{8b}$ is phenyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4) (C1-C4) dialkylamino. In a still further aspect, $R^{8b}$, when present, is phenyl substituted with 0, 1, or 2 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In yet a further aspect, $R^{8b}$, when present, is phenyl substituted with 0 or 1 group selected from halogen, —NH$_2$, —OH, C1-C4 alkyl, C1-C4 haloalkyl, C1-C4 alkoxy, C1-C4 alkylamino, and (C1-C4) (C1-C4) dialkylamino. In an even further aspect, $R^{8b}$, when present, is phenyl monosubstituted with a group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, $R^{8b}$, when present, is unsubstituted phenyl.

In a further aspect, $R^{8a}$, when present, is —CO$_2$H.

In a further aspect, $R^{8b}$, when present, is —CO$_2$H.

In a further aspect, each of $R^{8a}$ and $R^{8b}$ together comprise =O.

l. $R^9$ Groups

In one aspect, $R^9$ is hydrogen, C1-C4 alkyl, or Cy$^4$. In a further aspect, $R^9$ is hydrogen.

In a further aspect, $R^9$ is C1-C4 alkyl. In a still further aspect, $R^9$ is methyl, ethyl, n-propyl, i-propyl, n-butyl, i-butyl, s-butyl, or t-butyl. In yet a further aspect, $R^9$ is methyl, ethyl, n-propyl, or i-propyl. In an even further aspect, $R^8$ is methyl or ethyl. In a still further aspect, $R^9$ is ethyl. In yet a further aspect, $R^9$ is methyl.

In a still further aspect, $R^9$ is Cy$^4$.

m. CY$^1$ Groups

In one aspect, Cy$^1$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a further aspect, Cy$^1$, when present, is C3-C6 cycloalkyl, C2-C5 heterocycloalkyl, or aryl, and is substituted with 0, 1, or 2 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^1$, when present, is C3-C6 cycloalkyl, C2-C5 heterocycloalkyl, or aryl, and is substituted with 0 or 1 group selected from halogen, —NH$_2$, —OH, C1-C4 alkyl, C1-C4 haloalkyl, C1-C4 alkoxy, C1-C4 alkylamino, and (C1-C4) (C1-C4) dialkylamino. In yet a further aspect, Cy$^1$, when present, is C3-C6 cycloalkyl, C2-C5 heterocycloalkyl, or aryl, and is monosubstituted with a group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In an even further aspect, Cy$^1$, when present, is C3-C6 cycloalkyl, C2-C5 heterocycloalkyl, or aryl, and is unsubstituted.

In a further aspect, Cy$^1$, when present, is C3-C6 cycloalkyl or C2-C5 heterocycloalkyl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^1$, when present, is C3-C6 cycloalkyl or C2-C5 heterocycloalkyl, and is substituted with 0, 1, or 2 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In yet a further aspect, Cy$^1$, when present, is C3-C6 cycloalkyl or C2-C5 heterocycloalkyl, and is substituted with 0 or 1 group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In an even further aspect, Cy$^1$, when present, is C3-C6 cycloalkyl or C2-C5 heterocycloalkyl, and is monosubstituted with a group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^1$, when present, is C3-C6 cycloalkyl or C2-C5 heterocycloalkyl, and is unsubstituted.

In a further aspect, Cy$^1$, when present, is C3-C6 cycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^1$, when present, is C3-C6 cycloalkyl substituted with 0, 1, or 2 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In yet a further aspect, Cy$^1$, when present, is C3-C6 cycloalkyl substituted with 0 or 1 group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In an even further aspect, Cy$^1$, when present, is C3-C6 cycloalkyl monosubstituted with a group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^1$, when present, is unsubstituted C3-C6 cycloalkyl.

In a further aspect, Cy$^1$, when present, is cyclopropyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^1$, when present, is cyclopropyl substituted with 0, 1, or 2 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In yet a further aspect, Cy$^1$, when present, is cyclopropyl substituted with 0 or 1 group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In an even further aspect, Cy$^1$, when present, is cyclopropyl monosubstituted with a group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^1$, when present, is unsubstituted cyclopropyl.

In a further aspect, Cy$^1$, when present, is C2-C5 heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^1$, when present, is C2-C5 heterocycloalkyl substituted with 0, 1, or 2 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In yet a further aspect, Cy$^1$, when present, is C2-C5 heterocycloalkyl substituted with 0 or 1 group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In an even further aspect, Cy$^1$, when present, is C2-C5 heterocycloalkyl monosubstituted with a group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^1$, when present, is unsubstituted C2-C5 heterocycloalkyl.

In a further aspect, Cy$^1$, when present, is morpholinyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^1$, when present, is morpholinyl substituted with 0, 1, or 2 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In yet a further aspect, Cy$^1$, when present, is morpholinyl substituted with 0 or 1 group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In an even further aspect, Cy$^1$, when present, is morpholinyl monosubstituted with a group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^1$, when present, is unsubstituted morpholinyl.

In a further aspect, Cy$^1$, when present, is aryl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^1$, when present, is aryl substituted with 0, 1, or 2 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In yet a further aspect, Cy$^1$, when present, is aryl substituted with 0 or 1 group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In an even further aspect, Cy$^1$, when present, is aryl monosubstituted with a group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^1$, when present, is unsubstituted aryl.

In a further aspect, Cy$^1$, when present, is phenyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^1$, when present, is phenyl substituted with 0, 1, or 2 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In yet a further aspect, Cy$^1$, when present, is phenyl substituted with 0 or 1 group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In an even further aspect, Cy$^1$, when present, is phenyl monosubstituted with a group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^1$, when present, is unsubstituted phenyl.

n. CY$^2$ Groups

In one aspect, Cy$^2$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a further aspect, Cy$^2$, when present, is C3-C6 cycloalkyl, C2-C5 heterocycloalkyl, or aryl, and is substituted with 0, 1, or 2 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^2$, when present, is C3-C6 cycloalkyl, C2-C5 heterocycloalkyl, or aryl, and is substituted with 0 or 1 group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In yet a further aspect, Cy$^2$, when present, is C3-C6 cycloalkyl, C2-C5 heterocycloalkyl, or aryl, and is monosubstituted with a group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In an even further aspect, Cy$^2$, when present, is C3-C6 cycloalkyl, C2-C5 heterocycloalkyl, or aryl, and is unsubstituted.

In a further aspect, Cy$^2$, when present, is C3-C6 cycloalkyl or C2-C5 heterocycloalkyl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^2$, when present, is C3-C6 cycloalkyl or C2-C5 heterocycloalkyl, and is substituted with 0, 1, or 2 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In yet a further aspect, Cy$^2$, when present, is C3-C6 cycloalkyl or C2-C5 heterocycloalkyl, and is substituted with 0 or 1 group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In an even further aspect, Cy$^2$, when present, is C3-C6 cycloalkyl or C2-C5 heterocycloalkyl, and is monosubstituted with a group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^2$, when present, is C3-C6 cycloalkyl or C2-C5 heterocycloalkyl, and is unsubstituted.

In a further aspect, Cy$^2$, when present, is C3-C6 cycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^2$, when present, is C3-C6 cycloalkyl substituted with 0, 1, or 2 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In yet a further aspect, Cy$^2$, when present, is C3-C6 cycloalkyl substituted with 0 or 1 group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In an even further aspect, Cy$^2$, when present, is C3-C6 cycloalkyl monosubstituted with a group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^2$, when present, is unsubstituted C3-C6 cycloalkyl.

In a further aspect, Cy$^2$, when present, is cyclopropyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^2$, when present, is cyclopropyl substituted with 0, 1, or 2 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In yet a further aspect, Cy$^2$, when present, is cyclopropyl substituted with 0 or 1 group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In an even further aspect, Cy$^2$, when present, is cyclopropyl monosubstituted with a group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^2$, when present, is unsubstituted cyclopropyl.

In a further aspect, Cy$^2$, when present, is C2-C5 heterocycloalkyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^2$, when present, is C2-C5 heterocycloalkyl substituted with 0, 1, or 2 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In yet a further aspect, Cy$^2$, when present, is C2-C5 heterocycloalkyl substituted with 0 or 1 group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In an even further aspect, Cy$^2$, when present, is C2-C5 heterocycloalkyl monosubstituted with a group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^2$, when present, is unsubstituted C2-C5 heterocycloalkyl.

In a further aspect, Cy$^2$, when present, is aryl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^2$, when present, is aryl substituted with 0, 1, or 2 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In yet a further aspect, Cy$^2$, when present, is aryl substituted with 0 or 1 group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In an even further aspect, Cy$^2$, when present, is aryl monosubstituted with a group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^2$, when present, is unsubstituted aryl.

In a further aspect, Cy$^2$, when present, is phenyl substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^2$, when present, is phenyl substituted with 0, 1, or 2 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In yet a further aspect, Cy$^2$, when present, is phenyl substituted with 0 or 1 group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In an even further aspect, Cy$^2$, when present, is phenyl monosubstituted with a group selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a still further aspect, Cy$^2$, when present, is unsubstituted phenyl.

o. CY$^3$ Groups

In one aspect, Cy$^3$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino. In a further aspect, $Cy^3$, when present, is C3-C6 cycloalkyl, C2-C5 heterocycloalkyl, or aryl, and is substituted with 0, 1, or 2 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^3$, when present, is C3-C6 cycloalkyl, C2-C5 heterocycloalkyl, or aryl, and is substituted with 0 or 1 group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In yet a further aspect, $Cy^3$, when present, is C3-C6 cycloalkyl, C2-C5 heterocycloalkyl, or aryl, and is monosubstituted with a group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In an even further aspect, $Cy^3$, when present, is C3-C6 cycloalkyl, C2-C5 heterocycloalkyl, or aryl, and is unsubstituted.

In a further aspect, $Cy^3$, when present, is C3-C6 cycloalkyl or C2-C5 heterocycloalkyl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^3$, when present, is C3-C6 cycloalkyl or C2-C5 heterocycloalkyl, and is substituted with 0, 1, or 2 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In yet a further aspect, $Cy^3$, when present, is C3-C6 cycloalkyl or C2-C5 heterocycloalkyl, and is substituted with 0 or 1 group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In an even further aspect, $Cy^3$, when present, is C3-C6 cycloalkyl or C2-C5 heterocycloalkyl, and is monosubstituted with a group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^3$, when present, is C3-C6 cycloalkyl or C2-C5 heterocycloalkyl, and is unsubstituted.

In a further aspect, $Cy^3$, when present, is C3-C6 cycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^3$, when present, is C3-C6 cycloalkyl substituted with 0, 1, or 2 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In yet a further aspect, $Cy^3$, when present, is C3-C6 cycloalkyl substituted with 0 or 1 group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In an even further aspect, $Cy^3$, when present, is C3-C6 cycloalkyl monosubstituted with a group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^3$, when present, is unsubstituted C3-C6 cycloalkyl.

In a further aspect, $Cy^3$, when present, is C2-C5 heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^3$, when present, is C2-C5 heterocycloalkyl substituted with 0, 1, or 2 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In yet a further aspect, $Cy^3$, when present, is C2-C5 heterocycloalkyl substituted with 0 or 1 group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In an even further aspect, $Cy^3$, when present, is C2-C5 heterocycloalkyl monosubstituted with a group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^3$, when present, is unsubstituted C2-C5 heterocycloalkyl.

In a further aspect, $Cy^3$, when present, is morpholinyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^3$, when present, is morpholinyl substituted with 0, 1, or 2 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In yet a further aspect, $Cy^3$, when present, is morpholinyl substituted with 0 or 1 group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In an even further aspect, $Cy^3$, when present, is morpholinyl monosubstituted with a group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^3$, when present, is unsubstituted morpholinyl.

In a further aspect, $Cy^3$, when present, is aryl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^3$, when present, is aryl substituted with 0, 1, or 2 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In yet a further aspect, $Cy^3$, when present, is aryl substituted with 0 or 1 group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In an even further aspect, $Cy^3$, when present, is aryl monosubstituted with a group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^3$, when present, is unsubstituted aryl.

In a further aspect, $Cy^3$, when present, is phenyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^3$, when present, is phenyl substituted with 0, 1, or 2 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In yet a further aspect, $Cy^3$, when present, is phenyl substituted with 0 or 1 group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In an even further aspect, $Cy^3$, when present, is phenyl monosubstituted with a group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^3$, when present, is unsubstituted phenyl.

In a further aspect, $Cy^3$, when present, is pyridinyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4)

dialkylamino. In a still further aspect, $Cy^3$, when present, is pyridinyl substituted with 0, 1, or 2 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In yet a further aspect, $Cy^3$, when present, is pyridinyl substituted with 0 or 1 group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In an even further aspect, $Cy^3$, when present, is pyridinyl monosubstituted with a group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^3$, when present, is unsubstituted pyridinyl.

In a further aspect, $Cy^3$, when present, is oxazolyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^3$, when present, is oxazolyl substituted with 0, 1, or 2 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In yet a further aspect, $Cy^3$, when present, is oxazolyl substituted with 0 or 1 group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In an even further aspect, $Cy^3$, when present, is oxazolyl monosubstituted with a group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^3$, when present, is unsubstituted oxazolyl.

In a further aspect, $Cy^3$, when present, is C3-C6 cycloalkyl or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^3$, when present, is C3-C6 cycloalkyl or aryl, and is substituted with 0, 1, or 2 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In yet a further aspect, $Cy^3$, when present, is C3-C6 cycloalkyl or aryl, and is substituted with 0 or 1 group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In an even further aspect, $Cy^3$, when present, is C3-C6 cycloalkyl or aryl, and is monosubstituted with a group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^3$, when present, is C3-C6 cycloalkyl or aryl, and is unsubstituted.

p. $CY^4$ Groups

In one aspect, $Cy^4$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a further aspect, $Cy^4$, when present, is C3-C6 cycloalkyl, C2-C5 heterocycloalkyl, or aryl, and is substituted with 0, 1, or 2 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^4$, when present, is C3-C6 cycloalkyl, C2-C5 heterocycloalkyl, or aryl, and is substituted with 0 or 1 group selected from halogen, —$NH_2$, —OH, C1-C4 alkyl, C1-C4 haloalkyl, C1-C4 alkoxy, C1-C4 alkylamino, and (C1-C4) (C1-C4) dialkylamino. In yet a further aspect, $Cy^4$, when present, is C3-C6 cycloalkyl, C2-C5 heterocycloalkyl, or aryl, and is monosubstituted with a group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In an even further aspect, $Cy^4$, when present, is C3-C6 cycloalkyl, C2-C5 heterocycloalkyl, or aryl, and is unsubstituted.

In a further aspect, $Cy^4$, when present, is C3-C6 cycloalkyl or C2-C5 heterocycloalkyl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^4$, when present, is C3-C6 cycloalkyl or C2-C5 heterocycloalkyl, and is substituted with 0, 1, or 2 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In yet a further aspect, $Cy^4$, when present, is C3-C6 cycloalkyl or C2-C5 heterocycloalkyl, and is substituted with 0 or 1 group selected from halogen, —$NH_2$, —OH, C1-C4 alkyl, C1-C4 haloalkyl, C1-C4 alkoxy, C1-C4 alkylamino, and (C1-C4) (C1-C4) dialkylamino. In an even further aspect, $Cy^4$, when present, is C3-C6 cycloalkyl or C2-C5 heterocycloalkyl, and is monosubstituted with a group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^4$, when present, is C3-C6 cycloalkyl or C2-C5 heterocycloalkyl, and is unsubstituted.

In a further aspect, $Cy^4$, when present, is C3-C6 cycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4) (C1-C4) dialkylamino. In a still further aspect, $Cy^4$, when present, is C3-C6 cycloalkyl substituted with 0, 1, or 2 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In yet a further aspect, $Cy^4$, when present, is C3-C6 cycloalkyl substituted with 0 or 1 group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In an even further aspect, $Cy^4$, when present, is C3-C6 cycloalkyl monosubstituted with a group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^4$, when present, is unsubstituted C3-C6 cycloalkyl.

In a further aspect, $Cy^4$, when present, is cyclopropyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^4$, when present, is cyclopropyl substituted with 0, 1, or 2 groups independently selected from halogen, —$NH_2$, —OH, C1-C4 alkyl, C1-C4 haloalkyl, C1-C4 alkoxy, C1-C4 alkylamino, and (C1-C4) (C1-C4) dialkylamino. In yet a further aspect, $Cy^4$, when present, is cyclopropyl substituted with 0 or 1 group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In an even further aspect, $Cy^4$, when present, is cyclopropyl monosubstituted with a group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^4$, when present, is unsubstituted cyclopropyl.

In a further aspect, $Cy^4$, when present, is C2-C5 heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^4$, when present, is C2-C5 heterocycloalkyl substituted with 0, 1, or 2 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In yet a further aspect, $Cy^4$, when present, is C2-C5 heterocycloalkyl substituted with 0 or 1 group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In an even further aspect, $Cy^4$, when present, is C2-C5 heterocycloalkyl monosubstituted with a group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^4$, when present, is unsubstituted C2-C5 heterocycloalkyl.

In a further aspect, $Cy^4$, when present, is morpholinyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^4$, when present, is morpholinyl substituted with 0, 1, or 2 groups independently selected from halogen, —$NH_2$, —OH, C1-C4 alkyl, C1-C4 haloalkyl, C1-C4 alkoxy, C1-C4 alkylamino, and (C1-C4) (C1-C4) dialkylamino. In yet a further aspect, $Cy^4$, when present, is morpholinyl substituted with 0 or 1 group selected from halogen, —$NH_2$, —OH, C1-C4 alkyl, C1-C4 haloalkyl, C1-C4 alkoxy, C1-C4 alkylamino, and (C1-C4) (C1-C4) dialkylamino. In an even further aspect, $Cy^4$, when present, is morpholinyl monosubstituted with a group selected from halogen, —$NH_2$, —OH, C1-C4 alkyl, C1-C4 haloalkyl, C1-C4 alkoxy, C1-C4 alkylamino, and (C1-C4) (C1-C4) dialkylamino. In a still further aspect, $Cy^4$, when present, is unsubstituted morpholinyl.

In a further aspect, $Cy^4$, when present, is aryl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^4$, when present, is aryl substituted with 0, 1, or 2 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In yet a further aspect, $Cy^4$, when present, is aryl substituted with 0 or 1 group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In an even further aspect, $Cy^4$, when present, is aryl monosubstituted with a group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^4$, when present, is unsubstituted aryl.

In a further aspect, $Cy^4$, when present, is phenyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^4$, when present, is phenyl substituted with 0, 1, or 2 groups independently selected from halogen, —$NH_2$, —OH, C1-C4 alkyl, C1-C4 haloalkyl, C1-C4 alkoxy, C1-C4 alkylamino, and (C1-C4) (C1-C4) dialkylamino. In yet a further aspect, $Cy^4$, when present, is phenyl substituted with 0 or 1 group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In an even further aspect, $Cy^4$, when present, is phenyl monosubstituted with a group selected from halogen, —$NH_2$, —OH, C1-C4 alkyl, C1-C4 haloalkyl, C1-C4 alkoxy, C1-C4 alkylamino, and (C1-C4)(C1-C4) dialkylamino. In a still further aspect, $Cy^4$, when present, is unsubstituted phenyl.

2. Example Compounds

In one aspect, a compound can be present as one or more of the following structures:

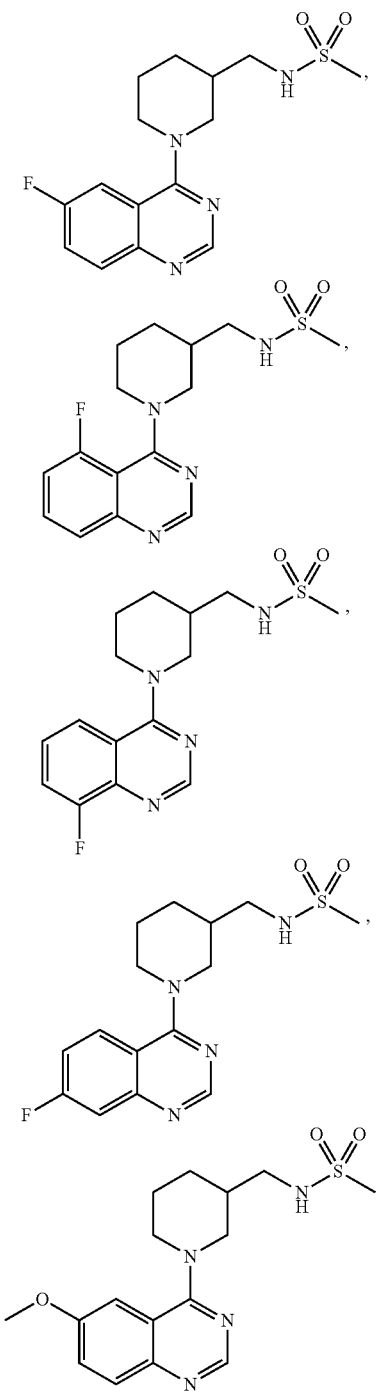

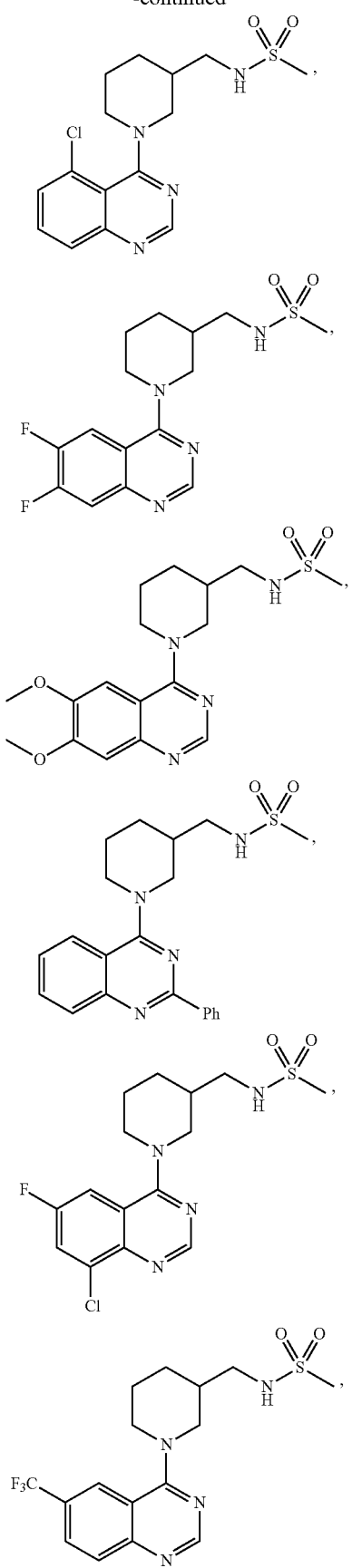
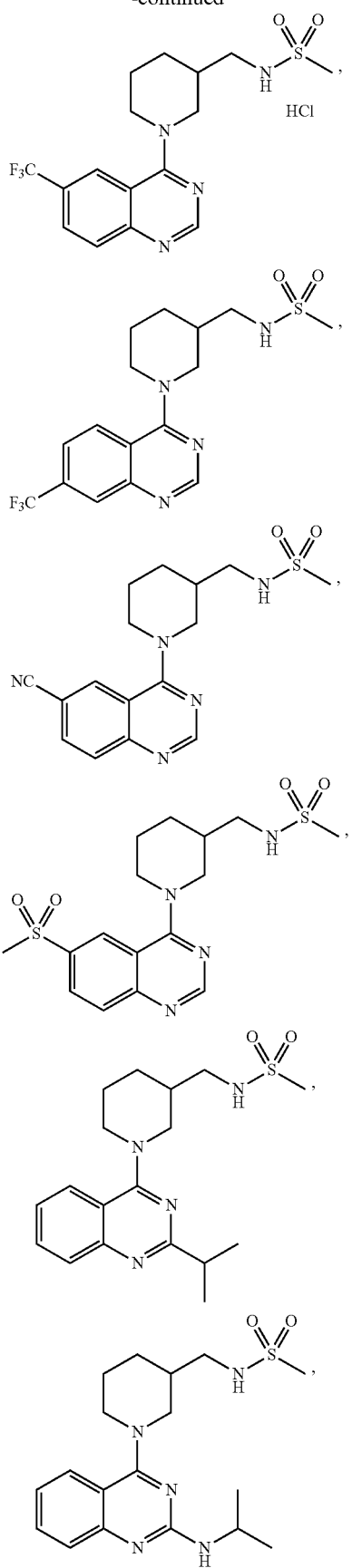

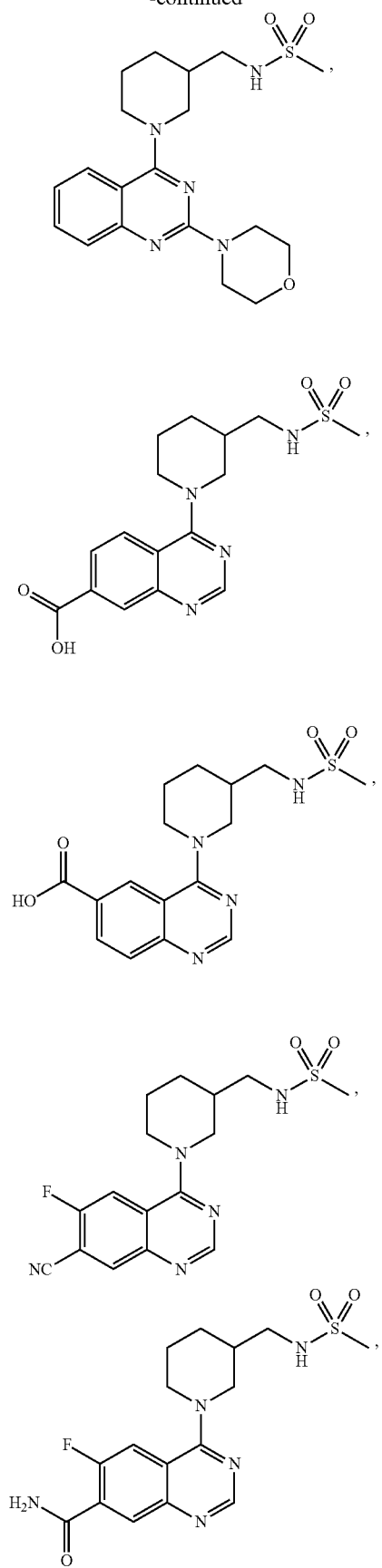
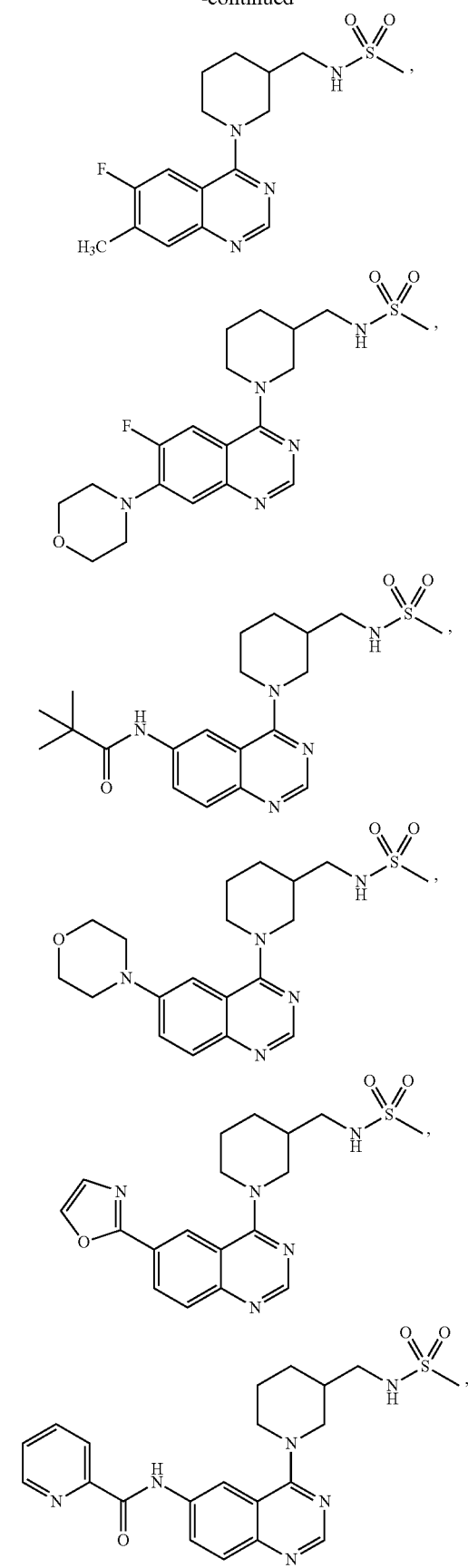

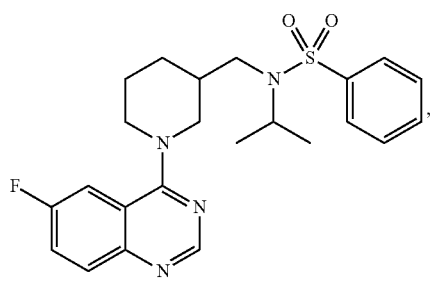
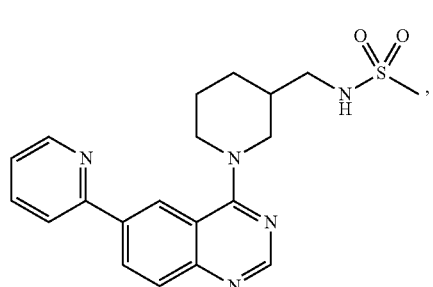
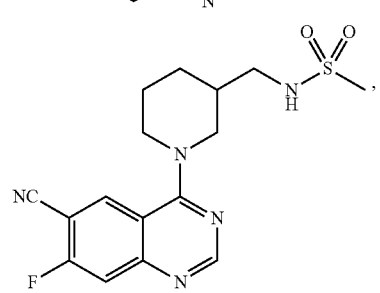
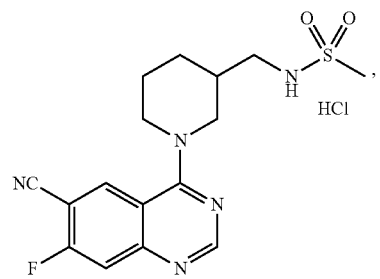
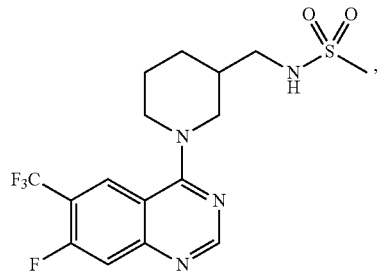
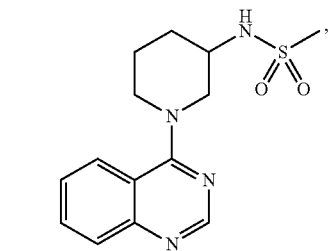
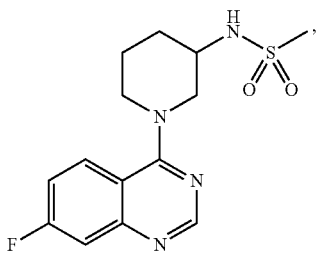
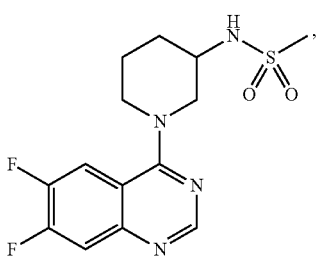
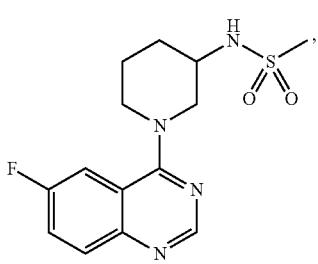
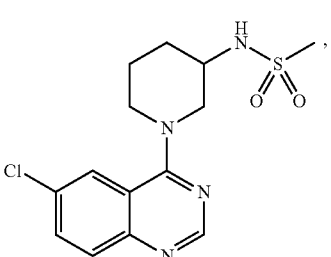
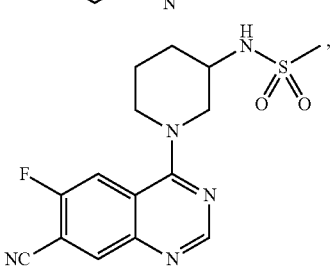
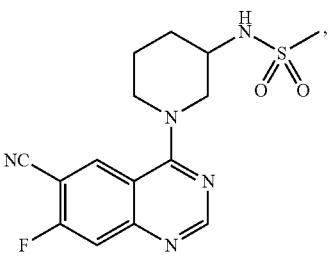

-continued
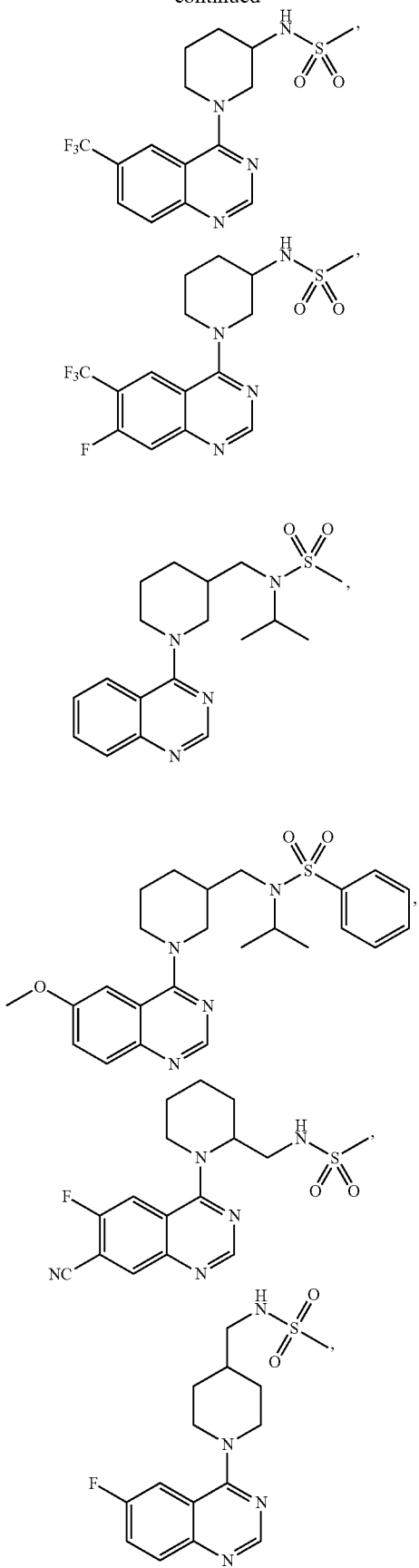
-continued
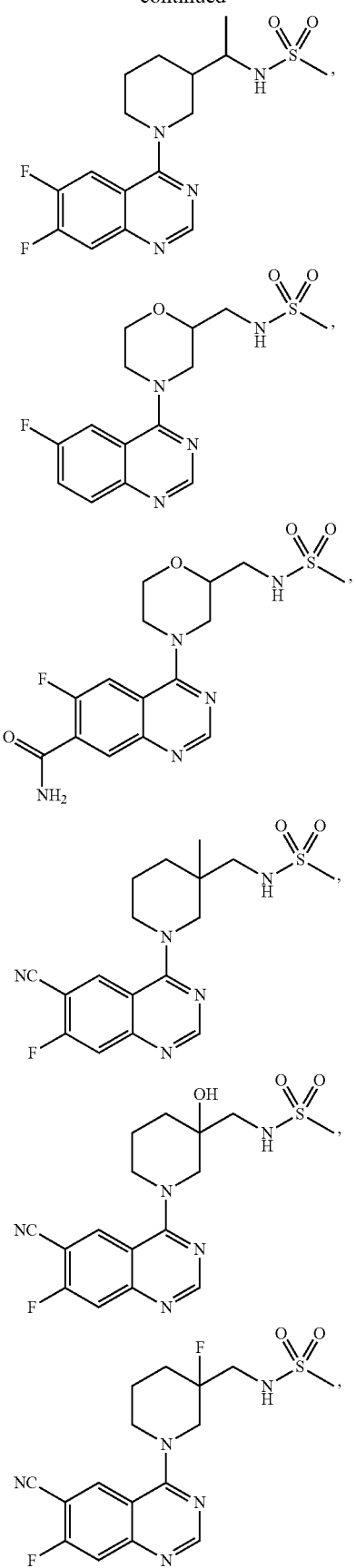

107
-continued
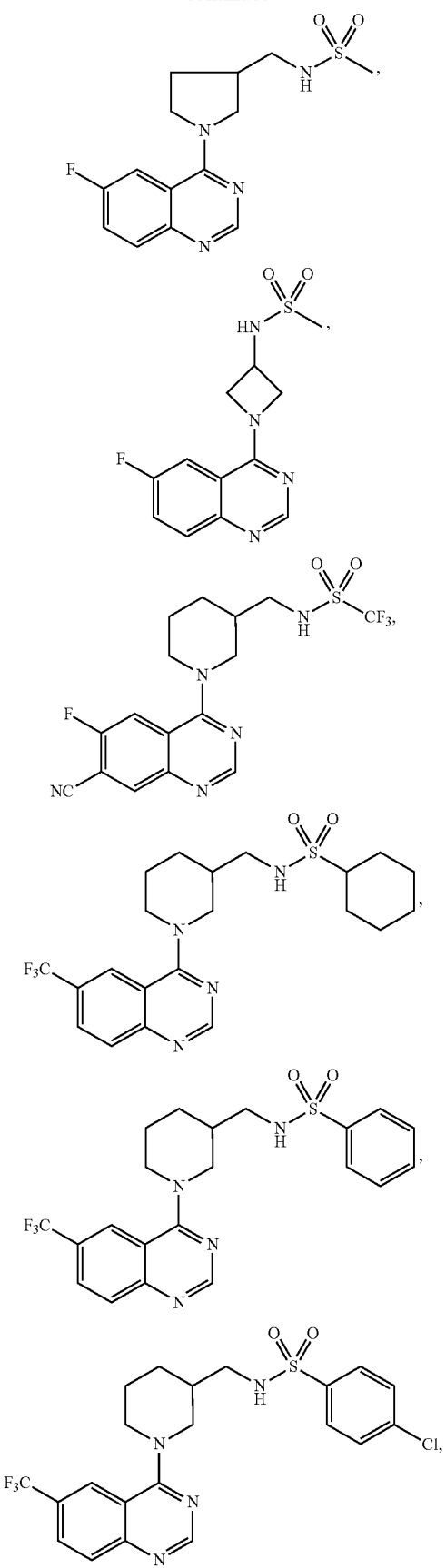
108
-continued
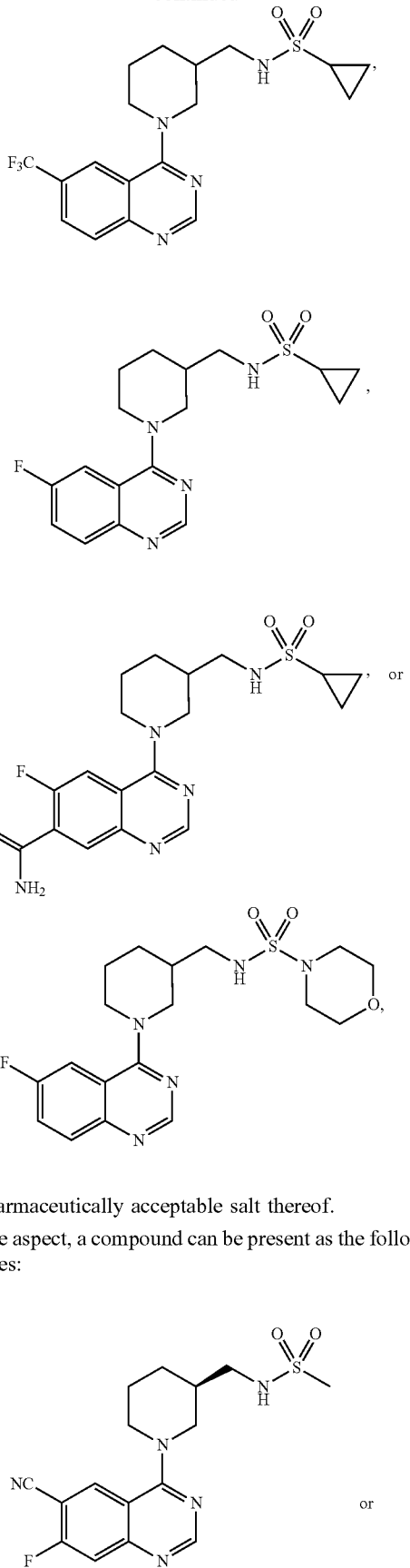
or a pharmaceutically acceptable salt thereof.
In one aspect, a compound can be present as the following structures:
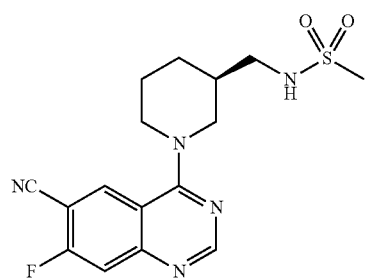
or

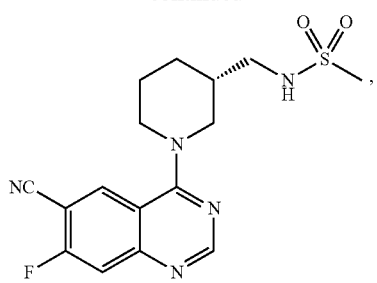
or a pharmaceutically acceptable salt thereof.
In one aspect, a compound can be present as one or more of the following structures:
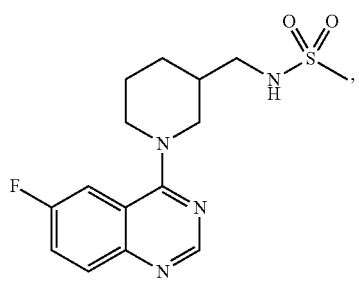
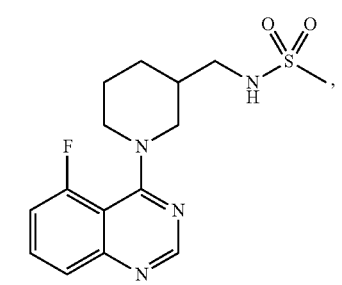
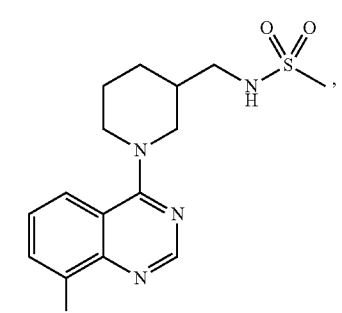
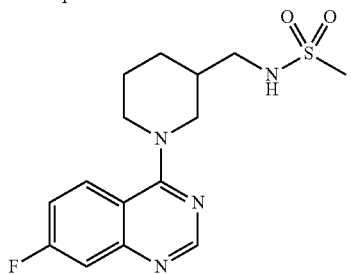
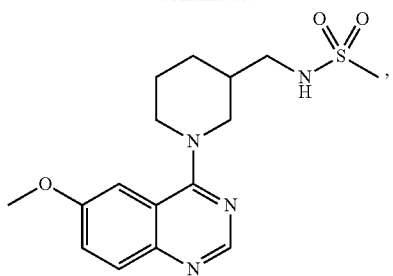
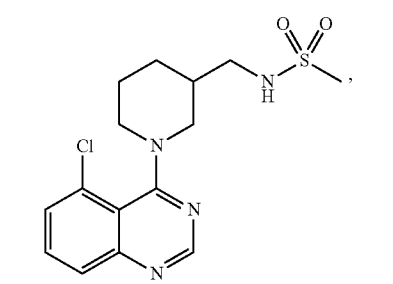
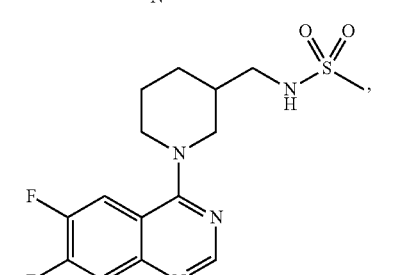
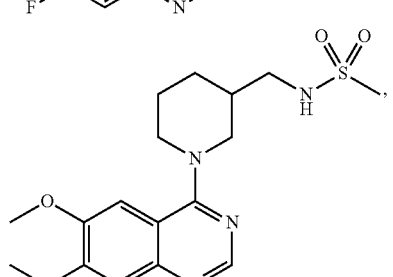
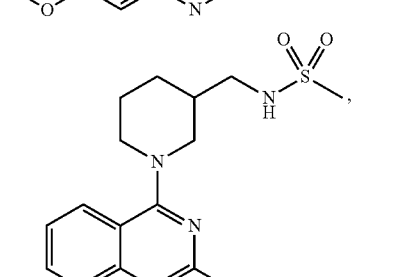
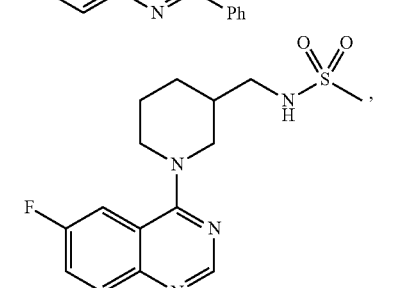

111
-continued
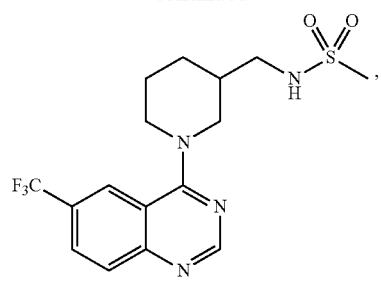
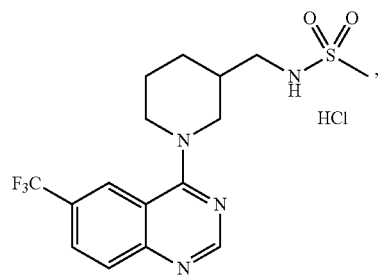
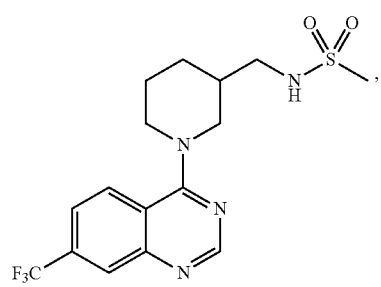
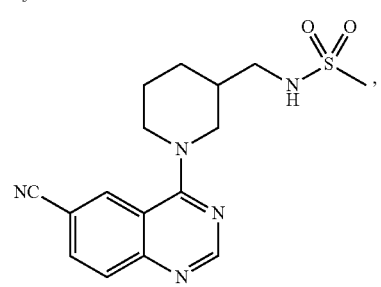
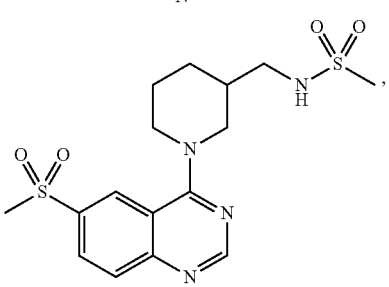
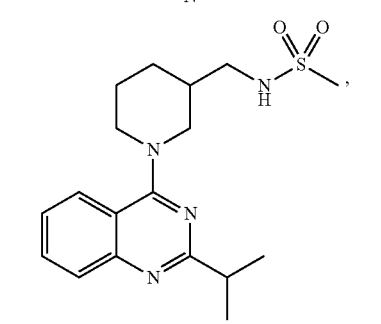
112
-continued
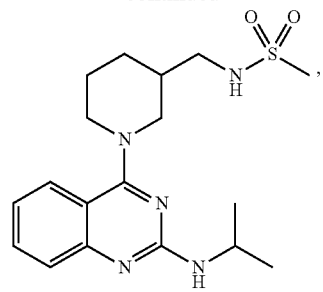
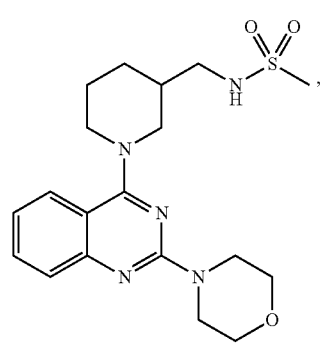
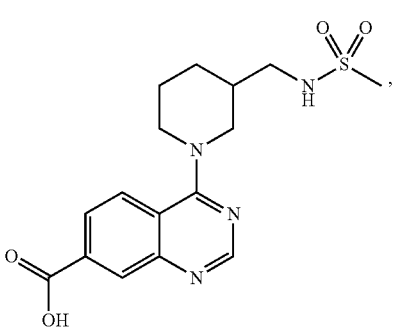
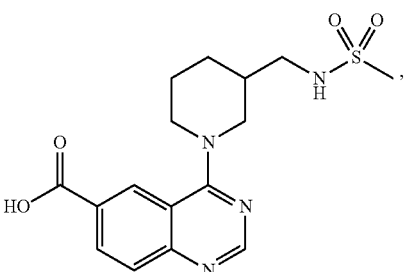
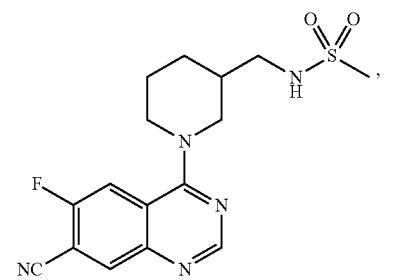

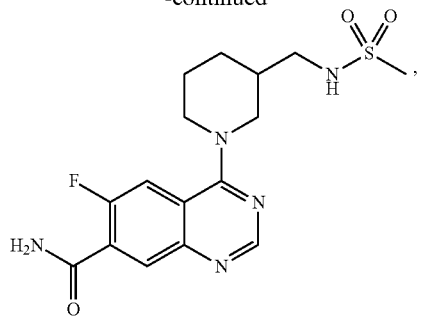
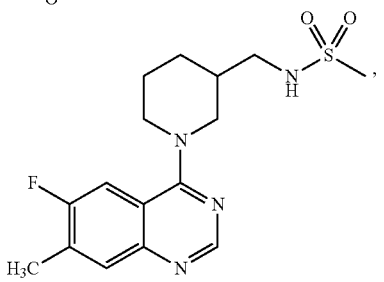
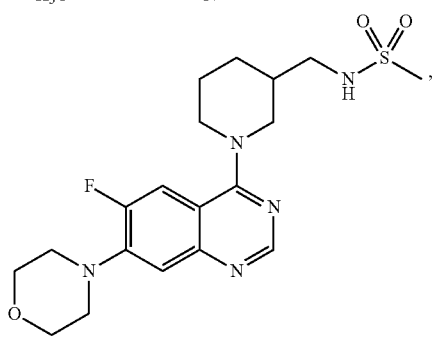
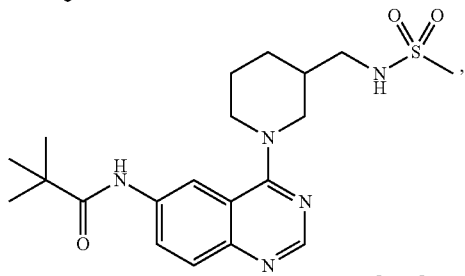
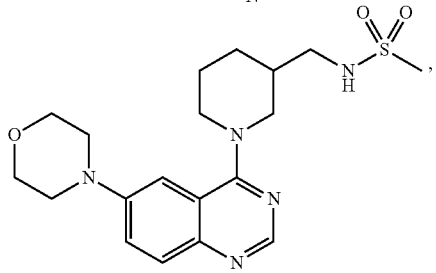
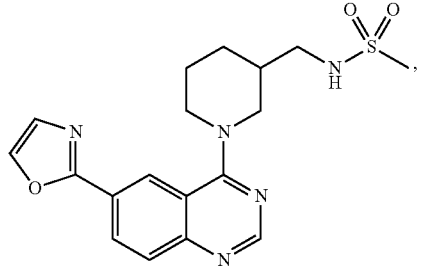
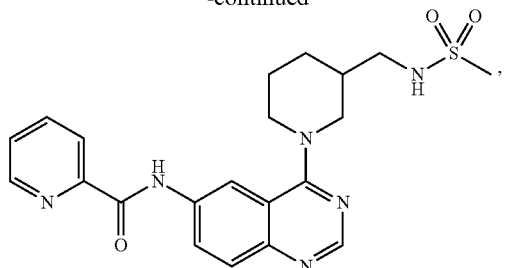
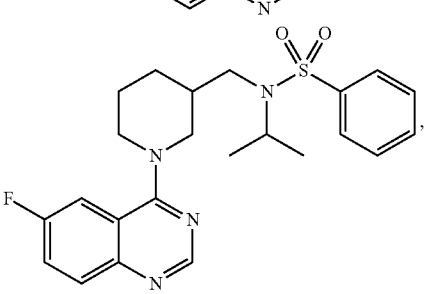
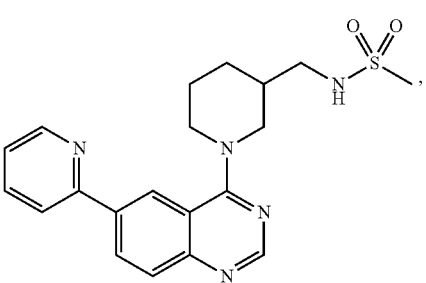
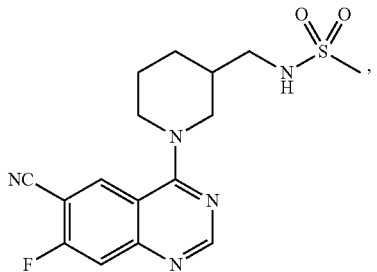
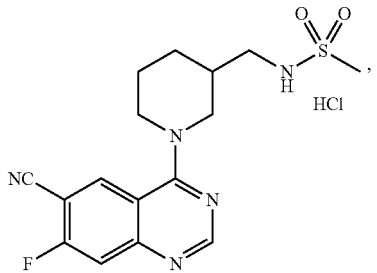
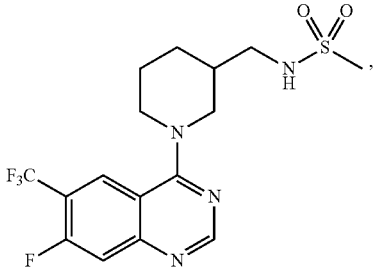

115
-continued
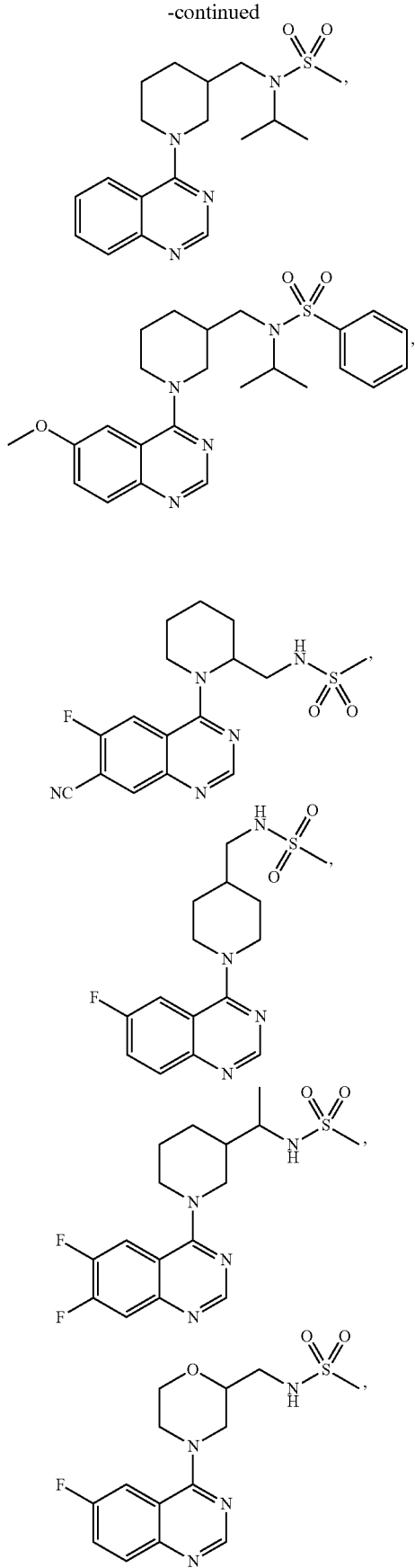
116
-continued
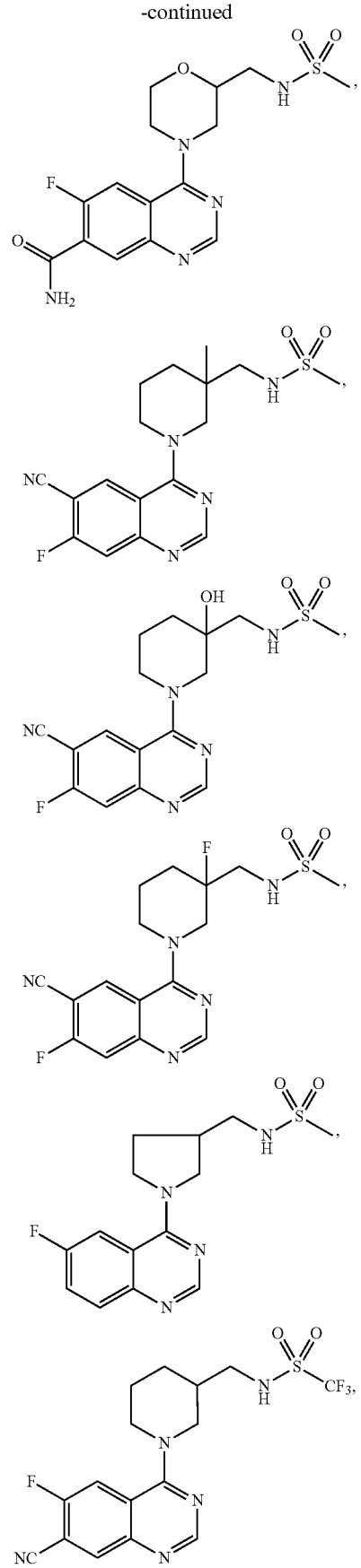

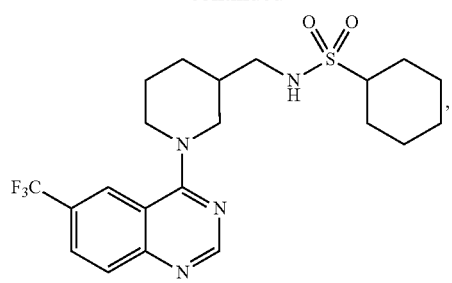
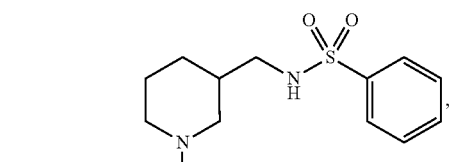
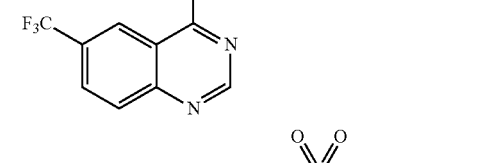
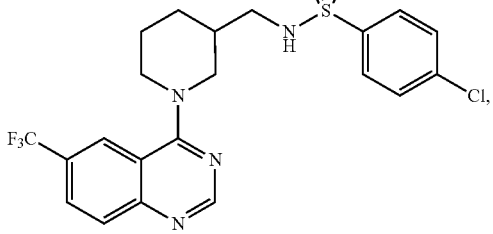
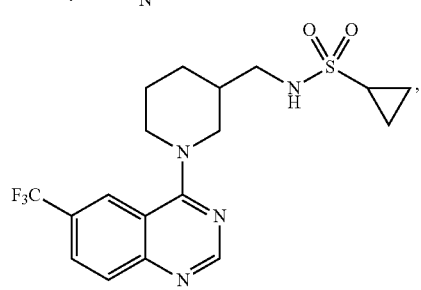
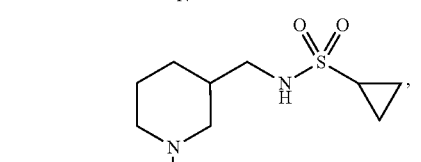
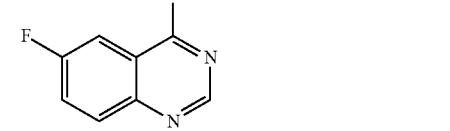
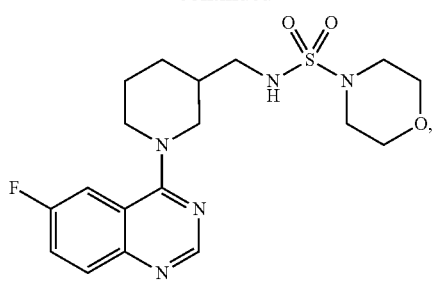
or a pharmaceutically acceptable salt thereof.
In one aspect, a compound can be present as one or more of the following
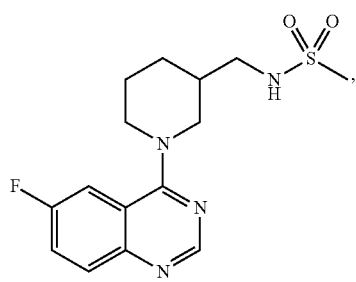
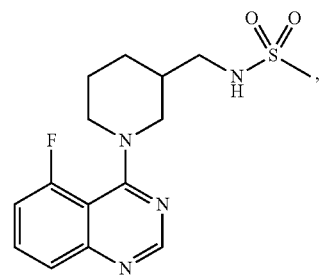
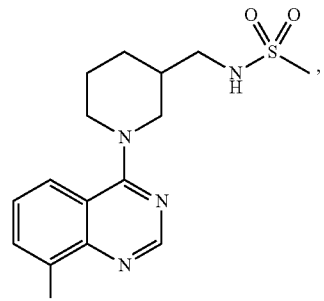
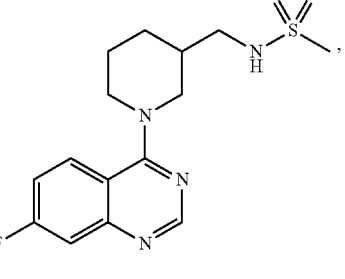

119
-continued
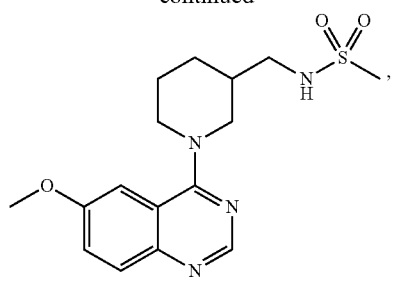
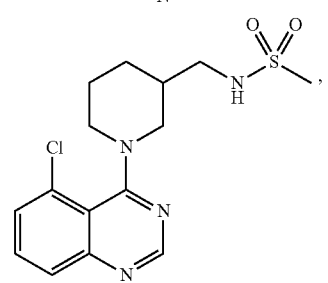
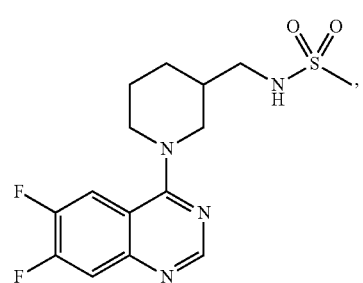
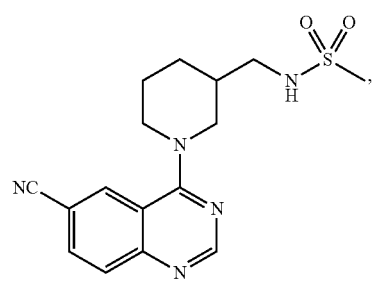
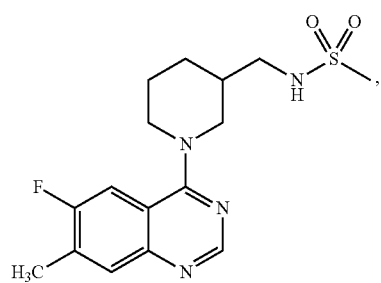
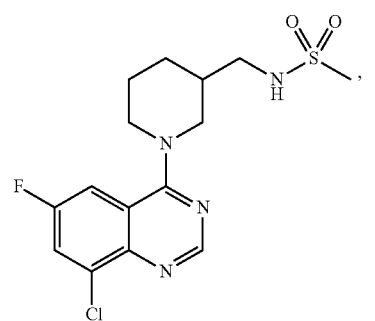
120
-continued
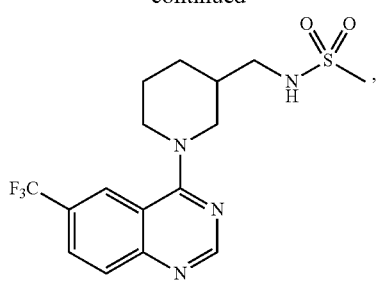
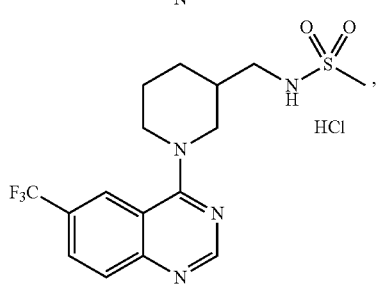
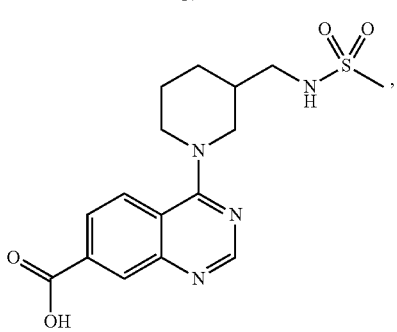
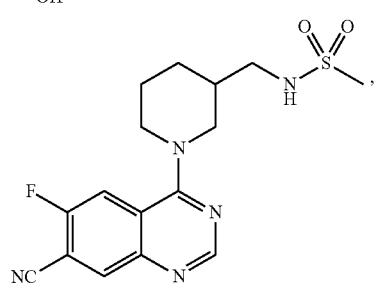
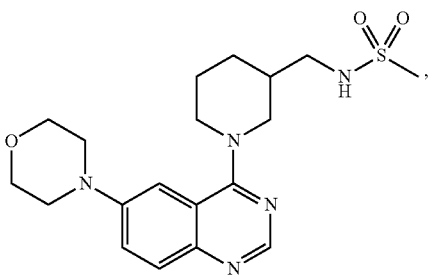
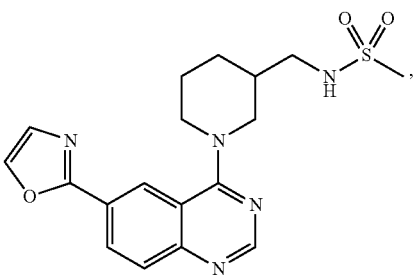

121
-continued
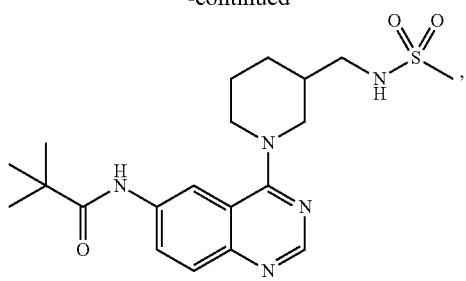
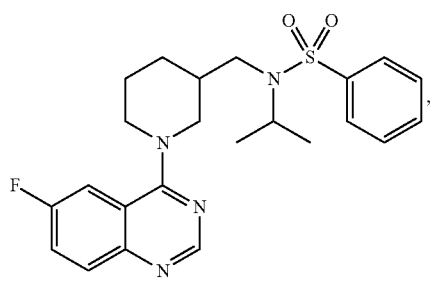
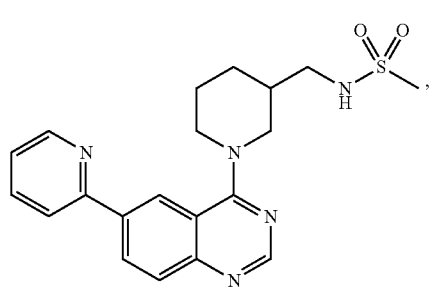
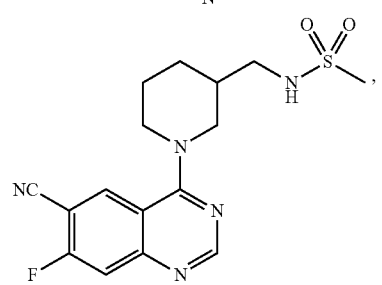
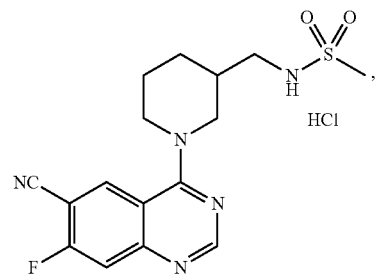
HCl
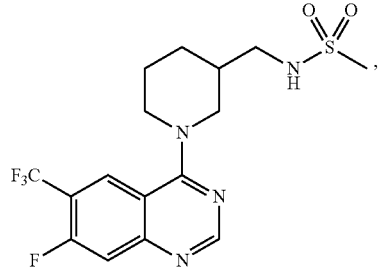
122
-continued
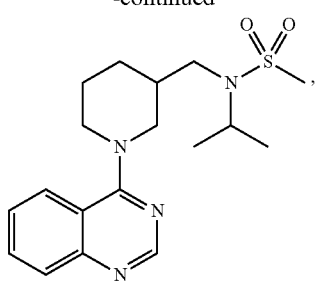
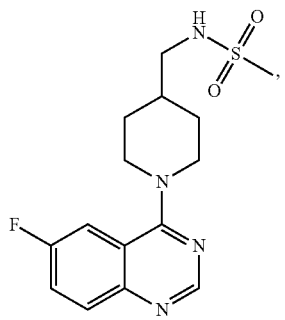
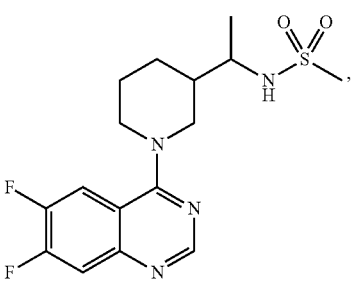
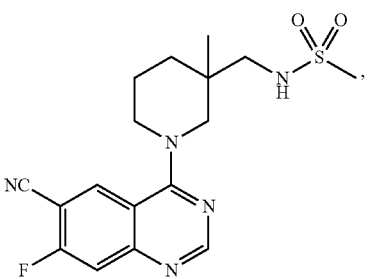
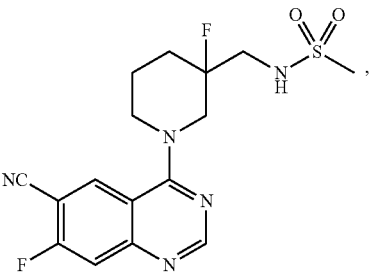
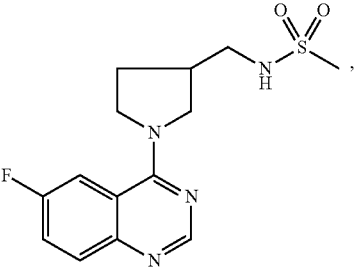

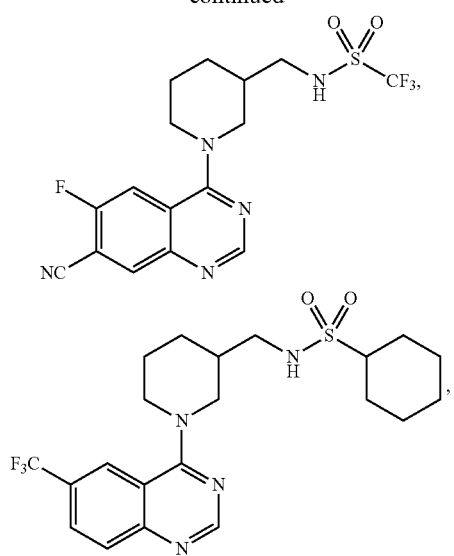
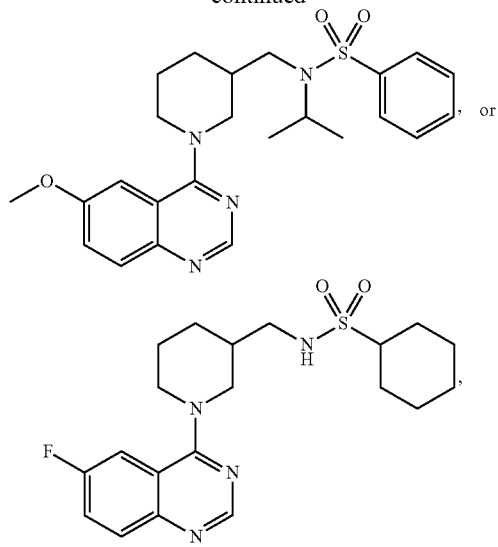
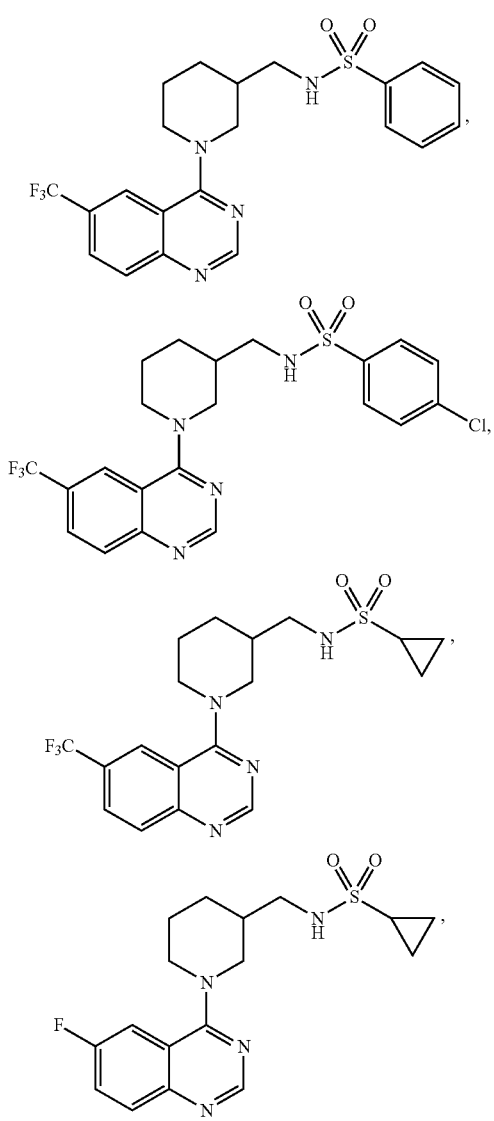
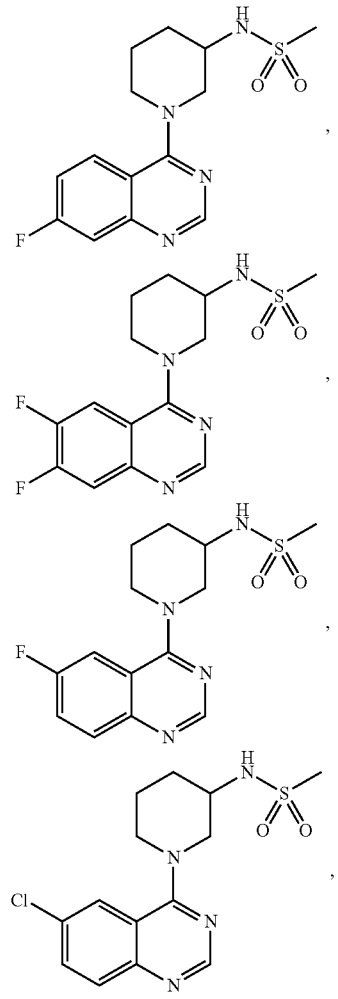
or a pharmaceutically acceptable salt thereof.
In one aspect, a compound can be present as one or more of the following structures:

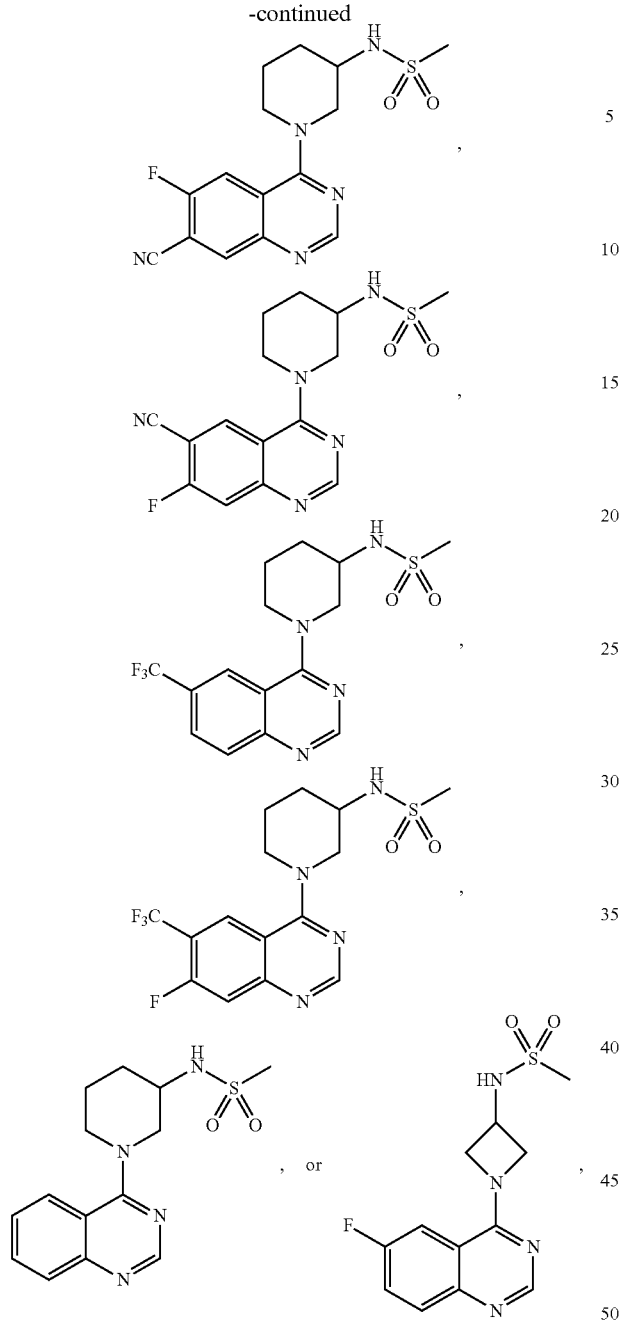
or a pharmaceutically acceptable salt thereof.
In one aspect, a compound can be present as one or more of the following structures:
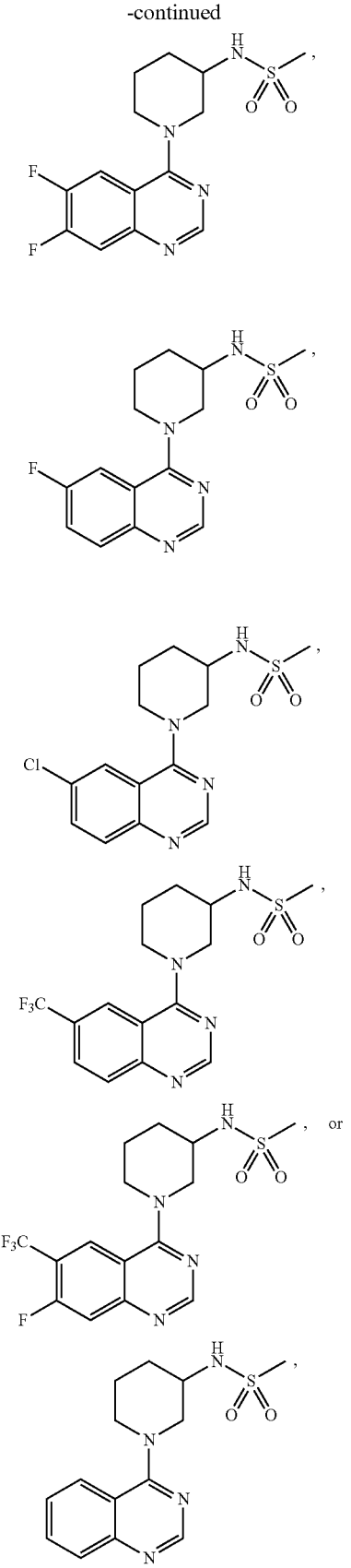
or a pharmaceutically acceptable salt thereof.

In one aspect, a compound can be present as one or more of the following structures:

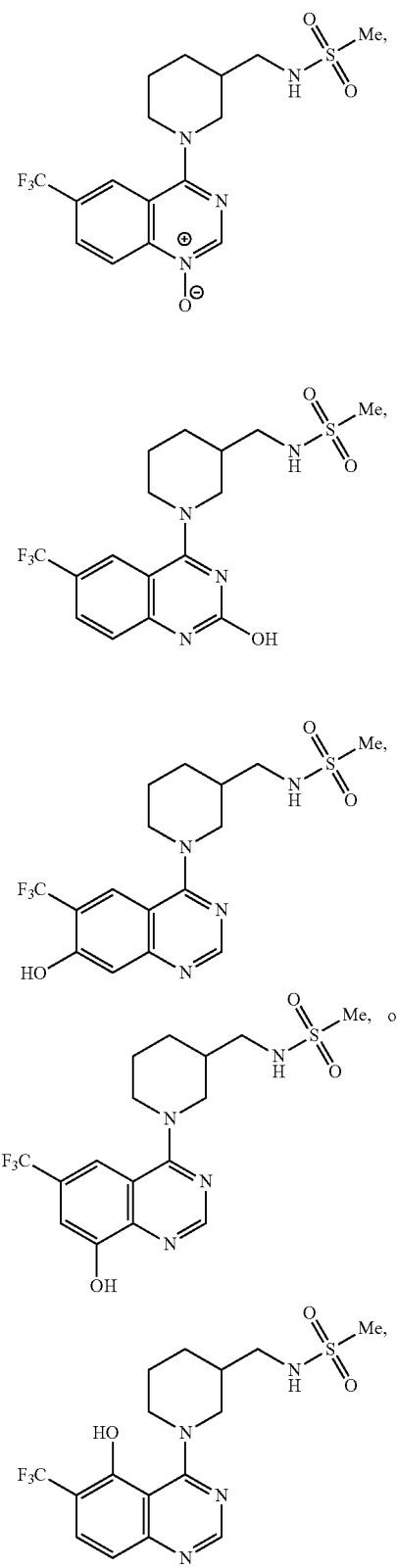

or a pharmaceutically acceptable salt thereof.

3. Prophetic Compound Examples

The following compound examples are prophetic, and can be prepared using the synthesis methods described herein above and other general methods as needed as would be known to one skilled in the art. It is anticipated that the prophetic compounds would be active as inhibitors of TXNIP activity, and such activity can be determined using the assay methods described herein below.

In one aspect, a compound can be selected from:

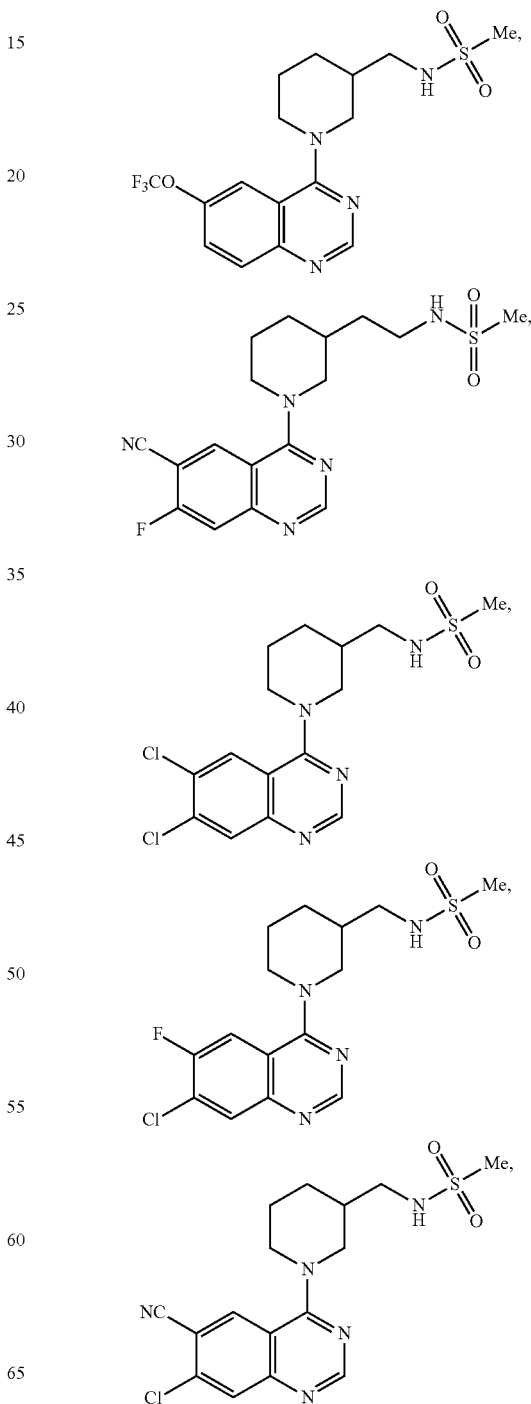

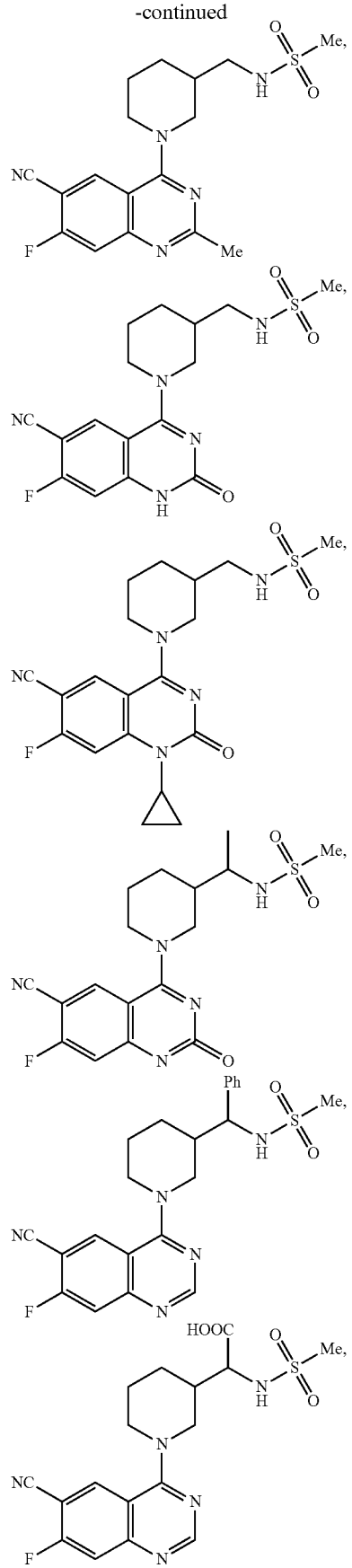
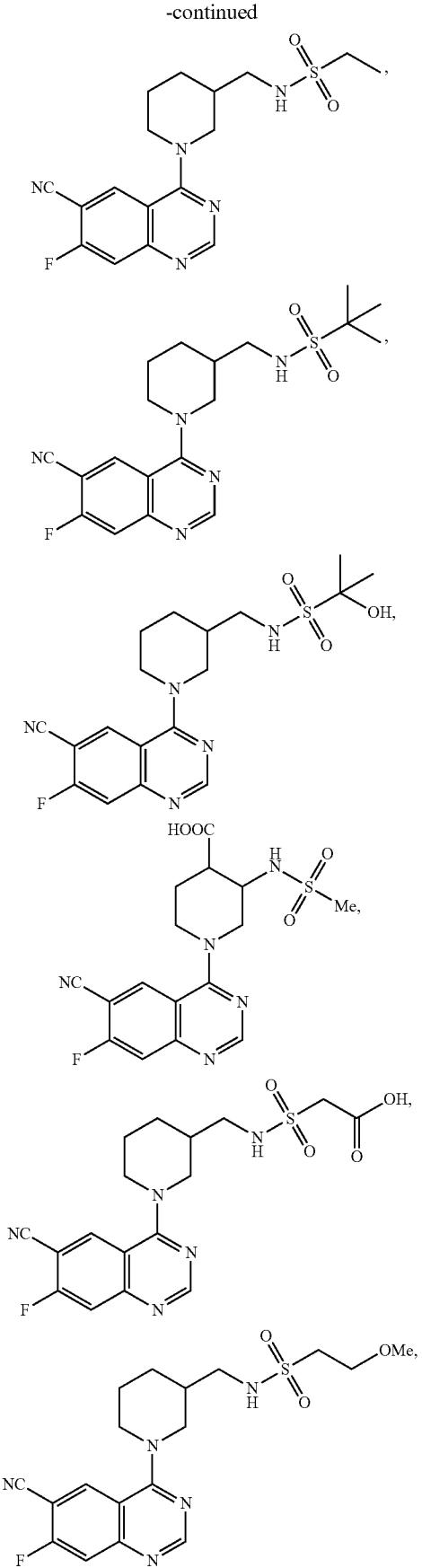

131
-continued
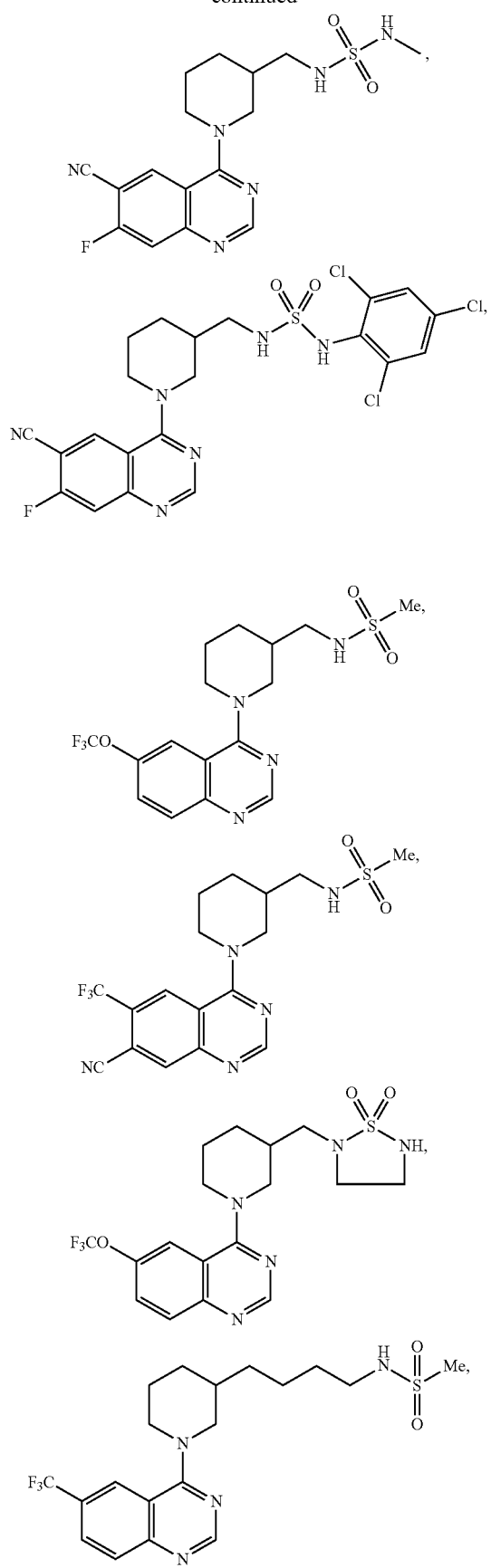
132
-continued
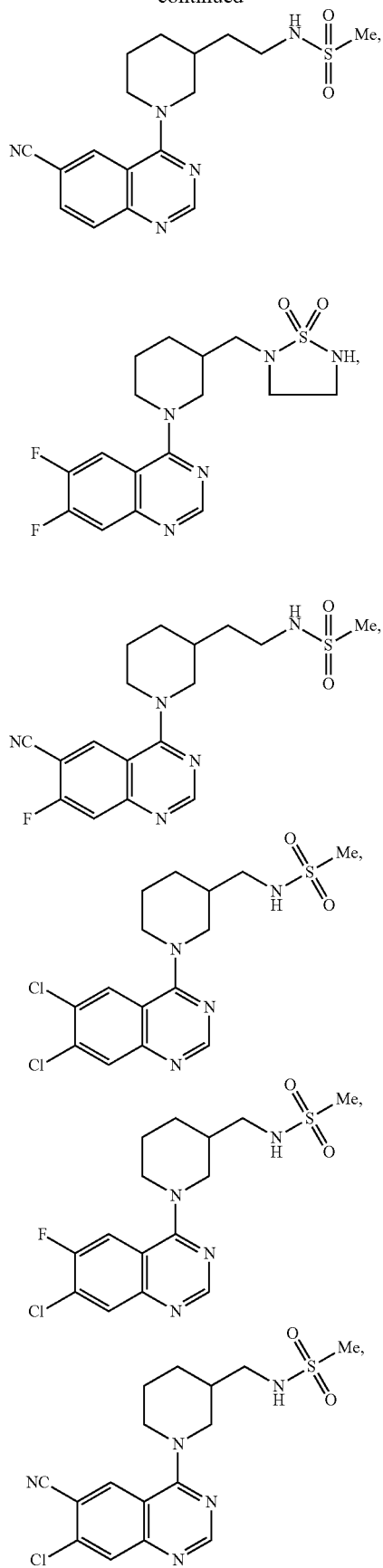

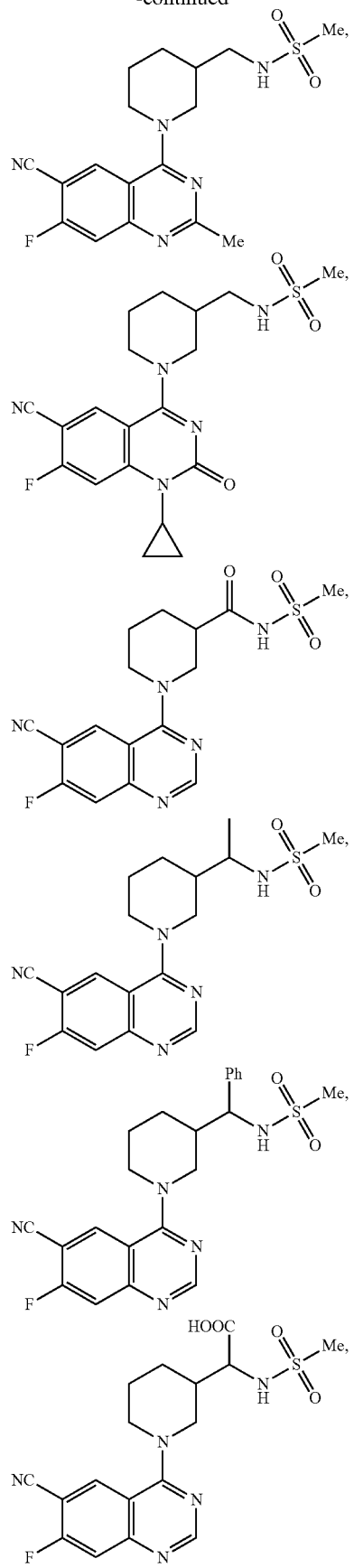
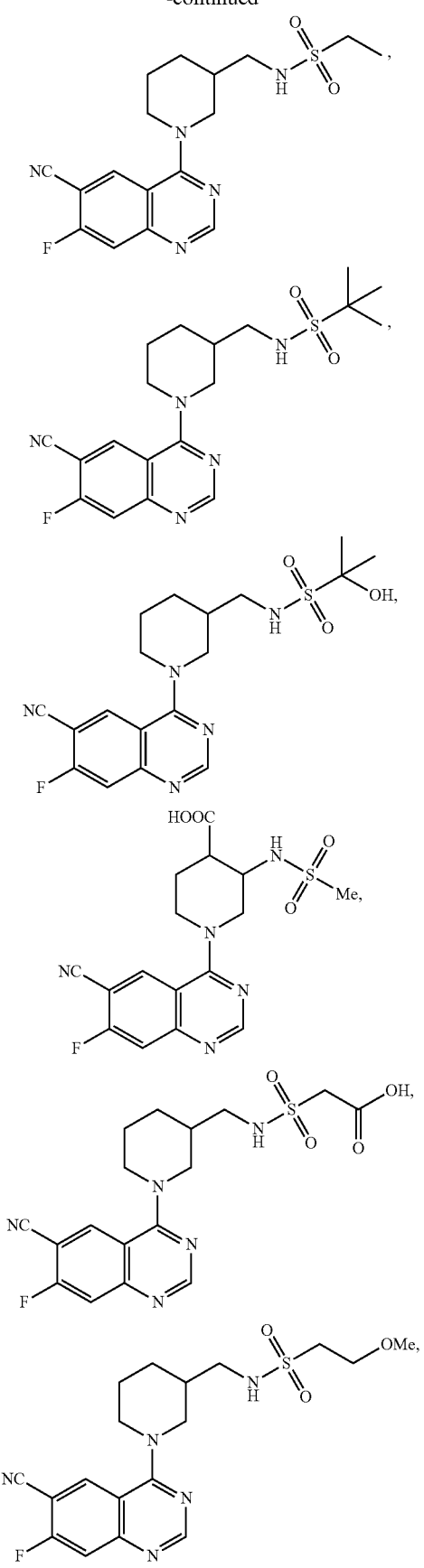

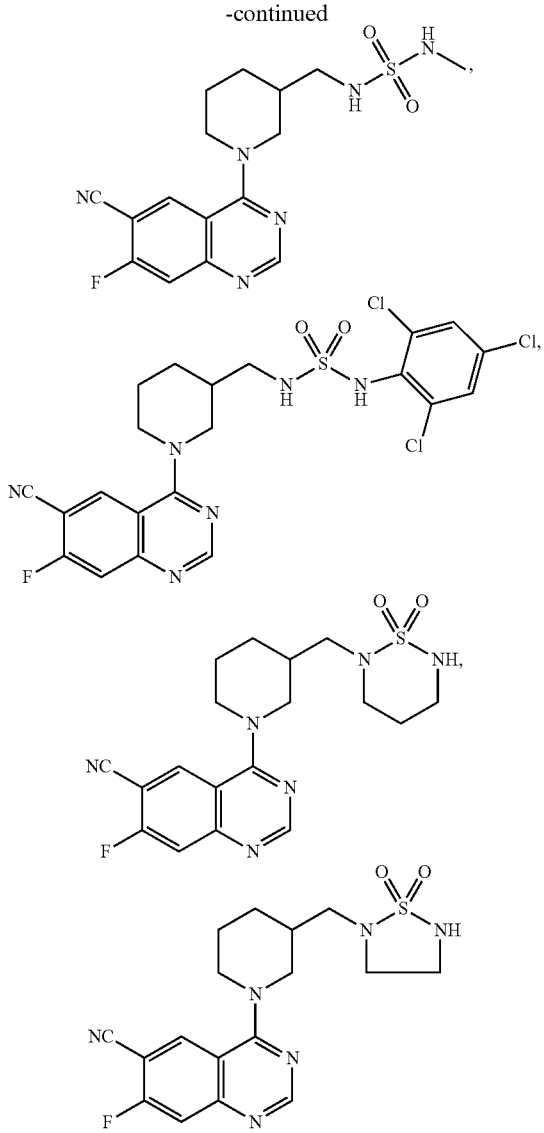

or a subgroup thereof.

It is contemplated that one or more compounds can optionally be omitted from the disclosed invention.

It is understood that the discloses compounds can be used in connection with the disclosed methods, compostions, kits, and uses.

It is understood that pharmaceutical acceptable derivatives of the disclosed compounds can be used also in connection with the disclosed methods, compostions, kits, and uses. The pharmaceutical acceptable derivatives of the compounds can include any suitable derivative, such as a pharmaceutically acceptable salts as discussed below, isomers, radiolabeled analogs, tautomers, and the like.

H. METHODS OF MAKING A COMPOUND

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Routes I-IX, as described and exemplified below. The following examples are provided so that the invention might be more fully understood, are illustrative only, and should not be construed as limiting.

1. Route I

In one aspect, substituted quinazoline sulfonamides can be prepared as shown below.

SCHEME 1A.

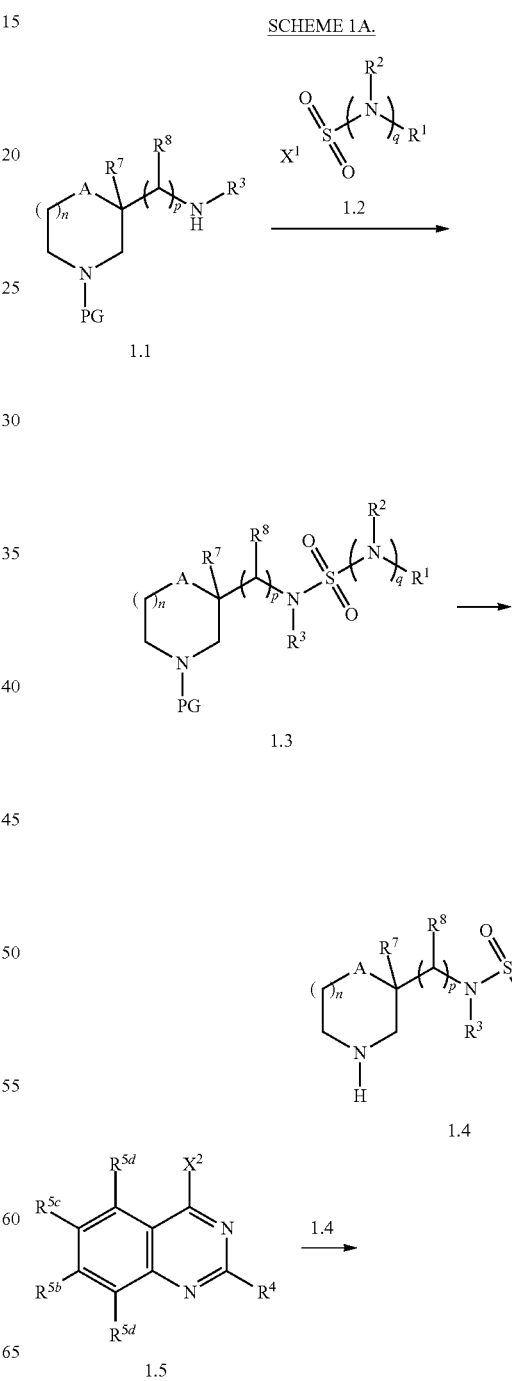

-continued

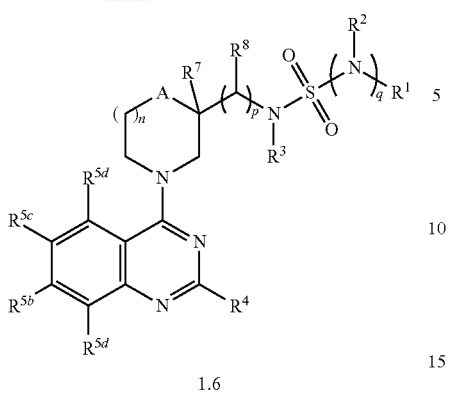

1.6

Compounds are represented in generic form, wherein PG is an amino protecting group, each of $X^1$ and $X^2$ is independently Cl or Br, and with other substituents as noted in compound descriptions elsewhere herein. A more specific example is set forth below.

SCHEME 1B.

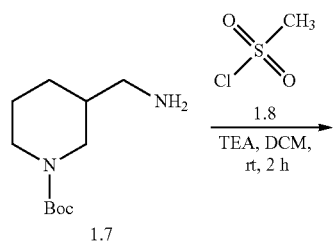

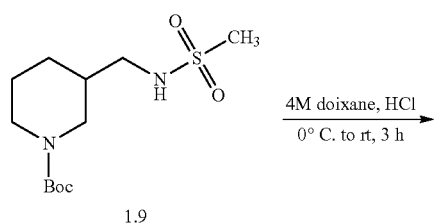

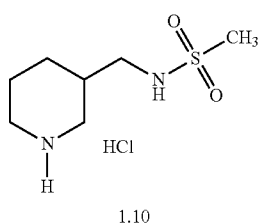

-continued

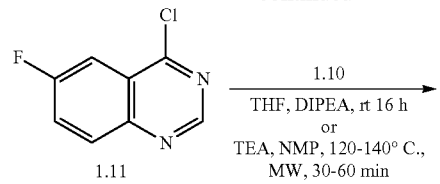

1.12

In one aspect, compounds of type 1.6, and similar compounds, can be prepared according to reaction Scheme 1B above. Thus, compounds of type 1.3 can be prepared by a sulfonylation reaction of an appropriate amine, e.g., 1.1 as shown above, and an appropriate sulfonyl halide, e.g., 1.2 as shown above. Appropriate amines and appropriate sulfonyl halides are commercially available or prepared by methods known to one skilled in the art. In certain cases, a sulfonyl anhydride can also be used. The sulfonylation reaction is carried out in the presence of an appropriate base, e.g., triethylamine (TEA), in an appropriate solvent, e.g., dichloromethane (DCM), for an appropriate period of time, e.g., 2 hours. Compounds of type 1.4 can be prepared by a deprotection reaction of an appropriate protected amine, e.g., 1.3 as shown above. The deprotection reaction is carried out in the presence of an appropriate deprotecting agent, e.g., hydrochloric acid (HCl) as shown above, in an appropriate solvent, e.g., dioxane, for an appropriate period of time, e.g., 3 hours. Compounds of type 1.6 can be prepared by a coupling reaction of an appropriate quinazoline derivative, e.g., 1.5 as shown above, and an appropriate amine, e.g., 1.4 as shown above. Appropriate quinazoline derivatives are commercially available or prepared by methods known to one skilled in the art. The coupling reaction is carried out in the presence of an appropriate base, e.g., N,N-diisopropylethylamine (DIPEA) or triethylamine, in an appropriate solvent, e.g., tetrahydrofuran (THF) or N-methyl-2-pyrrolidone. As can be appreciated by one skilled in the art, the above reaction provides an example of a generalized approach wherein compounds similar in structure to the specific reactants above (compounds similar to compounds of type 1.7, 1.8, 1.9, 1.10, and 1.11), can be substituted in the reaction to provide substituted quinazoline sulfonamides similar to Formula 1.12.

2. Route II

In one aspect, substituted quinazoline sulfonamides can be prepared as shown below.

SCHEME 2A.
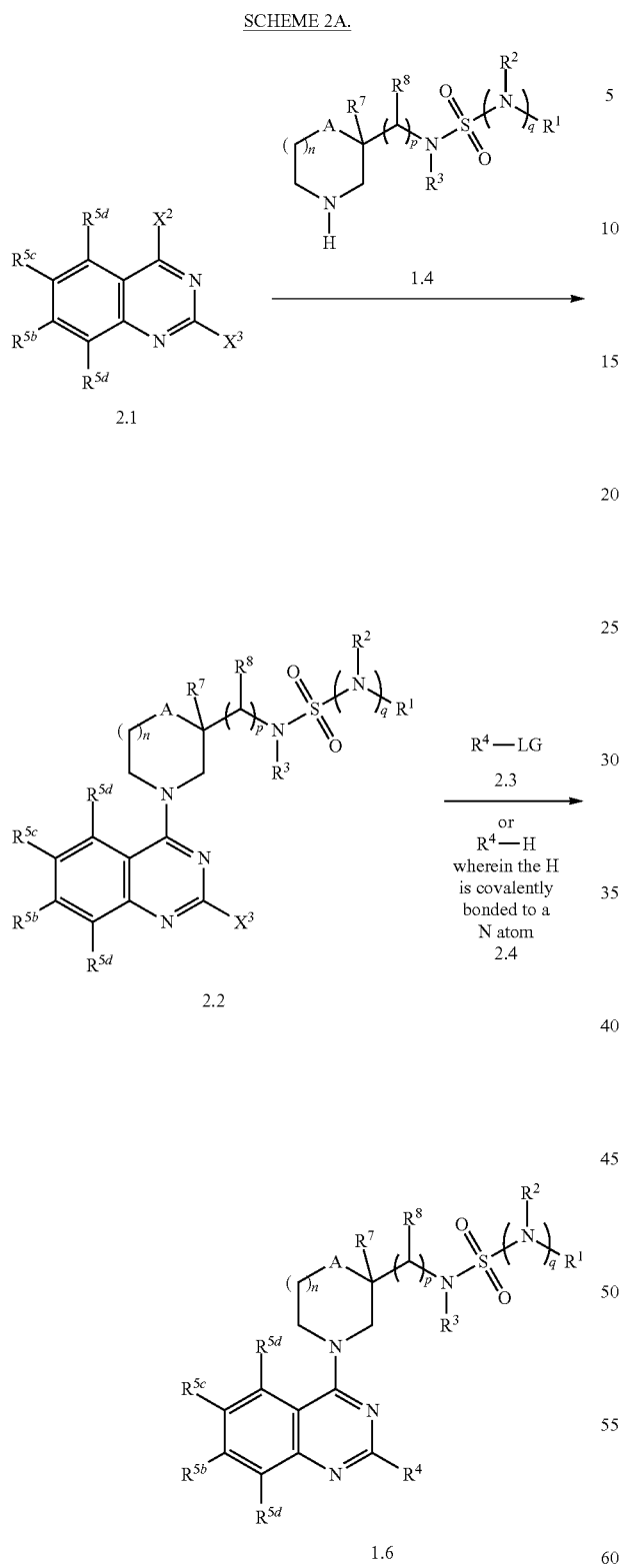
2.1
2.2
1.6
Compounds are represented in generic form, wherein each of $X^2$ and $X^3$ is independently Cl or Br, wherein LG is a leaving group, and with other substituents as noted in compound descriptions elsewhere herein. More specific examples are set forth below.
SCHEME 2B.
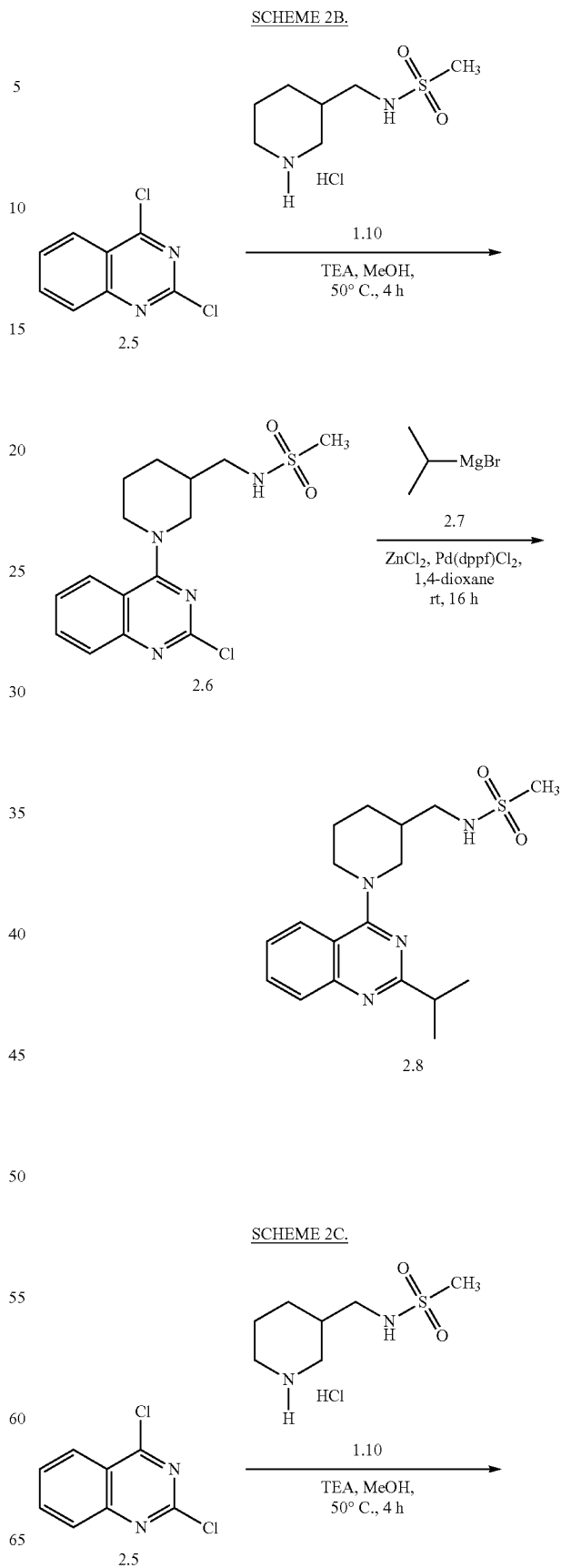
SCHEME 2C.

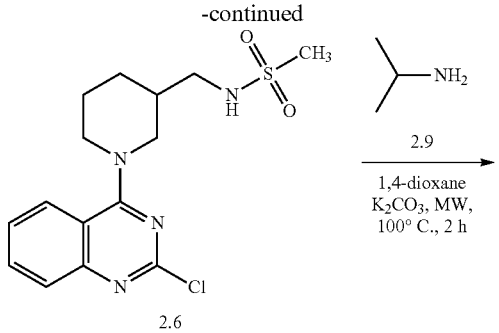

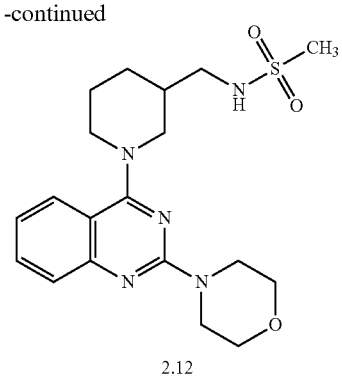

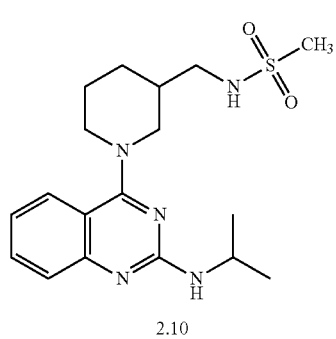

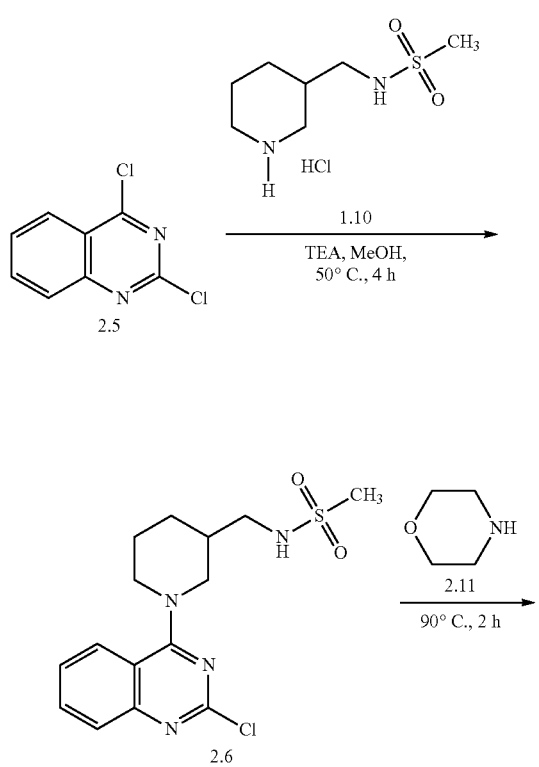

In one aspect, compounds of type 1.6, and similar compounds, can be prepared according to reaction Schemes 2B, 2C, and 2D above. Thus, compounds of type 2.2 can be prepared by a coupling reaction of an appropriate quinazoline derivative, e.g., 2.1 as shown above, and an appropriate amine, e.g., 1.4 as shown above. Appropriate quinazoline derivatives and appropriate amines are commercially available or prepared by methods known to one skilled in the art. The coupling reaction is carried out in the presence of an appropriate base, e.g., triethylamine, in an appropriate solvent, e.g., methanol, at an appropriate temperature, e.g., 50° C., for an appropriate period of time, e.g., 4 hours. As shown in Scheme 2B, compounds of type 1.6 can be prepared by a Grignard reaction of an appropriate halide, e.g., 2.2 as shown above, and an appropriate Grignard reagent, e.g., 2.3 as shown above. Appropriate Grignard reagents are commercially available or prepared by methods known to one skilled in the art. The Grignard reaction is carried out in the presence of an appropriate metal salt, e.g., zinc chloride, and an appropriate catalyst, e.g., [1,1'-bis(diphenylphosphino)ferrocene]dichloropalladium, in an appropriate solvent, e.g., 1,4-dioxane, for an appropriate period of time, e.g., 16 hours. Alternatively, as shown in Schemes 2C and 2D, compounds of type 1.6 can be prepared by a coupling reaction of an appropriate halide, e.g., 2.2 as shown above, and an appropriate amine, e.g., 2.4 as shown above. Appropriate amines are commercially available or prepared by methods known to one skilled in the art. As shown in Scheme 2C, the coupling reaction is carried out in the presence of an appropriate base, e.g., potassium carbonate, in an appropriate solvent, e.g., 1,4-dioxane, at an appropriate temperature, e.g., 100° C., for an appropriate period of time, e.g., 2 hours. Alternatively, as shown in Scheme 2D, the coupling reaction is carried out at an appropriate temperature, e.g., 90° C., for an appropriate period of time, e.g., 2 hours. As can be appreciated by one skilled in the art, the above reaction provides an example of a generalized approach wherein compounds similar in structure to the specific reactants above (compounds similar to compounds of type 1.10, 2.5, 2.6, 2.7, 2.9, and 2.11), can be substituted in the reaction to provide substituted quinazoline sulfonamides similar to Formulas 2.8, 2.10, and 2.12.

3. Route III

In one aspect, substituted quinazoline sulfonamides can be prepared as shown below.

SCHEME 3A.

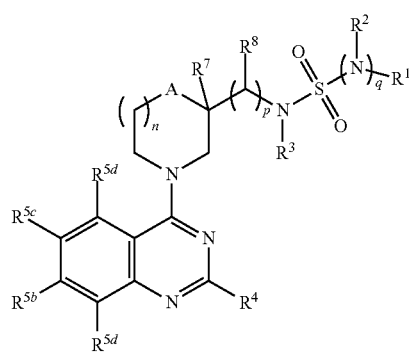

3.1
wherein one or more
of $R^{5a-5d} = CO_2(C_1$—$C_4$ alkyl)

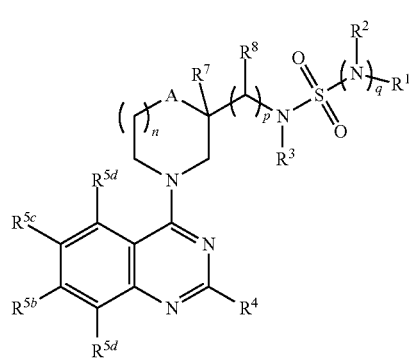

3.2
wherein each occurence of
of $R^{5a-5d} = CO_2(C_1$—$C_4$ alkyl) is now
$R^{5a-5d} = CO_2H$ Compounds are represented in generic form, with substituents as noted in compound descriptions elsewhere herein. A more specific example is set forth below.

SCHEME 3B.

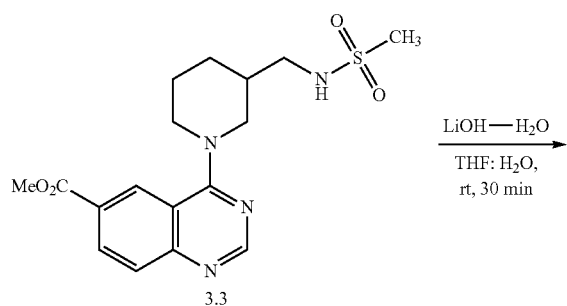

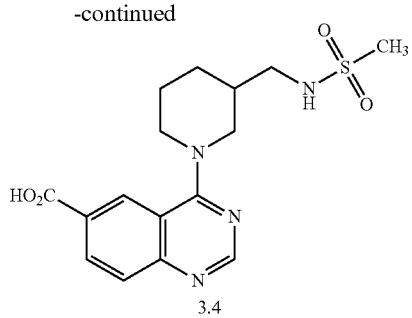

3.4

In one aspect, compounds of type 3.2, and similar compounds, can be prepared according to reaction Scheme 3B above. Thus, compounds of type 3.2 can be prepared by reduction of an appropriate ester, e.g., 3.1 as shown above. The reduction is carried out in the presence of an appropriate base, e.g., lithium hydroxide, in an appropriate solvent system, e.g., tetrahydrofuran and water, for an appropriate period of time, e.g., 3 hours. As can be appreciated by one skilled in the art, the above reaction provides an example of a generalized approach wherein compounds similar in structure to the specific reactants above (compounds similar to compound of type 3.3), can be substituted in the reaction to provide substituted quinazoline sulfonamides similar to Formula 3.4.

4. Route IV

In one aspect, substituted quinazoline sulfonamides can be prepared as shown below.

SCHEME 4A.

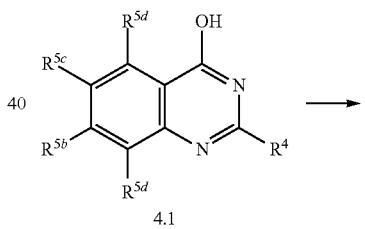

4.1

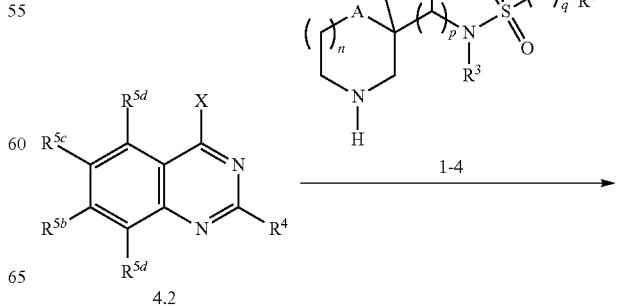

4.2

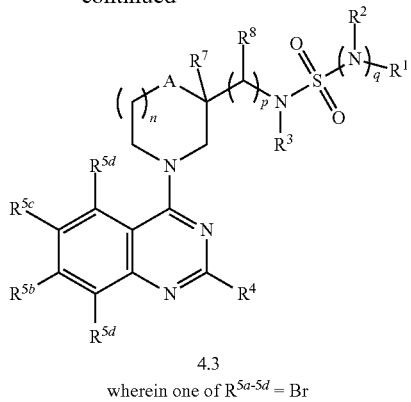

4.3 wherein one of $R^{5a-5d}$ = Br

Compounds are represented in generic form, wherein X is a halogen and with other substituents as noted in compound descriptions elsewhere herein. A more specific example is set forth below.

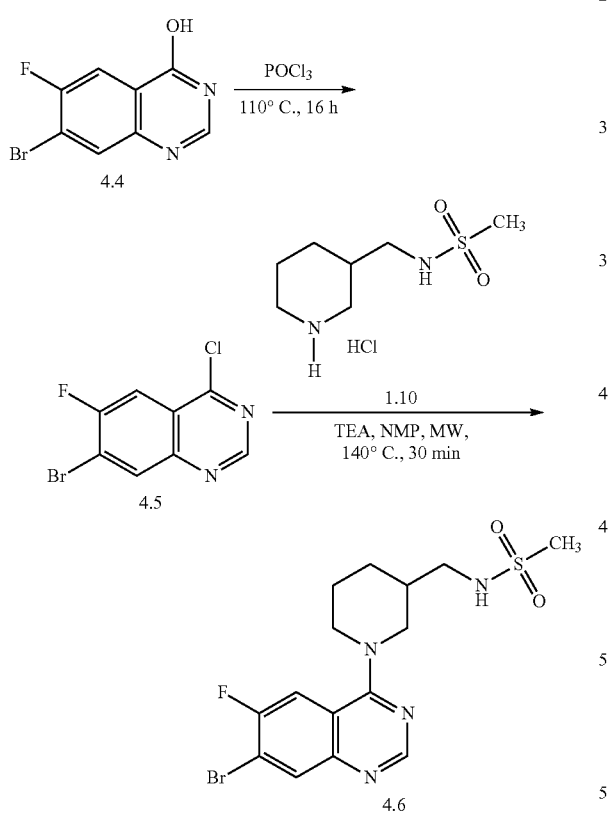

In one aspect, compounds of type 4.3, and similar compounds, can be prepared according to reaction Scheme 4B above. Thus, compounds of type 4.2 can be prepared by a substitution reaction of an appropriate hydroxyl, e.g., 4.3 as shown above. Appropriate hydroxyls are commercially available or prepared by methods known to one skilled in the art. The substitution reaction is carried out in the presence of an appropriate halide source, e.g., phosphoryl chloride, at an appropriate temperature, e.g., 110° C., for an appropriate period of time, e.g., 16 hours. Compounds of type 4.3 can be prepared by a coupling reaction of an appropriate quinazoline derivative, e.g., 4.2 as shown above, and an appropriate amine, e.g., 1.4 as shown above. The coupling reaction is carried out in the presence of an appropriate base, e.g., triethylamine, in an appropriate solvent, e.g., N-methyl-2-pyrrolidone, at an appropriate temperature, e.g., 140° C., for an appropriate period of time, e.g., 30 minutes. As can be appreciated by one skilled in the art, the above reaction provides an example of a generalized approach wherein compounds similar in structure to the specific reactants above (compounds similar to compounds of type 1.10, 4.4, and 4.5), can be substituted in the reaction to provide substituted quinazoline sulfonamides similar to Formula 4.6.

5. Route V

In one aspect, substituted quinazoline sulfonamides can be prepared as shown below.

SCHEME 5A.

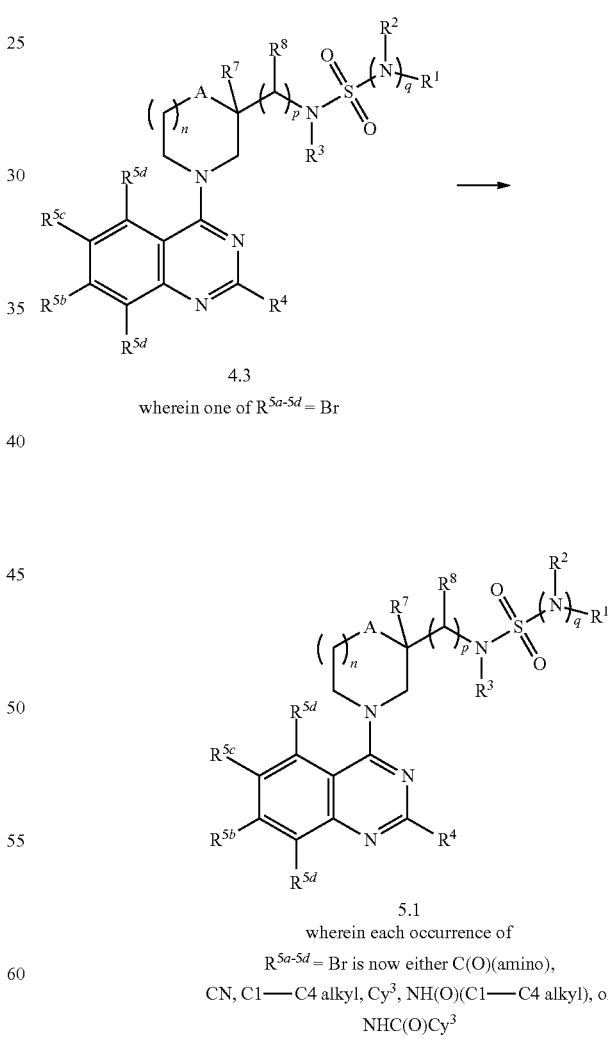

5.1 wherein each occurrence of $R^{5a-5d}$ = Br is now either C(O)(amino), CN, C1—C4 alkyl, $Cy^3$, NH(O)(C1—C4 alkyl), or NHC(O)$Cy^3$ Compounds are represented in generic form, with substituents as noted in compound descriptions elsewhere herein. A more specific example is set forth below.

SCHEME 5B.

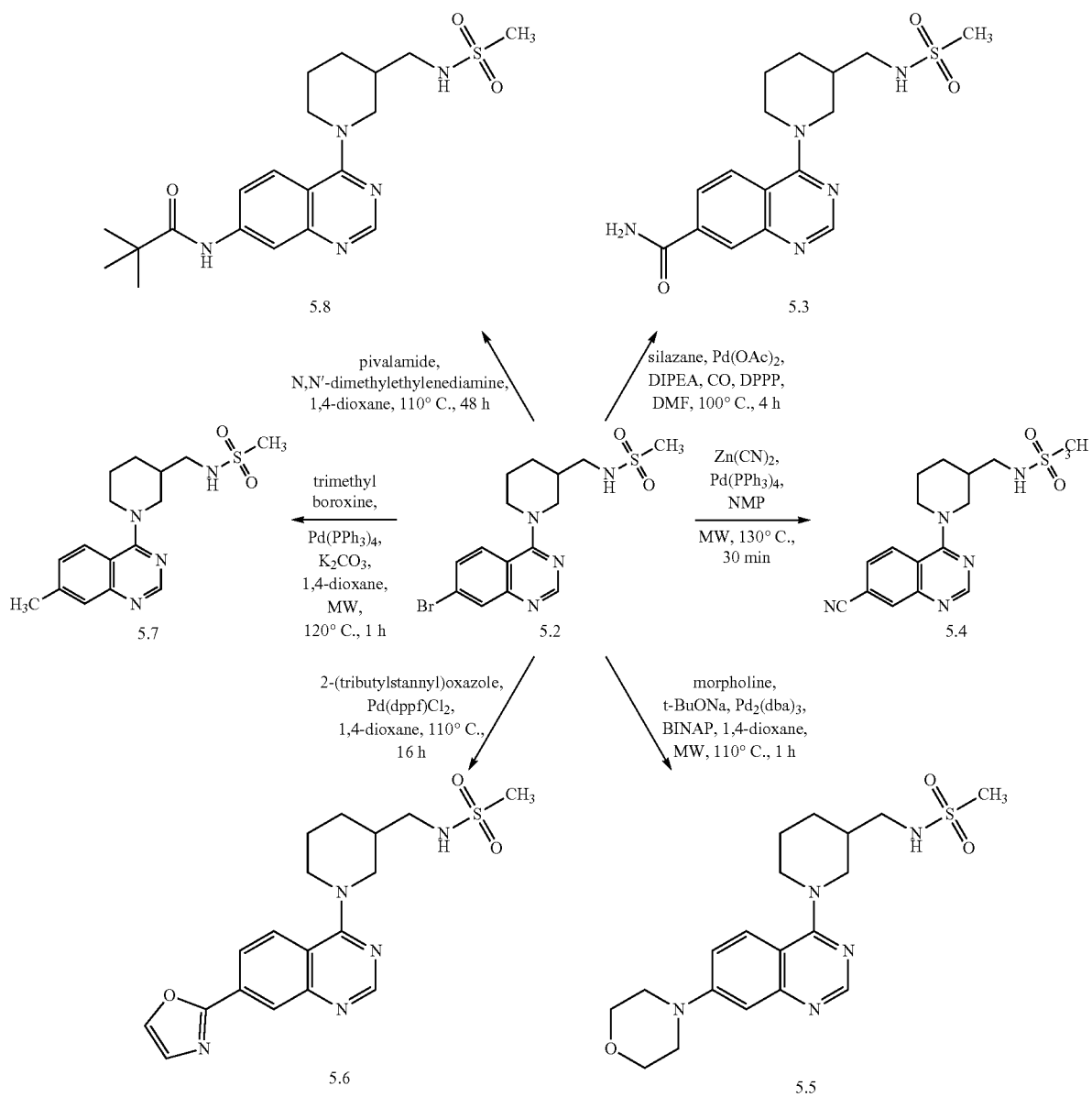

In one aspect, compounds of type 5.3-5.8, and similar compounds, can be prepared according to reaction Scheme 5B above. Thus, compounds of type 5.3 can be prepared by a carbonylation reaction of an appropriate aryl bromide, e.g., 5.2 as shown above, and an appropriate amine, e.g., silazane. Appropriate amines are commercially available or prepared by methods known to one skilled in the art. The carbonylation reaction is carried out in the presence of an appropriate catalyst, e.g., palladium (II) acetate, an appropriate ligand, e.g., 1,3-bis(diphenylphosphino)propane, and an appropriate base, e.g., N,N-diisopropylethylamine, at an appropriate temperature, e.g., 100° C., for an appropriate period of time, e.g., 4 hours. Compounds of type 5.4 can be prepared by a cyanation reaction of an appropriate aryl bromide, e.g., 5.2 as shown above. The cyanation reaction is carried out in the presence of an appropriate metal cyanide, e.g., zinc cyanide, and an appropriate catalyst, e.g., tetrakis (triphenylphosphine)palladium (0), in an appropriate solvent, e.g., N-methyl-2-pyrrolidone, at an appropriate temperature, e.g., 130° C., for an appropriate period of time, e.g., 30 minutes. Compounds of type 5.5 can be prepared by a coupling reaction of an appropriate aryl bromide, e.g., 5.2 as shown above, and an appropriate amine, e.g., morpholine as shown above. Appropriate amines are commercially available or prepared by methods known to one skilled in the art. The coupling reaction is carried out in the presence of an appropriate base, e.g., sodium tert-butoxide, an appropriate catalyst, e.g., tris(dibenzylideneacetone)dipalladium (0), and an appropriate ligand, e.g., 2,2'-bis(diphenylphosphino)-1,1'-binaphthyl (BINAP), in an appropriate solvent, e.g., 1,4-dioxane, at an appropriate temperature, e.g., 110° C., for an appropriate period of time, e.g., 1 hour. Compounds of type 5.6 can be prepared by a coupling reaction of an appropriate aryl bromide, e.g., 5.2 as shown above, and an appropriate organotin reagent, e.g., 2-(tributylstannyl)oxazole as shown above. Appropriate organotin reagents are commercially available or prepared by methods known to one skilled in the art. The coupling reaction is carried out in the presence of an appropriate catalyst, e.g., tris(dibenzylideneacetone)dipalladium (0), in an appropriate solvent, e.g., 1,4-dioxane, at an appropriate temperature, e.g., 110° C., for an appropriate period of time, e.g., 30 minutes. Compounds of type 5.7 can be prepared by a coupling reaction of an appropriate aryl bromide, e.g., 5.2 as shown above, and an appropriate organoborane, e.g., trimethyl boroxime as shown above. Appropriate organoboranes are commercially available or prepared by methods known to one skilled in the art. The coupling reaction is carried out in the presence of an appropriate catalyst, e.g., tetrakis(triphenylphosphine)palladium (0), and an appropriate base, e.g., potassium carbonate, in an appropriate solvent, e.g., 1,4-dioxane, at an appropriate temperature, e.g., 120° C., for an appropriate period of time, e.g., 1 hour. Compounds of type 5.8 can be prepared by a coupling reaction of an appropriate aryl bromide, e.g., 5.2, and an appropriate amide, e.g., pivalamide as shown above. Appropriate amides are commercially available or prepared by one skilled in the art. The coupling reaction is carried out in the presence of an appropriate catalyst, e.g., copper (I) iodide, an appropriate ligand, e.g., N,N'-dimethylethylenediamine, and an appropriate salt, e.g., tripotassium phosphate, in an appropriate solvent, e.g., 1.4-dioxane, at an appropriate temperature, e.g., 100° C., for an appropriate period of time, e.g., 16 hours. As can be appreciated by one skilled in the art, the above reaction provides an example of a generalized approach wherein compounds similar in structure to the specific reactants above (compounds similar to compounds of type 5.2), can be substituted in the reaction to provide substituted quinazoline sulfonamides similar to Formulas 5.3, 5.4, 5.5, 5.6, 5.7, and 5.8.

6. Route VI

In one aspect, substituted quinazoline sulfonamides can be prepared as shown below.

SCHEME 6A.

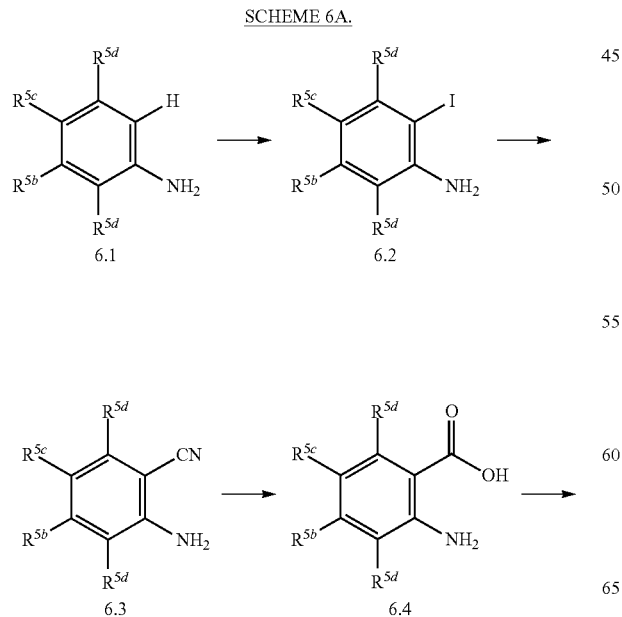

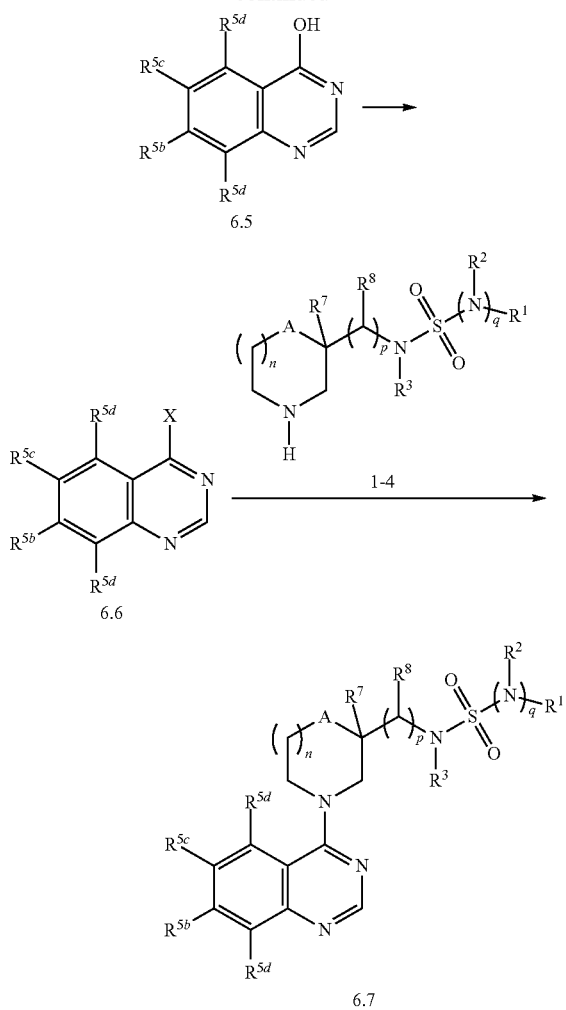

Compounds are represented in generic form, wherein X is halogen and with other substituents as noted in compound descriptions elsewhere herein. A more specific example is set forth below.

SCHEME 6B.

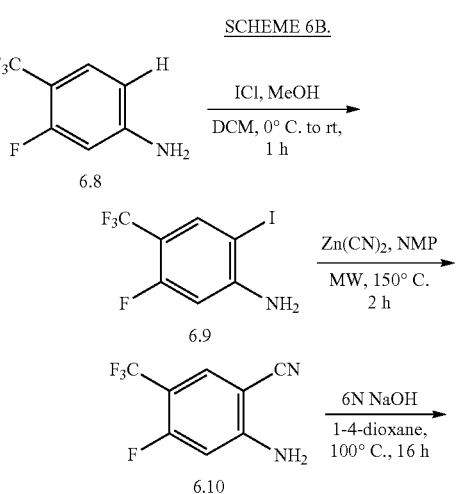

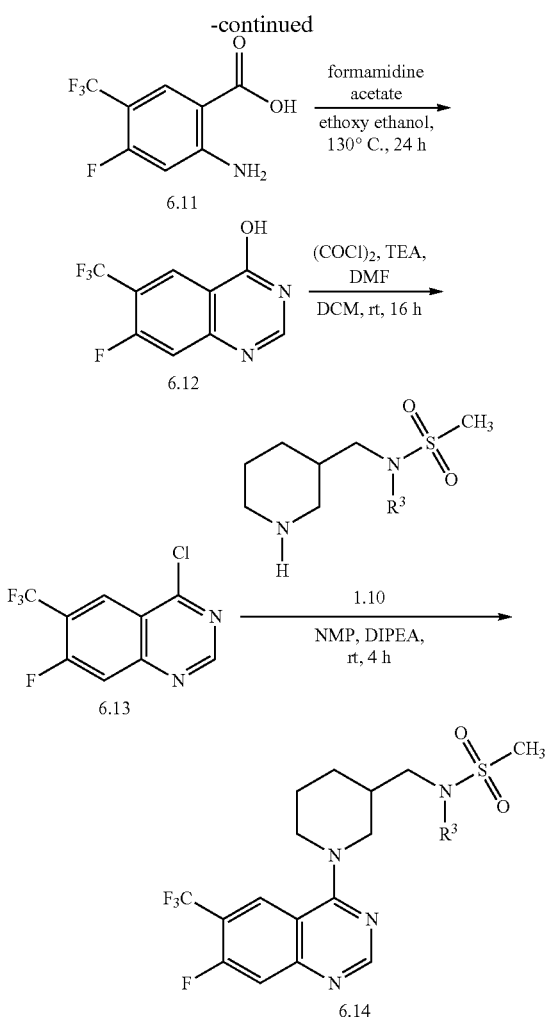

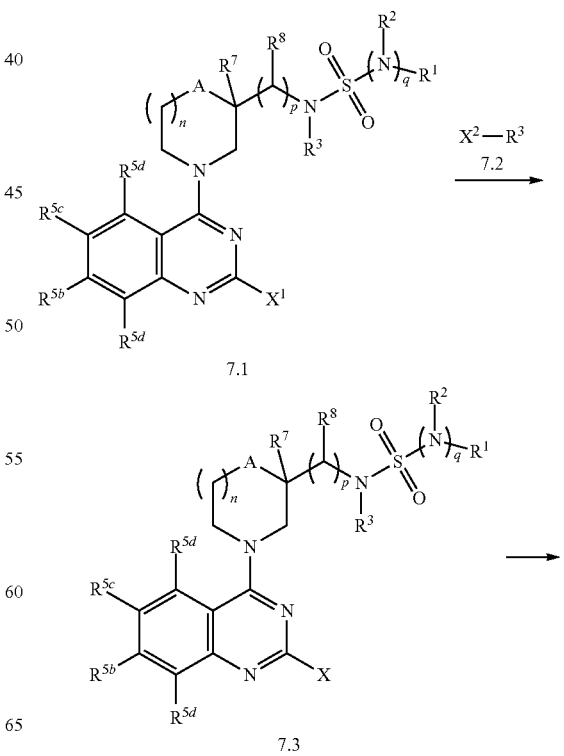

In one aspect, compounds of type 6.7, and similar compounds, can be prepared according to reaction Scheme 6B above. Thus, compounds of type 6.2 can be prepared by electrophilic aromatic substitution of an appropriate arene, e.g., 6.1 as shown above. Appropriate arenes are commercially available or prepared by methods known to one skilled in the art. The electrophilic aromatic substitution is carried out in the presence of an appropriate electrophile, e.g., iodine monochloride, and an appropriate base, e.g., methanol, in an appropriate solvent, e.g., dichloromethane, for an appropriate period of time, e.g., 1 hour. Compounds of type 6.3 can be prepared by a cyanation reaction of an appropriate aryl iodide, e.g., 6.2 as shown above. The cyanation reaction is carried out in the presence of an appropriate metal cyanide, e.g., zinc cyanide, in an appropriate solvent, e.g., N-methyl-2-pyrrolidone, at an appropriate temperature, e.g., 150° C., for an appropriate period of time, e.g., 2 hours. Compounds of type 6.4 can be prepared by hydrolysis of an appropriate aryl cyanide, e.g., 6.3 as shown above. The hydrolysis is carried out in the presence of an appropriate base, e.g., 6N sodium hydroxide, in an appropriate solvent, e.g., 1,4-dioxane, at an appropriate temperature, e.g., 100° C., for an appropriate period of time, e.g., 16 hours. Compounds of type 6.5 can be prepared by cyclization of an appropriate aryl carboxylic acid, e.g., 6.4 as shown above, and an appropriate amidine, e.g., formamidine acetate as shown above. Appropriate amidines are commercially available or prepared by methods known to one skilled in the art. The cyclization is carried out in the presence of an appropriate solvent, e.g., ethoxy ethanol, at an appropriate temperature, e.g., 130° C., for an appropriate period of time, e.g., 24 hours. Compounds of type 6.6 can be prepared by a substitution reaction of an appropriate aryl alcohol, e.g., 6.5 as shown above, and an appropriate electrophile, e.g., oxalyl dichloride as shown above. The substitution reaction is carried out in the presence of an appropriate base, e.g., triethylamine, and an appropriate solvent system, e.g., dimethylformamide (DMF) and dichloromethane, for an appropriate period of time, e.g., 16 hours. Compounds of type 6.7 can be prepared by a coupling reaction of an appropriate aryl halide, e.g., 6.6 as shown above, and an appropriate amine, e.g., 1.4 as shown above. The coupling reaction is carried out in the presence of an appropriate base, e.g., N,N-diisopropylethylamine, in an appropriate solvent, e.g., N-methyl-2-pyrrolidinone, for an appropriate period of time, e.g., 4 hours. As can be appreciated by one skilled in the art, the above reaction provides an example of a generalized approach wherein compounds similar in structure to the specific reactants above (compounds similar to compounds of type 1.10, 6.8, 6.9, 6.10, 6.11, 6.12, and 6.13), can be substituted in the reaction to provide substituted quinazoline sulfonamides similar to Formula 6.14.

7. Route VII

In one aspect, substituted quinazoline sulfonamides can be prepared as shown below.

SCHEME 7A.

-continued

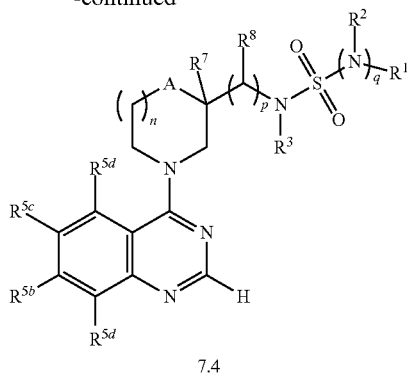

7.4

Compounds are represented in generic form, wherein each of $X^1$ and $X^2$ is independently halogen and with other substituents as noted in compound descriptions elsewhere herein. A more specific example is set forth below.

SCHEME 7B.

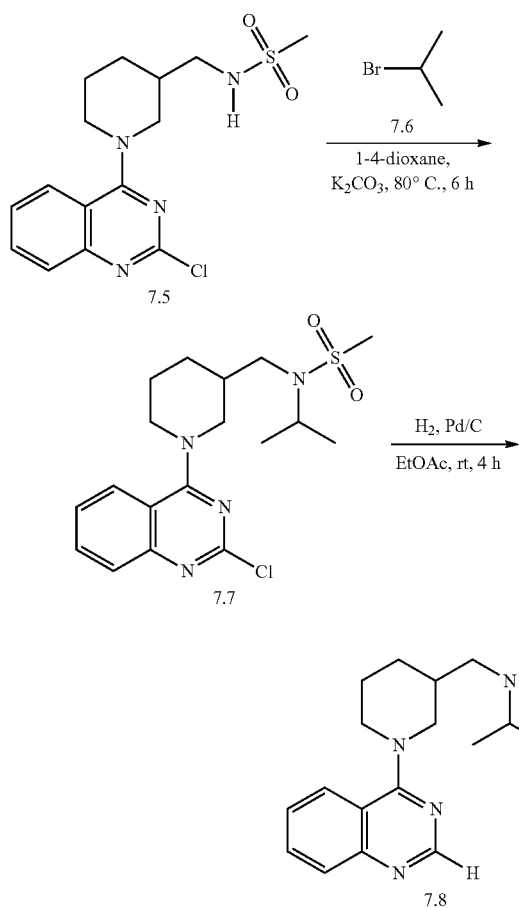

In one aspect, compounds of type 7.4, and similar compounds, can be prepared according to reaction Scheme 7B above. Thus, compounds of type 7.3 can be prepared by an alkylation reaction of an appropriate amine, e.g., 7.1 as shown above, and an appropriate alkyl halide, e.g., 7.2 as shown above. Appropriate alkyl halides are commercially available or prepared by methods known to one skilled in the art. The alkylation reaction is carried out in the presence of an appropriate base, e.g., potassium carbonate, in an appropriate solvent, e.g., 1,4-dioxane, at an appropriate temperature, e.g., 80° C., for an appropriate period of time, e.g., 6 hours. Compounds of type 7.4 can be prepared by hydrogenation of an appropriate aryl halide, e.g., 7.3 as shown above. The hydrogenation is carried out in the presence of an appropriate hydrogen source, e.g., hydrogen gas, and an appropriate catalyst, e.g., palladium on carbon, in an appropriate solvent, e.g., ethyl acetate, for an appropriate period of time, e.g., 4 hours. As can be appreciated by one skilled in the art, the above reaction provides an example of a generalized approach wherein compounds similar in structure to the specific reactants above (compounds similar to compounds of type 7.5, 7.6, and 7.7), can be substituted in the reaction to provide substituted quinazoline sulfonamides similar to Formula 7.8.

8. Route VIII

In one aspect, substituted quinazoline sulfonamides can be prepared as shown below.

SCHEME 8A.

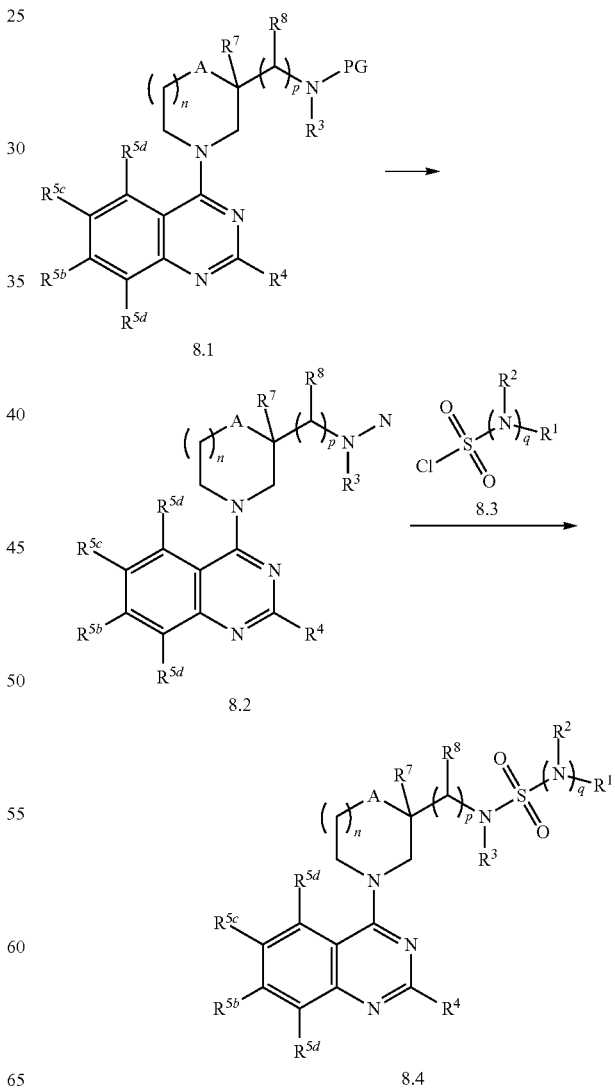

Compounds are represented in generic form, wherein PG is an amino protecting group and with other substituents as noted in compound descriptions elsewhere herein. A more specific example is set forth below.

9. Route IX

In one aspect, substituted quinazoline sulfonamides can be prepared as shown below.

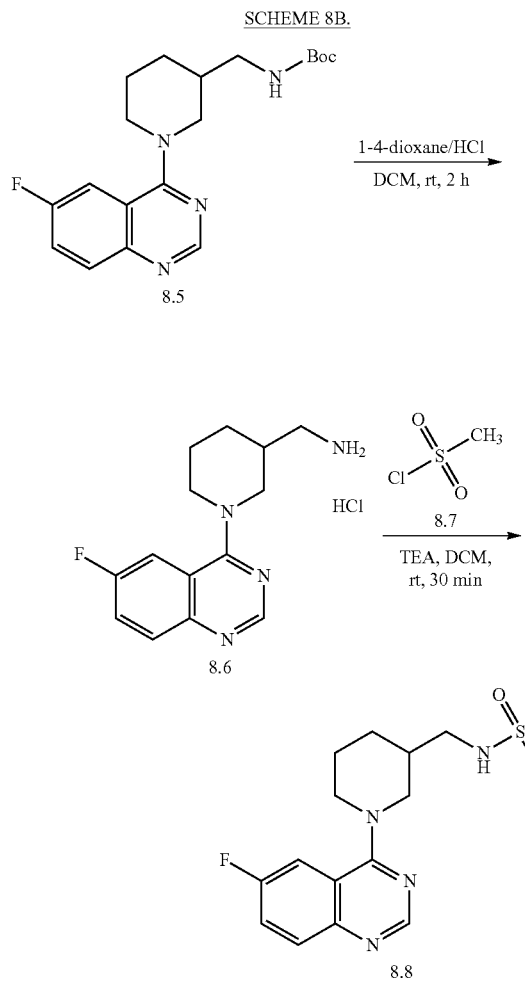

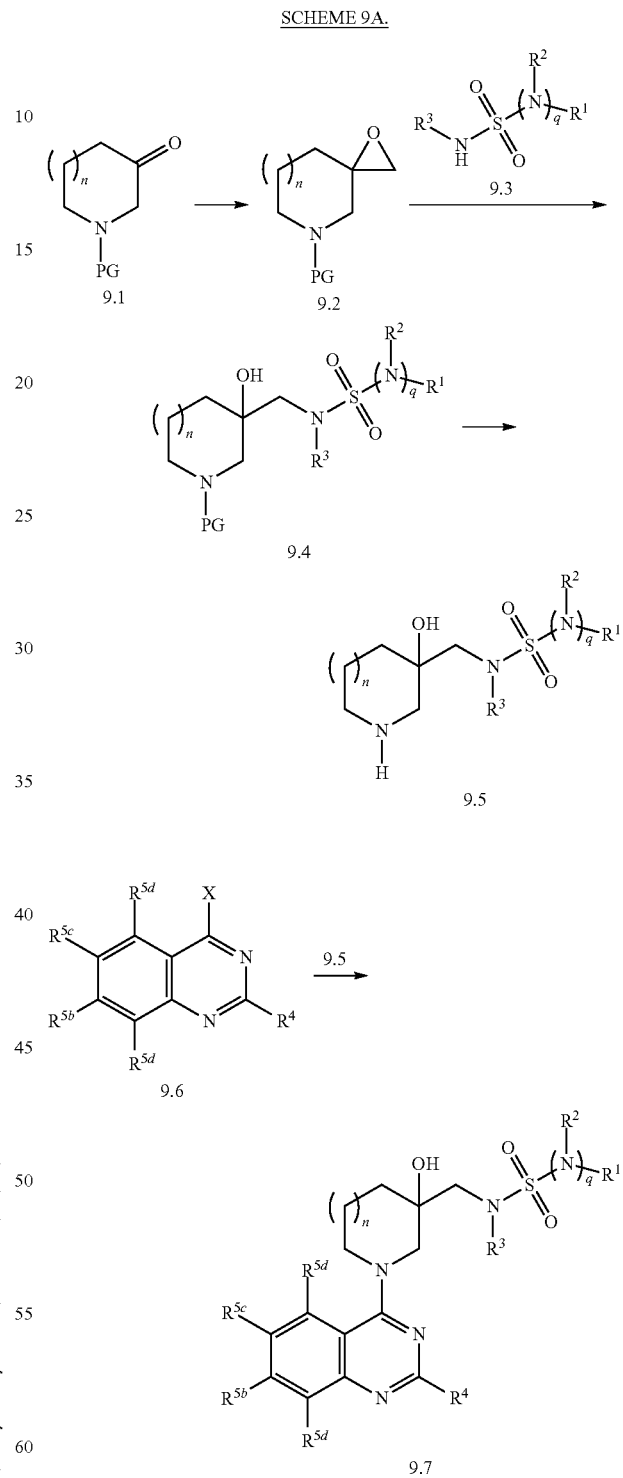

In one aspect, compounds of type 8.4, and similar compounds, can be prepared according to reaction Scheme 8B above. Thus, compounds of type 8.2 can be prepared by deprotection of an appropriate amine, e.g., 8.1 as shown above. The deprotection is carried out in the presence of an appropriate deprotecting agent, e.g., hydrochloric acid, in an appropriate solvent system, e.g., 1,4-dioxane and dichloromethane, for an appropriate period of time, e.g., 2 hours. Compounds of type 8.4 can be prepared by a sulfonylation reaction of an appropriate amine, e.g., 8.2 as shown above, and an appropriate sulfonyl halide, e.g., 8.3 as shown above. The sulfonylation reaction is carried out in the presence of an appropriate base, e.g., triethylamine, in an appropriate solvent, e.g., dichloromethane, for an appropriate period of time, e.g., 30 minutes. As can be appreciated by one skilled in the art, the above reaction provides an example of a generalized approach wherein compounds similar in structure to the specific reactants above (compounds similar to compounds of type 8.1, 8.2, and 8.3), can be substituted in the reaction to provide substituted quinazoline sulfonamides similar to Formula 8.4.

Compounds are represented in generic form, wherein PG is an amino protecting group, X is halogen, and with other substituents as noted in compound descriptions elsewhere herein. A more specific example is set forth below.

SCHEME 9B.

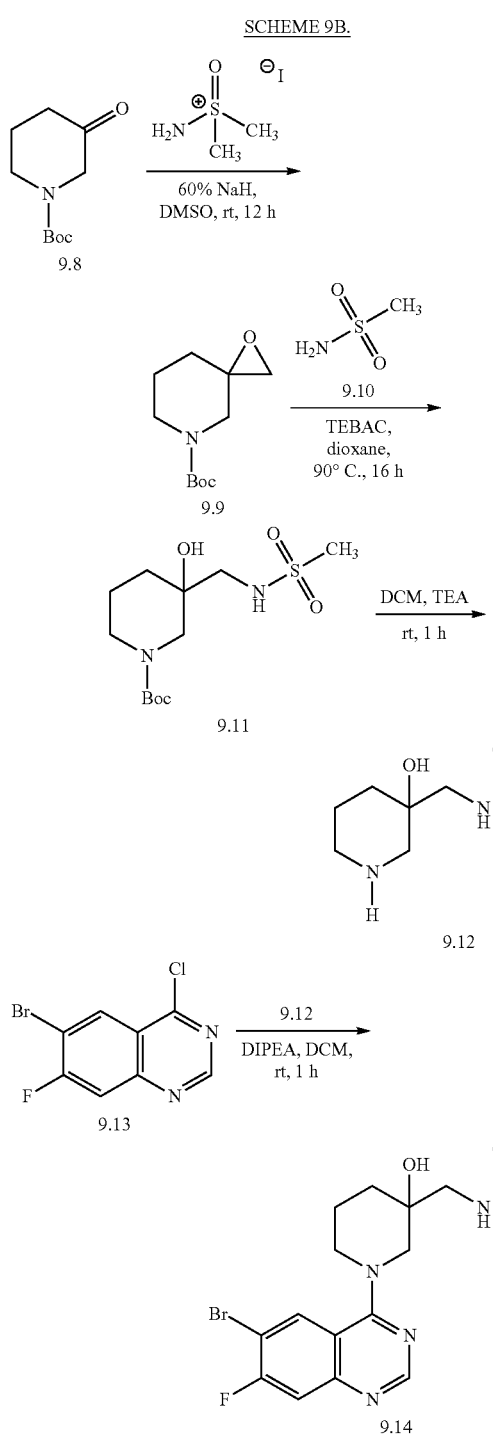

In one aspect, compounds of type 9.7, and similar compounds, can be prepared according to reaction Scheme 9B above. Thus, compounds of type 9.2 can be prepared by epoxidation of an appropriate ketone, e.g., 9.1 as shown above. Appropriate ketones are commercially available or prepared by methods known to one skilled in the art. The epoxidation is carried out in the presence of an appropriate sulfoxonium agent, e.g., trimethylsulfoxonium iodide, and an appropriate base, e.g., 60% sodium hydride, in an appropriate solvent, e.g., dimethylsulfoxide (DMSO), for an appropriate period of time, e.g., 12 hours. Compounds of type 9.4 can be prepared by a nucleophilic substitution reaction of an appropriate epoxide, e.g., 9.2 as shown above, and an appropriate nucleophile, e.g., 9.3 as shown above. The nucleophilic substitution reaction is carried out in the presence of an appropriate base, e.g., benzyl triethylammonium chloride (TEBAC), in an appropriate solvent, e.g., dioxane, at an appropriate temperature, e.g., 90° C., for an appropriate period of time, e.g., 16 hours. Compounds of type 9.5 can be prepared by deprotection of an appropriate amine, e.g., 9.4 as shown above. The deprotection is carried out in the presence of an appropriate deprotecting agent, e.g., trifluoroacetic acid (TFA), in an appropriate solvent, e.g., dichloromethane, for an appropriate period of time, e.g., 1 hour. Compounds of type 9.7 can be prepared by a coupling reaction of an appropriate aryl halide, e.g., 9.6 as shown above, and an appropriate amine, e.g., 9.5 as shown above. The coupling reaction is carried out in the presence of an appropriate base, e.g., N,N-diisopropylethylamine, in an appropriate solvent, e.g., dichloromethane, for an appropriate period of time, e.g., 1 hour. As can be appreciated by one skilled in the art, the above reaction provides an example of a generalized approach wherein compounds similar in structure to the specific reactants above (compounds similar to compounds of type 9.8, 9.9, 9.10, 9.11, 9.12, and 9.13), can be substituted in the reaction to provide substituted quinazoline sulfonamides similar to Formula 9.14.

I. METHODS OF USING THE COMPOSITIONS

Provided are methods of using of a disclosed composition or medicament. In one aspect, the method of use is directed to the treatment of a disorder. In a further aspect, the disclosed compounds can be used as single agents or in combination with one or more other drugs in the treatment, prevention, control, amelioration, or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

The pharmaceutical compositions and methods of the present invention can further comprise other therapeutically active compounds as noted herein which are usually applied in the treatment of the above mentioned pathological conditions.

1. Manufacture of a Medicament

In one aspect, the invention relates to a method for the manufacture of a medicament for treating or preventing a disorder associated with elevated TXNIP and/or glucagon in a mammal, the method comprising combining a therapeutically effective amount of a disclosed compound or product of a disclosed method with a pharmaceutically acceptable carrier or diluent.

In a further aspect, the disorder associated with elevated TXNIP and/or glucagon is a disorder affecting regulation of hepatic glucose production. In a still further aspect, the disorder associated with elevated TXNIP is diabetes. In yet a further aspect, the diabetes is selected from Type I diabetes, Type II diabetes, and gestational diabetes. In an even further aspect, the diabetes is Type I diabetes. In a still further aspect, the diabetes is Type II diabetes. In yet a further aspect, the diabetes is gestational diabetes.

As regards these applications, the present method includes the administration to an animal, particularly a mammal, and more particularly a human, of a therapeutically effective amount of the compound effective in the inhibition of TXNIP expression and TXNIP protein signaling. The dose administered to an animal, particularly a human, in the context of the present invention should be sufficient to affect a therapeutic response in the animal over a reasonable time frame. One skilled in the art will recognize that dosage will depend upon a variety of factors including the condition of the animal, the body weight of the animal, as well as the severity and stage of the disorder.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

2. Use of Compounds and Compositions

Also provided are the uses of the disclosed compounds and compositions. Thus, in one aspect, the invention relates to the uses for inhibition of TXNIP expression or function and/or reduction of glucagon levels. In a further aspect, the use is treatment of a disorder associated with elevated TXNIP and/or glucagon (e.g., diabetes or diabetes related disorders).

In a further aspect, the invention relates to the use of a disclosed compound or product of a disclosed method in the manufacture of a medicament for the treatment of a disorder associated with TXNIP activity such as, for example, a disorder associated with elevated TXNIP (e.g., diabetes or diabetes related disorders).

In a further aspect, the disorder associated with elevated TXNIP and/or glucagon is a disorder affecting the regulation of hepatic glucose production. In a still further aspect, the disorder associated with elevated TXNIP is diabetes. In yet a further aspect, the diabetes is selected from Type I diabetes, Type II diabetes, and gestational diabetes. In an even further aspect, the diabetes is Type I diabetes. In a still further aspect, the diabetes is Type II diabetes. In an even further aspect, the disorder is gestational diabetes.

Also provided are uses of the disclosed compounds and compositions for treating hyperlipidemia and/or fatty liver disease (e.g., nonalcoholic fatty liver disease). The hyperlipidemia and/or fatty liver disease is optionally associated with elevated TXNIP and/or glucagon, but is not necessarily so associated. Further, the hyperlipidemia and/or fatty liver disease is optionally related with diabetes, but is not necessarily related to diabetes.

In a further aspect, the use relates to a process for preparing a pharmaceutical composition comprising a therapeutically effective amount of a disclosed compound or a product of a disclosed method, and a pharmaceutically acceptable carrier, for use as a medicament.

In a further aspect, the use relates to a process for preparing a pharmaceutical composition comprising a therapeutically effective amount of a disclosed compound or a product of a disclosed method, wherein a pharmaceutically acceptable carrier is intimately mixed with a therapeutically effective amount of the disclosed compound or the product of a disclosed method.

In various aspects, the use relates to the treatment of a disorder in a vertebrate animal. In a further aspect, the use relates to the treatment of a disorder in a human subject.

It is understood that the disclosed uses can be employed in connection with the disclosed compounds, methods, compositions, and kits. In a further aspect, the invention relates to the use of a disclosed compound or composition of a medicament for the treatment of a disorder associated with elevated TXNIP and/or glucagon and or for treatment of hyperlipidemia and/or fatty liver disease in a mammal.

3. Kits

In one aspect, disclosed are kits comprising an effective amount of a compound having a structure represented by a formula:

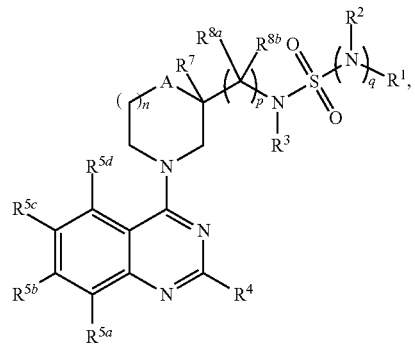

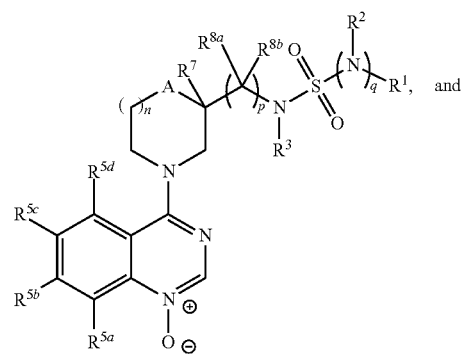

and

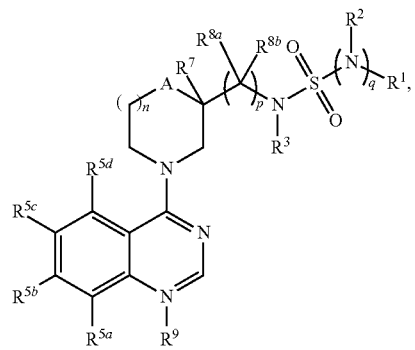

wherein n is 0, 1, or 2; wherein p is 0, 1, 2, 3, or 4; wherein q is 0 or 1; wherein $R^1$ is —$NH_2$, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)$CO_2H$, or $Cy^1$; wherein $Cy^1$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^2$ is hydrogen or C1-C4 alkyl, or wherein each of $R^1$ and $R^2$ are covalently bonded together and, together with the intermediate atoms, comprise a 3- to 6-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^3$ is hydrogen or C1-C4 alkyl, or wherein each of $R^1$ and $R^3$ are covalently bonded together and, together with the intermediate atoms, comprise a 5- to 7-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^4$ is hydrogen, halogen, —$NH_2$, —OH, C1-C4 alkyl, C1-C4 alkoxy, C1-C4 alkylamino, (C1-C4)(C1-C4) dialkylamino, or $Cy^2$; wherein $Cy^2$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein each of $R^{5a}$, $R^{5b}$, $R^{5c}$, and $R^{5d}$ is independently hydrogen, halogen, —$NH_2$, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —$CO_2$(C1-C4 alkyl), —$CO_2H$, —$CO_2NH_2$, —NHC(O)$Cy^3$, —NHC(O)(C1-C4 alkyl), or $Cy^3$; wherein $Cy^3$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein A is O, $NR^{6a}$, or $CHR^{6b}$; wherein $R^{6a}$ is hydrogen or C1-C4 alkyl; and wherein $R^{6b}$ is hydrogen, C1-C4 alkyl, C1-C4 haloalkyl, C1-C4 alkoxy, C1-C4 alkylamino, (C1-C4)(C1-C4) dialkylamino, or —$CO_2H$; wherein $R^7$ is hydrogen, halogen, —OH, C1-C4 alkyl, C1-C4 haloalkyl, or C1-C4 alkoxy; wherein each occurrence of $R^{8a}$ and $R^{8b}$, when present, is independently hydrogen, C1-C4 alkyl, C1-C4 haloalkyl, phenyl, or —$CO_2H$; or wherein p is 1 and each of $R^{8a}$ and $R^{8b}$ together comprise =O; and wherein $R^9$ is hydrogen, C1-C4 alkyl, or $Cy^4$, wherein $Cy^4$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino, or a pharmaceutically acceptable salt thereof, and one or more of: (a) at least one agent known to treat a disorder associated with elevated TXNIP; (b) at least one agent known to reduce TXNIP; and (c) instructions for treating or preventing a disorder associated with elevated TXNIP.

In another aspect, disclosed are kits comprising an effective amount of a compound having a structure represented by a formula:

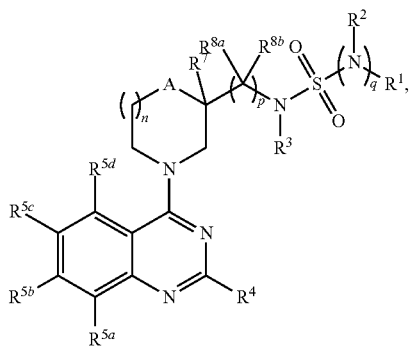

wherein n is 0, 1, or 2; wherein each of p and q is independently 0 or 1; wherein $R^1$ is —$NH_2$, —OH, C1-C4 alkyl, C1-C4 haloalkyl, C1-C4 alkoxy, C1-C4 alkylamino, (C1-C4)(C1-C4) dialkylamino, or $Cy^1$; wherein $Cy^1$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein $R^2$ is hydrogen or C1-C4 alkyl, or wherein each of $R^1$ and $R^2$ are covalently bonded together and, together with the intermediate atoms, comprise a 3- to 6-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, (C1-C4)(C1-C4) dialkylamino; wherein $R^3$ is hydrogen or C1-C4 alkyl; wherein $R^4$ is hydrogen, halogen, —$NH_2$, —OH, C1-C4 alkyl, C1-C4 alkoxy, C1-C4 alkylamino, (C1-C4)(C1-C4) dialkylamino, or $Cy^2$; wherein $Cy^2$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein each of $R^{5a}$, $R^{5b}$, $R^{5c}$, and $R^{5d}$ is independently hydrogen, halogen, —$NH_2$, —CN, —OH, C1-C4 alkyl, C1-C4 haloalkyl, C1-C4 alkoxy, C1-C4 alkylamino, (C1-C4)(C1-C4) dialkylamino, —$CO_2$(C1-C4 alkyl), —$CO_2H$, —$CO_2NH_2$, —NHC(O)$Cy^3$, —NHC(O)(C1-C4 alkyl), or $Cy^3$; wherein $Cy^3$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino; wherein A is O, $NR^{6a}$, or $CHR^{6b}$; wherein $R^{6a}$ is hydrogen or C1-C4 alkyl; and wherein $R^{6b}$ is hydrogen, C1-C4 alkyl, C1-C4 haloalkyl, C1-C4 alkoxy, C1-C4 alkylamino, or (C1-C4)(C1-C4) dialkylamino; wherein $R^7$ is hydrogen, halogen, —OH, C1-C4 alkyl, C1-C4 haloalkyl, or C1-C4 alkoxy; wherein $R^8$ is hydrogen, C1-C4 alkyl, or C1-C4 haloalkyl, or a pharmaceutically acceptable salt thereof, and one or more of: (a) at least one agent known to treat a disorder associated with elevated TXNIP; (b) at least one agent known to reduce TXNIP; and (c) instructions for treating or preventing a disorder associated with elevated TXNIP.

In various aspects, the agents and pharmaceutical compositions described herein can be provided in a kit. The kit can also include combinations of the agents and pharmaceutical compositions described herein.

In various aspects, the informational material can be descriptive, instructional, marketing or other material that relates to the methods described herein and/or to the use of the agents for the methods described herein. For example, the informational material may relate to the use of the agents herein to treat a subject who has, or who is at risk for developing, a disorder associated with elevated TXNIP. The kits can also include paraphernalia for administering the agents of this invention to a cell (in culture or in vivo) and/or for administering a cell to a patient.

In various aspects, the informational material can include instructions for administering the pharmaceutical composition and/or cell(s) in a suitable manner to treat a human, e.g., in a suitable dose, dosage form, or mode of administration (e.g., a dose, dosage form, or mode of administration described herein). In a further aspect, the informational material can include instructions to administer the pharmaceutical composition to a suitable subject, e.g., a human having, or at risk for developing, a disorder associated with elevated TXNIP.

In various aspects, the composition of the kit can include other ingredients, such as a solvent or buffer, a stabilizer, a preservative, a fragrance or other cosmetic ingredient. In such aspects, the kit can include instructions for admixing the agent and the other ingredients, or for using one or more compounds together with the other ingredients.

In a further aspect, the compound and the at least one agent known are co-formulated. In a still further aspect, the compound and the at least one agent are co-packaged.

In a further aspect, the kit further comprises a plurality of dosage forms, the plurality comprising one or more doses; wherein each dose comprises an effective amount of the compound and the at least one agent. In a still further aspect, the effective amount is a therapeutically effective amount. In yet a further aspect, the effective amount is a prophylactically effective amount. In an even further aspect, each dose of the compound and the at least one agent are co-packaged. In a still further aspect, each dose of the compound and the at least one agent are co-formulated.

4. Subjects

In various aspects, the subject of the herein disclosed methods is a vertebrate, e.g., a mammal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

In some aspects of the disclosed methods, the subject has been diagnosed with a need for treatment prior to the administering step. In some aspects of the disclosed method, the subject has been diagnosed with a disorder associated with elevated TXNIP prior to the administering step. In some aspects of the disclosed methods, the subject has been identified with a need for treatment prior to the administering step. In one aspect, a subject can be treated prophylactically with a compound or composition disclosed herein, as discussed herein elsewhere.

a. Dosage

Toxicity and therapeutic efficacy of the agents and pharmaceutical compositions described herein can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio $LD_{50}/ED_{50}$.

Data obtained from cell culture assays and further animal studies can be used in formulating a range of dosage for use in humans. The dosage of such compounds lies preferably within a range of circulating concentrations that include the $ED_{50}$ with little or no toxicity, and with little or no adverse effect on a human's ability to hear. The dosage may vary within this range depending upon the dosage form employed and the route of administration utilized. For any agents used in the methods described herein, the therapeutically effective dose can be estimated initially from cell culture assays. A dose can be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Exemplary dosage amounts of a differentiation agent are at least from about 0.01 to 3000 mg per day, e.g., at least about 0.00001, 0.0001, 0.001, 0.01, 0.1, 1, 2, 5, 10, 25, 50, 100, 200, 500, 1000, 2000, or 3000 mg per kg per day, or more.

The formulations and routes of administration can be tailored to the disease or disorder being treated, and for the specific human being treated. For example, a subject can receive a dose of the agent once or twice or more daily for one week, one month, six months, one year, or more. The treatment can continue indefinitely, such as throughout the lifetime of the human. Treatment can be administered at regular or irregular intervals (once every other day or twice per week), and the dosage and timing of the administration can be adjusted throughout the course of the treatment. The dosage can remain constant over the course of the treatment regimen, or it can be decreased or increased over the course of the treatment.

In various aspects, the dosage facilitates an intended purpose for both prophylaxis and treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., (1990) Chapter 27 in Remington's Pharmaceutical Sciences, 18th Ed., Gennaro, ed., Mack Publishing Co., Easton, Pa.). In general, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., (1996) Chapter 3, In: Goodman & Gilman's The Pharmacological Basis of Therapeutics, 9th Ed., Hardman et al., eds., McGraw-Hill, New York, N.Y.).

b. Routes of Administration

Also provided are routes of administering the disclosed compounds and compositions. The compounds and compositions of the present invention can be administered by direct therapy using systemic administration and/or local administration. In various aspects, the route of administration can be determined by a patient's health care provider or clinician, for example following an evaluation of the patient. In various aspects, an individual patient's therapy may be customized, e.g., the type of agent used, the routes of administration, and the frequency of administration can be personalized. Alternatively, therapy may be performed using a standard course of treatment, e.g., using pre-selected agents and pre-selected routes of administration and frequency of administration.

Systemic routes of administration can include, but are not limited to, parenteral routes of administration, e.g., intravenous injection, intramuscular injection, and intraperitoneal injection; enteral routes of administration e.g., administration by the oral route, lozenges, compressed tablets, pills, tablets, capsules, drops (e.g., ear drops), syrups, suspensions and emulsions; rectal administration, e.g., a rectal suppository or enema; a vaginal suppository; a urethral suppository; transdermal routes of administration; and inhalation (e.g., nasal sprays).

In various aspects, the modes of administration described above may be combined in any order.

J. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Biology Experimentals

As an overview, the following steps were taken to identify and optimize lead compounds: (1) primary screening (compound library screen using an INS-1 cell line stably transfected with human TXNIP promoter luciferase reporter system and cultured in low (5 mM) or high glucose (25 mM) glucose; counter screen to exclude hits that also inhibit general transcription); (2) secondary screen of hits (dose response and cytotoxicity screen determining IC50 and cell death using (untransfected) INS-1 cells); (3) manual confirmation of hits by (a) performing transient co-transfection experiments using human TXNIP promoter driven firefly luciferase and pRK-TK driven renilla luciferase reporter constructs in the presence or absence of compound followed by dual luciferase reporter assays; (b) using quantitative real-time RT-PCR to determine the ability of hits to inhibit endogenous TXNIP mRNA expression); (c) Western blotting to confirm TXNIP inhibition at the protein level; (d) assessing TXNIP expression at low and high glucose in primary human islets treated with and without the compound; (e) apoptosis assays, to assess putative TXNIP inhibitors functionally for the capacity to protect against β-cell apoptosis e.g. by cleaved caspase-3 analysis; (4) animal testing (lead compounds from the previous screens and chemical optimization that have proven sufficiently potent in the cell model were tested in vivo in mice using STZ-diabetic mice including analysis of glucose homeostasis by blood glucose monitoring. Agents were selected based on efficacy, desirable pharmacokinetic properties, and lack of toxicity and off-target binding. Additional details are provided below.

a. Cell Culture and Treatment

The Rat INS-1 cell line was obtained from UAB and maintained in RPMI-1640 (Invitrogen #11875) supplemented with 10% fetal bovine serum (FBS), 100 U/ml penicillin and 100 mg/ml streptomycin, 10 mM HEPES, 1 mM Sodium Pyruvate, 50 μM 2-Mercaptoethanol, and 11.1 mM Glucose in a humidified incubator with a 5% $CO_2$ atmosphere at 37° C. $4 \times 10^4$ cells per well were seeded to 96-well plate and incubated at 37° C. overnight. A subset of the cells were then cultured in medium with 5 mM Glucose for 24 hrs and then treated in medium with 25 mM glucose with or without compounds to be tested for another 24 hrs.

For seeding cells, the cell composition is calculated and cells are diluted to $4 \times 10^5$ cells/ml. 100 μl are then added to each well and diluted to $4 \times 10^4$ cells/well.

b. Cell Transcfection

The human TXNIP promoter region including −1518 bp upstream of the ATG start codon was subcloned into the pGL4.17 [luc2/Neo] vector (Promega) to generate the luciferase reporter plasmid and was verified by sequencing.

To generate a stable cell line, INS-1 cells were transfected with this pGL4.17-human TXNIP promoter luciferase plasmid (0.4 μg/well) using DharmaFECT Duo transfection reagent (1 μl/well; Dharmacon). 48 h after transfection, Geneticin (100 μg/ml, Invitrogen) was added to select stable transfected cells. After all Geneticin-sensitive cells of the control wells (no transfection) had died, single clones were picked and the dose of Geneticin was reduced to the maintenance dose of 50 μg/ml, which was used thereafter for expansion and culture of these cells. Cells were maintained in medium containing 500 ml RPMI 1640 with 11.1 mM of glucose (Invitrogen, #11875), 50 ml FBS (Invitrogen, #16140), 5 ml Pen/Strep (Invitrogen, #15140), 5.5 ml 1M HEPES solution (Invitrogen, #15630), 5.5 ml 100× Sodium Pyruvate (Invitrogen, #11360), and 150 mg L-glutamine (Sigma, #G3126-100G) and for each 10 ml of medium, 35 μl of 1:1000 diluted 3-Mercaptoethanol (Fisher, #ICN19470583) as well as 10 μl of Geneticin (Invitrogen, #10131) were freshly added each time.

c. Luciferase Assay In certain assays in which cells were transfected with two promoters to determine specificity, a Dual-Luciferase® Reporter Assay System (Promega, CAT #E1960) was used according to commercial instructions. Briefly, 24 h after the transfection growth media was removed from the cultured cells. Cells were then rinsed with 200p PBS. After decanting the PBS, the cells were incubated in 25 μl of PLB with gentle rocking for 15 min at RT. Then 20 μl of cell lysate in PLB were transferred to Eppendorf tubes containing 100 μl of LAR (i.e., Luciferase Assay Substrate in Luciferase Assay Buffer). Cell lysates were then vortexed and firefly luciferase activity was measure. Then 100 μl of Stop&Glow solution were added to each sample. Samples were vortexed and Renilla luciferase activity was measured using a GLOMAX 20/20 Luminometer, with protocol "DLR-0-INJ".

d. Screening Assays

For the primary high throughput screening (HTS) assay, stably transfected, monoclonal INS-1 cells were split using Trypsin (2 ml per T75 flask) and seeded at a density of $10^4$/well in a 384-well plate and incubated overnight at low, 5 mM glucose. The next day, the medium was changed to high glucose (25 mM) or high glucose plus the small molecules to be tested and luciferase assays were performed 24 h later. Compounds capable of inhibiting glucose-induced TXNIP promoter activity by >50%, but found to be inactive in a counter-screen for general transcriptional inhibitors were further tested in a secondary qPCR HTS for their ability to reduce glucose-induced endogenous TXNIP expression in a dose-dependent manner. For secondary screens, total RNA was extracted from 96-well cultured cells using RNeasy 96 kit (Qiagen #74181) following the manufacturer's protocol using spin technology. Then a one-step qRT-PCR amplification was performed using QuantiFast SYBR Green RT-PCR kit (Qiagen #204154) and was carried out in a 10 µl reaction which consisted of 2 µl RNA, 0.5 µM each of primers (Rat TXNIP 5' primer: CGAGT-CAAAGCCGTCAGGAT (SEQ ID NO:1) and Rat TXNIP 3' primer: TTCATAGCGCAAGTAGTCCAAGGT (SEQ ID NO:2); Or Rat 18S rRNA 5' primer: AGTCCCTGCCCTTTGTACACA (SEQ ID NO:3) and Rat 18S rRNA 3' primer: GATCCGAGGGCCTCACTAAAC) (SEQ ID NO:4), 5 µl 2×SYBR Green Master Mix, 0.1 µl 10× QuantiFast RT Mix. The SYBR Green assay was performed using a LightCycler 480 II (Roche Applied Science) with an initial incubation at 50° C. for 10 min for RT followed by denaturation at 95° C. for 5 min. Forty cycles of amplification were performed using a thermal cycling profile of 95° C. for 10 s, 60° C. for 30 s. Subsequently, a melting curve was recorded by holding at 95° C. for 60 s, cooling to 60° C. for 60 s, and then heating at 0.11° C./s up to 95° C. The data was collected and analyzed using the LightCycler 480 Software Release 1.5.0 SP3. The relative amount of TXNIP mRNA was normalized to 18 s rRNA level as a housekeeping gene, and the data was analyzed according to the $2^{-\Delta\Delta CT}$ method (1). The transformed data was expressed as % inhibition and compound $IC_{50}$ calculated by a 4-parameter logistic fit of the data using GraphPad Prism 7.

The TXNIP inhibitory effect of lead compounds and derivatives was further confirmed manually using dual-luciferase assays including a control renilla luciferase plasmid, quantitative real-time RT-PCR and Western blotting with the anti-TXNIP IgG (JY2; #K0205-3; 1:1000; MBL, Woburn, Mass.), to assure compound-induced TXNIP inhibition also at the protein level.

e. Cell Viability Analysis

INS-1 cell viability was determined based on quantification of ATP using Cell Titer-Glo Luminescent Cell Viability Assay kit (Promega #G7572), which indicates the presence of metabolically active cells. Briefly, INS-1 cells were seeded into 96-well plates at a cell density of $4.5 \times 10^4$ and $3.5 \times 10^4$ cells per well and incubated overnight at 37° C. with 5% CO2. On the following day, cells were treated with compounds for 24 hrs and 72 hrs respectively. Cell Titer-Glo reagent was added to the cells and Luminescence was acquired on Synergy 4 Reader (PerkinElmer).

f. Primary Cell Cultures

Isolated primary human islets were cultured in the presence or absence of compound #11 (Table 1). The compound specifically inhibited glucose-induced TXNIP expression, as shown in FIG. 1. Compound #11 also protected human islets against Type 1 diabetes associated pro-inflammatory cytokine-induced TXNIP expression and 3-cell apoptosis, as shown in FIG. 2.

g. In Vivo Administration Decreases Blood Glucose Levels and Serum Glucagon Levels and Lowers Hepatic Glucose Production in Wild-Type Mice Compound #11a was administered for three weeks in the drinking water of wild-type mice at about 100 mg/kg/d. The treated mice showed no change in body weight as compared to untreated controls and no gross abnormalities in organs upon sacrifice. However, the treated mice showed a small but significant decrease in blood glucose levels. Fasting serum glucagon levels were decreased in treated mice as compared to control mice, suggesting compound #11a affected alpha cell glucagon secretion. Indeed, incubation of alpha TC1-6 cells with compound #11a resulted in decreased glucagon secretion.

Further studies of hepatic glucose production and whole body glucose turnover, i.e., peripheral glucose uptake into muscle and adipose tissue, were performed using hyperinsulinemic-euglycemic clamp studies. The treated mice showed a significant decrease in basal hepatic glucose production as compared to control. These results indicate compound #11a decreases serum glucagon levels and lowers hepatic glucose production.

h. In Vivo Administration Lowers Circulating Lipid Levels and Liver Triglycerides Oral administration of compound #11a to wild-type mice resulted in significantly lower levels of non-esterified fatty acids and of triglycerides in the serum as compared to control mice not receiving compound treatment. In addition, liver triglyceride levels in compound-treated mice were two-fold lower than in control mice.

i. In Vivo Administration Prevents/Reverses Diabetes in Two Different Models of Diabetes Oral administration of compound #11a (100 mg/kg/d) to mice starting after completion of the multiple low-dose STZ regimen, effectively protected against diabetes (FIG. 3). Of note, the mice maintained a normal body weight and no detrimental effects or abnormalities were noticed in response to compound treatment throughout the experiment or upon sacrifice and dissection.

Obese, insulin-resistant and diabetic, leptin receptor-deficient db/db mice were administered compound #11a as described above for 4 weeks. Similar to the STZ-treated mice, the db/db mice showed no difference in body weight as compared to untreated db/db mice. However, blood glucose levels in the treated animals decreased significantly within days of starting treatment with compound #11a and remained within the normal range for the remainder of the study (FIG. 3). The treated mice showed a significant decrease in fasting serum glucagon levels similar to the decrease observed in lean wild-type mice. Thus, certain substituted quinazoline sulfonamides possess good pharmacokinetic properties and are capable of effectively inhibiting TXNIP expression, lowering glucagon levels and hepatic glucose production and of treating and preventing diabetes. In addition, they can lower liver and serum lipid levels j. In Vivo Administration Improves STZ-Induced Diabetes in a Dose Dependent Manner After having been rendered overtly diabetic by multiple low-dose STZ injections, mice received compound #11a by gavage at a dose of 100 mg/kg b.i.d or 30 mg/kg b.i.d. or received a vehicle control. Blood glucose levels significantly decreased in a dose-dependent manner in the mice receiving compound #11a, whereas hyperglycemia continued to worsen in vehicle treated mice.

2. Chemistry Experimentals a. General Synthesis of Substituted (quinazolin-4-yl)piperidin-3-yl)methyl)methanesulfonamides (Cmpds 1-14)

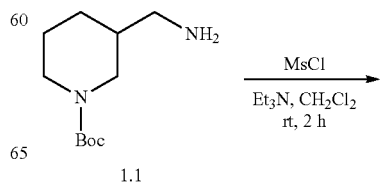

1.1

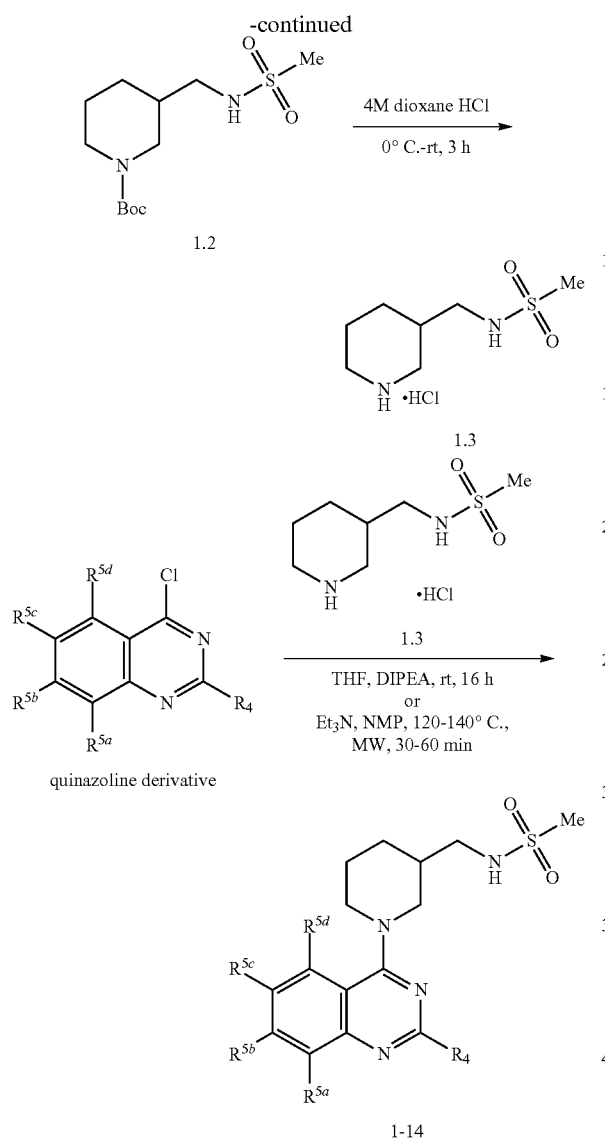

anhydrous $Na_2SO_4$ and concentrated under reduced pressure to afford 1.2 (2.0 g, crude) as a thick colorless liquid. MS (MM): m/z=193.0 [M-Boc]$^+$.

ii. Preparation of tert-butyl 3-(methylsulfonamidomethyl)piperidine-1-carboxylate (1.3)

To a stirred solution of 1.2 (2.0 g, 6.81 mmol) in 1, 4-dioxane HCl (4M, 2 mL) was stirred at RT for 2 h. Upon complete consumption of starting material, the reaction mixture was concentrated under reduced pressure. The residue was co-distilled with toluene (3×25 mL) to afford 1.3 (1.5 g, crude) as a white solid. $^1$H NMR (300 MHz, DMSO-d$_6$): δ 9.18-8.98 (m, 1H), 7.23 (t, J=6.0 Hz, 1H), 3.23-3.15 (m, 2H), 3.23-315 (m, 2H), 2.89-2.73 (m, 1H), 2.70 (s, 3H), 2.68-2.56 (m, 3H), 1.91-1.62 (m, 4H), 1.22-1.16 (m, 1H).

iii. Preparation of Compounds 1-14

To a solution of 1.3 (0.548 mmol) and DIEA (0.15 ml) in THF/NMP (8 mL) was added the appropriate quinazoline (0.548 mmol) and the reaction mixture was stirred at RT for 16 h or irradiated at 120-140° C. for 30-60 minutes. Upon complete consumption of the starting material, the reaction mixture was poured into water (20 mL), extracted with EtOAc (2×20 mL). The organic extracts were washed with water (2×20 mL), brine (20 mL), dried over anhydrous $Na_2SO_4$ and concentrated under reduced pressure. The residue was purified by silica gel column chromatography to afford desired compounds 1-14.

a. N-((1-(6-fluoroquinazolin-4-yl)piperidin-3-yl)methyl)methanesulfonamide (1)

Yield: 48%; 1H NMR (400 MHz, DMSO-d6) δ 8.62 (s, 1H), 7.89 (dd, J=9.2, 5.6 Hz, 1H), 7.75 (ddd, J=9.2, 8.3, 2.8 Hz, 1H), 7.65 (dd, J=9.8, 2.8 Hz, 1H), 7.13 (t, J=6.2 Hz, 1H), 4.26 (d, J=12.9 Hz, 1H), 4.13 (d, J=13.2 Hz, 1H), 3.15 (td, J=13.1, 12.3, 2.8 Hz, 1H), 3.01-2.82 (m, 2H), 2.89 (s, 3H), 1.92-1.77 (m, 3H), 1.68 (q, J=12.5, 12.0 Hz, 1H), 1.37-1.22 b. N-((1-(5-fluoroquinazolin-4-yl)piperidin-3-yl)methyl)methanesulfonamide (2)

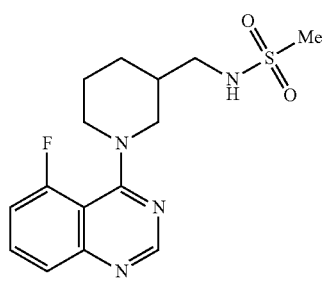

Yield: 44%; 1H NMR (400 MHz, DMSO-d6) δ 8.62 (s, 1H), 7.89 (dd, J=9.2, 5.6 Hz, 1H), 7.75 (ddd, J=9.2, 8.3, 2.8 Hz, 1H), 7.65 (dd, J=9.8, 2.8 Hz, 1H), 7.13 (t, J=6.2 Hz, 1H), 4.26 (d, J=12.9 Hz, 1H), 4.13 (d, J=13.2 Hz, 1H), 3.15 (td, J=13.1, 12.3, 2.8 Hz, 1H), 3.01-2.82 (m, 2H), 2.89 (s, 3H), 1.92-1.77 (m, 3H), 1.68 (q, J=12.5, 12.0 Hz, 1H), 1.37-1.22 (m, 1H); FABMS (M+H) calculated for $C_{15}H_{19}FN_4O_2S.H$ was 339.1286 found 339.1294; HPLC purity >99 (% of AUC), $t_R$=2.3, 2.41 minutes.

c. N-((1-(8-fluoroquinazolin-4-yl)piperidin-3-yl)methyl)methanesulfonamide (3)

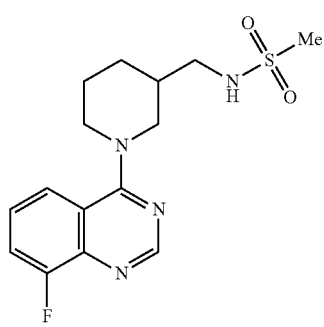

Yield: 62%; 1H NMR (400 MHz, DMSO-d6) δ 8.61 (s, 1H), 7.77 (dt, J=8.4, 1.1 Hz, 1H), 7.64 (ddd, J=10.6, 7.9, 1.1 Hz, 1H), 7.53-7.42 (m, 1H), 7.11 (t, J=6.1 Hz, 1H), 4.37-4.28 (m, 1H), 4.20 (d, J=13.2 Hz, 1H), 3.17 (ddd, J=13.1, 11.4, 2.9 Hz, 1H), 3.00-2.80 (m, 2H), 2.88 (s, 3H), 1.91-1.75 (m, 3H), 1.65 (q, J=11.5 Hz, 1H), 1.38-1.22 (m, 1H); FABMS (M+H) calculated for $C_{15}H_{19}FN_4O_2S.H$ was 339.1286 found 339.1288; HPLC purity >96 (% of AUC), $t_R$=2.23, 2.52 minutes.

d. N-((1-(7-fluoroquinazolin-4-yl)piperidin-3-yl)methyl)methanesulfonamide (4)

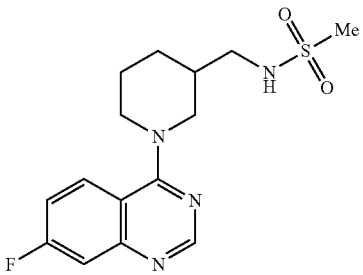

Yield: 38%; 1H NMR (400 MHz, DMSO-d6) δ 8.57 (s, 1H), 8.03 (dd, J=9.3, 6.2 Hz, 1H), 7.51 (dd, J=10.2, 2.7 Hz, 1H), 7.38 (ddd, J=9.2, 8.4, 2.8 Hz, 1H), 7.10 (t, J=6.1 Hz, 1H), 4.29 (d, J=13.3 Hz, 1H), 4.16 (d, J=13.2 Hz, 1H), 3.17 (s, 1H), 3.00-2.80 (m, 3H), 2.88 (s, 3H), 1.91-1.74 (m, 3H), 1.65 (d, J=12.9 Hz, 1H); FABMS (M+H) calculated for $C_{15}H_{19}FN_4O_2S.H$ was 339.1286 found 339.1296; HPLC purity >96 (% of AUC), $t_R$=1.2, 2.38 minutes.

e. N-((1-(6-methoxyquinazolin-4-yl)piperidin-3-yl)methyl)methanesulfonamide (5)

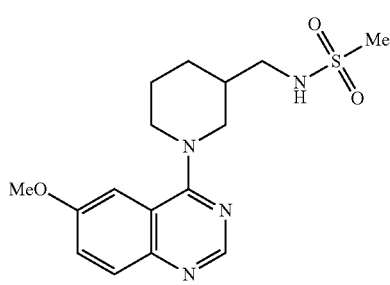

Yield: 28%; 1H NMR (400 MHz, DMSO-d6) δ 8.5 (s, 1H), 7.74 (d, J=9.1 Hz, 1H), 7.46 (dd, J=9.1, 2.8 Hz, 1H), 7.17-7.09 (m, 2H), 4.25 (d, J=12.8 Hz, 1H), 4.09 (d, J=13.2 Hz, 1H), 3.30 (s, 11H), 3.08-2.88 (m, 1H), 2.89-2.69 (m, 1H), 1.95-1.77 (m, 1H), 1.32-1.14 (m, 1H); FABMS (M+H) calculated for $C_{16}H_{22}N_4O_3S.H$ was 351.1485 found 351.1479; HPLC purity >95 (% of AUC), $t_R$=2.65, 2.72 minutes.

f. N-((1-(5-chloroquinazolin-4-yl)piperidin-3-yl)methyl)methanesulfonamide (6)

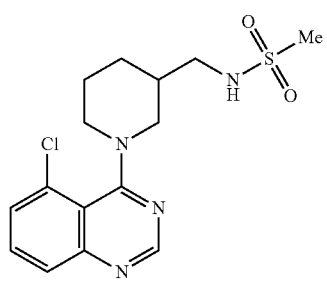

Yield: 40%; ¹H NMR (400 MHz, DMSO-d₆) δ 8.57 (s, 1H), 8.46 (s, 1H), 7.77-7.63 (m, 3H), 7.62 (d, J=4.1 Hz, 0H), 7.54 (d, J=6.7 Hz, 1H), 7.08-6.99 (m, 1H), 4.11-3.95 (m, 2H), 3.92 (d, J=13.0 Hz, 1H), 3.81 (d, J=12.9 Hz, 1H), 3.33 (s, 1H), 3.14 (t, J=11.7 Hz, 1H), 2.53 (d, J=11.5 Hz, 1H), 1.97 (s, 1H), 1.86 (d, J=12.4 Hz, 1H), 1.79 (s, 1H), 1.73 (s, OH), 1.63 (d, J=17.6 Hz, 1H), 1.30 (s, 2H), 1.14 (q, J=8.0, 7.6 Hz, 1H); FABMS (M+H) calculated for $C_{15}H_{19}ClN_4O_2S \cdot H$ was 355.0990 found 355.0982; HPLC purity >99 (% of AUC), $t_R$=2.77 minutes.

g. N-((1-(6,7-difluoroquinazolin-4-yl)piperidin-3-L)methyl)methanesulfonamide (7)

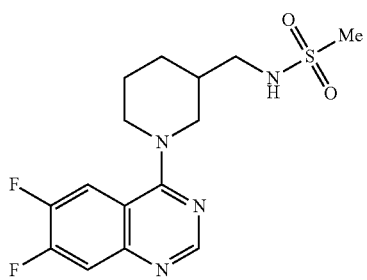

Yield: 32%; 1H NMR (400 MHz, DMSO-d6) δ 8.59 (s, 1H), 7.89 (dd, J=11.5, 8.7 Hz, 1H), 7.80 (dd, J=11.6, 7.9 Hz, 1H), 7.10 (t, J=6.1 Hz, 1H), 4.28-4.19 (m, 1H), 4.11 (d, J=13.2 Hz, 1H), 3.16 (ddd, J=13.0, 11.3, 2.9 Hz, 1H), 3.00-2.86 (m, 2H), 2.87 (s, 4H), 2.85 (d, J=6.3 Hz, 1H), 1.89-1.73 (m, 2H), 1.64 (q, J=11.9 Hz, 1H), 1.35-1.20 (m, 1H); FABMS (M+H) calculated for $C_{15}H_{18}F_2N_4O_2S \cdot H$ was 357.1191 found 357.1183; HPLC purity >98 (% of AUC), $t_R$=3.11 minutes.

h. N-((1-(6,7-dimethoxyquinazolin-4-yl)piperidin-3-yl)methyl)methanesulfonamide (8)

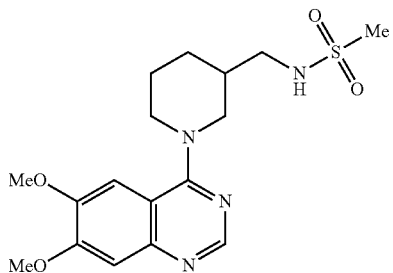

1H NMR (400 MHz, Chloroform-d) δ 8.61 (d, J=1.0 Hz, 1H), 7.27 (d, J=7.0 Hz, 1H), 7.07 (s, 1H), 4.84 (s, 1H), 4.17-4.05 (m, 2H), 4.04-3.93 (m, 6H), 3.13 (ddd, J=15.9, 9.6, 2.8 Hz, 2H), 3.03 (ddd, J=14.0, 7.7, 6.3 Hz, 1H), 2.93 (dd, J=12.9, 9.9 Hz, 1H), 2.00-1.74 (m, 2H), 1.41 (s, 10H), 1.39-1.21 (m, 1H); MS (MM) m/z 402.2 (M+H)⁺.

i. N-((1-(2-phenylquinazolin-4-yl)piperidin-3-yl)methyl)methanesulfonamide (9)

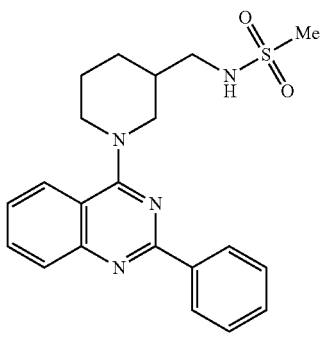

Yield: 29%; 1H NMR (400 MHz, DMSO-d6) δ 8.50 (d, J=6.5 Hz, 2H), 7.98 (d, J=8.3 Hz, 1H), 7.86 (d, J=7.8 Hz, 1H), 7.80 (d, J=7.6 Hz, 1H), 7.49 (s, 2H), 7.18 (t, J=6.2 Hz, 1H), 4.43 (d, J=12.8 Hz, 1H), 4.29 (d, J=12.9 Hz, 1H), 3.22 (d, J=12.6 Hz, 1H), 2.99 (d, J=14.5 Hz, 3H), 2.89 (s, 3H), 1.97 (s, 1H), 1.85 (d, J=20.6 Hz, 3H), 1.70 (s, 1H), 1.32 (d, J=11.3 Hz, 1H); FABMS (M+H) calculated for $C_{21}H_{24}N_4O_2S \cdot H$ was 397.1693 found 397.1688; HPLC purity >99 (% of AUC), $t_R$=3.66 minutes.

j. N-((1-(8-chloro-6-fluoroquinazolin-4-yl)piperidin-3-yl)methyl)methanesulfonamide (10)

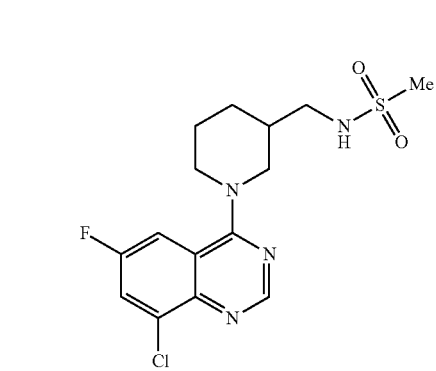

Yield: 34%; ¹H NMR (400 MHz, DMSO-d6): δ 8.67 (s, 1H), 8.09 (dd, J=2.8 Hz, J=8.4 Hz, 1H), 7.65 (dd, J=2.8 Hz, J=9.6 Hz, 1H), 7.11 (t, J=6.0 Hz, 1H), 4.27 (d, J=12.8 Hz, 1H), 4.14 (d, J=12.8 Hz, 1H), 3.24-3.16 (m, 1H), 2.98-2.89 (m, 6H), 1.91-1.78 (m, 3H), 1.71-1.65 (m, 1H), 1.35-1.26 (m, 1H); MS (MM) m/z 373.0 [M]⁺; HPLC purity: >99 (% of AUC).

k. N-((1-(6-(trifluoromethyl)quinazolin-4-yl)piperidin-3-yl)methyl)methanesulfonamide (11)

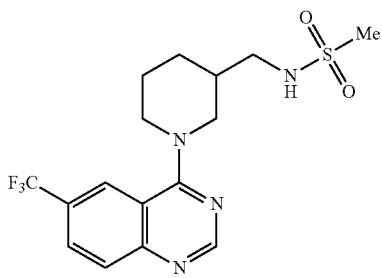

11

Yield: 19%; 1H NMR (400 MHz, DMSO-d6) δ 8.66 (s, 1H), 8.22-8.16 (m, 1H), 8.04 (dd, J=8.8, 1.9 Hz, 1H), 7.97-7.90 (m, 1H), 7.08 (t, J=6.2 Hz, 1H), 4.38 (d, J=13.0 Hz, 1H), 4.21 (d, J=13.2 Hz, 1H), 3.31-3.18 (m, 1H), 3.01 (dd, J=13.1, 10.1 Hz, 1H), 2.98-2.80 (m, 2H), 2.87 (s, 3H), 1.85 (m, 3H), 1.79 (s, 1H), 1.62 (s, 1H); FABMS (M+H) calculated for $C_{16}H_{19}F_3N_4O_2S.H$ was 389.1254 found 389.1243; HPLC purity >92 (% of AUC), $t_R$=3.99 minutes.

l. N-((1-(7-(trifluoromethyl)quinazolin-4-yl)piperidin-3-yl)methyl)methanesulfonamide (12)

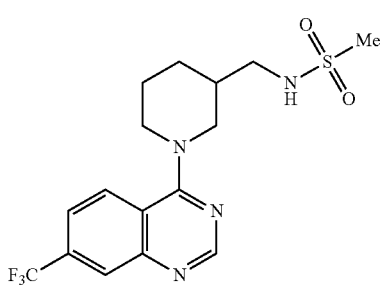

12

Yield: 77%; 1H NMR (400 MHz, DMSO-d6) δ 8.66 (s, 1H), 8.17 (d, J=8.7 Hz, 1H), 8.08 (dd, J=2.0, 1.0 Hz, 1H), 7.73 (dd, J=8.8, 2.0 Hz, 1H), 7.16-7.08 (m, 1H), 4.41-4.32 (m, 1H), 4.23 (d, J=13.3 Hz, 1H), 3.47-3.28 (m, 1H), 3.28-3.16 (m, 1H), 3.04-2.81 (m, 2H), 2.88 (s, 3H), 1.91-1.75 (m, 3H), 1.66 (q, J=12.3, 11.9 Hz, 1H), 1.40-1.25 (m, 1H); FABMS (M+H) calculated for $C_{16}H_{19}F_3N_4O_2S.H$ was 389.1254 found 389.1246; HPLC purity >96 (% of AUC), $t_R$=10.71 minutes.

m. N-((1-(6-cyanoquinazolin-4-yl)piperidin-3-yl)methyl)methanesulfonamide (13)

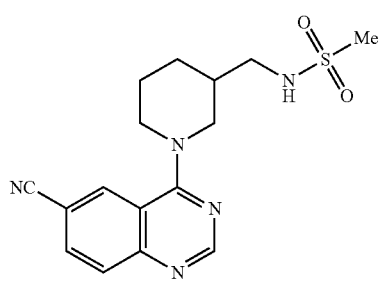

13

Yield: 79%; 1H NMR (400 MHz, DMSO-d6) δ 8.66 (s, 1H), 8.17 (d, J=8.7 Hz, 1H), 8.08 (dd, J=2.0, 1.0 Hz, 1H), 7.73 (dd, J=8.8, 2.0 Hz, 1H), 7.16-7.08 (m, 1H), 4.41-4.32 (m, 1H), 4.23 (d, J=13.3 Hz, 1H), 3.47-3.28 (m, 1H), 3.28-3.16 (m, 1H), 3.04-2.81 (m, 2H), 2.88 (s, 3H), 1.91-1.75 (m, 3H), 1.66 (q, J=12.3, 11.9 Hz, 1H), 1.40-1.25 (m, 1H); FABMS (M+H) calculated for $C_{16}H_{19}N_5O_2S.H$ was 389.1254 found 389.1246; HPLC purity >99 (% of AUC), $t_R$=1.44 minutes.

n. N-((1-(6-(methylsulfonyl)quinazolin-4-yl)piperidin-3-yl)methyl)methanesulfonamide (14)

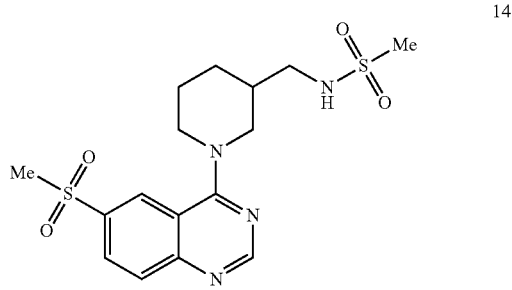 [SMILES: CS(=O)(=O)NCC1CCCN(c2ncnc3ccc(S(C)(=O)=O)cc23)C1]

14

Yield: 26%; $^1$H NMR (400 MHz, DMSO-d$_6$): δ 8.69 (s, 1H), 8.43 (s, 1H), 8.23 (dd, J=1.6 Hz, J=8.8 Hz, 1H), 7.96 (d, J=8.8 Hz, 1H), 7.12 (t, J=6.0 Hz, 1H), 4.46 (d, J=13.2 Hz, 1H), 4.27 (d, J=12.8 Hz, 1H), 3.40-3.33 (m, 4H), 3.12-3.06 (m, 1H), 2.97-2.94 (m, 2H), 2.89 (s, 3H), 1.94-1.82 (m, 3H), 1.67-1.65 (m, 1H), 1.45-1.35 (m, 1H); MS (MM) m/z 399.1 [M+H]$^+$.

b. Synthesis of N-((1-(6-(trifluoromethyl)quinazolin-4-yl)piperidin-3-yl)methyl)methanesulfonamide hydrochloride (11A)

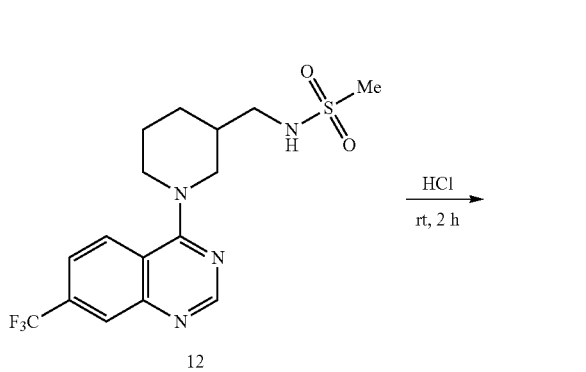

12

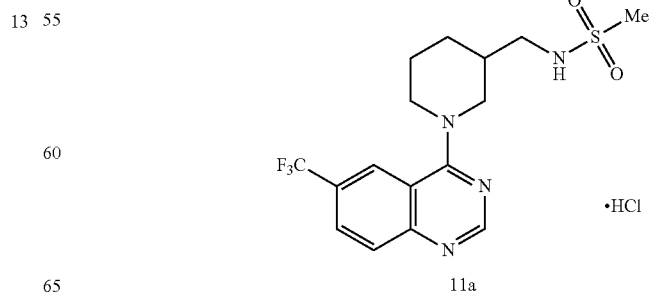

11a

A stirred solution of 12 (50 mg, mmol) in HCl (4.0 M in 1, 4-dioxane) (2 mL) was stirred at RT for 2 h. Upon complete consumption of starting material, the reaction mixture was concentrated under reduced pressure to afford 11a (30 mg, 34% as a yellow solid. $^1$H NMR (300 MHz, DMSO-$d_6$): δ 8.86 (s, 1H), 8.36 (s, 1H), 8.27 (d, J=9.0 Hz, 1H), 8.03 (d, J=8.7 Hz, 1H), 7.18 (t, J=6.0 Hz, 1H), 4.70 (d, J=10.2 Hz, 1H), 4.49 (d, J=12.0 Hz, 1H), 3.63 (t, J=11.7 Hz, 1H), 3.36 (t, J=10.8 Hz, 1H), 2.96 (t, J=7.2 Hz, 1H), 2.92 (s, 3H), 2.0-1.8 (m, 3H), 1.78-1.64 (m, 1H), 1.47-1.38 (m, 1H); MS (MM) m/z 389.1 [M+H]$^+$; HPLC Purity: >99 (% of AUC).

c. Synthesis of N-((1-(2-isopropylquinazolin-4-yl)piperidin-3-yl)methyl)methanesulfonamide (15)

i. Preparation of N-((1-(2-chloroquinazolin-4-yl)piperidin-3-yl)methyl)methanesulfonamide

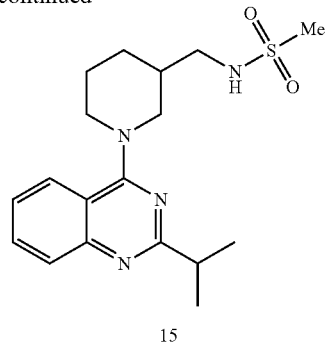

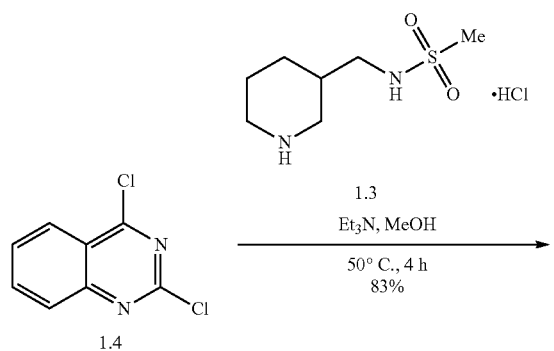

To a stirred solution of 2,4-dichloroquinazoline 1.4 (500 mg, 2.48 mmol) in MeOH (50 mL) was added 1.3 (621 mg, 2.73 mmol) and Et$_3$N (0.95 mL, 7.44 mmol) at RT. The reaction mixture was stirred at 50° C. for 4 h. Upon complete consumption of starting material, the reaction mixture was poured into water (25 mL), extracted with EtOAc (2×25 mL). The organic extracts were washed with saturated NaHCO$_3$ (25 mL), water (25 mL), brine (25 mL), dried over anhydrous Na$_2$SO$_4$ and concentrated under reduced pressure. The residue was purified by silica gel column chromatography (gradient elution 5-10% of MeOH in CH$_2$Cl$_2$) to afford 1.5 (735 mg, 83%).

ii. Preparation of N-((1-(2-isopropylquinazolin-4-yl)piperidin-3-yl)methyl)methanesulfonamide (15)

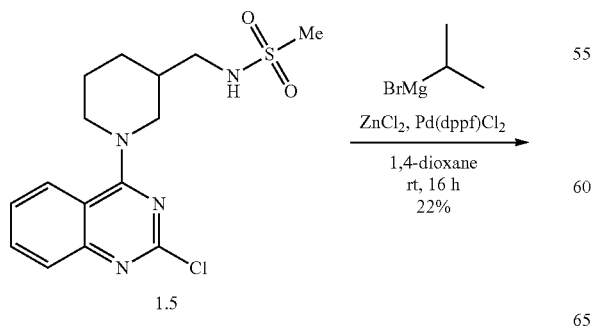

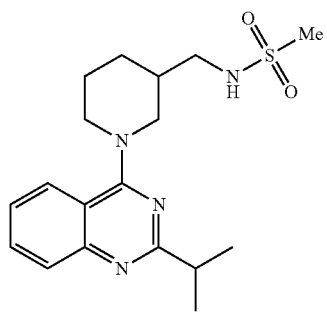

To a suspension of ZnCl$_2$ (1 mL, 1.05 mmol) in 1,4-dioxane (2 mL) was added isopropyl magnesium bromide (1 mL) and 1.5 (150 mg, 0.42 mmol) at RT. The reaction mixture as stirred at RT for 16 h. Upon complete consumption of the starting material, the reaction mixture was filtered through celite pad. The filtrate was diluted with EtOAc (25 mL), washed with saturated NaHCO$_3$ (25 mL), water (25 mL), brine (25 mL), dried over anhydrous Na$_2$SO$_4$ and concentrated under reduced pressure. The residue was purified by silica gel column chromatography (gradient elution 5-10% of MeOH in methylene chloride) to afford 15 (36 mg, 22%) as off-white solid. $^1$H NMR (400 MHz, MeOD): δ 7.66 (d, J=8.4 Hz, 1H), 7.42 (t, J=4.4 Hz, 1H), 7.28 (d, J=8.4 Hz, 1H), 7.01-6.98 (m, 1H), 4.23-4.05 (m, 3H), 3.10-2.85 (m, 3H), 2.82 (s, 3H), 2.78-2.51 (m, 1H), 1.96-1.85 (m, 2H), 1.78-1.73 (m, 1H), 1.70-1.59 (m, 1H), 1.31-1.16 (m, 1H), 1.15 (d, J=5.6 Hz, 6H); MS (MM) m/z 363.2 [M+H]$^+$; HPLC purity: >95 (% of AUC).

d. Synthesis of N-((1-(2-(isopropylamino)quinazolin-4-yl)piperidin-3-yl)methyl)methanesulfonamide (16)

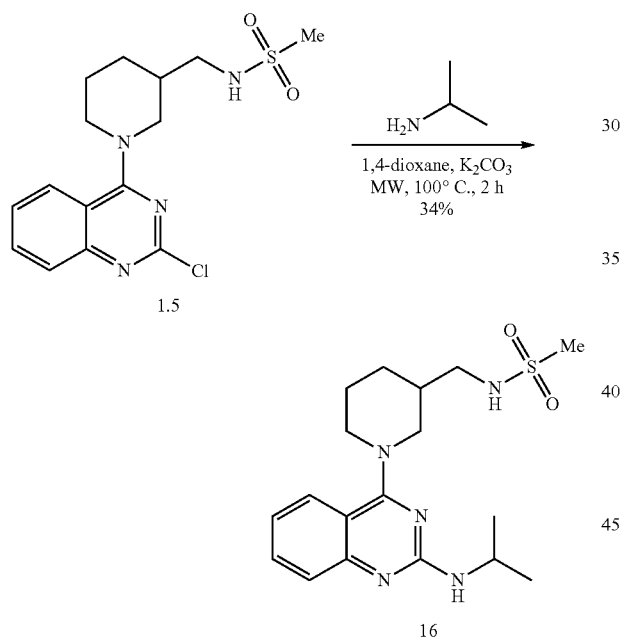

To a stirred solution of 1.5 (200 mg, 0.56 mmol) in 1,4-dioxane (2 mL) taken in a microwave vial was added isopropyl amine (99 mg, 1.68 mmol) and K$_2$CO$_3$ (232 mg, 1.68 mmol). The microwave vial was sealed and irradiated at 100° C. for 2 h in CEM-microwave instrument. Upon complete consumption of starting material, the reaction mixture was poured into water (20 mL), extracted with EtOAc (2×25 mL). The organic extracts were washed with saturated NaHCO$_3$ (25 mL), water (25 mL), brine (25 mL), dried over anhydrous Na$_2$SO$_4$ and concentrated under reduced pressure. The residue was purified by silica gel column chromatography (gradient elution 90-100% of EtOAc in hexanes) to afford 16 (73 mg, 34%) as an off-white solid. $^1$H NMR (400 MHz, CDCl$_3$): δ 7.57 (d, J=8.4 Hz, 1H), 7.44-7.39 (m, 2H), 6.96 (t, J=6.8 Hz, 1H), 4.90 (d, J 7.2 Hz, 1H), 4.20-4.15 (m, 1H), 3.78 (brs, 2H), 3.47-3.40 (m, 2H), 3.05-2.95 (m, 2H), 2.87 (s, 3H), 2.02 (brs, 1H), 1.86 (brs, 1H), 1.65-1.58 (m, 2H), 1.38-1.36 (m, 1H), 1.25-1.16 (m, 6H); MS (MM) m/z 378.1 [M+H]$_+$; HPLC purity: >94 (% of AUC).

e. Synthesis of N-((1-(2-morpholinoquinazolin-4-yl)piperidin-3-yl)methyl)methanesulfonamide (17)

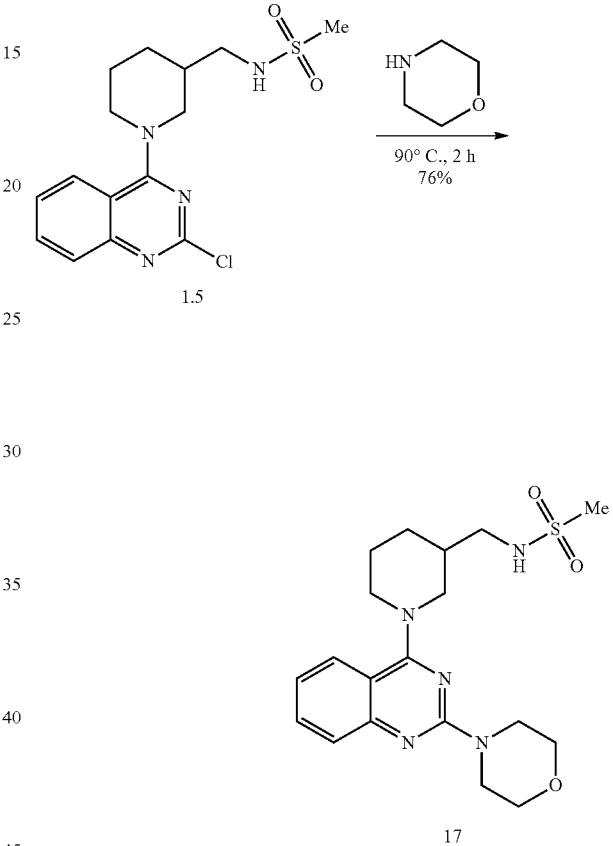

A stirred solution of 1.5 (200 mg, 0.56 mmol) in morpholine (0.20 mL) was allowed to stir at 90° C. for 2 h. Upon complete consumption of starting material, the reaction mixture was poured into water, extracted with EtOAc (2×20 mL). The combined extracts were washed with saturated NaHCO$_3$ (20 mL), water (20 mL), brine (20 mL), dried over anhydrous Na$_2$SO$_4$ and concentrated under reduced pressure. The residue was purified by silica gel column chromatography (gradient elution 70-80% of EtOAc in hexanes) to afford 17 (173 mg, 76%) as off white solid. $^1$H NMR (400 MHz, DMSO-d6): δ 7.75 (d, J=8 Hz, 1H), 7.57-7.53 (m, 1H), 7.40-7.36 (m, 1H), 7.17-7.09 (m, 2H), 4.19 (d, J=12.4 Hz, 1H), 4.06 (d, J=13.2 Hz, 1H), 3.76-3.74 (m, 4H), 3.67-3.65 (m, 4H), 3.09 (t, J=10.8 Hz, 1H), 2.96-2.92 (m, 1H), 2.89 (s, 3H), 2.88-2.77 (m, 2H), 1.91-1.85 (m, 2H), 1.79-1.76 (m, 1H), 1.67-1.58 (m, 1H), 1.34-1.23 (m, 1H); MS (MM) m/z 406.1 [M+H]$^+$; HPLC purity: >98 (% of AUC).

f. Synthesis of 4-(3-(methylsulfonamidomethyl) piperidin-1-yl)quinazoline-7-carboxylic acid (18)

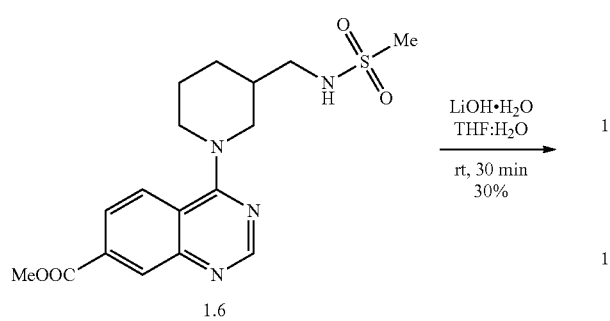

iii. Preparation of 4-(3-(methylsulfonamidomethyl) piperidin-1-yl)quinazoline-7-carboxylic acid (18)

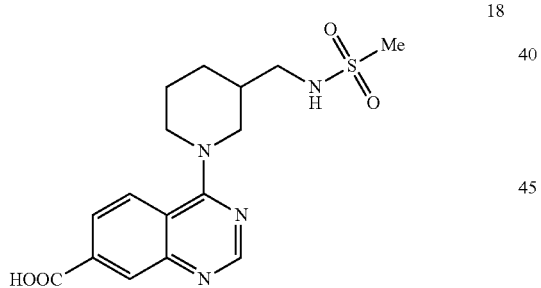

To a stirred solution of 1.6 (60 mg, 0.15 mmol) in THF (5 mL), H₂O (5 mL) and was added LiOH.H₂O (13.3 mg, 0.31 mmol), at RT. The reaction mixture was stirred at RT for 30 min. Upon complete consumption of starting material, the reaction mixture was concentrated under reduced pressure. The residue was diluted with water (5 mL) and acidified with 2N HCl to $P^H$ 2-3. The precipitated solid was filtered and vacuum dried to afford 18 (17 mg, 30%) as an off-white solid. ¹H NMR (400 MHz, DMSO-d6): δ 8.86 (s, 1H), 8.63 (s, 1H), 8.36 (d, J=1.6 Hz, 1H), 8.23 (d, J=8.8 Hz, 1H), 8.08 (dd, J=1.6 Hz, J=8.4 Hz, 1H), 7.26 (t, J=6.4 Hz, 1H), 4.71 (t, J=12.4 Hz, 2H), 3.52 (br s, 2H), 3.30 (t, J=12 Hz, 1H), 3.05-3.00 (m, 1H), 2.91 (s, 3H), 1.99 (br s, 1H), 1.90 (d, J=4.8 Hz, 2H), 1.72 (d, J=13.6 Hz, 1H), 1.48-1.39 (m, 1H); MS (MM) m/z 365.1 [M+H]⁺; HPLC purity >97 (% of AUC).

g. Synthesis of 4-(3-(methylsulfonamidomethyl) piperidin-1-yl)quinazoline-6-carboxylic acid (19)

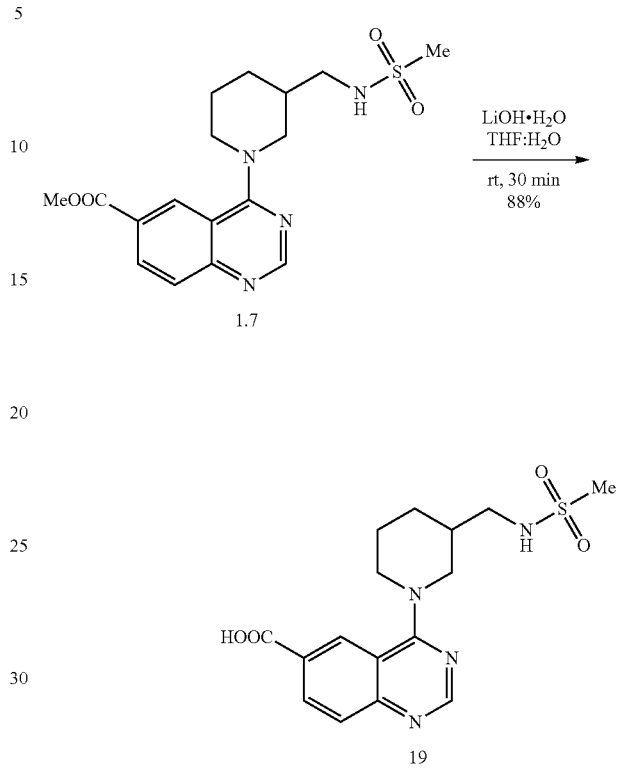

i. Preparation of methyl 4-(3-(methylsulfonamidomethyl)piperidin-1-yl)quinazoline-6-carboxylate (1.7)

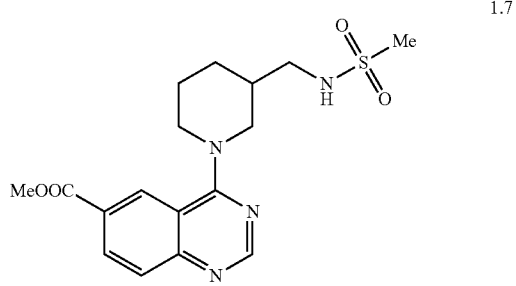 [SMILES: COC(=O)c1ccc2ncnc(N3CCCC(CNS(C)(=O)=O)C3)c2c1]

1.7 was made following the same procedure described above for compounds 1-14. Yield: 51% as a white solid; ¹H NMR (400 MHz, CDCl₃): δ 8.68 (s, 1H), 8.62 (s, 1H), 8.28 (dd, J=1.6 Hz, J=8.4 Hz 1H), 7.87 (d, J=8.8 Hz, 1H), 5.61 (t, J=6.4 Hz, 1H), 4.23-4.12 (m, 2H), 3.98 (s, 3H), 3.66-3.55 (m, 2H), 3.24-3.11 (m, 2H), 2.99 (s, 3H), 2.22-2.19 (m, 1H), 2.04-21.99 (m, 1H), 1.81-1.79 (m, 3H), 1.55-1.51 (m, 1H); MS (MM) m/z 379.1 [M+H]⁺.

ii. Preparation of 4-(3-(methylsulfonamidomethyl)piperidin-1-yl)quinazoline-6-carboxylic acid (19)

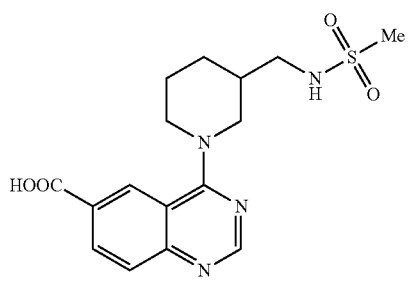

To a stirred solution of 1.7 (75 mg, 0.13 mmol) in THF (5 mL), H$_2$O (5 mL) and was added LiOH.H$_2$O (11 mg, 0.26 mmol) at RT. The reaction mixture was stirred at RT for 30 min. Upon complete consumption of starting material, the reaction mixture was concentrated under reduced pressure. The residue was diluted with water (5 mL), acidified with 2N HCl to P$^H$ 2-3. The precipitated solid was filtered and vacuum dried to get the 19 (63 mg, 88%) as a white solid. $^1$H NMR (300 MHz, DMSO-d6): δ 8.84 (s, 1H), 8.63 (s, 1H), 8.42 (d, J=8.1 Hz, 1H), 8.09 (d, J=8.4 Hz, 1H), 7.28 (br s, 1H), 4.76 (br s, 1H), 4.48 (d, J=11.7 Hz, 1H), 3.68 (d, J=12 Hz, 2H), 2.95 (br s, 2H), 2.89 (s, 3H), 1.90 (d, J=8.1 Hz, 3H), 1.72 (d, J=9.3 Hz, 1H), 1.46 (d, J=9.0 Hz, 1H); MS (MM) m/z 365.1 [M+H]$^+$; HPLC purity >95 (% of AUC).

h. Synthesis of N-((1-(7-cyano-6-fluoroquinazolin-4-yl)piperidin-3-yl)methyl)methanesulfonamide (20)

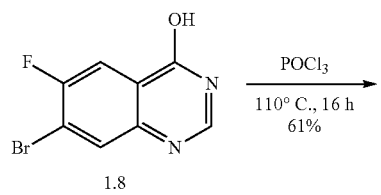

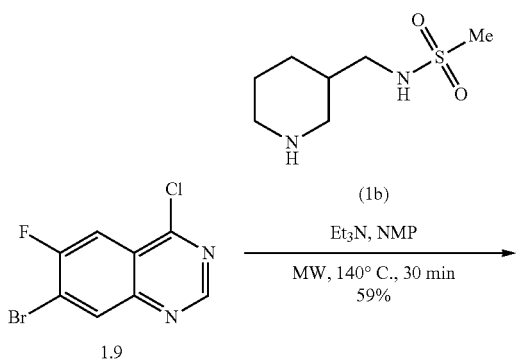

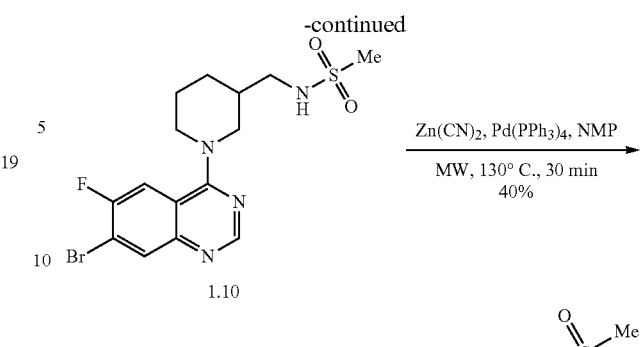

i. Preparation of N-((1-(7-bromo-6-fluoroquinazolin-4-yl)piperidin-3-yl)methyl)methane-sulfonamide (1.10)

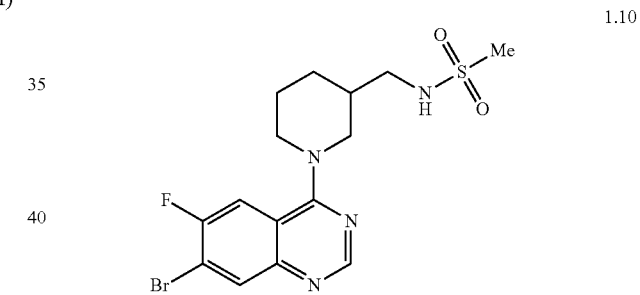

A stirred solution of 7-bromo-6-fluoroquinazolin-4-ol 1.8 (2.0 g, 8.33 mmol) in POCl$_3$ (10 mL) was stirred at 110° C. for 16 h. Upon complete consumption of starting material, the reaction mixture was concentrated under reduced pressure, the residue was taken in ice cold water (20 mL), extracted with EtOAc (2×25 mL). The organic extracts were washed with water (2×25 mL), brine (25 mL), dried over anhydrous Na$_2$SO$_4$ and concentrated under reduced pressure. The residue was purified by silica gel column chromatography (gradient elution 30-40% of EtOAc in hexanes) to afford 7-bromo-4-chloro-6-fluoroquinazoline 1.9 (1.3 g, 61%) as a yellow solid. To a stirred solution of 1.9 (200 mg, 0.77 mmol) in NMP (2 mL) taken in a microwave vial was added 1.3 (225 mg, 0.99 mmol) and Et$_3$N (0.29 mL, 2.32 mmol). The microwave vial was sealed and irradiated at 140° C. for 30 min in CEM-microwave instrument. Upon complete consumption of the starting material, the reaction mixture was poured into water (20 mL), extracted with EtOAc (2×20 mL). The organic extracts were washed with water (2×20 mL), brine (20 mL), dried over anhydrous Na$_2$SO$_4$ and concentrated under reduced pressure. The residue was purified by silica gel column chromatography (gradient elution 70-80% of EtOAc in hexanes) to afford 1.10 (190 mg, 59%) as a yellow solid.

ii. Preparation of N-((1-(7-cyano-6-fluoroquinazolin-4-yl)piperidin-3-yl)methyl)methanesulfonamide (20)

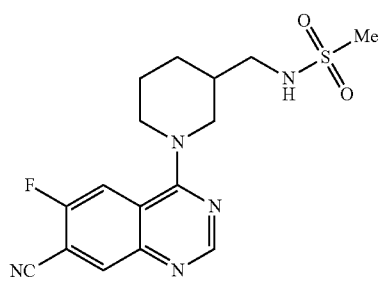

20

To a stirred solution of 1.10 (100 mg, 0.24 mmol) in NMP (2 mL) taken in a microwave vial was added Zn(CN)₂ (56 mg, 0.48 mmol). Argon gas was purged through septum and the reaction was degassed for about 5 min. To the reaction mixture Pd(PPh₃)₄ (55 mg, 0.048 mmol) was added under inert atmosphere and purged again with argon gas for 5 min. The microwave vial was sealed and irradiated at 130° C. for 30 min in CEM-microwave instrument. Upon complete consumption of the starting material, the reaction mixture was poured into water (20 mL), extracted with EtOAc (2×20 mL). The organic extracts were washed with water (2×20 mL), brine (20 mL), dried over anhydrous Na₂SO₄ and concentrated under reduced pressure. The residue was purified by silica gel column chromatography (gradient elution 5-10% of CH₃OH in CH₂Cl₂) to afford 20 (35 mg, 40%) as pale yellow solid. ¹H NMR (300 MHz, DMSO-d6): δ; 8.67 (s, 1H), 8.50 (d, J=6.3 Hz, 1H), 7.92 (d, J=10.2 Hz, 1H), 7.11 (t, J=6 Hz, 1H), 4.30 (d, J=13.2 Hz, 1H), 4.17 (d, J=13.2 Hz, 1H), 3.24-3.16 (m, 1H), 3.03-2.92 (m, 6H), 1.88-1.78 (m, 3H), 1.68-1.59 (m, 1H), 1.36-1.23 (m, 1H); MS (MM) m/z 362.0 [M–H]⁺; HPLC purity: >98 (% AUC).

i. Synthesis of 6-fluoro-4-(3-(methylsulfonamidomethyl)piperidin-1-yl)quinazoline-7-carboxamide (21)

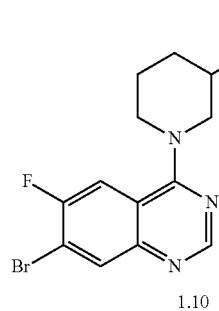

1.10

Silazane, Pd(OAc)₂
DIPEA, CO, DPPP
DMF, 100° C., 4 h
→

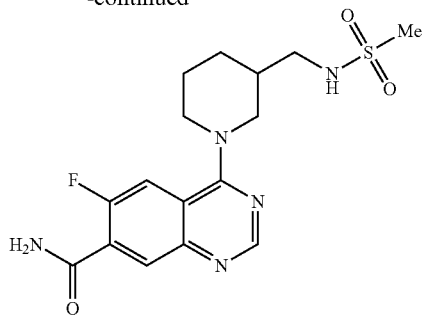

21

To a stirred solution of 1.10 (150 mg, 0.36 mmol) in DMF (2 mL) taken in a steel bomb added silazane (0.17 mL, 1.08 mmol) and DIPEA (177 mg, 1.08 mmol). Argon gas was purged and the reaction was degassed for about 5 min. added Pd(OAc) (7 mg, 0.036 mmol), DPPP (10 mg), CO was filled up to 250 Psi, allowed to stir at 100° C. for 4 h. Upon complete consumption of starting material, the reaction mixture was poured into water (25 mL), extracted with EtOAc (2×25 mL). The organic extracts were washed with saturated NaHCO₃ (20 mL), water (20 mL), brine (20 mL), dried over anhydrous Na₂SO₄ and concentrated under reduced pressure. The residue was purified by silica gel column chromatography (gradient elution 80-90% of EtOAc in hexanes) to afford 21 (13 mg, 9%). ¹H NMR (300 MHz, CH₃OD): δ 8.46 (s, 1H), 8.04 (d, J=4.88 Hz, 1H), 7.65 (d, J=10.8 Hz, 1H), 7.45-7.40 (m, 1H), 4.33 (d, J=12.6 Hz, 1H), 4.20 (d, J=10.2 Hz, 1H), 3.10-2.92 (m, 4H), 2.84 (s, 3H), 1.98-1.61 (m, 4H), 1.38-1.29 (m, 1H); MS (MM) m/z 380.1 [M–H]⁺; HPLC purity: >98 (% of AUC).

j. Synthesis of N-((1-(6-fluoro-7-methylquinazolin-4-yl)piperidin-3-yl)methyl)methanesulfonamide (22)

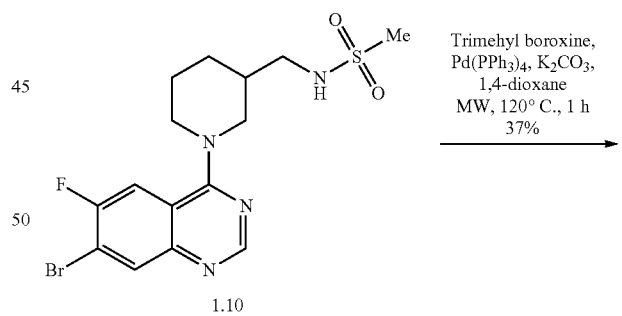

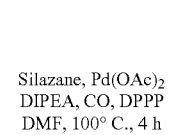 

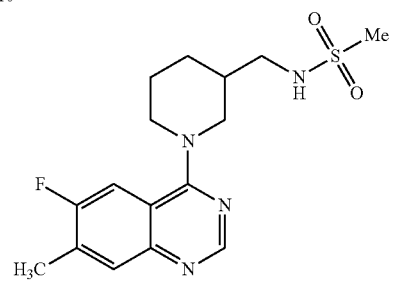

22

To a stirred solution of 1.10 (200 mg, 0.47 mmol) in 1,4-dioxane (10 mL) in a microwave vial was added trimethylboroxine (120 mg, 0.96 mmol) and K₂CO₃ (200 mg, 1.43 mmol). Argon gas was purged through septum and the reaction was degassed for about 5 min. To the reaction mixture Pd (PPh₃)₄ (110 mg, 0.095 mmol) was added under inert atmosphere, purged with argon for 5 more min. The microwave vial was sealed and irradiated at 120° C. for 1 h in CEM-microwave instrument. Upon complete consumption of starting material, the reaction mixture was poured into water (25 mL), extracted with EtOAc (2×25 mL). The organic extracts were washed with saturated NaHCO₃ (25 mL), water (25 mL), brine (25 mL), dried over anhydrous Na₂SO₄ and concentrated under reduced pressure. The residue was purified by silica gel column chromatography (gradient elution 90-100% of EtOAc in hexanes) to afford 22 (62 mg, 37%) as yellow solid. ¹H NMR (400 MHz, DMSO-d6): δ 8.58 (s, 1H), 7.73 (d, J=7.6 Hz, 1H), 7.59 (d, J=10.8 Hz, 1H), 7.12 (t, J=6.4 Hz, 1H), 4.24 (d, J=12.8 Hz, 1H), 4.11 (d, J=12.8 Hz, 1H), 3.15-3.09 (m, 1H), 2.98-2.87 (m, 2H), 2.89 (s, 3H), 2.87-2.84 (m, 1H), 2.42 (s, 3H), 1.88-1.78 (m, 3H), 1.71-1.62 (m, 1H), 1.33-1.23 (m, 1H); MS (MM) m/z 353.1 [M+H]⁺; HPLC purity: >98 (% AUC).

k. Synthesis of N-((1-(6-fluoro-7-morpholinoquinazolin-4-yl)piperidin-3-yl)methyl)methanesulfonamide (23)

material the reaction mixture was poured into water (10 mL) and extracted with EtOAc (2×15 mL). The combined organic extracts were washed with water (2×10 mL), brine (10 mL), dried over anhydrous Na₂SO₄ and, concentrated under reduced pressure. The residue was purified by silica gel column chromatography eluting (EtOAc:hexanes; 9:1). Fractions containing the product were combined and concentrated under reduced pressure to afford 23 (8 mg, 6%) as a yellow solid. ¹H NMR (400 MHz, CDCl₃): δ 8.54 (s, 1H), 7.57 (d, J=8.0 Hz, 1H), 7.49 (d, J=14.4 Hz, 1H), 6.04 (br s, 1H), 4.63 (d, J=12.8 Hz, 1H), 4.41 (d, J=10.4 Hz, 1H), 3.87 (s, 4H), 3.52 (t, J=13.6 Hz, 1H), 3.41-3.33 (m, 5H), 3.22-3.05 (m, 2H), 2.98 (s, 3H), 2.12 (br s, 1H), 2.04-1.92 (m, 2H), 1.95-1.92 (m, 1H), 1.77-1.69 (m, 1H); MS (MM) m/z 425.0; HPLC Purity: 97.82 (% of AUC).

l. Synthesis of N-((1-(6-morpholinoquinazolin-4-yl)piperidin-3-yl)methyl)methanesulfonamide (24)

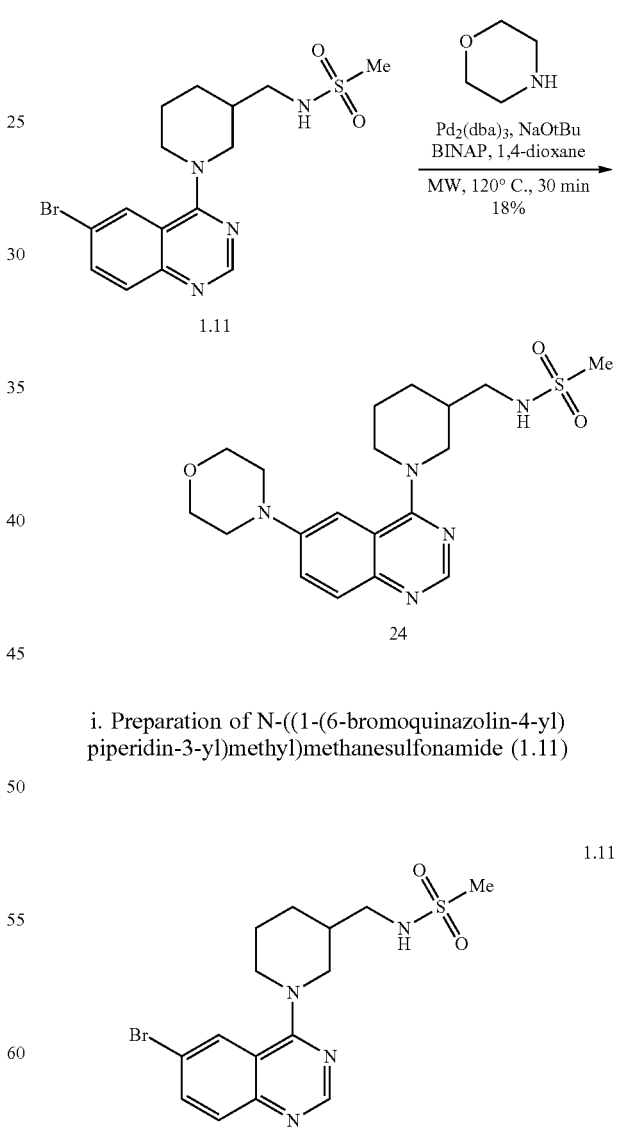

i. Preparation of N-((1-(6-bromoquinazolin-4-yl)piperidin-3-yl)methyl)methanesulfonamide (1.11)

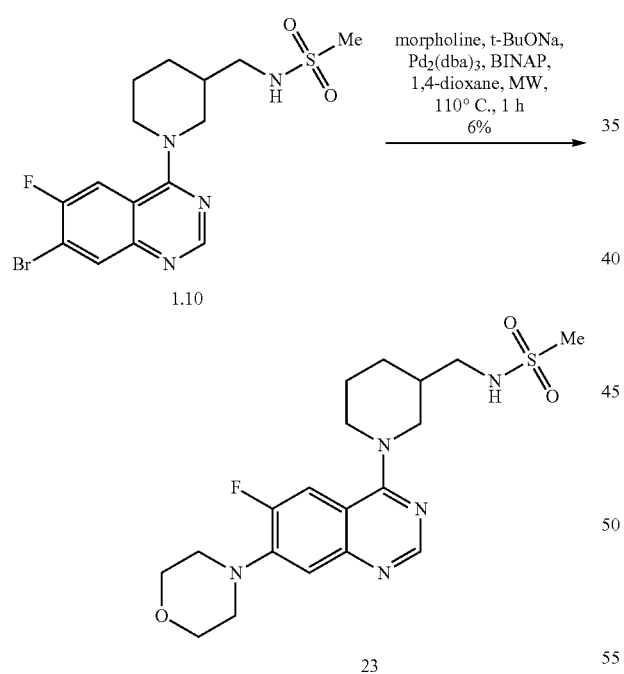

1.11 was made following the same procedure described above for compounds 1-14. Yield: 36%; MS (MM) m/z 399.0 [M+H]⁺.

ii. Preparation of N-((1-(6-morpholinoquinazolin-4-yl)piperidin-3-yl)methyl)methanesulfonamide (24)

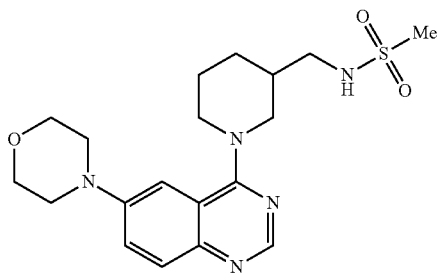

To a stirred solution of 1.11 (100 mg, 0.25 mmol) in 1,4-dioxane (10 mL) taken in a microwave vial added morpholine (21.8 mg, 0.25) and NaOtBu (72 mg, 0.75 mmol). Argon gas was purged through septum and the reaction was degassed for about 5 min. To the reaction mixture, BINAP (4.7 mg, 0.007 mmol) and Pd$_2$(dba)$_3$ (10.2 mg, 0.01 mmol) were added under inert atmosphere. The reaction mixture was purged with argon gas again for 5 min. The microwave vial was sealed and irradiated at 120° C. for 30 min. in CEM-microwave instrument. Upon complete consumption of starting material, the reaction mixture was filtered through celite pad, washed with EtOAc (50 mL) and the filtrate was concentrated under reduced pressure. The residue was purified by silica gel column chromatography (gradient elution 2-5% of MeOH in CH$_2$Cl$_2$) to afford 24 (18 mg, 18%) as a yellow solid. $^1$H NMR (300 MHz, CDCl$_3$): δ 8.59 (s, 1H), 7.82 (d, J=9.6 Hz, 1H), 7.49 (d, J=9.6 Hz, 1H), 7.07 (s, 1H), 5.40 (s, 1H), 4.01-3.90 (m, 6H), 3.52-3.34 (m, 2H), 3.26-3.07 (m, 6H), 2.97 (s, 3H), 2.17 (s, 1H), 2.01-1.97 (m, 1H), 1.77-1.68 (m, 2H), 1.46-1.44 (m, 1H); MS (MM) m/z 406.1 [M+H]$^+$; HPLC purity >94 (% AUC).

m. Synthesis of N-(4-(3-(methylsulfonamidomethyl)piperidin-1-yl)quinazolin-6-yl)pivalamide (25)

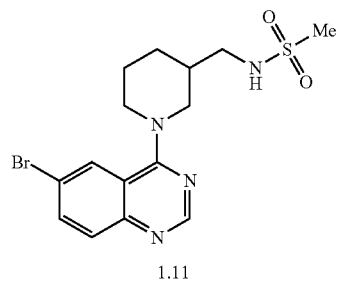

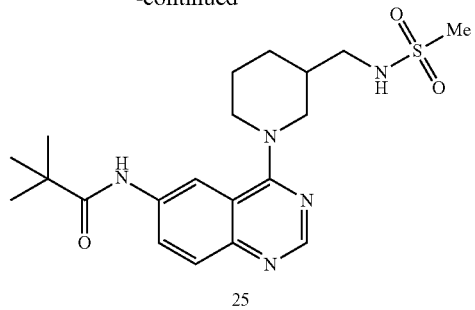

To a stirred solution of 1.11 (100 mg, 0.25 mmol) in 1,4-dioxane (10 mL) taken in a sealed tube added pivalamide (30 mg, 0.30 mmol), K$_3$PO$_4$ (159 mg, 0.75 mmol), N-N'-dimethylethylenediamine (2.3 mg, 0.025 mmol) and CuI (4.75 mg, 0.025 mmol). The sealed tube equipped with pressure gauge was sealed and heated at 110° C. for 48 h. Upon complete consumption of starting material, the reaction mixture was poured into water (15 mL), extracted with EtOAc (2×20 mL). The combined organic extracts were washed with water (2×20 mL), brine (20 mL), dried over anhydrous Na$_2$SO$_4$ and concentrated under reduced pressure. The residue was purified by silica gel column chromatography eluting (EtOAc:hexanes; 8:2). Fractions containing the product were combined and concentrated under reduced pressure to afford 25 (25 mg, 24%) as a yellow solid. $^1$H NMR (400 MHz, CDCl$_3$): δ 8.82 (s, 1H), 8.65 (s, 1H), 7.85 (d, J=8.8 Hz, 1H), 7.66 (s, 1H), 7.33-7.30 (m, 1H), 6.16 (d, J=8.4 Hz, 1H), 4.55 (d, J=14 Hz, 1H), 3.26-3.22 (m, 1H), 3.13-2.98 (m, 2H), 2.92 (s, 3H), 2.92-2.75 (m, 2H), 2.41-2.36 (m, 1H), 2.04-1.92 (m, 2H), 1.82-1.72 (m, 1H), 1.37 (m, 9H), 1.34-1.31 (m, 1H); MS (MM) m/z 420.3[M+H]$^+$; HPLC Purity: 98.16 (% of AUC).

n. Synthesis of N-((1-(6-(oxazol-2-yl)quinazolin-4-yl)piperidin-3-yl)methyl)methanesulfonamide (26)

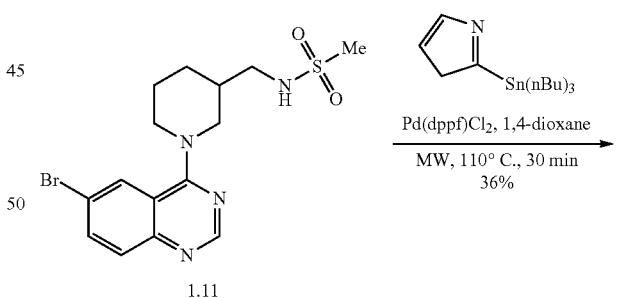

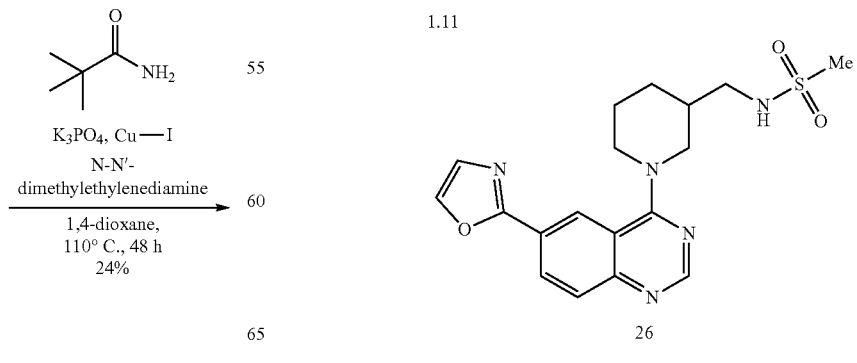

To a stirred solution of 1.11 (100 mg, 0.25 mmol) in 1,4-dioxane (10 mL) taken a microwave vial was added 2-(tributylstannyl)oxazole (108 mg, 0.30 mmol). Ar (g) was purged through septum and the reaction was degassed for about 5 min. To the reaction mixture Pd(dppf)Cl$_2$ (18 mg, 0.025 mmol) was added under Ar (g) atmosphere. The reaction mixture was purged with Ar (g) again for 5 min. The microwave vial was sealed and irradiated at 110° C. in CEM-microwave instrument for 30 min. Upon complete consumption of starting material, the reaction mixture was filtered through pad of celite, washed with EtOAc (50 mL) and the filtrate was concentrated under reduced pressure. The residue was purified by silica gel column chromatography eluting (MeOH:CH$_2$Cl$_2$; 0.3:9.7). Fractions containing the product were combined and concentrated under reduced pressure to afford 26 (55 mg, 36%) as a white solid. $^1$H NMR (300 MHz, DMSO-d$_6$): δ 8.64 (s, 1H), 8.51 (s, 1H), 8.34 (d, J=9.0 Hz, 1H), 8.31 (s, 1H), 7.90 (d, J=8.7 Hz, 1H), 7.45 (s, 1H), 7.12 (t, J=5.7 Hz, 1H), 4.39 (d, J=14.7 Hz, 1H), 4.24 (d, J=13.5 Hz, 1H), 3.30-3.26 (m, 1H), 3.07-2.94 (m, 3H), 2.90 (s, 3H), 1.95-1.68 (m, 4H), 1.41-1.34 (m, 1H); MS (MM) m/z 388.1 [M+H]$^+$; HPLC Purity: 93.58 (% of AUC).

o. Synthesis of N-((1-(6-(pyridin-2-yl)quinazolin-4-yl)piperidin-3-yl)methyl)methanesulfonamide (27)

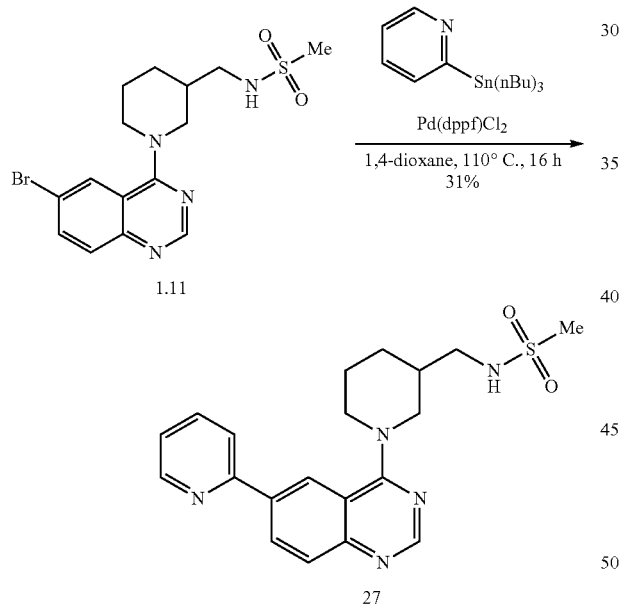

To a stirred solution of 1.11 (200 mg, 0.50 mmol) in 1,4-dioxane (15 mL) taken in a sealed tube fitted with pressure gauge, vial added 2-(tributylstannyl)pyridine (221 mg, 0.60). Ar (g) was purged through septum and the reaction was degassed for about 5 min. To the reaction mixture Pd(dppf)Cl$_2$ (40 mg, 0.05 mmol) was added under Ar (g) atmosphere, purged with Ar (g) again for 5 min. The reaction mixture was stirred at 110° C. for 16 h. Upon complete consumption of starting material, the reaction mixture was filtered through celite pad, washed with EtOAc (50 mL) and the filtrate was concentrated under reduced pressure. The residue was purified by silica gel column chromatography eluting (MeOH:CH$_2$Cl$_2$; 0.5:9.5). Fractions containing the product were combined and concentrated under reduced pressure to afford 27 (62 mg, 31%) as a pink solid. $^1$H NMR (400 MHz, DMSO-d$_6$): δ 8.74-8.72 (m, 1H), 8.62 (s, 2H), 8.51 (dd, J=2.0 Hz, J=8.8 Hz, 1H), 8.12 (d, J=8.0 Hz, 1H), 7.96-7.92 (m, 1H), 7.88 (d, J=8.8 Hz, 1H), 7.42-7.39 (m, 1H), 7.13 (t, J=6.0 Hz, 1H), 4.41 (d, J=12 Hz, 1H), 4.26 (d, J=13.6 Hz, 1H), 3.29-3.22 (m, 1H), 3.03-2.92 (m, 3H), 2.88 (s, 3H), 1.98-1.70 (m, 4H), 1.38-1.30 (m, 1H); MS (MM) m/z 398.0 [M+H]$^+$; HPLC Purity: 95.49 (% of AUC).

p. Synthesis of N-(4-(3-(methylsulfonamidomethyl)piperidin-1-yl)quinazolin-6-yl)picolinamide (28)

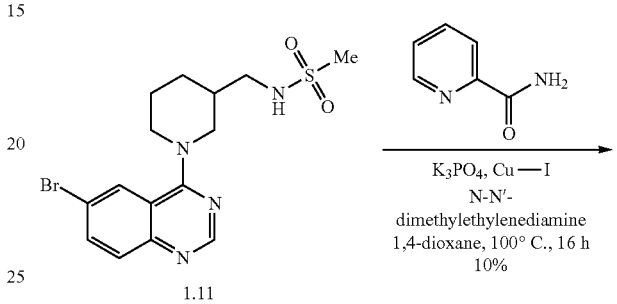

To a stirred solution of 1.11 (400 mg, 1.00 mmol) in 1,4-dioxane (10 mL) taken in a sealed tube added picolinamide (146 mg, 1.20 mmol), K$_3$PO$_4$ (637 mg, 3.01 mmol), N-N'-dimethylethylenediamine (26 mg, 0.3 mmol) and CuI (95 mg, 0.50 mmol). The sealed tube was fitted with pressure gauge was sealed and heated at 100° C. for 16 h. Upon complete consumption of starting material, the reaction mixture was poured into water (15 mL), extracted with EtOAc (2×20 mL). The combined organic extracts were washed with saturated NaHCO$_3$ (20 mL), water (20 mL), brine (20 mL), dried over anhydrous Na$_2$SO$_4$ and concentrated under reduced pressure. The residue was purified by silica gel column chromatography eluting (EtOAc:hexanes; 9:1). Fractions containing the product were combined and concentrated under reduced pressure to afford 28 (40 mg, 10%) as an off-white solid. $^1$H NMR (400 MHz, DMSO-d$_6$): δ 11.13 (s, 1H), 8.78 (br s, 1H), 8.33 (s, 1H), 8.22 (s, 1H), 8.11 (t, J=7.2 Hz, 1H), 7.72 (s, 1H), 7.07 (t, J=5.6 Hz, 1H), 4.29 (d, J=13.2 Hz, 1H), 4.19 (d, J=10.4 Hz, 1H), 3.19-3.3.14 (m, 1H), 2.98 (t, J=6 Hz, 2H), 2.91 (m, 4H), 1.94-1.74 (m, 4H), 1.37-1.33 (m, 1H); MS (MM) m/z 441.1 [M+H]$^+$; HPLC Purity: 97.19 (% of AUC).

q. Synthesis of N-((1-(6-cyano-7-fluoroquinazolin-4-yl)piperidin-3-yl)methyl)methanesulfonamide (29)

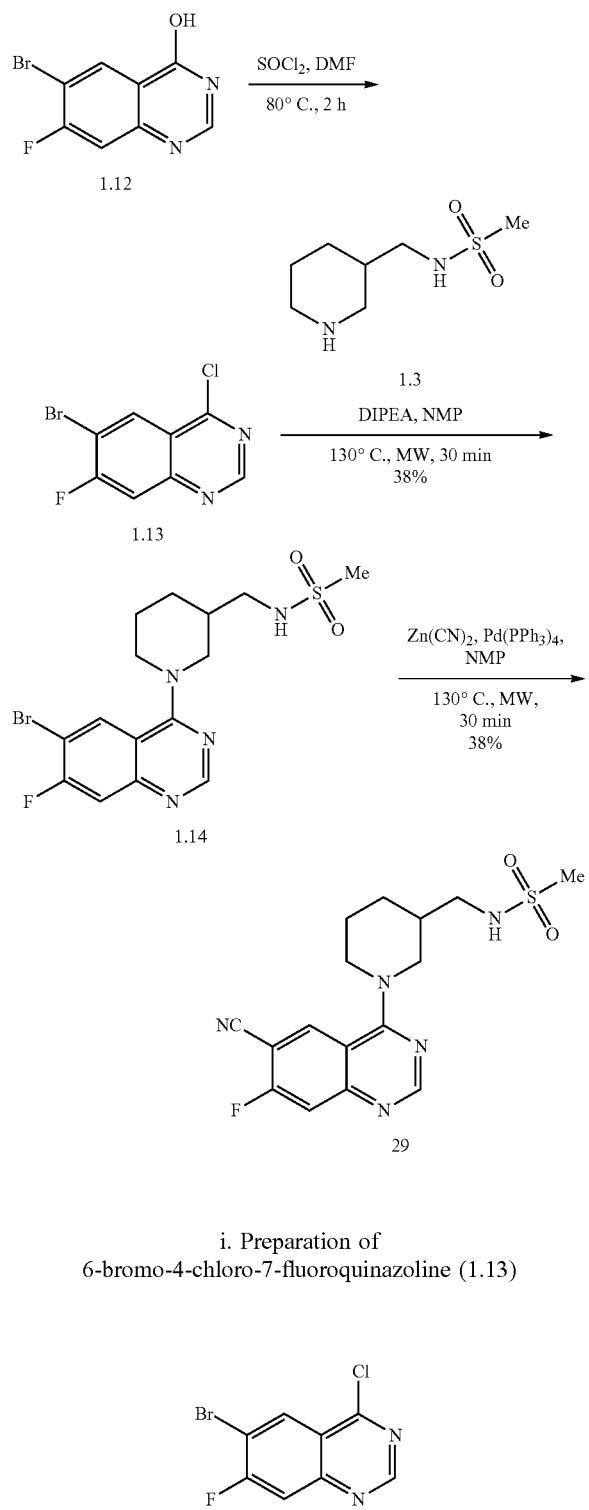

i. Preparation of 6-bromo-4-chloro-7-fluoroquinazoline (1.13)

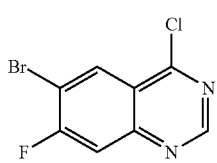

To a stirred solution of 6-bromo-7-fluoroquinazolin-4-ol 1.12 (200 mg, 0.81 mmol) in SOCl₂ (5.0 mL) was added DMF (0.1 mL) (catalytic) at 0° C., the reaction mixture was stirred at 80° C. for 2 h. Upon complete consumption of starting material, the reaction mixture was concentrated under reduced pressure. Co-distilled with toluene (3×25 mL) to afford 1.13 (180 mg, crude) as a yellow solid. MS (MM): m/z=262.9 [M+H]$^+$.

ii. Preparation of N-((1-(6-bromo-7-fluoroquinazolin-4-yl)piperidin-3-yl)methyl)methane-sulfonamide (1.14)

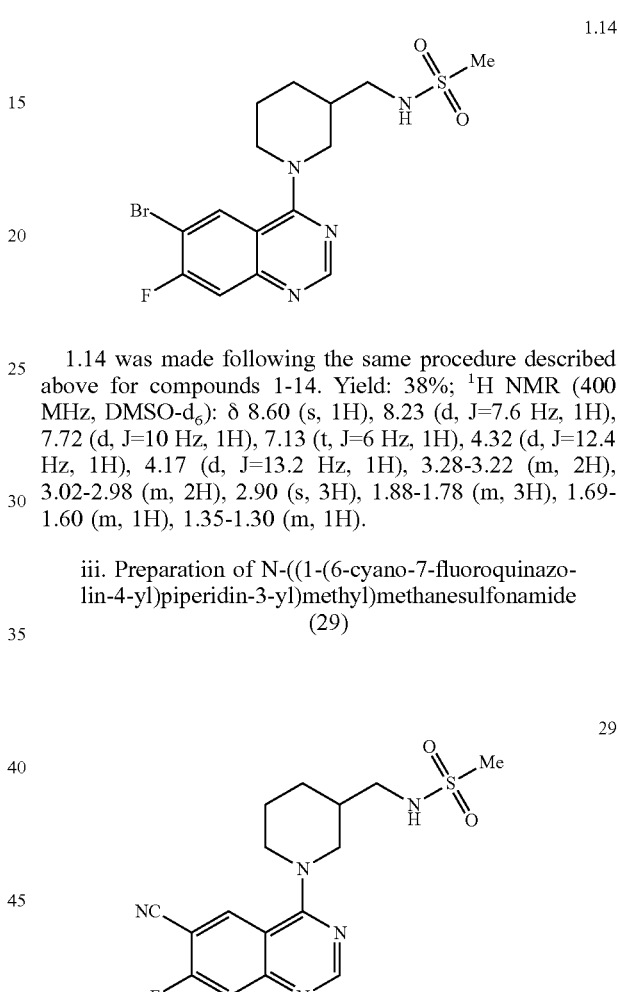

1.14 was made following the same procedure described above for compounds 1-14. Yield: 38%; $^1$H NMR (400 MHz, DMSO-d$_6$): δ 8.60 (s, 1H), 8.23 (d, J=7.6 Hz, 1H), 7.72 (d, J=10 Hz, 1H), 7.13 (t, J=6 Hz, 1H), 4.32 (d, J=12.4 Hz, 1H), 4.17 (d, J=13.2 Hz, 1H), 3.28-3.22 (m, 2H), 3.02-2.98 (m, 2H), 2.90 (s, 3H), 1.88-1.78 (m, 3H), 1.69-1.60 (m, 1H), 1.35-1.30 (m, 1H).

iii. Preparation of N-((1-(6-cyano-7-fluoroquinazolin-4-yl)piperidin-3-yl)methyl)methanesulfonamide (29)

To a stirred solution of 1.15 (100 mg, 0.23 mmol) in NMP (5.0 mL) taken in a microwave vial was added Zn(CN)₂ (28 mg, 0.23 mmol). Argon gas was purged through septum and the reaction mixture was degassed for about 10 min. To the reaction mixture added Pd(PPh₃)₄ (13.8 mg, 0.01) under inert atmosphere. The reaction mixture was purged with argon gas again for 5 min. The microwave vial was sealed and irradiated at 130° C. for 30 min in CEM-microwave instrument. Upon complete consumption of starting material, the reaction mixture was poured into water (20 mL), extracted with EtOAc (2×20 mL). The organic extracts were washed with saturated NaHCO₃ (20 mL), water (20 mL), brine (20 mL), dried over anhydrous Na₂SO₄ and concentrated under reduced pressure. The residue was purified by silica gel column chromatography (gradient elution 70-80% of EtOAc in hexanes) to afford 29 (43 mg, 38%) as an off-white solid. $^1$H NMR (400 MHz, DMSO-d$_6$): δ 8.61 (s, 1H), 8.56 (d, J=7.2 Hz, 1H), 7.66 (d, J=10.8 Hz, 1H), 7.12 (t, J=6 Hz, 1H), 4.43 (d, J=10.8 Hz, 1H), 4.26 (d, J=13.6 Hz, 1H), 3.40-3.36 (m, 1H), 3.12-3.06 (m, 1H), 2.93-2.78 (m, 5H), 1.88-1.78 (m, 3H), 1.68-1.62 (m, 1H), 1.37-1.29 (m, 1H); MS (MM) m/z 364.1 [M+H]$^+$; HPLC purity >99 (% AUC).

r. Synthesis of N-((1-(6-cyano-7-fluoroquinazolin-4-yl)piperidin-3-yl)methyl)methanesulfonamide hydrochloride (29)

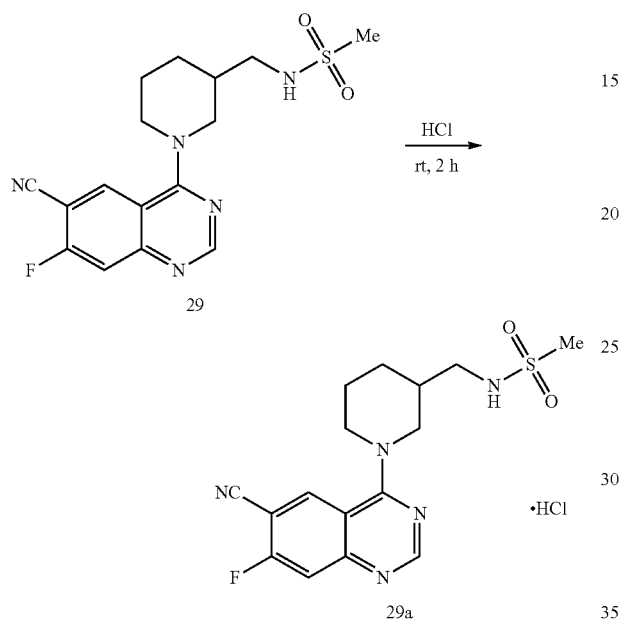

A stirred solution of 29 (1.26 g, 3.47 mmol) in 1,4-dioxane was added HCl (4.0 M in 1, 4-dioxane) (20 mL) was stirred at RT for 2 h. Upon complete consumption of starting material, the reaction mixture was concentrated under reduced pressure to afford 29a (1.36 g, 98%) as an off-white solid. $^1$H NMR (300 MHz, DMSO-d$_6$): δ 8.83 (s, 1H), 8.74 (d, J=6.3 Hz, 1H), 7.88 (d, J=9.6 Hz, 1H), 7.21 (t, J=6 Hz, 1H), 4.67 (d, J=12.6 Hz, 1H), 4.45 (d, J=13.5 Hz, 1H), 3.66 (t, J=10.8 Hz, 1H), 3.38 (t, J=12.3 Hz, 1H), 2.96-2.92 (m, 2H), 2.89 (s, 3H), 1.88-1.85 (m, 3H), 1.70-1.67 (m, 1H), 1.44-1.40 (m, 1H); MS (MM): m/z 364.1 [M+H]$^+$; HPLC Purity: 96.9 (% of AUC).

s. Synthesis of N-((1-(7-fluoro-6-(trifluoromethyl) quinazolin-4-yl)piperidin-3-yl)methyl)methane-sulfonamide (30)

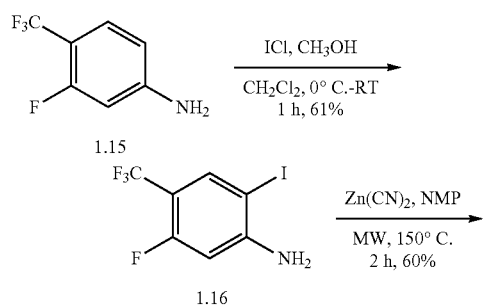

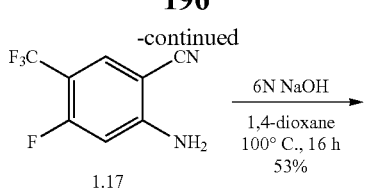

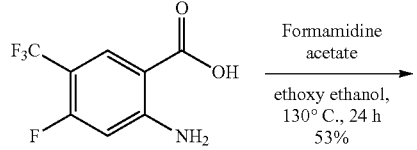

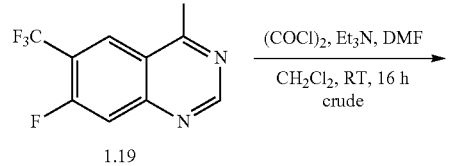

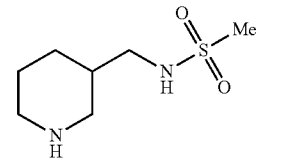

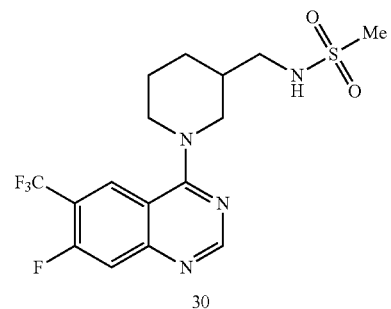

i. Preparation of 5-fluoro-2-iodo-4-(trifluoromethyl)aniline (1.16)

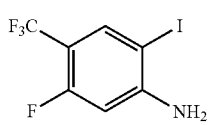

To a stirred solution of 3-fluoro-4-(trifluoromethyl)aniline 1.16 (1.0 g, 5.58 mmol) in CH$_3$OH (20 mL) at 0° C. was added IC$_1$ (904 mg, 5.58 mmol) in CH$_2$Cl$_2$ (10 mL). The reaction mixture was stirred at RT for 1 h. Upon complete consumption of starting material, the reaction mixture was poured into water (50 mL), extracted with EtOAc (2×50 mL). The organic extracts were washed with saturated water (50 mL), brine (50 mL), dried over anhydrous Na$_2$SO$_4$ and concentrated under reduced pressure. The residue was purified by silica gel column chromatography eluting (EtOAc: hexanes; 1:9). Fractions containing the product were combined and concentrated under reduced pressure to afford 1.16 (1.40 g, 61%) as yellow solid. $^1$H NMR (400 MHz, CDCl$_3$): δ 7.79 (d, J=8.0 Hz, 1H), 6.49 (d, J=12.0 Hz, 1H), 4.52 (br s, 2H).

ii. Preparation of 2-amino-4-fluoro-5-(trifluoromethyl)benzonitrile (1.17)

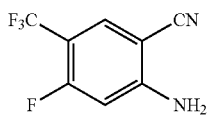

1.17

To a stirred solution of 1.16 (1.0 g, 3.28 mmol) in NMP (10 mL) taken in a microwave vial was charged with Zn(CN)$_2$ (424 mg, 3.61 mmol) and was degassed with Ar (g) for 10 min. Pd(PPh$_3$)$_4$ (189 mg, 0.164 mmol) was added to the reaction mixture under Ar (g) atmosphere and the reaction mixture was again purged with Ar (g) for 5 min. The microwave vial was sealed and irradiated at 150° C. in CEM-microwave instrument for 2 h. Upon complete consumption of starting material, the reaction mixture was poured into water (10 mL), extracted with EtOAc (2×20 mL). The combined organic extracts were washed with water (25 mL), brine (25 mL), dried over anhydrous Na$_2$SO$_4$ and concentrated under reduced pressure. The residue was purified by silica gel column chromatography eluting (EtOAc:hexanes; 2:8). Fractions containing the product were combined and concentrated under reduced pressure to afford 1.17 (408 mg, 60%) as a light yellow solid. MS (MM) m/z 203.0 [M−H]$^+$.

iii. Preparation of 2-amino-4-fluoro-5-(trifluoromethyl)benzoic acid (1.18)

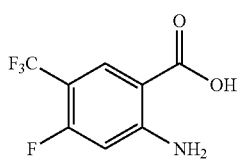

1.18

To a stirred solution of 1.17 (1.10 g, 5.37 mmol) in 1, 4-dioxane (11 mL) at RT added 6N NaOH solution (11 mL). The reaction mixture was stirred at 100° C. for 16 h. Upon complete consumption of starting material, the reaction mixture was poured into water (50 mL), neutralized with 2N HCl and extracted with EtOAc (2×50 mL). The combined organic extracts were washed with saturated water (50 mL), brine (50 mL), dried over anhydrous Na$_2$SO$_4$ and concentrated under reduced pressure. The residue was purified by silica gel column chromatography eluting (EtOAc:hexanes; 1:9). Fractions containing the product were combined and concentrated under reduced pressure to afford 1.18 (635 mg, 53%) as a yellow solid. MS (MM) m/z 221.0 [M−H]$^+$.

iv. Preparation of 7-fluoro-6-(trifluoromethyl)quinazolin-4-ol (1.19)

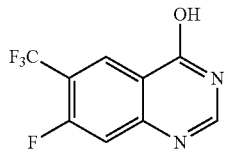

1.19

To a stirred solution of 1.18 (620 mg, 2.76 mmol) in ethoxy ethanol (12 mL) at RT was added formamidine acetate (576 mg, 5.53 mmol). The reaction mixture was stirred at 130° C. for 24 h. Upon complete consumption of starting material, the reaction mixture was poured into water (50 mL), the solid precipitated was collected by filtration and dried to afford 1.19 (575 mg, crude) as a white solid. MS (MM) m/z 233.0 [M+H]$^+$.

v. Preparation of 4-chloro-7-fluoro-6-(trifluoromethyl)quinazoline (1.20)

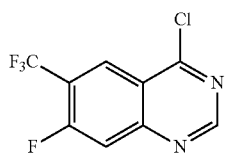

1.20

To a stirred solution of 1.19 (50 mg, 0.22 mmol) in CH$_2$Cl$_2$ (10 mL) were added Et$_3$N (44 mg, 0.44 mmol), DMF (catalytic) and (COCl)$_2$ (41.9 mg, 0.33 mmol) at RT for 16 h. Upon complete consumption of starting material, the reaction mixture was concentrated under reduced pressure. Co-distilled with toluene (3×25 mL) to afford 1.20 (62 mg, crude) as a brown solid. MS (MM) m/z 250.9 [M]$^+$.

vi. Preparation of N-((1-(7-fluoro-6-(trifluoromethyl)quinazolin-4-yl)piperidin-3-yl)methyl)methane-sulfonamide (30)

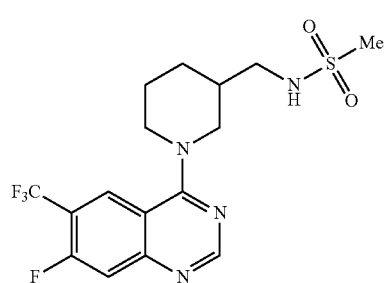

30

To a stirred solution of 1.20 (100 mg, 0.40 mmol) in NMP (5 mL) was added 1.3 (146 mg, 0.48 mmol) and DIPEA (154 mg, 1.2 mmol) at RT. The reaction mixture was stirred at RT for 4 h. Upon complete consumption of starting material, the reaction mixture was poured into water (25 mL), extracted with EtOAc (2×25 mL). The organic extracts were washed with saturated NaHCO$_3$ (25 mL), water (25 mL), brine (25 mL), dried over anhydrous Na$_2$SO$_4$ and concentrated under reduced pressure. The residue was purified by mass trigger HPLC to afford 30 (4.2 mg, 3%) as an off-white solid. $^1$H NMR (400 MHz, CDCl$_3$): δ 8.61 (s, 1H), 8.08 (d, J=7.2 Hz, 1H), 7.54 (d, J=11.2 Hz, 1H), 5.27 (t, J=6 Hz, 1H), 4.03-3.99 (m, 2H), 3.62-3.52 (m, 2H), 3.16-3.10 (m, 1H), 3.05-2.99 (m, 1H), 2.11-2.06 (m, 1H), 1.98-1.91 (m, 1H), 1.66-1.60 (m, 1H); MS (MM) m/z 407.1 [M+H]$^+$; HPLC Purity: 96.4 (% of AUC).

t. General Synthesis of Substituted (quinazolin-4-yl)piperidin-3-yl)methanesulfonamides 31-35, 38, and 39

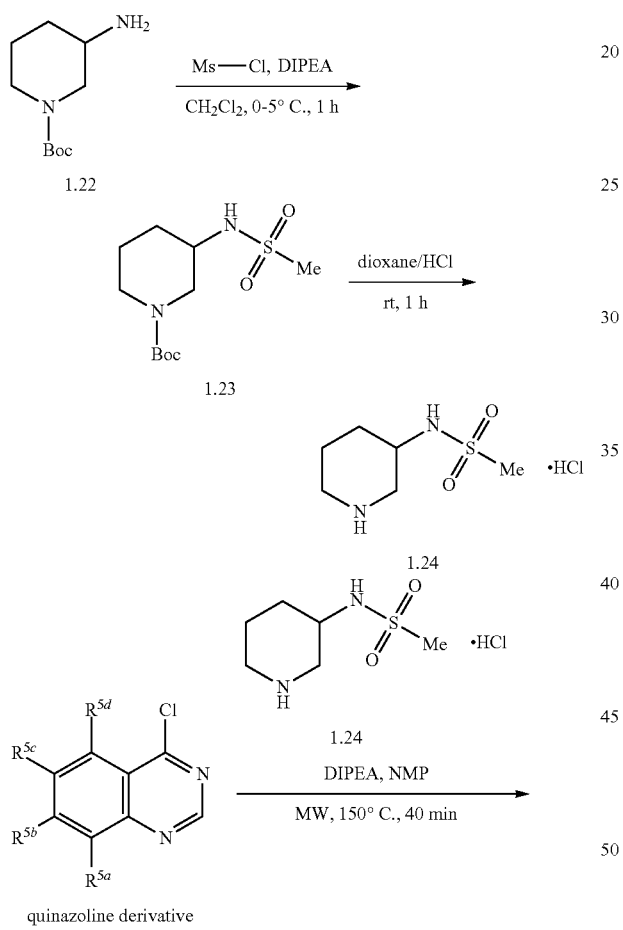

i. Preparation of tert-butyl 3-(methylsulfonamido)piperidine-1-carboxylate (1.22)

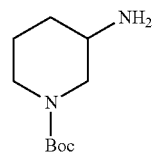

To a stirred solution of tert-butyl 3-aminopiperidine-1-carboxylate 1.21 (500 mg, 2.49 mmol) in CH$_2$Cl$_2$ (25 mL) were added Et$_3$N (504 mg, 4.99 mmol) and methane sulphonyl chloride (428 mg, 3.74 mmol) at 0° C. The reaction mixture was stirred at RT 1 h. Upon complete consumption of starting material, the reaction mixture was diluted water (40 mL), the mixture was extracted with CH$_2$Cl$_2$ (2×40 mL). The organic extracts were washed with saturated NaHCO$_3$ (20 mL), water (20 mL), brine (20 mL), dried over anhydrous Na$_2$SO$_4$ and concentrated under reduced pressure. The residue was purified by silica gel column chromatography (gradient elution 30-40% of EtOAc in hexanes) to afford 1.22 (500 mg, 72%) as a thick colorless liquid. MS (MM) m/z 277.1 [M−H]$^+$.

ii. Preparation of N-(piperidin-3-yl)methanesulfonamide (1.23)

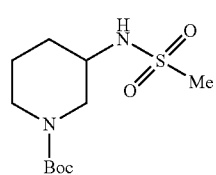

A solution of 1.22 (500 mg, 1.70 mmol) in 1, 4-dioxane HCl (4M, 2 mL) was stirred at RT for 2 h. Upon complete consumption of starting material, the reaction mixture was concentrated under reduced pressure. The residue was co-distilled with toluene (3×25 mL) to afford 1.23 (280 mg, crude) as a white solid. MS (MM) m/z 179.1 [M+H]$^+$.

iii. Preparation of Compounds 31-35, 38, and 39

To a stirred solution of appropriate quinazoline derivative (0.74 mmol) in NMP (3 mL) taken in a microwave vial was added 1.23 (174 mg, 0.82 mmol) and DIPEA (0.36 mL, 2.23 mmol). The microwave vial was sealed and irradiated at 150° C. for 40 min. in a CEM-microwave instrument. Upon complete consumption of starting material, the reaction mixture was poured into water (25 mL), extracted with EtOAc (2×25 mL). The organic extracts were washed with saturated NaHCO$_3$ (25 mL), water (25 mL), brine (25 mL), dried over anhydrous Na$_2$SO$_4$ and concentrated under reduced pressure. The residue was purified by silica gel column chromatography (gradient elution 80-90% of EtOAc in hexanes) to afford the desired targets 31-35, 38, and 39.

a. N-(1-(quinazolin-4-yl)piperidin-3-yl)methanesulfonamide (31)

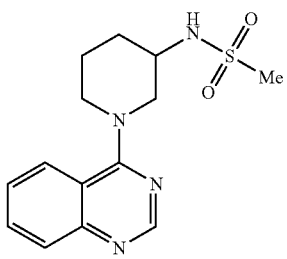

Yield: 36%; 1H NMR (400 MHz, DMSO-d6) δ 8.61 (s, 1H), 8.00 (dt, J=8.4, 1.1 Hz, 1H), 7.85-7.74 (m, 1H), 7.52 (ddd, J=8.3, 5.4, 2.9 Hz, 1H), 7.32 (d, J=7.0 Hz, 1H), 4.25-4.16 (m, 1H), 4.01 (d, J=13.4 Hz, 1H), 3.52 (ddd, J=13.1, 9.8, 5.7 Hz, 1H), 3.23-3.04 (m, 2H), 2.97 (s, 3H), 2.07-1.94 (m, 1H), 1.86 (dt, J=13.0, 3.9 Hz, 1H), 1.78-1.63 (m, 1H), 1.69 (s, 1H), 1.54 (ddd, J=23.3, 10.9, 4.1 Hz, 1H); FABMS (M+H) calculated for $C_{14}H_{18}N_4O_2S \cdot H$ was 307.1223 found 307.1225; HPLC purity >96 (% of AUC), $t_R$=1, 1.44 minutes.

b. N-(1-(7-fluoroquinazolin-4-yl)piperidin-3-yl)methanesulfonamide (32)

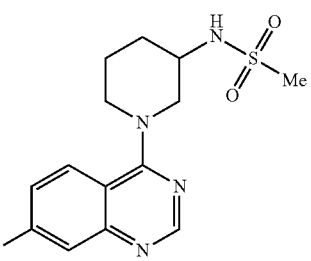

Yield: 53%; 1H NMR (400 MHz, DMSO-d6) δ 8.59 (s, 1H), 8.08 (dd, J=9.3, 6.1 Hz, 1H), 7.52 (dd, J=10.2, 2.7 Hz, 1H), 7.40 (ddd, J=9.3, 8.4, 2.7 Hz, 1H), 7.32 (d, J=7.0 Hz, 1H), 4.00 (d, J=13.1 Hz, 1H), 3.55-3.47 (m, 1H), 3.31-3.09 (m, 2H), 2.96 (s, 3H), 2.06-1.96 (m, 1H), 1.86 (dt, J=12.8, 3.9 Hz, 1H), 1.76-1.61 (m, 1H), 1.55 (ddd, J=23.5, 11.7, 4.0 Hz, 1H); FABMS (M+H) calculated for $C_{14}H_{17}FN_4O_2S \cdot H$ was 325.1129 found 325.1124; HPLC purity >99 (% of AUC), $t_R$=1.2, 2.33 minutes.

c. N-(1-(6,7-difluoroquinazolin-4-yl)piperidin-3-yl)methanesulfonamide (33)

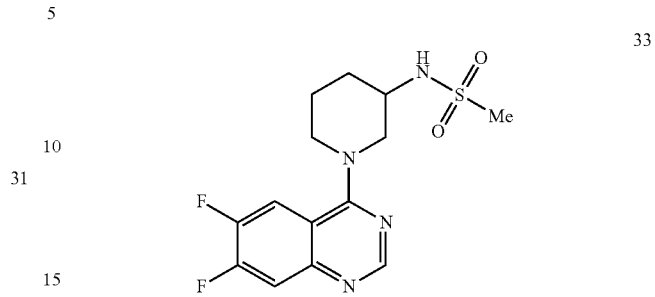

Yield: 43%; $^1$H NMR (300 MHz, DMSO-d6): δ 8.63 (s, 1H), 7.98 (t, J=11.1 Hz, 1H), 7.87-7.81 (m, 1H), 7.36 (d, J=6.6 Hz, 1H), 4.12 (d, J=11.4 Hz, 1H), 3.95 (d, J=12.9 Hz, 1H), 3.55 (br s, 1H), 3.27-3.12 (m, 2H), 2.99 (s, 3H), 2.03-1.87 (m, 2H), 1.72-1.55 (m, 2H); MS (MM) m/z 343.0 [M+H]$^+$; HPLC purity: >98 (% of AUC).

d. N-(1-(6-fluoroquinazolin-4-yl)piperidin-3-yl)methanesulfonamide (34)

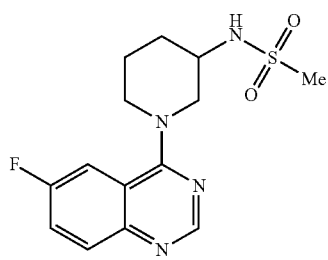

Yield: 36%; $^1$H NMR (300 MHz, DMSO-d6): δ 8.64 (s, 1H), 7.92-7.87 (m, 1H), 7.79-7.72 (m, 2H), 7.36 (d, J=7.2 Hz, 1H), 4.13 (d, J=9.9 Hz, 1H), 3.94 (d, J=13.5 Hz, 1H), 3.57-3.55 (m, 1H), 3.24-3.09 (m, 2H), 2.98 (s, 3H), 2.03-1.99 (m, 1H), 1.91-1.87 (m, 1H), 1.77-1.65 (m, 1H), 1.62-1.51 (m, 1H); MS (MM) m/z 325.0 [M+H]$^+$; HPLC purity: >99 (% of AUC).

e. N-(1-(6-chloroquinazolin-4-yl)piperidin-3-yl)methanesulfonamide (35)

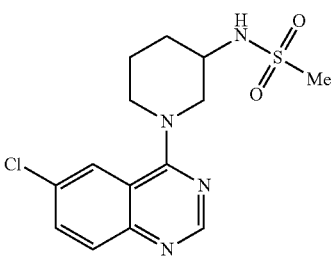

Yield: 38%; $^1$H NMR (300 MHz, DMSO-d6): δ 8.64 (s, 1H), 8.01 (s, 1H), 7.84 (s, 2H), 7.36 (d, J=6.9 Hz, 1H), 4.13

(d, J=13.2 Hz, 1H), 3.94 (d, J=13.5 Hz, 1H), 3.56 (br s, 1H), 3.26-3.15 (m, 2H), 2.98 (s, 3H), 2.03-1.88 (m, 2H), 1.75-1.55 (m, 2H); MS (MM) m/z 341.0 [M]⁺; HPLC purity: >98 (% of AUC).

f. N-(1-(6-(trifluoromethyl)quinazolin-4-yl)piperidin-3-yl)methanesulfonamide (38)

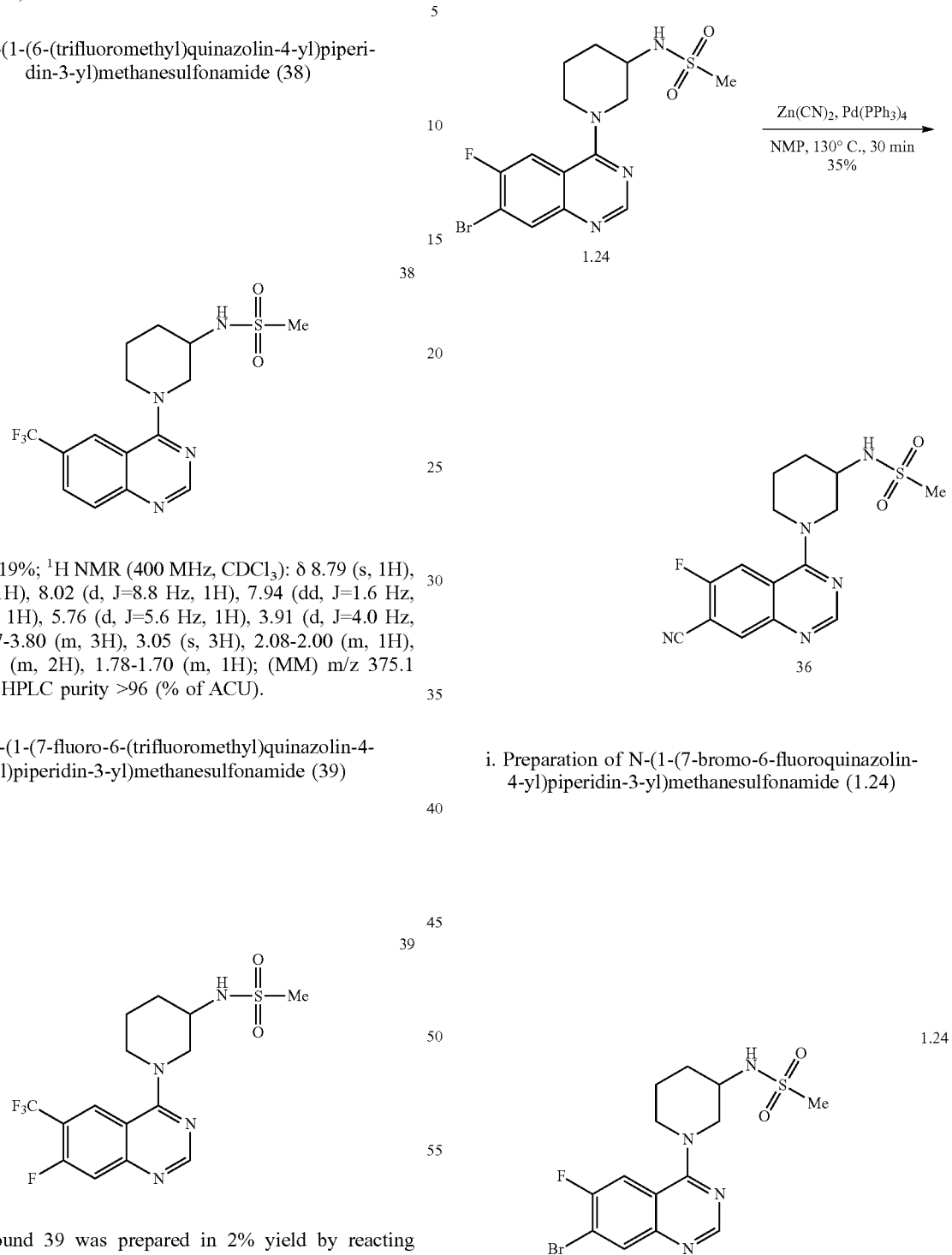

Yield: 19%; ¹H NMR (400 MHz, CDCl₃): δ 8.79 (s, 1H), 8.18 (s, 1H), 8.02 (d, J=8.8 Hz, 1H), 7.94 (dd, J=1.6 Hz, J=8.8 Hz 1H), 5.76 (d, J=5.6 Hz, 1H), 3.91 (d, J=4.0 Hz, 2H), 3.87-3.80 (m, 3H), 3.05 (s, 3H), 2.08-2.00 (m, 1H), 1.97-1.88 (m, 2H), 1.78-1.70 (m, 1H); (MM) m/z 375.1 [M+H]⁺; HPLC purity >96 (% of ACU).

g. N-(1-(7-fluoro-6-(trifluoromethyl)quinazolin-4-yl)piperidin-3-yl)methanesulfonamide (39)

Compound 39 was prepared in 2% yield by reacting N-(piperidin-3-yl)cyclopropanesulfonamide 1.23 and quinazoline 1.20, following the same procedure described in scheme 2. ¹H NMR (400 MHz, CDCl₃): δ 8.68 (s, 1H), 8.12 (d, J=7.2 Hz, 1H), 7.58 (d, J=11.2 Hz, 1H), 5.57 (d, J=5.6 Hz, 1H), 3.85-3.76 (m, 2H), 3.73-3.68 (m, 2H), 2.98 (s, 3H), 2.02-1.95 (m, 1H), 1.91-1.83 (m, 2H), 1.71-1.64 (m, 1H), 1.23-1.22 (m, 1H); MS (MM) m z 393.1 [M+H]⁺; HPLC Purity: 94.4 (% of AUC).

u. Synthesis of N-(1-(7-cyano-6-fluoroquinazolin-4-yl)piperidin-3-yl)methanesulfonamide (36)

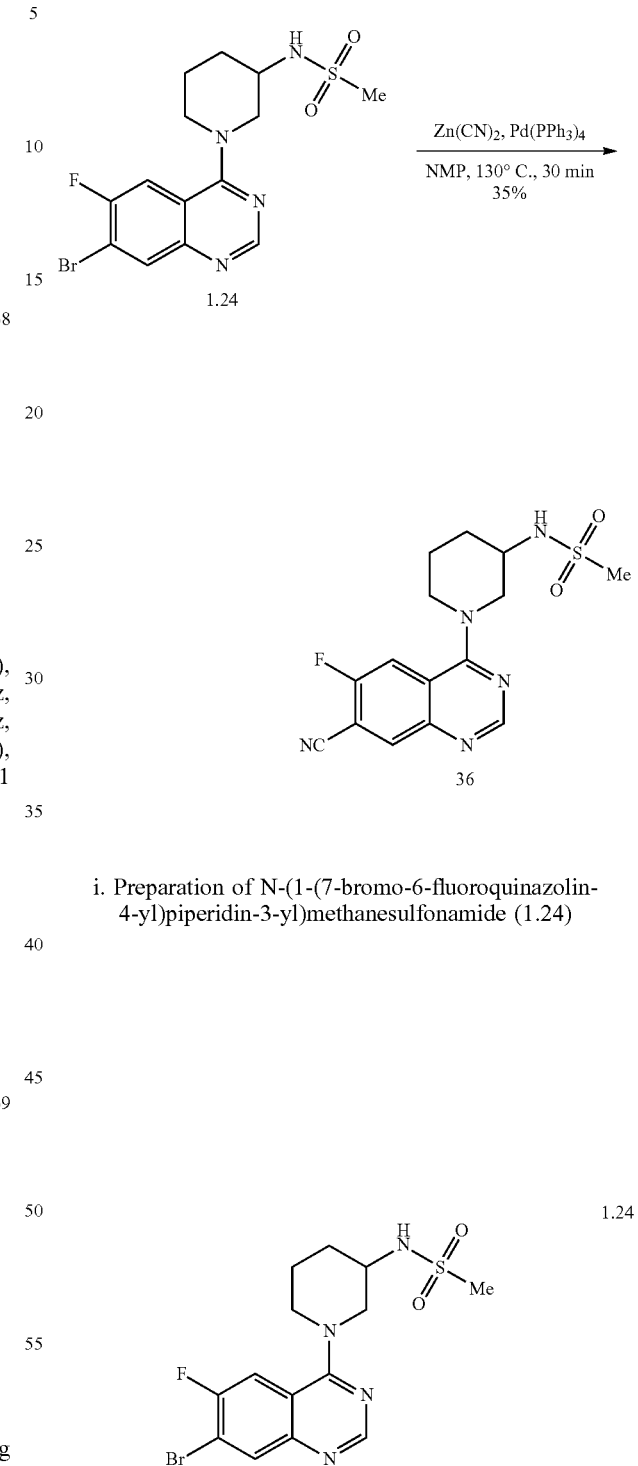

i. Preparation of N-(1-(7-bromo-6-fluoroquinazolin-4-yl)piperidin-3-yl)methanesulfonamide (1.24)

Intermediate 1.24 was made following the same procedure described above for compounds 31-35, 38, and 39. Yield: 52%; ¹H NMR (300 MHz, CDCl₃): δ 8.71 (s, 1H), 8.19 (d, J=6.9 Hz, 1H), 7.6 (d, J=9.0 Hz, 1H), 5.82 (d, J=6.3 Hz, 1H), 3.91-3.63 (m, 5H), 3.05 (s, 3H), 2.07-1.97 (m, 5H); MS (MM) m/z 405.0 [M+2]⁺.

ii. Preparation of N-(1-(7-cyano-6-fluoroquinazolin-4-yl)piperidin-3-yl)methanesulfonamide (36)

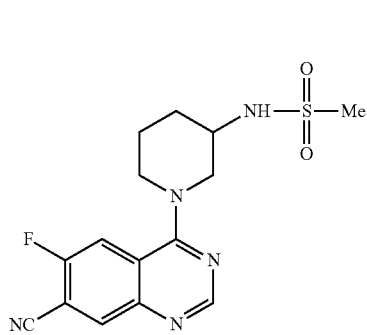

Starting from 1.24 and following the same procedure described for preparation of 29. Yield: 35% as an off-white solid; $^1$H NMR (400 MHz, DMSO-d$_6$): δ 8.71 (s, 1H), 8.52 (d, J=6.4 Hz, 1H), 7.99 (d, J=10.4 Hz, 1H), 7.36 (d, J=7.2 Hz, 1H), 4.15 (dd, J=2.8 Hz, J=12.8 Hz, 1H), 3.98 (d, J=13.2 Hz, 1H), 3.60-3.52 (m, 1H), 3.30-3.20 (m, 2H), 2.95 (s, 3H), 2.03-1.99 (m, 1H), 1.89 (dd, J=4.8 Hz, J=9.2 Hz, 1H), 1.74-1.68 (m, 1H), 1.62-1.53 (m, 1H); MS (MM): m/z 350.0 [M+H]$^+$; HPLC: >99 (% of AUC).

v. Synthesis of N-(1-(6-cyano-7-fluoroquinazolin-4-yl)piperidin-3-yl)methanesulfonamide (37)

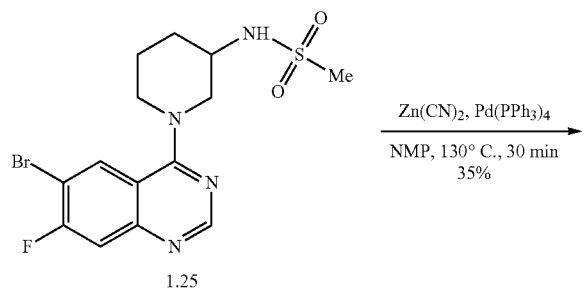

i. Preparation of N-(1-(6-bromo-7-fluoroquinazolin-4-yl)piperidin-3-yl)methanesulfonamide (1.25)

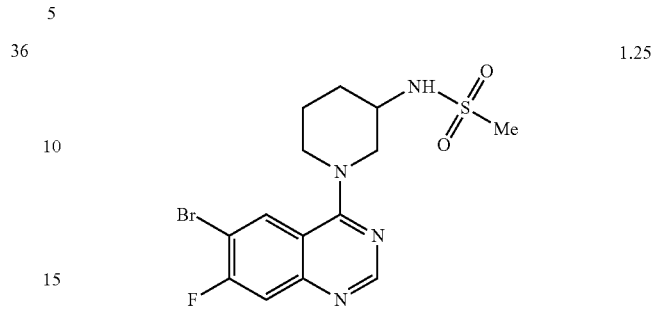

1.25 was made following the same procedure described above for compounds 31-35, 38, and 39.

ii. Preparation of N-(1-(6-cyano-7-fluoroquinazolin-4-yl)piperidin-3-yl)methanesulfonamide (37)

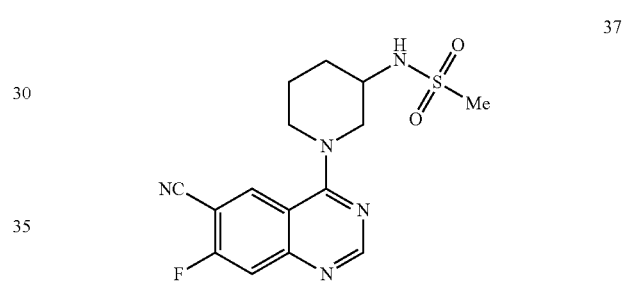

Compound 37 was synthesized from 1.25 according to the same protocol described for 29. Yield: 55%; $^1$H NMR (300 MHz, DMSO-d$_6$): δ 8.64 (s, 1H), 8.61 (d, J=6.9 Hz, 1H), 7.76 (d, J=10.8 Hz, 1H), 7.36 (d, J=6.9 Hz, 1H), 4.23 (d, J=12.0 Hz, 1H), 4.09 (d, J=13.5 Hz, 1H), 3.57 (br s, 1H), 3.43-3.37 (m, 2H), 2.9 (s, 3H), 2.03-1.88 (m, 2H), 1.70-1.55 (m, 2H); MS (MM) m/z 350.1[M+H]$^+$; HPLC Purity: 95.43 (% of AUC).

w. Synthesis of N-isopropyl-N-((1-(quinazolin-4-yl)piperidin-3-yl)methyl)methanesulfonamide (40)

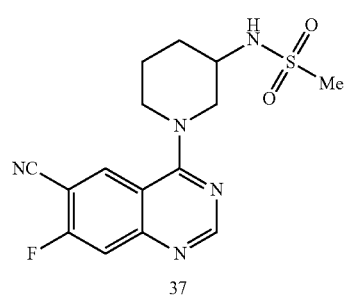 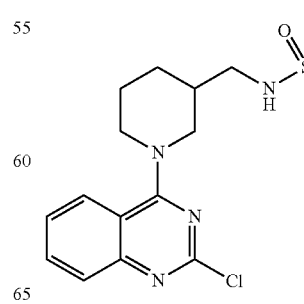 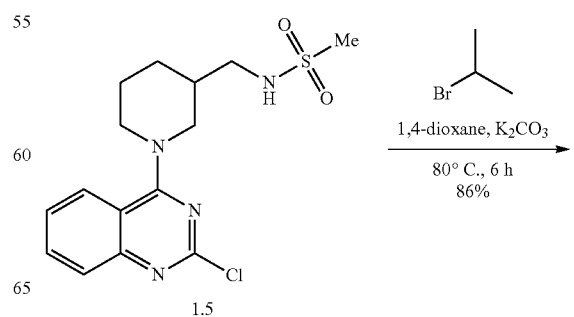

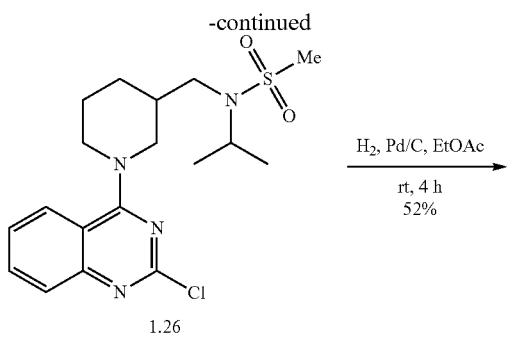

1.26

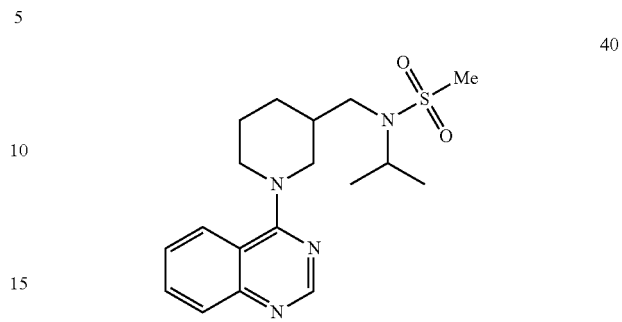

ii. Preparation of N-isopropyl-N-((1-(quinazolin-4-yl)piperidin-3-yl)methyl)methanesulfonamide 40

To a stirred solution of 1.26 (100 mg, 0.25 mmol) in EtOAc (2 mL) was added 10% Pd/C (20 mg, 20% w/w) under inert atmosphere and subjected to hydrogenation at −50 Psi pressure using hydrogen bladder at RT for 4 h. Upon complete consumption of the starting material, the reaction mixture was filtered through celite pad and the filtrate was concentrated under reduced pressure. The residue was purified by silica gel column chromatography (gradient elution 70-80% of EtOAc in hexanes) to afford 40 (47 mg, 52%/) as off-white solid. $^1$H NMR (400 MHz, CDCl$_3$): δ 9.53 (d, J=8.4 Hz, 1H), 8.90 (s, 1H), 7.88 (t, J=7.6 Hz, 1H), 7.75 (d, J=8.4 Hz, 1H), 7.45 (t, J=7.6 Hz, 1H), 4.67 (d, J=12 Hz, 1H), 4.44 (d, 12.4 Hz, 1H), 3.96-3.89 (m, 1H), 3.22 (t, J=12.4 Hz, 1H), 3.08-3.03 (m, 2H), 2.98-2.85 (m, 5H), 2.12 (br s, 1H), 1.96-1.92 (m, 1H), 1.85-1.81 (m, 1H), 1.61-1.58 (m, 1H), 1.22-1.17 (m, 6H); MS (MM) m/z 363.2 [M+H]$^+$; HPLC purity: >98 (% of AUC)

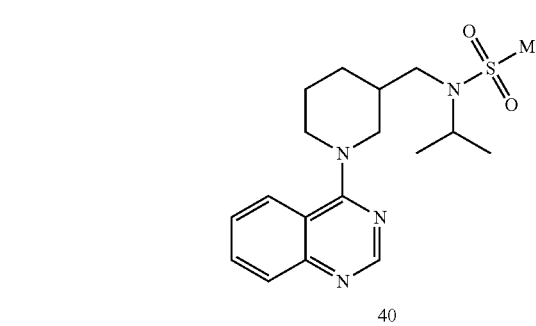

40 i. Preparation of N-((1-(2-chloroquinazolin-4-yl)piperidin-3-yl)methyl)-N-isopropylmethanesulfonamide (1.26)

x. Synthesis of N-isopropyl-N-((1-(6-methoxyquinazolin-4-yl)piperidin-3-yl)methyl)benzene-sulfonamide (41)

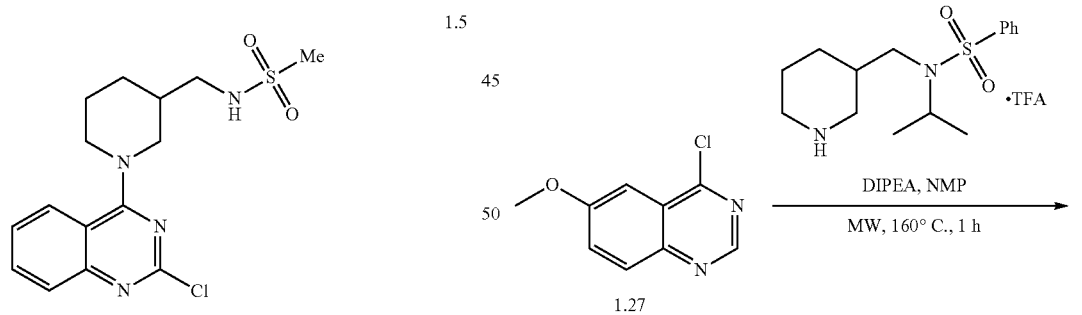

1.5        1.27

To a stirred solution of 1.5 (150 mg, 0.42 mmol) in DMF (1.5 mL) was added bromo isopropyl (103 mg, 0.84 mmol) and K$_2$CO$_3$ (174 mg, 1.26 mmol) at 80° C. for 6 h. Upon complete consumption of starting material, the reaction mixture was poured into water (25 mL), extracted with EtOAc (2×25 mL). The organic extracts were washed with saturated NaHCO$_3$ (25 mL), water (25 mL), brine (25 mL) dried over anhydrous Na$_2$SO$_4$ and concentrated under reduced pressure. The residue was purified by silica gel column chromatography (gradient elution 70-80% of EtOAc in hexanes) to afford 1.26 (144 mg, 86%) as an off-white solid.

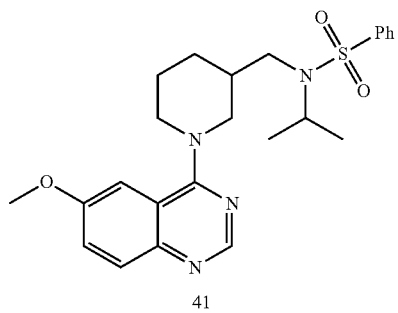

41

Compound 41 was synthesized from reaction of To a stirred solution of 4-chloro-6-methoxyquinazoline 1.27 and N-isopropyl-N-(piperidin-3-ylmethyl)benzenesulfonamide according the same procedure described in scheme 1. Yield: 23%; $^1$H NMR (400 MHz, CDCl$_3$): δ 8.61 (s, 1H), 7.77-7.72 (m, 3H), 7.49-7.38 (m, 2H), 7.35 (d, J=2.8 Hz, 1H), 7.33 (d, J=2.4 Hz, 1H), 7.14 (d, J=2.8 Hz, 1H), 4.30 (d, J=12.8 Hz, 1H), 4.10 (d, J=13.2 Hz, 1H), 3.98-3.93 (m, 1H), 3.90 (s, 3H), 3.05-3.02 (m, 1H), 2.99-2.96 (m, 2H), 2.78-2.73 (m, 1H), 2.28-2.20 (m, 1H), 2.00-1.97 (m, 1H), 1.88-1.83 (m, 1H), 1.80-1.73 (m, 1H), 1.26-1.20 (m, 1H), 0.92 (d, J=6.8 Hz, 3H), 0.87 (d, J=6.8 Hz, 3H); MS (MM) m/z 454.8 [M]$^+$; HPLC purity: >98 (% of AUC).

y. Synthesis of N-((1-(6-fluoroquinazolin-4-yl)piperidin-3-yl)methyl)-N-isopropylbenzenesulfonamide (42)

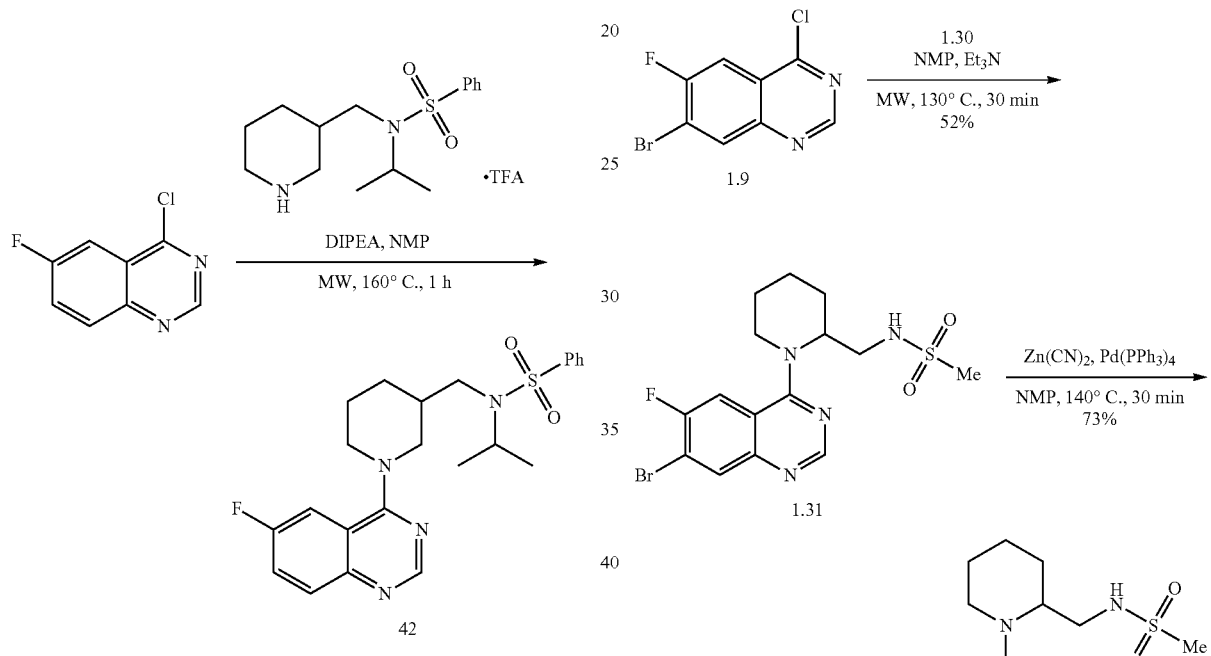

Same procedure described for 41. Yield: 18%; $^1$H NMR (400 MHz, CDCl$_3$): δ 8.71 (s, 1H), 7.92-7.89 (m, 1H), 7.82-7.80 (m, 2H), 7.55-7.51 (m, 3H), 7.49-7.46 (m, 2H), 4.39-4.35 (m, 1H), 4.20 (d, J=14.2 Hz, 1H), 3.15-3.07 (m, 3H), 2.86-2.80 (m, 1H), 2.32-2.26 (m, 1H), 2.08-2.05 (m, 1H), 1.95-1.90 (m, 1H), 1.82-1.71 (m, 1H), 1.35-1.26 (m, 2H), 1.08 (d, J=6.8 Hz, 3H), 1.03 (d, J=6.8 Hz, 3H); MS (MM) m/z 442.8 [M+H]$^+$; HPLC purity: >98 (% of AUC).

z. Synthesis of N-((1-(7-cyano-6-fluoroquinazolin-4-yl)piperidin-2-yl)methyl)methane-sulfonamide (43)

i. Preparation of tert-butyl 2-(methylsulfonamidomethyl)piperidine-1-carboxylate (1.29)

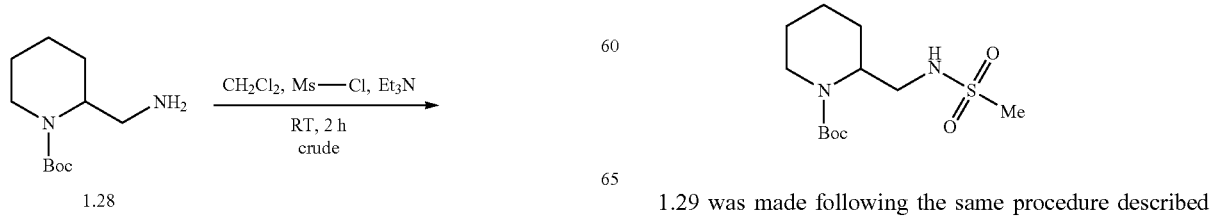

1.29 was made following the same procedure described above for 1.2. MS (MM): m/z=193.1 [M-Boc]$^+$.

ii. Preparation of
N-(piperidin-2-ylmethyl)methanesulfonamide (1.30)

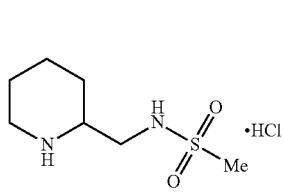

1.30 was made following the same procedure described above for 1.3. MS (MM): m/z=193.1 [M+H]$^+$.

iii. Preparation of N-((1-(7-bromo-6-fluoroquinazo-lin-4-yl)piperidin-2-yl)methyl)methane-sulfonamide (1.31)

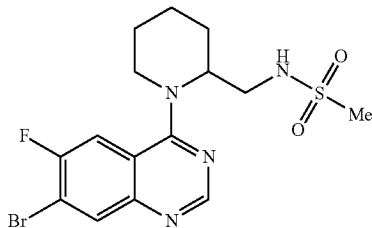

1.31 was made following the same procedure described above for compound 29. MS (MM): m/z=414.9 [M–H]$^+$.

iv. Preparation of N-((1-(7-cyano-6-fluoroquinazo-lin-4-yl)piperidin-2-yl)methyl)methane-sulfonamide (43)

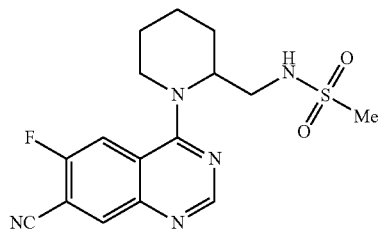

Compound 43 was made following the same procedure described above for compounds 1-14. Yield: 73% from 1.31; $^1$H NMR (300 MHz, CDCl$_3$): δ 8.68 (s, 1H), 8.24 (d, J=6.0 Hz, 1H), 7.64 (d, J=9.3 Hz, 1H), 5.88 (br s, 1H), 4.87 (br s, 1H), 4.09-3.85 (m, 2H), 3.59-3.49 (m, 1H), 3.34-3.26 (m, 1H), 2.95 (s, 3H), 2.05-1.71 (m, 6H); MS (MM) m/z 364.3 [M+H]$^+$; HPLC Purity: >99 (% of AUC).

aa. Synthesis of N-((1-(6-fluoroquinazolin-4-yl)piperidin-4-yl)methyl)methanesulfonamide (44)

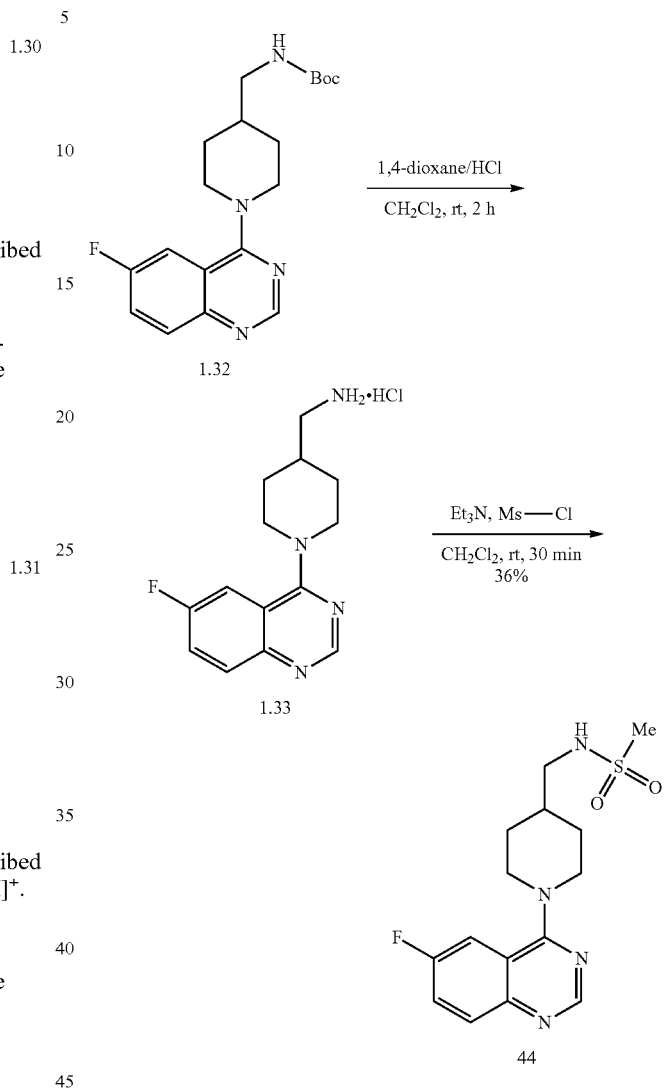

i. Preparation of (1-(6-fluoroquinazolin-4-yl)piperi-din-4-yl)methanamine hydrochloride (1.33)

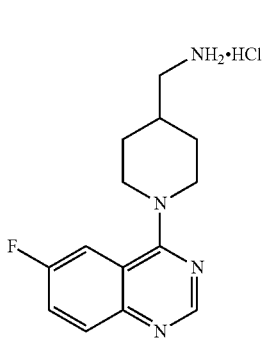

1.33 was made following as in the procedure described above for compounds 1-14.

ii. Preparation of N-((1-(6-fluoroquinazolin-4-yl)piperidin-4-yl)methyl)methanesulfonamide (44)

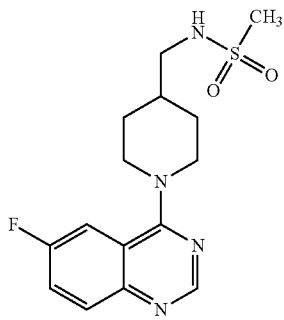

44

To a stirred solution of 1.33 (150 mg, 0.48 mmol) in CH$_2$Cl$_2$ (15 mL) added methane sulphonyl chloride (65.9 mg, 0.57 mmol) and Et$_3$N (145 mg, 1.44 mmol) at RT. The reaction mixture was stirred at RT for 30 min. Upon complete consumption of starting material, the reaction mixture was poured into water (20 mL), extracted with CH$_2$Cl$_2$ (2×20 mL). The organic extracts were washed with saturated NaHCO$_3$ (10 mL), water (20 mL) and brine (20 mL), dried over anhydrous Na$_2$SO$_4$ and concentrated under reduced pressure. The residue was purified by silica gel column chromatography (gradient elution 80-90% of EtOAc in hexanes) to afford 44 (62 mg, crude, 36%) as an off-white solid. $^1$H NMR (300 MHz, CDCl$_3$): δ 8.72 (s, 1H), 7.93-7.88 (m, 1H), 7.54-7.45 (m, 2H), 4.41-4.29 (m, 3H), 3.15-3.11 (m, 4H), 2.99 (s, 3H), 1.97-1.73 (m, 3H), 1.55-1.42 (m, 2H); MS (MM) m/z 339.0 [M+H]$^+$; HPLC purity: >94 (% of AUC).

bb. Synthesis of N-(1-(1-(6,7-difluoroquinazolin-4-yl)piperidin-3-yl)ethyl)methanesulfonamide (45)

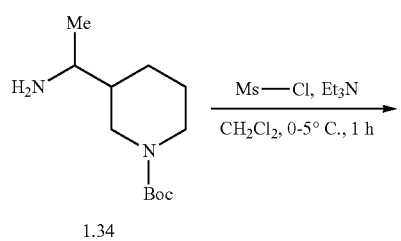

1.34

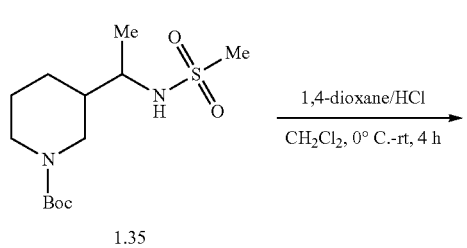

1.35

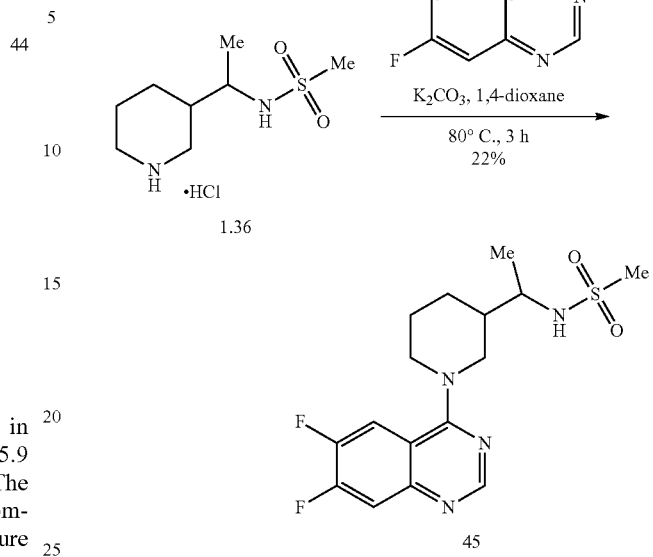

i. Preparation of N-(1-(piperidin-3-yl)ethyl)methanesulfonamide (1.36)

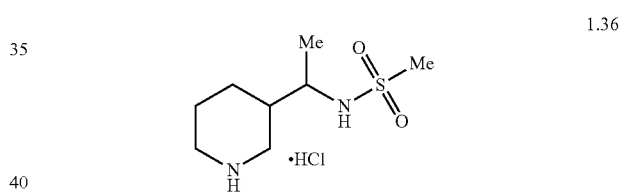

1.36

1.36 was made following the same procedure described above for 1.3.

ii. Preparation of N-(1-(1-(6,7-difluoroquinazolin-4-yl)piperidin-3-yl)ethyl)methanesulfonamide (45)

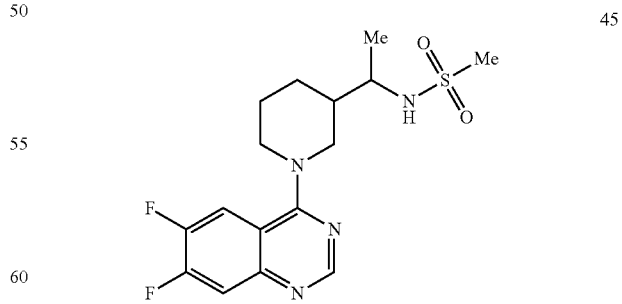

45

To a stirred solution of 1.36 (20 mg, 0.09 mmol) in 1,4-dioxane (2 mL) added 4-chloro-6,7-difluoroquinazoline (22 mg, 0.11 mmol) and K$_2$CO$_3$ (68 mg, 0.49 mmol) at RT. The reaction mixture was stirred at 80° C. for 3 h. Upon complete consumption of starting material, the reaction mixture was poured into water (25 mL), extracted with EtOAc (25 mL). The organic extracts were washed with saturated NaHCO₃ (25 mL), water (25 mL), brine (25 mL), dried over anhydrous Na₂SO₄ and concentrated under reduced pressure. The residue was purified by silica gel column chromatography (gradient elution 80-90% of EtOAc in hexanes) to afford 45 (8 mg, 22%). ¹H NMR (400 MHz, DMSO-d6): δ 8.60 (s, 1H), 7.91-7.79 (m, 2H), 7.07 (t, J=8.8 Hz, 1H), 4.31 (d, J=13.8 Hz, 1H), 4.02 (t, J=12.8 Hz, 1H), 3.20-3.10 (m, 2H), 2.92-2.89 (m, 4H), 1.92-1.78 (m, 3H), 1.65-1.59 (m, 1H), 1.39-1.30 (m, 1H), 1.19-1.11 (m, 3H); MS (MM) m/z 371.1[M+H]⁺; HPLC purity: >98 (% AUC).

cc. Synthesis of N-((4-(6-fluoroquinazolin-4-yl)morpholin-2-yl)methyl)methanesulfonamide (46)

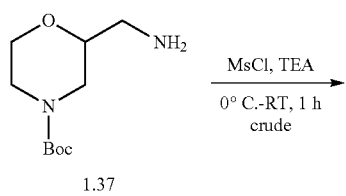

1.37

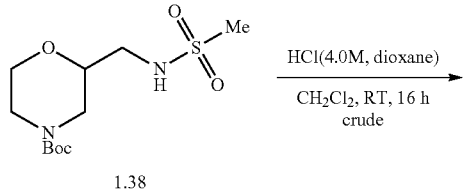

1.38

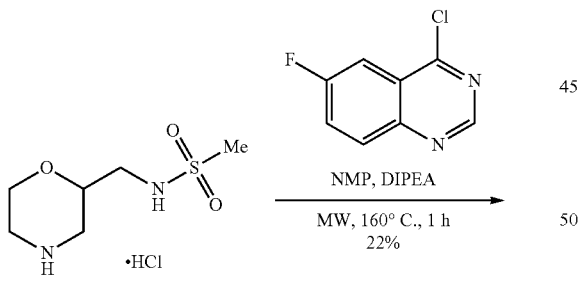

1.39

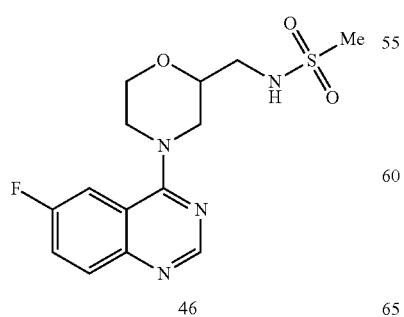

46 i. Preparation of tert-butyl 2-(methylsulfonamidomethyl)morpholine-4-carboxylate (1.38)

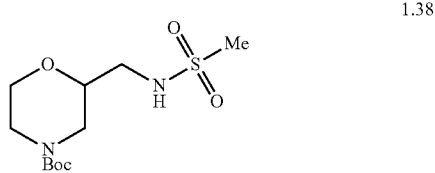 [SMILES: CC(C)(C)OC(=O)N1CCOC(CNS(C)(=O)=O)C1]

1.38

1.38 was made following the same procedure described above for 1.2. MS (MM): m/z 195.1[M-Boc]⁺.

ii. Preparation of N-(morpholin-2-ylmethyl)methanesulfonamide (1.39)

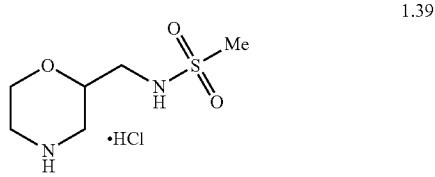 [SMILES: CS(=O)(=O)NCC1CNCCO1 ; Cl]

1.39

1.39 was made following the same procedure described above for compound 1.3. MS (MM):(MM) m/z 195.1[M+H]⁺.

iii. Preparation of N-((4-(6-fluoroquinazolin-4-yl)morpholin-2-yl)methyl)methanesulfonamide (46)

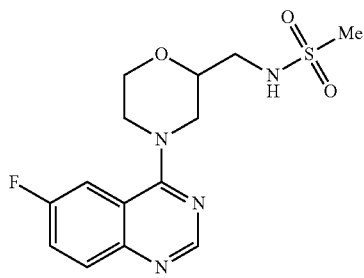

46

Compound 46 was prepared from reaction of 1.39 and 4-chloro-6-fluoro-quinazoline according to the same procedure described for compounds 1-14. Yield: 22% as a yellow solid; ¹H NMR (400 MHz, DMSO-d₆): δ 8.67 (s, 1H), 7.94-7.92 (m, 1H), 7.80-7.74 (m, 2H), 7.21 (t, J=6.0 Hz, 1H), 4.23-4.20 (m, 1H), 4.11-4.07 (m, 1H), 3.97-3.94 (m, 1H), 3.77-3.69 (m, 2H), 3.34-3.27 (m, 1H), 3.12 (t, J=6.0 Hz, 2H), 3.06-3.01 (m, 1H), 2.93 (s, 3H); MS (MM) m/z 341.1 [M+H]⁺; HPLC Purity: >99 (% of AUC).

dd. Synthesis of 6-fluoro-4-(2-(methylsulfona-midomethyl)morpholino)quinazoline-7-carboxamide (47)

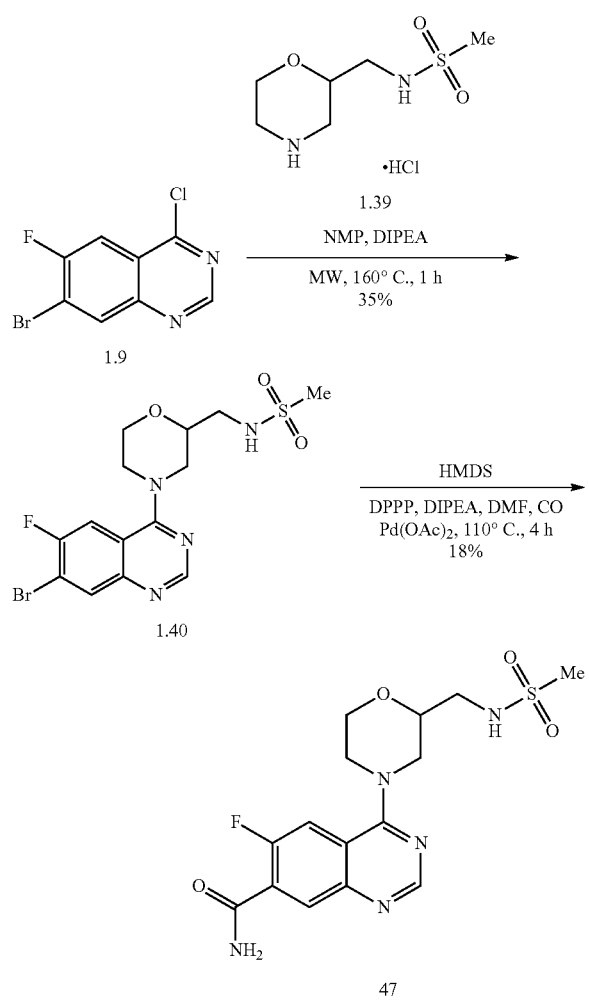

i. Preparation of N-((4-(7-bromo-6-fluoroquinazo-lin-4-yl)morpholin-2-yl)methyl)methanesulfonamide (1.40)

Compound 1.40 was prepared according to the same procedure described for compounds 1-14. Yield: 35% as an off-white solid; $^1$H NMR (400 MHz, DMSO-d$_6$): δ 8.65 (s, 1H), 8.23 (d, J=6.8 Hz, 1H), 7.93 (d, J=9.6 Hz, 1H), 7.21 (t, J=6.4 Hz, 1H), 4.27-4.24 (m, 1H), 4.15-4.11 (m, 1H), 3.96-3.93 (m, 1H), 3.75-3.68 (m, 2H), 3.37-3.34 (m, 1H), 3.13-3.09 (m, 2H), 3.07-3.04 (m, 1H), 2.93 (s, 3H); MS (MM): m/z 419.0 [M]$^+$; HPLC Purity: 97.4 (% of AUC).

ii. Preparation of 6-fluoro-4-(2-(methylsulfona-midomethyl)morpholino)quinazoline-7-carboxamide (47)

To a stirred solution of 1.40 (100 mg, 0.23 mmol) in DMF (10 mL) taken in a steel bomb was added hexamethyldisi-lazane (110 mg, 0.71 mmol) and DIPEA (0.09 mg, 0.71 mmol). Ar (g) gas was purged and the reaction was degassed for about 5 min. added Pd(OAc) (16 mg, 0.023 mmol), DPPP (10 mg). CO was filled up to 250 Psi, stirred at 110° C. for 4 h. Upon complete consumption of starting material, the reaction mixture was poured into water (20 mL), extracted with EtOAc (2×20 mL). The organic extracts were washed with water (2×20 mL), brine (20 mL), dried over anhydrous Na$_2$SO$_4$ and concentrated under reduced pressure. The residue was purified by silica gel column chromatography (gradient elution 80-90% of EtOAc in hexanes) to afford 47 (16 mg, 18%) as an off-white solid. $^1$H NMR (400 MHz, MeOD): δ 8.68 (s, 1H), 8.08 (br s, 1H), 8.01 (d, J=6.8 Hz, 1H), 7.84 (s, 1H), 7.82 (s, 1H), 7.21 (t, J=6.0 Hz, 1H), 4.27-4.24 (m, 1H), 4.15-4.11 (m, 1H), 3.97-3.94 (m, 1H), 3.76-3.70 (m, 2H), 3.37-3.35 (m, 1H), 3.13-3.04 (m, 4H), 2.93 (s, 3H); MS (MM): m/z 384.1 [M+H]$^+$; HPLC Purity: 97.4 (% of AUC).

ee. Synthesis of N-((1-(6-bromo-7-fluoroquinazolin-4-yl)-3-methylpiperidin-3-yl)methyl)methanesulfo-namide (48)

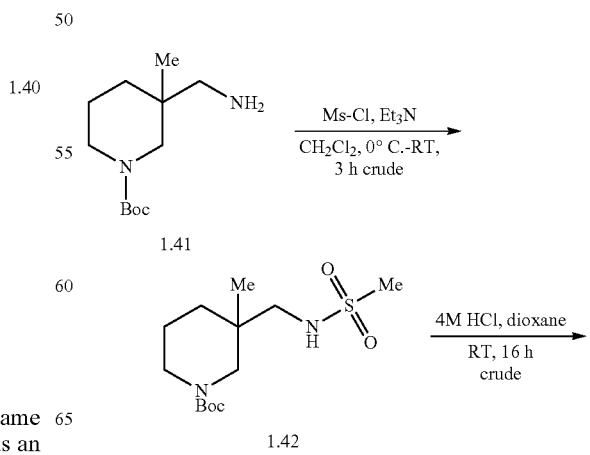

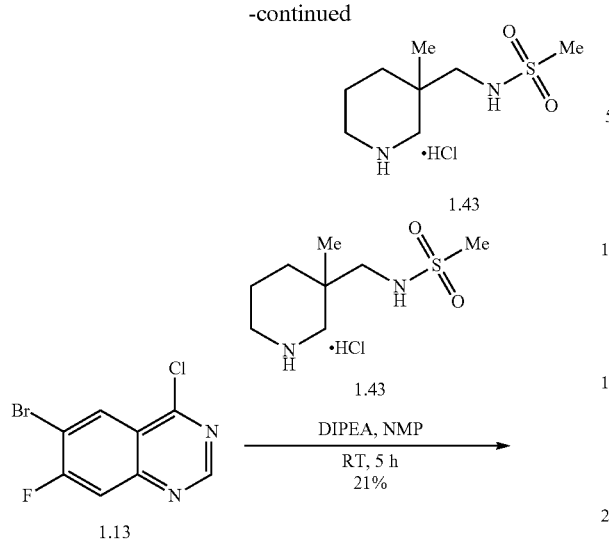

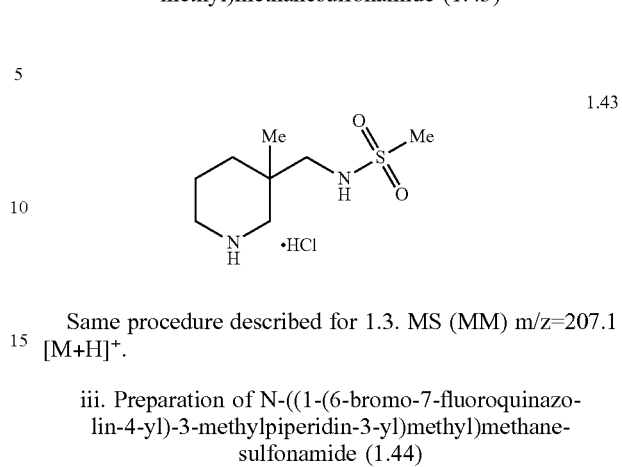

ii. Preparation of N-((3-methylpiperidin-3-yl)methyl)methanesulfonamide (1.43)

Same procedure described for 1.3. MS (MM) m/z=207.1 [M+H]⁺.

iii. Preparation of N-((1-(6-bromo-7-fluoroquinazolin-4-yl)-3-methylpiperidin-3-yl)methyl)methanesulfonamide (1.44)

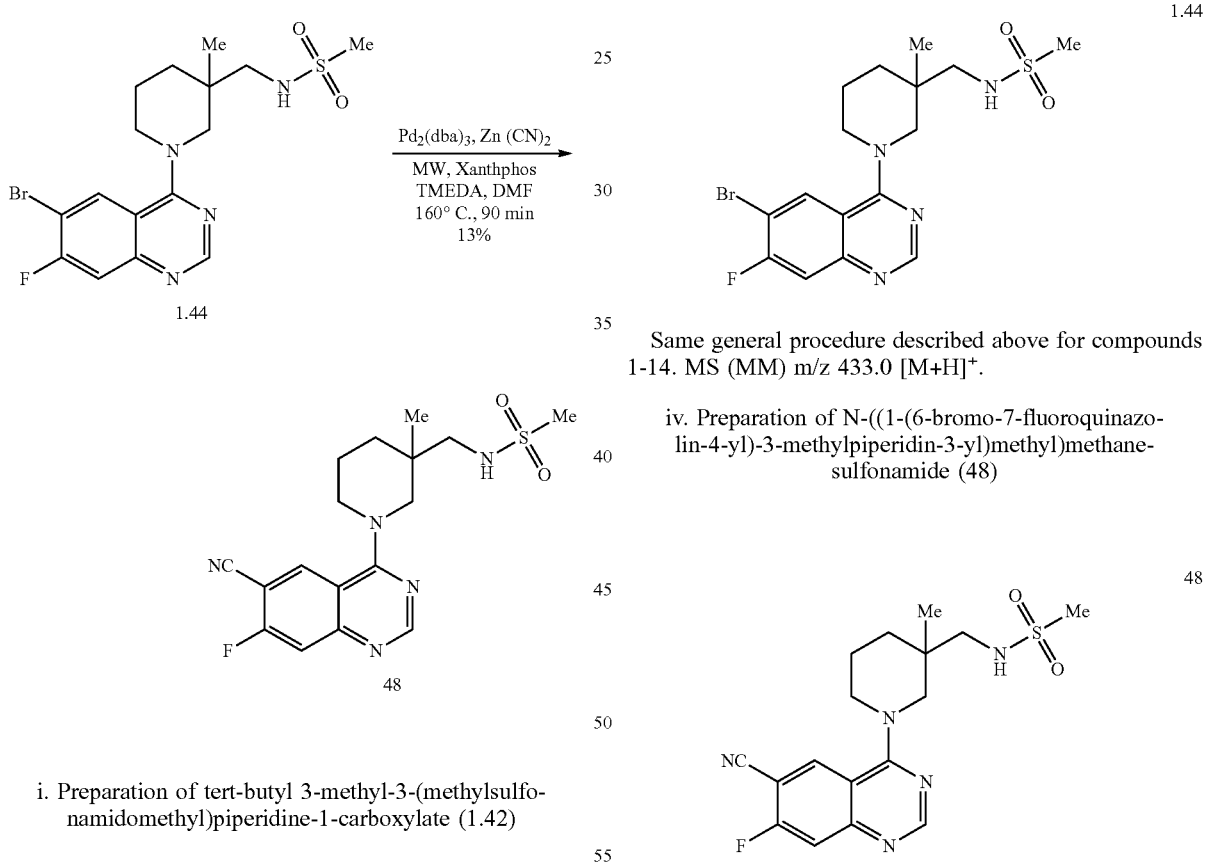

Same general procedure described above for compounds 1-14. MS (MM) m/z 433.0 [M+H]⁺.

iv. Preparation of N-((1-(6-bromo-7-fluoroquinazolin-4-yl)-3-methylpiperidin-3-yl)methyl)methanesulfonamide (48)

i. Preparation of tert-butyl 3-methyl-3-(methylsulfonamidomethyl)piperidine-1-carboxylate (1.42)

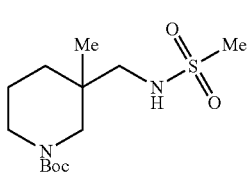

Same procedure described for 1.2. MS (MM) m/z=305.1 [M−H]⁺.

To a stirred solution of 1.44 (75 mg, 0.17 mmol) in NMP (7.0 mL) was added Zn(CN)₂ (40 mg, 0.34 mmol) purged with Ar (g) for 10 min and then added Pd₂(dba)₃ (15 mg, 0.016 mmol), Xantphos (9 mg, 0.016 mmol) and tetramethylethylenediamine (TMEDA) (3 mg, 0.033 mmol) under Ar (g) atmosphere and subjected to microwave at 200 W, 200 psi, 160° C. for 90 min. After 90 min, the reaction mixture was cooled to RT, water (100 mL) was added and the mixture was extracted with EtOAc (2×250 mL). The organic extracts were washed with water (20 mL), brine (20 mL), dried over anhydrous Na₂SO₄ and concentrated under reduced pressure. The residue was purified by mass triggered prep HPLC to afford 48 (9 mg, 13%) as an off-white solid. ¹H NMR (400 MHz, DMSO-d₆) δ: 8.59 (s, 1H), 8.56 (d, J=7.20 Hz, 1H), 7.73 (d, J=10.8 Hz, 1H), 7.00 (t, J=6.8 Hz, 1H), 3.89-3.86 (m, 1H), 3.75-3.71 (m, 2H), 3.61-3.58 (m, 1H), 2.83 (br s, 5H), 1.78-1.76 (m, 2H), 1.64-1.61 (m, 1H), 1.46-1.41 (m, 1H), 1.23-1.22 (m, 3H). LCMS (ESI): m/z=378 [M+H]⁺, HPLC: 96.7% (AUC).

ff. Synthesis of N-((1-(6-cyano-7-fluoroquinazolin-4-yl)-3-hydroxypiperidin-3-yl)methyl)methanesulfonamide (49)

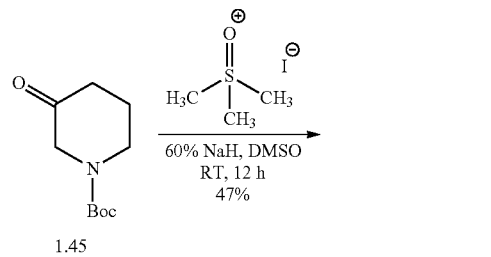

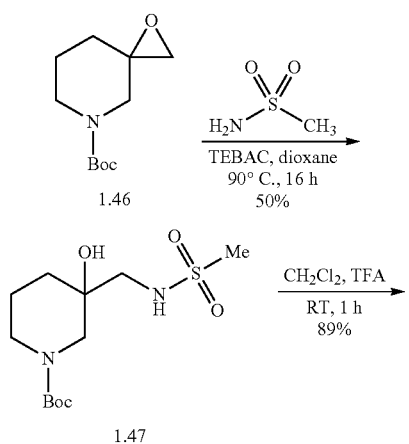

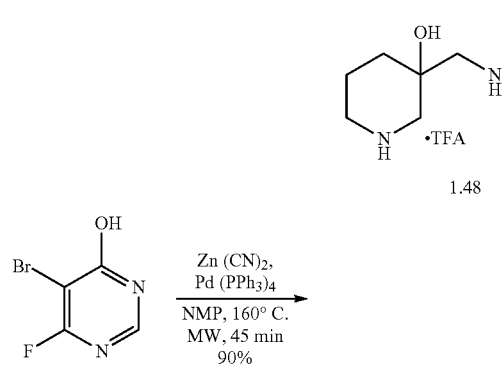

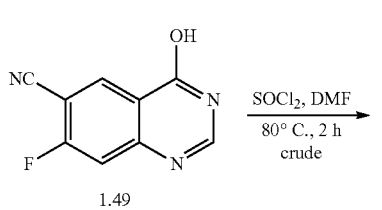

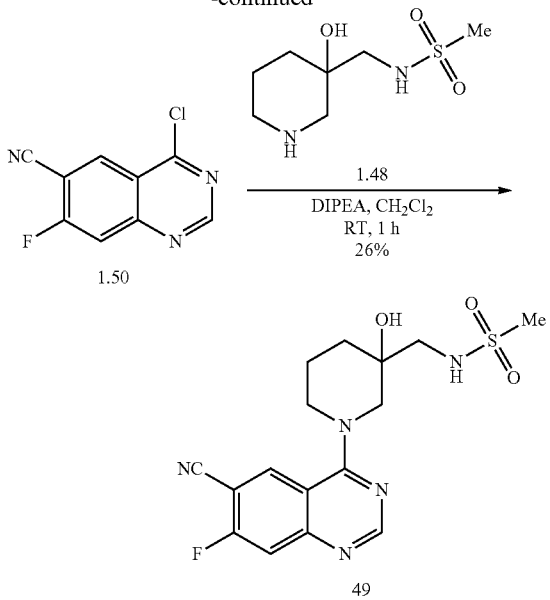

i. Preparation of tert-butyl 1-oxo-5-azaspiro[2.5]octane-5-carboxylate (1.46)

To a stirred solution of trimethylsulfoxonium iodide (650 mg, 2.50 mmol) in DMSO (15 mL) was added 60% NaH (138 mg, 3.01 mmol) stirred for 30 min at RT. 1 (500 mg, 2.50 mmol) was added. The reaction mixture was stirred at RT for 12 h. Upon complete consumption of starting material, the reaction mixture was poured into water (25 mL), extracted with CH₂Cl₂ (2×25 mL). The organic extracts were washed with saturated NaHCO₃ (25 mL), water (25 mL), brine (25 mL), dried over anhydrous Na₂SO₄ and concentrated under reduced pressure to afford 1.46 (250 mg, 47%) as a brown gummy liquid. ¹H NMR (400 MHz, CDCl₃): δ: 3.46-3.43 (m, 3H), 3.36-3.33 (m, 1H), 2.75 (br s, 1H), 2.66 (d, J=4.4 Hz, 1H), 1.86-1.80 (m, 1H), 1.74-1.60 (m, 3H), 1.45 (s, 9H).

ii. Preparation of tert-butyl 3-hydroxy-3-(methylsulfonamidomethyl)piperidine-1-carboxylate (1.47)

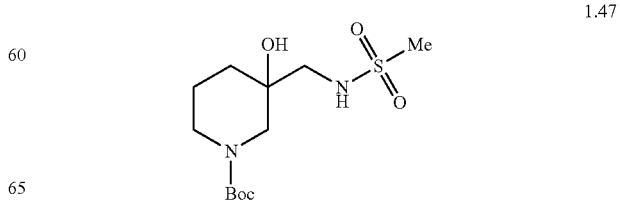

To a stirred solution of 1.46 (250 mg, 1.17 mmol) in 1,4-dioxane (2.5 mL) were added compound methanesulfonamide (167 mg, 1.75 mmol), Tetraethylbenzylammoniumchloride (TEBAC) (26 mg, 0.11 mmol) and K₂CO₃ (16 mg, 0.11 mmol) at RT. The reaction mixture was allowed to stir at 90° C. for 16 h. Upon complete consumption of starting material, the reaction mixture was poured into water (25 mL), extracted with CH₂Cl₂ (2×25 mL). The organic extracts were washed with saturated NaHCO₃ (25 mL), water (25 mL), brine (25 mL), dried over anhydrous Na₂SO₄ and concentrated under reduced pressure. The residue was purified by silica gel column chromatography eluting (EtOAc:hexanes; 5:5). Fractions containing the product were combined and concentrated under reduced pressure to afford 1.47 (180 mg, 50%) as a clear gummy liquid. $^1$H NMR (400 MHz, CDCl₃) δ: 3.36-3.33 (m, 2H), 3.25-3.22 (m, 2H), 3.07-3.04 (m, 2H), 2.93 (s, 3H), 1.68-1.61 (m, 3H), 1.43 (br s, 1H), 1.39 (s, 9H). LCMS (ESI): m/z=307 [M+H]⁺.

iii. Preparation of N-((3-hydroxypiperidin-3-yl)methyl)methanesulfonamide (1.48)

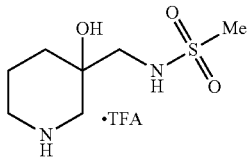

1.48

To a stirred solution of compound 1.47 (500 mg, 1.62 mmol) in CH₂Cl₂ (12.5 mL) was added TFA (786 mg, 8.10 mmol) at RT. The reaction mixture was stirred at RT for 1 h. Upon complete consumption of starting material, the reaction mixture was concentrated under reduced pressure. Co-distilled with toluene (3×50 mL) to afford 1.48 (300 mg, 1.44 mmol, 89%) as a brown gummy liquid. $^1$H NMR (400 MHz, CDCl₃) δ: 3.21 (br s, 2H), 3.12 (s, 3H), 2.98-2.88 (m, 4H), 2.06-2.01 (m, 1H), 1.87-1.84 (m, 1H), 1.56-1.39 (m, 2H). LCMS (ESI): m/z=209 [M+H]⁺.

iv. Preparation of 7-fluoro-4-hydroxyquinazoline-6-carbonitrile (1.49)

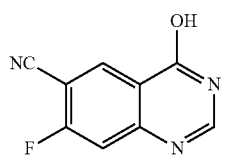

1.49

To a stirred solution of 1.12 (700 mg, 2.88 mmol) in NMP (17 mL) taken in a microwave vial was charged with Zn(CN)₂ (676 mg, 5.76 mmol) and was degassed with argon for 10 min. Pd(PPh₃)₄ (332 mg, 0.28 mmol) was added to the reaction mixture under Ar (g) atmosphere and the reaction mixture was again purged with argon for 5 min. The microwave vial was sealed and irradiated at 160° C. in CEM-microwave instrument for 1 h. Upon complete consumption of starting material, the reaction mixture was poured into water (25 mL), extracted with EtOAc (2×25 mL). The combined organic extracts were washed with water (25 mL), brine (25 mL), dried over anhydrous Na₂SO₄ and concentrated under reduced pressure. The residue was purified by silica gel column chromatography eluting (EtOAc:hexanes; 8:2). Fractions containing the product were combined and concentrated under reduced pressure to afford 1.49 (490 mg, 90%) as an off-white solid. $^1$H NMR (400 MHz, DMSO-d₆) δ: 12.73 (br s, 1H), 8.64 (d, J=7.2 Hz, 1H), 8.29 (d, J=3.6 Hz, 1H), 7.76 (d, J=10.4 Hz, 1H). LCMS (ESI): m/z=188 [M+H]⁺.

v. Preparation of 4-chloro-7-fluoroquinazoline-6-carbonitrile (1.50)

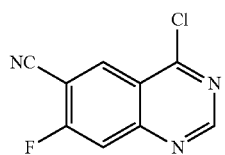

1.50

To a stirred solution of 8 (175 mg, 0.92 mmol) was added SOCl₂ (15 mL) at RT. The reaction mixture was stirred at 80° C. for 2 h. Upon complete consumption of starting material, the reaction mixture was concentrated under reduced pressure. Co-distilled with toluene (3×25 mL) to afford 1.50 (175 mg, crude) as brown gummy liquid. The crude product used directly in the next step without further analysis.

vi. Preparation of N-((1-(6-cyano-7-fluoroquinazolin-4-yl)-3-hydroxypiperidin-3-yl)methyl)methanesulfonamide (49)

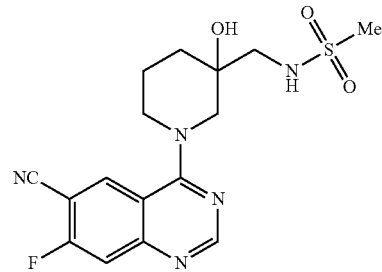

49

To a stirred solution of 1.50 (175 mg, 0.843 mmol) in CH₂Cl₂ (7.5 mL) were added 1.48 (175 mg, 0.843 mmol) and DIPEA (325 mg, 2.52 mmol) at RT. The reaction mixture was allowed to stir at RT for 1 h. Upon complete consumption of starting material, the reaction mixture was poured into water (25 mL), extracted with EtOAc (2×25 mL). The combined organic extracts were washed with water (25 mL), brine (25 mL), dried over anhydrous Na₂SO₄ and concentrated under reduced pressure. The residue was purified by silica gel column chromatography eluting (EtOAc:hexanes; 4:6). Fractions containing the product were combined and concentrated under reduced pressure to afford 49 (85 mg, 26%) as an off-white solid. $^1$H NMR (400 MHz, DMSO-d₆) δ: 8.74 (d, J=7.2 Hz, 1H), 8.58 (s, 1H), 7.72 (d, J=10.8 Hz, 1H), 7.00 (t, J=6.4 Hz, 1H), 4.88 (s, 1H), 4.31 (d, J=12.8 Hz, 1H), 4.00 (d, J=13.2 Hz, 1H), 3.49 (d, J=13.6 Hz, 1H), 3.25 (t, J=10.4 Hz, 1H), 2.96 (d, J=6.4 Hz, 2H), 2.90 (s, 3H), 1.98-1.96 (m, 1H), 1.74-1.64 (m, 3H). LCMS (ESI): m/z=378 [M+H]+. HPLC: 98.7% (AUC).

gg. Synthesis of N-((1-(6-cyano-7-fluoroquinazolin-4-yl)-3-fluoropiperidin-3-yl)methyl)methanesulfonamide (50)

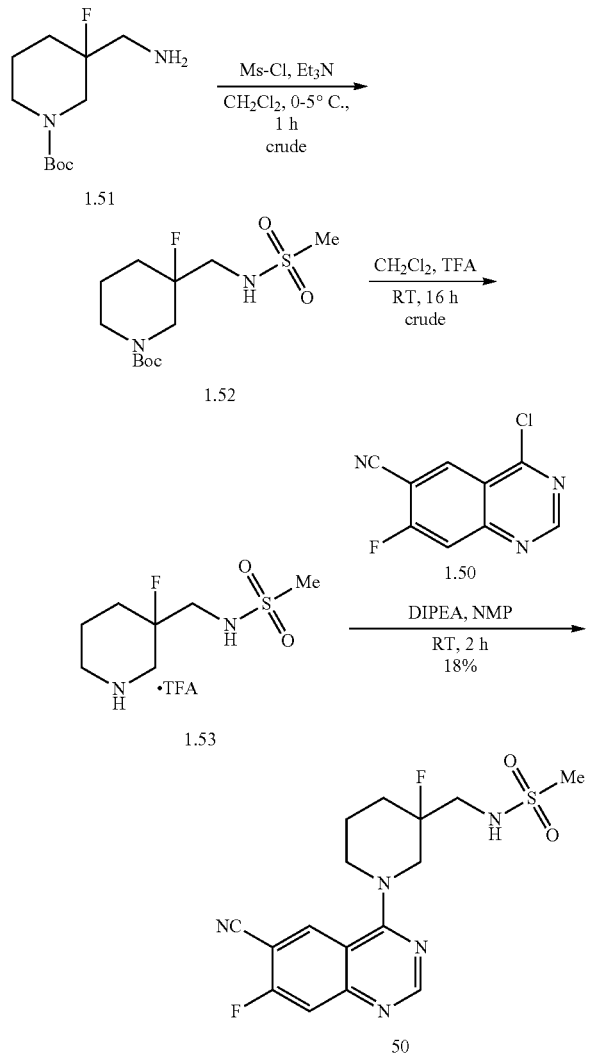

i. Preparation of tert-butyl 3-fluoro-3-(methylsulfonamidomethyl)piperidine-1-carboxylate (1.52)

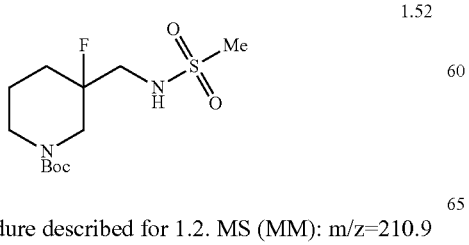

Same procedure described for 1.2. MS (MM): m/z=210.9 [M-Boc]+.

ii. Preparation of N-((3-fluoropiperidin-3-yl)methyl)methanesulfonamide (1.53)

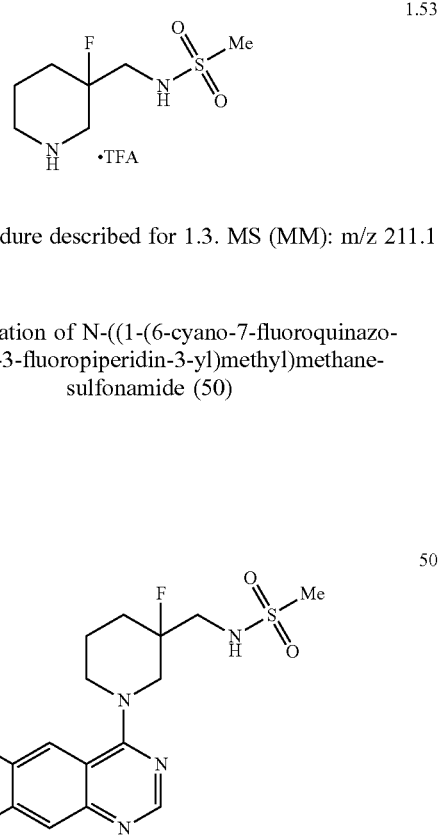

Same procedure described for 1.3. MS (MM): m/z 211.1 [M+H]+.

iii. Preparation of N-((1-(6-cyano-7-fluoroquinazolin-4-yl)-3-fluoropiperidin-3-yl)methyl)methanesulfonamide (50)

Same general procedure described for compounds 1-14 above. $^1$H NMR (400 MHz, DMSO-d$_6$): δ 8.64 (s, 1H), 8.57 (d, J=6.8 Hz, 1H), 7.77 (d, J=10.8 Hz, 1H), 7.39 (t, J=6.4 Hz, 1H), 4.46-4.34 (m, 2H), 3.67 (d, J=14.4 Hz, 1H), 3.36-3.33 (m, 1H), 3.29-3.24 (m, 1H), 3.23-3.21 (m, 1H), 2.89 (s, 3H), 1.98-1.87 (m, 2H), 1.81-1.75 (m, 2H); MS (MM): m/z 382.1 [M+H]+; HPLC purity: >98.7 (% of AUC).

hh. Synthesis of N-((1-(6-fluoroquinazolin-4-yl)pyrrolidin-3-yl)methyl)methanesulfonamide (51)

i. Preparation of (1-(6-fluoroquinazolin-4-yl)pyrrolidin-3-yl)methanamine (1.54)

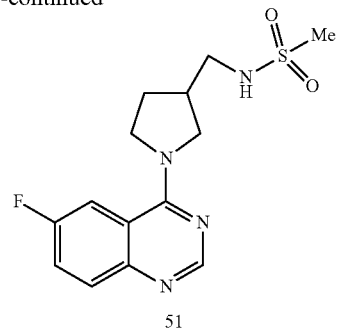

51

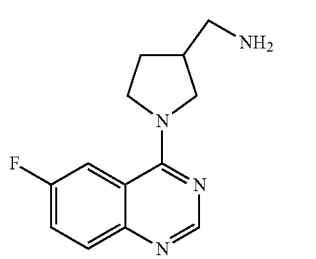

1.54

1.54 was prepared in two steps from 4-chloro-6-fluoroquinazoline following the same general procedure described for compounds 1-14 above. 1H NMR (400 MHz, DMSO-d6) δ 8.72 (s, 1H), 8.12 (dd, J=10.5, 2.5 Hz, 1H), 7.98-7.82 (m, 5H), 4.20 (dd, J=12.2, 7.2 Hz, 1H), 4.17-4.07 (m, 1H), 3.83 (t, J=10.0 Hz, 1H), 3.04-2.94 (m, 2H), 2.60 (dt, J=15.2, 7.6 Hz, 1H), 2.21 (dd, J=11.1, 5.6 Hz, 1H), 1.81 (dq, J=12.3, 8.5 Hz, 1H); FABMS (M+H) calculated for $C_{13}H_{15}FN_4 \cdot H$ was 247.1354 found 247.1346.

ii. Preparation of Synthesis of N-((1-(6-fluoroquinazolin-4-yl)pyrrolidin-3-yl)methyl)methanesulfonamide (51)

51

Same procedure described for 44. Yield from 1.54:32%; 1H NMR (400 MHz, DMSO-d6) δ 8.42 (s, 1H), 7.97 (dd, J=10.9, 2.7 Hz, 1H), 7.76 (dd, J=9.2, 5.9 Hz, 1H), 7.67 (ddd, J=9.2, 8.2, 2.7 Hz, 1H), 7.21 (t, J=6.1 Hz, 1H), 4.04-3.79 (m, 3H), 3.64 (dd, J=11.2, 7.4 Hz, 1H), 3.06 (h, J=6.7 Hz, 2H), 2.90 (s, 3H), 2.48-2.38 (m, 1H), 2.08 (dq, J=11.8, 6.5 Hz, 1H), 1.74 (dq, J=12.2, 8.1 Hz, 1H); FABMS (M+H) calculated for $C_{14}H_{17}FN_4O_2S \cdot H$ was 325.1129 found 325.1128; HPLC purity >99 (% of AUC), $t_R$=1.46, 1.73 minutes.

ii. Synthesis of N-(3-(6-fluoroquinazolin-4-yl)cyclobutyl)methanesulfonamide (52)

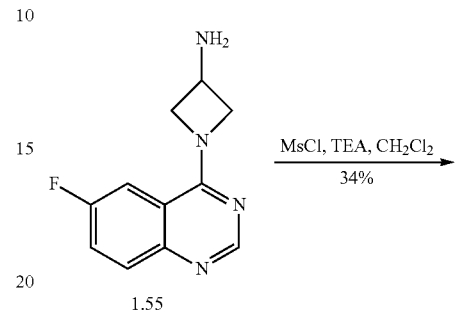

1.55

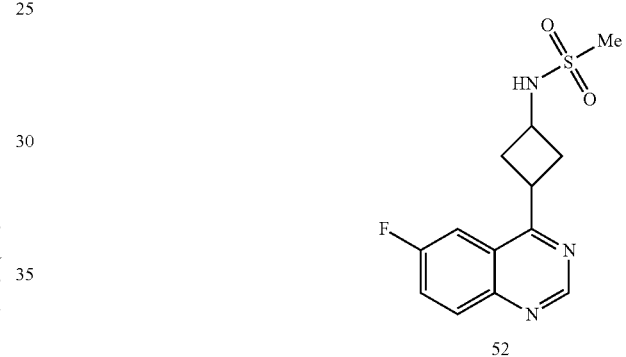

52 i. Preparation of 1-(6-fluoroquinazolin-4-yl)azetidin-3-amine (1.55)

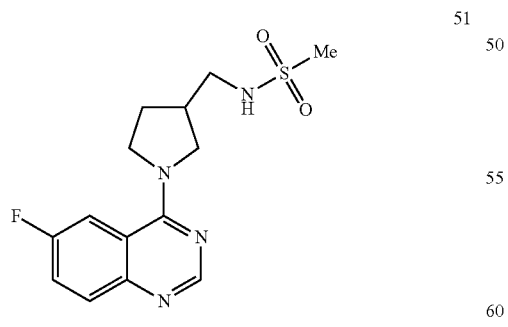

1.55

Intermediate 1.55 was prepared in two steps following the same general procedure described for compounds 1-14 above. FABMS (M+H) calculated for $C_{11}H_{11}FN_4 \cdot H$ was 219.1041 found 219.1042.

ii. Preparation of N-(3-(6-fluoroquinazolin-4-yl)cyclobutyl)methanesulfonamide (52)

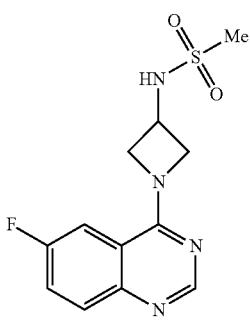

Compound 52 was prepared by mesylation of 1.55 following the same procedure described for preparation of 1.2 (Scheme 1). Yield from 1.55:34%; 1H NMR (400 MHz, DMSO-d6) δ 8.52 (s, 1H), 7.98 (d, J=8.0 Hz, 1H), 7.86-7.70 (m, 1H), 7.67 (dd, J=9.7, 2.7 Hz, 1H), 4.39 (s, 2H), 3.32 (s, 5H), 2.97 (s, 2H); FABMS (M+H) calculated for $C_{12}H_{13}FN_4O_2S.H$ was 297.0864 found 297.0814; HPLC purity=100 (% of AUC), $t_R$=1.73 minutes.

jj. Synthesis of N-((1-(7-cyano-6-fluoroquinazolin-4-yl)piperidin-3-yl)methyl)-1,1,1-trifluoromethanesulfonamide (53)

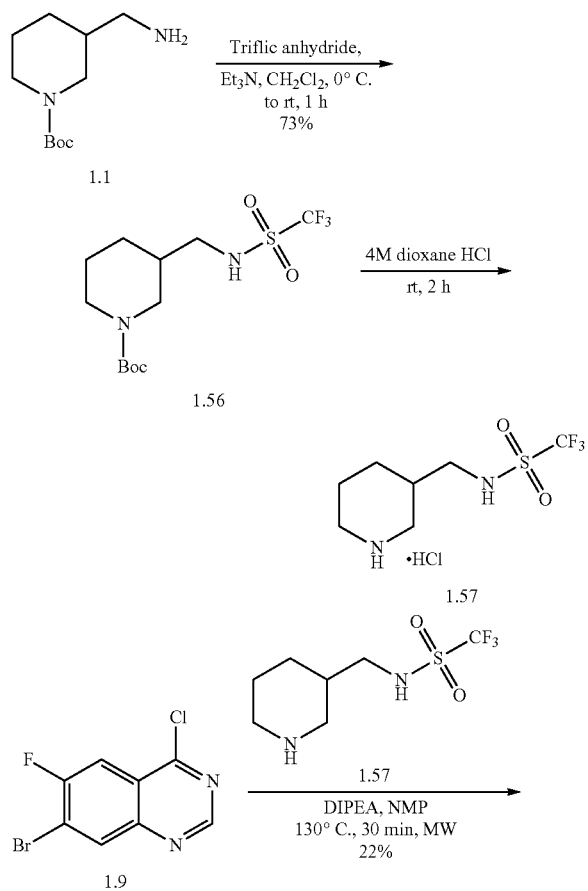

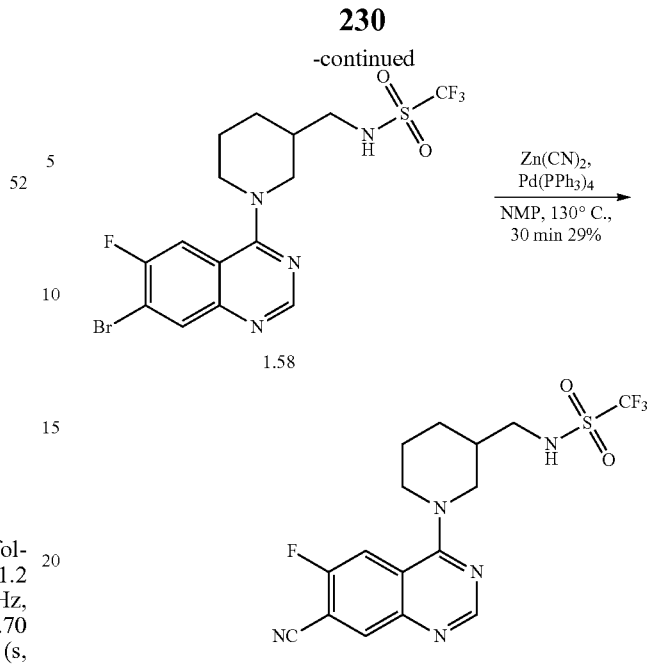

i. Preparation of tert-butyl 3-(((trifluoromethyl)sulfonamido)methyl)piperidine-1-carboxylate (1.56)

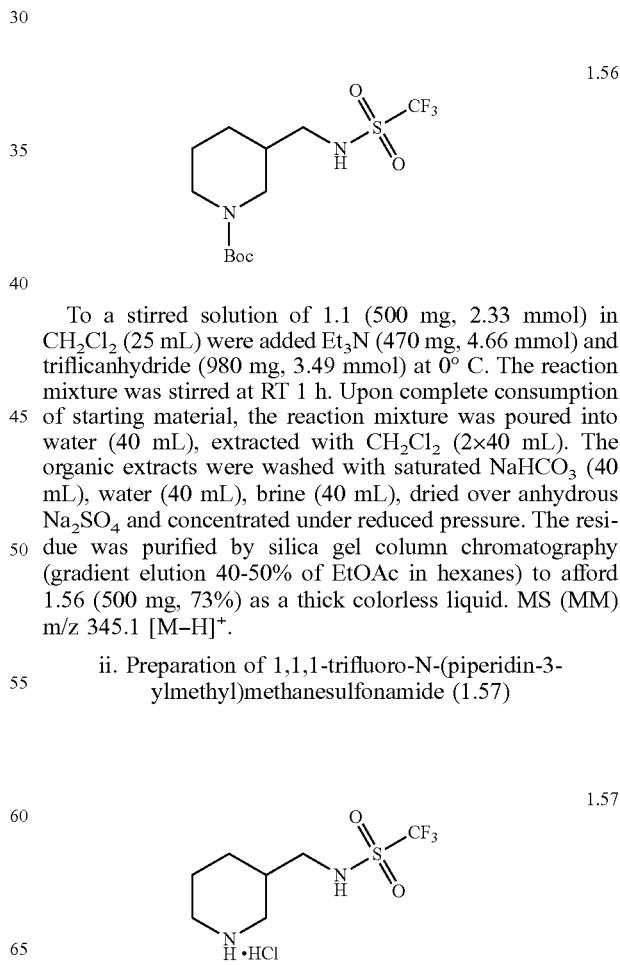

To a stirred solution of 1.1 (500 mg, 2.33 mmol) in $CH_2Cl_2$ (25 mL) were added $Et_3N$ (470 mg, 4.66 mmol) and triflicanhydride (980 mg, 3.49 mmol) at 0° C. The reaction mixture was stirred at RT 1 h. Upon complete consumption of starting material, the reaction mixture was poured into water (40 mL), extracted with $CH_2Cl_2$ (2×40 mL). The organic extracts were washed with saturated $NaHCO_3$ (40 mL), water (40 mL), brine (40 mL), dried over anhydrous $Na_2SO_4$ and concentrated under reduced pressure. The residue was purified by silica gel column chromatography (gradient elution 40-50% of EtOAc in hexanes) to afford 1.56 (500 mg, 73%) as a thick colorless liquid. MS (MM) m/z 345.1 [M−H]⁺.

ii. Preparation of 1,1,1-trifluoro-N-(piperidin-3-ylmethyl)methanesulfonamide (1.57)

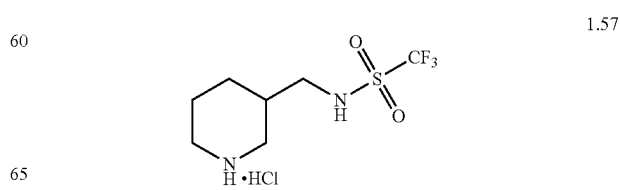

Same procedure described for 1.3. MS (MM) m/z 245.1 [M–H]⁺.

iii. Preparation of N-((1-(7-bromo-6-fluoroquinazolin-4-yl)piperidin-3-yl)methyl)-1,1,1-trifluoromethanesulfonamide (1.58)

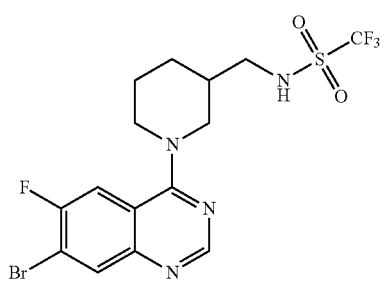

1.58

Same general procedure described for compounds 1-14 above. Yield from 1.9:22%; ¹H NMR (400 MHz, DMSO-$d_6$): δ 9.48 (s, 1H), 8.61 (s, 1H), 8.20 (d, J=7.2 Hz, 1H), 7.8 (d, J=9.6 Hz, 1H), 4.2 (d, J=11.6 Hz, 1H), 4.13 (d, J=13.6 Hz, 1H), 3.22-3.13 (m, 3H), 2.98 (dd, J=10.0 Hz, J=12.8 Hz, 1H), 1.92-1.79 (m, 3H), 1.71-1.64 (m, 1H), 1.35-1.27 (m, 1H); MS (MM) m/z 473.0 [M+2]⁺.

iv. Preparation of N-((1-(7-cyano-6-fluoroquinazolin-4-yl)piperidin-3-yl)methyl)-1,1,1-trifluoromethanesulfonamide (54)

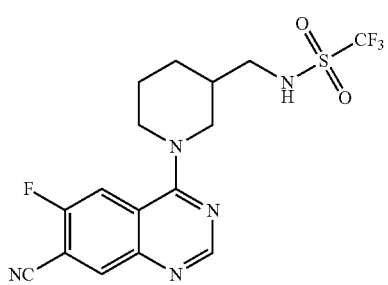

53

Same procedure described for 20. Yield from 1.58:29%; ¹H NMR (300 MHz, DMSO-$d_6$): δ 9.48 (s, 1H), 8.69 (s, 1H), 8.51 (d, J=6.3 Hz, 1H), 7.91 (d, J=10.2 Hz, 1H), 4.27 (d, J=12.3 Hz, 1H), 4.14 (d, J=13.5 Hz, 1H), 3.23 (d, J=11.4 Hz, 1H), 3.14 (d, J=6.3 Hz, 2H), 3.03 (t, J=10.8 Hz, 1H), 1.90-1.65 (m, 4H), 1.39-1.23 (m, 1H); MS (MM) m/z 416.1 [M+H]⁺; HPLC purity >98 (% of AUC).

kk. Synthesis of N-((1-(6-(trifluoromethyl)quinazolin-4-yl)piperidin-3-yl)methyl)benzenesulfonamide (54)

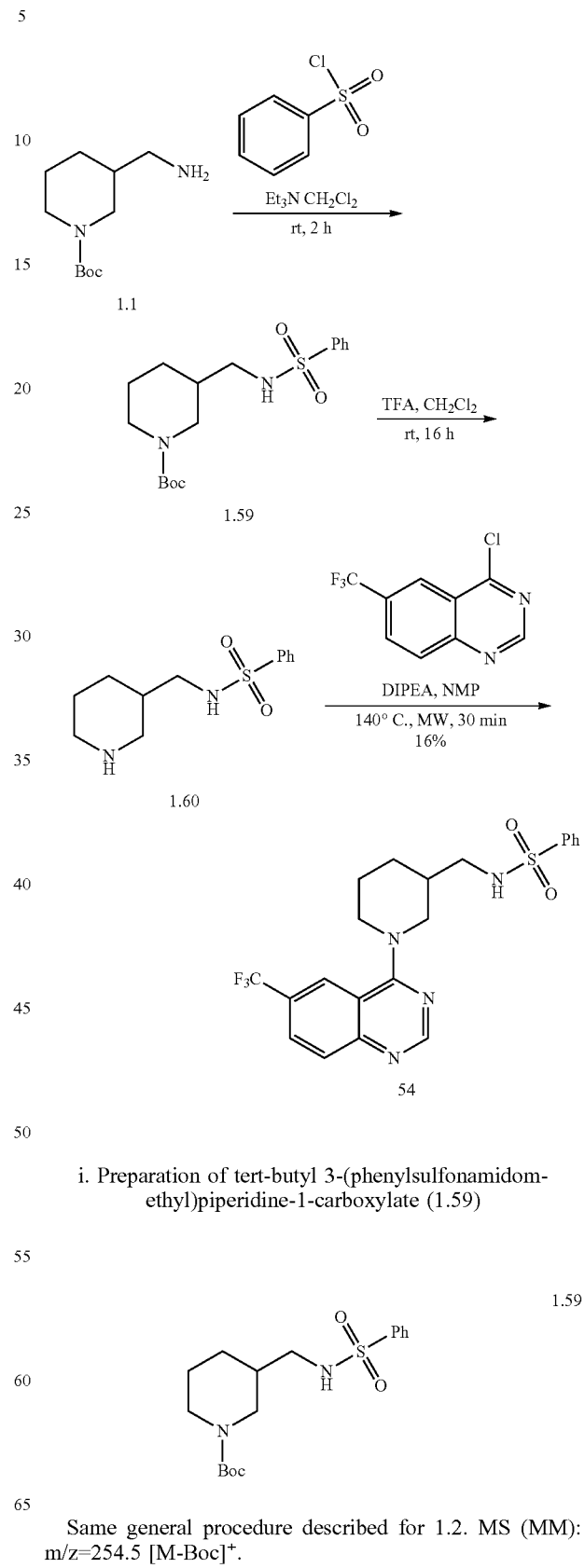

i. Preparation of tert-butyl 3-(phenylsulfonamidomethyl)piperidine-1-carboxylate (1.59)

Same general procedure described for 1.2. MS (MM): m/z=254.5 [M-Boc]⁺.

ii. Preparation of N-(piperidin-3-ylmethyl)benzenesulfonamide (1.60)

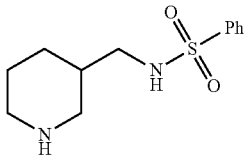

1.60

Same general procedure described for 1.3. MS (MM): m/z=255.1 [M+H]⁺.

iii. Preparation of N-((1-(6-(trifluoromethyl)quinazolin-4-yl)piperidin-3-yl)methyl)benzenesulfonamide (54)

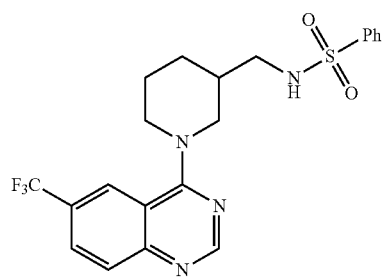

54

Same general procedure described above (Scheme 1). Yield from 1.60:16%; $^1$H NMR (400 MHz, CDCl$_3$): δ 8.68 (s, 1H), 8.09 (s, 1H), 7.96 (d, J=8.8 Hz, 1H), 7.90-7.86 (m, 3H), 7.56-7.47 (m, 3H), 5.68 (t, J=6.8 Hz, 1H), 4.0-3.90 (m, 2H), 3.65-3.56 (m, 2H), 3.08-3.01 (m, 1H), 2.92-2.85 (m, 1H), 2.11-2.08 (m, 1H), 1.97-1.91 (m, 1H), 1.73-1.68 (m, 1H), 1.52-1.46 (m, 1H); MS (MM) m/z 451.1 [M+H]⁺; HPLC purity >92 (% AUC).

ll. Synthesis of N-((1-(6-(trifluoromethyl)quinazolin-4-yl)piperidin-3-yl)methyl)cyclohexanesulfonamide (55)

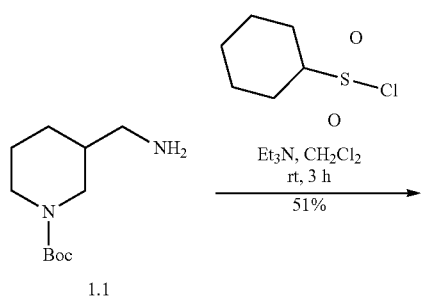

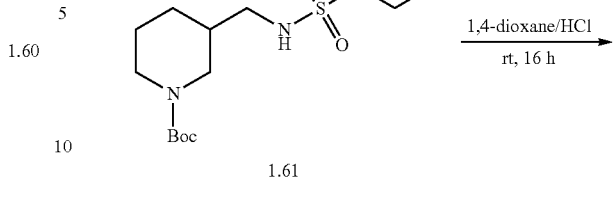

1.61

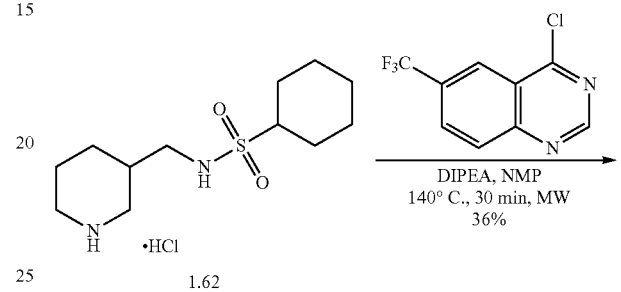

55 i. Preparation of tert-butyl 3-(cyclohexanesulfonamidomethyl)piperidine-1-carboxylate (1.61)

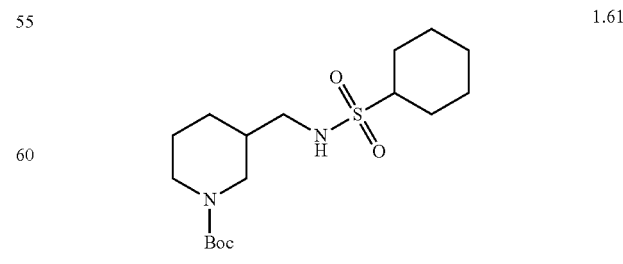

1.61

Same general procedure described for 1.2. MS (MM) m/z=261.2 [M+H]⁺.

ii. Preparation of
N-(piperidin-3-ylmethyl)cyclohexanesulfonamide
(1.62)

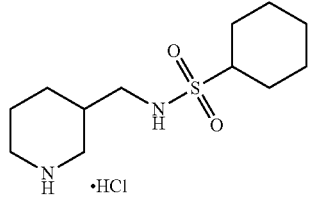

Same general procedure described for 1.3. MS (MM): m/z=261.2 [M+1]⁺.

iii. Preparation of N-((1-(6-(trifluoromethyl)quinazolin-4-yl)piperidin-3-yl)methyl)cyclohexanesulfonamide (55)

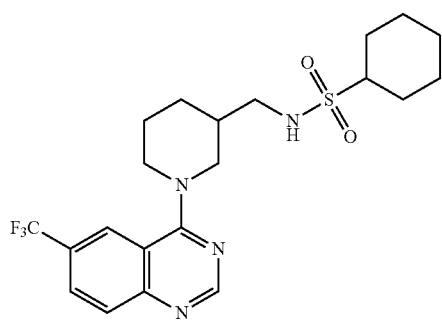

Same general procedure described for compounds 1-14 above. Yield from 1.62:36%; ¹H NMR (400 MHz, CDCl₃): δ 8.70 (s, 1H), 8.14 (s, 1H), 7.97 (d, J=8.8 Hz, 1H), 7.89 (dd, J=2.0 Hz, J=8.4 Hz, 1H), 5.23 (t, J=6.8 Hz, 1H), 4.09-4.01 (m, 2H), 3.71-3.64 (m, 2H), 3.22-3.15 (m, 1H), 3.11-3.04 (m, 1H), 2.92-2.86 (m, 1H), 2.22-2.13 (m, 3H), 2.02-1.97 (m, 1H), 1.91-1.87 (m, 1H), 1.79-1.69 (m, 2H), 1.67-1.48 (m, 3H), 1.33-1.1 (m, 4H); MS (MM) m/z 455.0 [M−H]⁺; HPLC purity >92 (% of ACU).

mm. Synthesis of 4-chloro-N-((1-(6-(trifluoromethyl)quinazolin-4-yl)piperidin-3-yl)methyl)benzenesulfonamide (56)

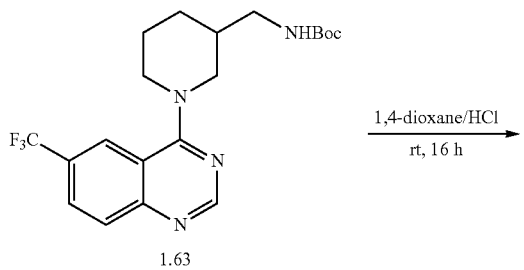

-continued

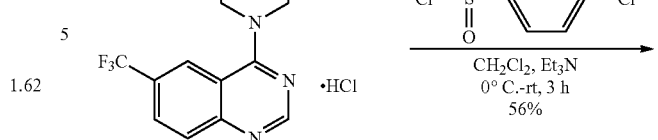

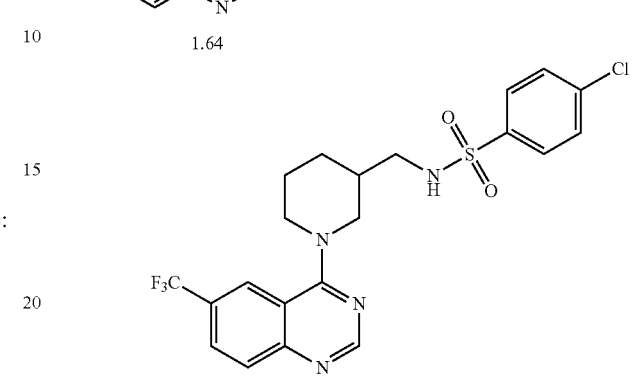

i. Preparation of tert-butyl ((1-(6-(trifluoromethyl)quinazolin-4-yl)piperidin-3-yl)methyl)carbamate (1.63)

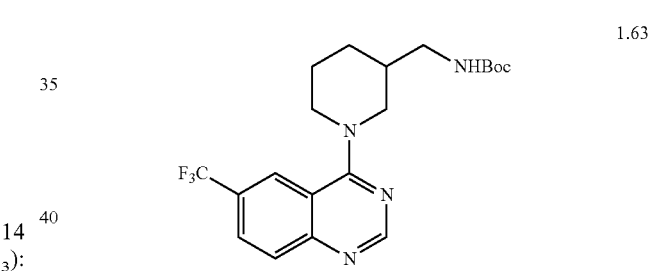

Same general procedure described for compounds 1-14 above. ¹H NMR (400 MHz, DMSO-d₆): δ 8.12 (s, 1H), 7.96 (d, J=8.8 Hz, 1H), 7.89 (d, J=2.0 Hz, 1H), 7.87 (d, J=2.0 Hz, 1H), 4.86 (br s, 1H), 4.23 (d, J=12.0 Hz, 2H), 3.31 (t, J=10.8 Hz, 1H), 3.21-3.\00 (m, 4H), 2.72 (s, 3H), 2.04-1.96 (m, 2H), 1.90-1.85 (m, 1H), 1.79-1.75 (m, 1H), 1.42 (s, 1H); MS (MM) m/z 411.2 [M+H]⁺.

ii. Preparation of (1-(6-(trifluoromethyl)quinazolin-4-yl)piperidin-3-yl)methanamine (1.64)

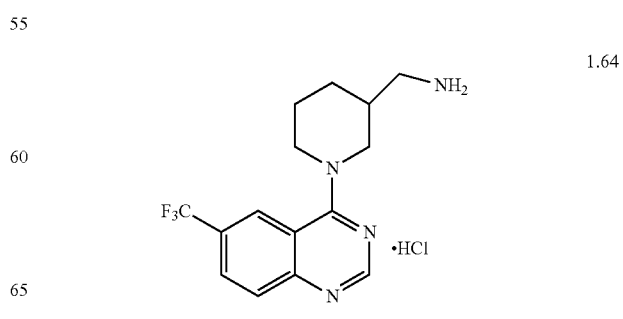

Same general procedure described for compounds 1-14 above. MS (MM) m/z=311.2 [M+H]⁺.

iii. Preparation of 4-chloro-N-((1-(6-(trifluoromethyl)quinazolin-4-yl)piperidin-3-yl)methyl)benzenesulfonamide (56)

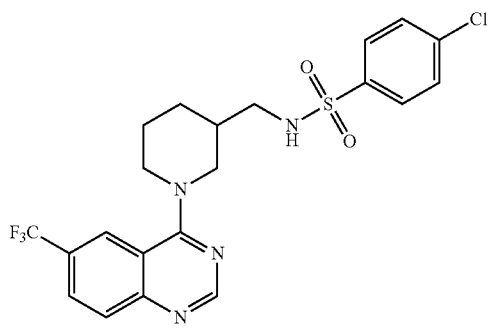

56

To a stirred solution of 1.64 (25 mg, 0.07 mmol) in CH₂Cl₂ (20 mL) were added Et₃N (14.5 mg, 0.14 mmol) and 4-chloro benzene sulphonyl chloride (18.2 mg, 0.08 mmol) at 0° C. The reaction mixture was stirred at RT for 1 h. Upon complete consumption of starting material, the reaction mixture was poured into water (20 mL), extracted with CH₂Cl₂ (2×20 mL). The organic extracts were washed with saturated NaHCO₃ (20 mL), water (20 mL), brine (20 mL), dried over anhydrous Na₂SO₄ and concentrated under reduced pressure. The residue was purified by silica gel column chromatography (gradient elution 30-40% of EtOAc in hexanes) to afford 55 (15 mg, 56%) as a white solid. ¹H NMR (300 MHz, CDCl₃): δ 8.69 (s, 1H), 8.10 (s, 1H), 7.97 (d, J=8.7 Hz, 1H), 7.89 (d, J=8.7 Hz, 1H), 7.81 (d, J=8.4 Hz, 2H), 7.47 (d, J=8.4 Hz, 2H), 5.81 (t, J=6.0 Hz, 1H), 4.03-3.96 (m, 1H), 3.89 (dd, J=2.7 Hz, J=8.7 Hz, 1H), 3.72-3.63 (m, 2H), 3.09-3.00 (m, 1H), 2.92-2.83 (m, 1H), 2.09 (d, J=3.99 Hz, 1H), 1.98-1.91 (m, 1H), 1.69-1.66 (m, 2H), 1.52-1.46 (m, 1H); MS (MM) m/z 485.0 [M+H]⁺; HPLC purity >95 (% of ACU).

nn. Synthesis of N-((1-(6-(trifluoromethyl)quinazolin-4-yl)piperidin-3-yl)methyl)cyclopropanesulfonamide (57)

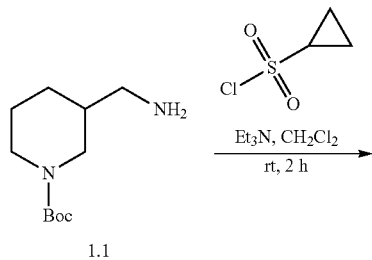

1.1

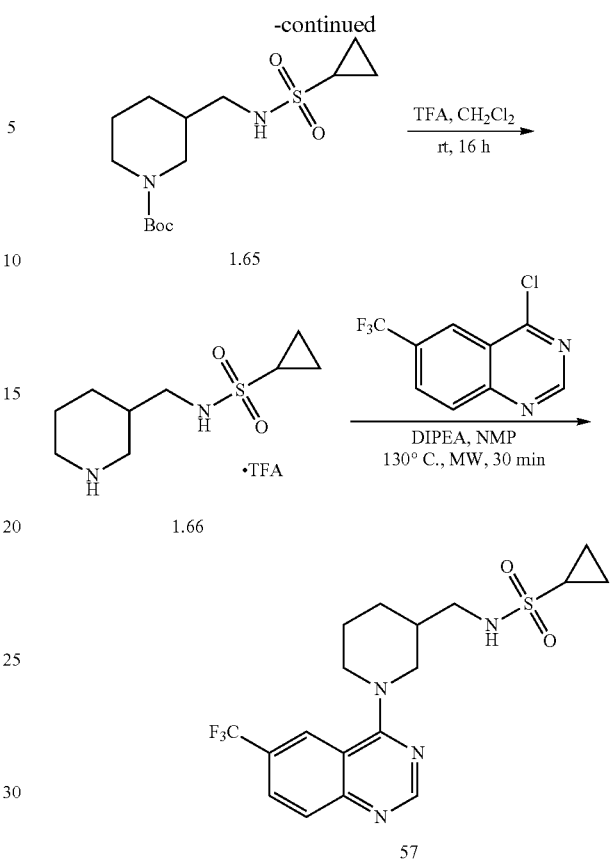

i. Preparation of tert-butyl 3-(cyclopropanesulfonamidomethyl)piperidine-1-carboxylate (1.65)

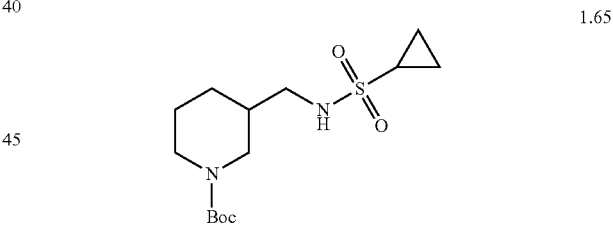

1.65

Same general procedure described for 1.2. MS (MM): m/z=218.1 [M-Boc]⁺.

ii. Preparation of N-(piperidin-3-ylmethyl)cyclopropanesulfonamide (1.66)

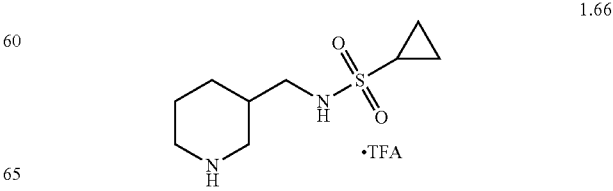

1.66

Same general procedure described for 1.3. MS (MM): m/z=219.1 [M+H]⁺.

iii. Preparation of N-((1-(6-(trifluoromethyl)quinazolin-4-yl)piperidin-3-yl)methyl)cyclopropanesulfonamide (57)

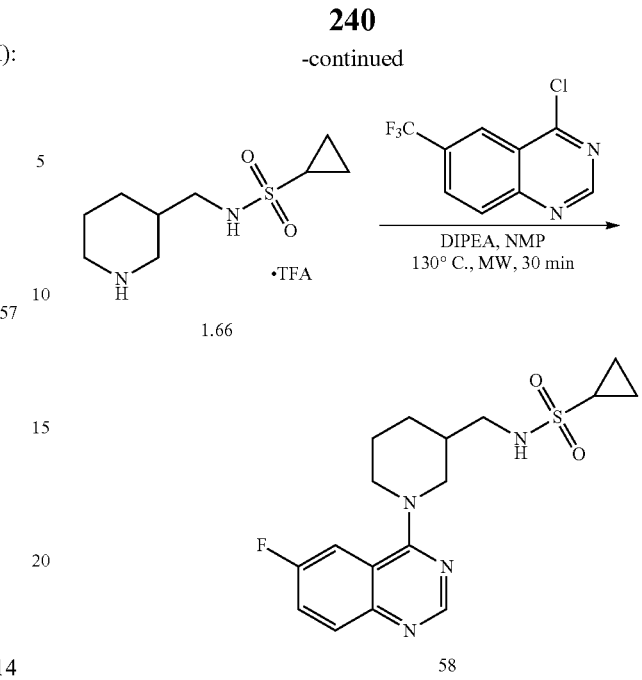

Same general procedure described for compounds 1-14 above. Yield from 1.66:23%; ¹H NMR (300 MHz, DMSO-$d_6$): δ 8.67 (s, 1H), 8.21 (s, 1H), 8.06 (d, J=8.7 Hz, 1H), 7.95 (d, J=8.7 Hz, 1H), 7.17 (t, J=6 Hz, 1H), 4.41 (d, J=12.9 Hz, 1H), 4.22 (d, J=13.2 Hz, 1H), 3.28 (d, J=12 Hz, 1H), 3.07-2.89 (m, 3H), 2.57 (m, 1H), 1.91-1.80 (m, 3H), 1.68-1.59 (m, 1H), 1.39-1.28 (m, 1H), 0.92-0.88 (m, 4H); MS (MM) m/z 415.1 [M+H]⁺; HPLC purity >99 (% AUC).

oo. Synthesis of N-((1-(6-fluoroquinazolin-4-yl)piperidin-3-yl)methyl)cyclopropanesulfonamide (58)

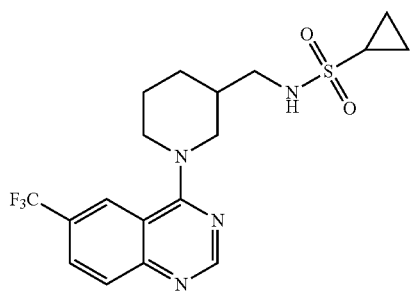

Same procedure described for 57. Yield: 39%; ¹H NMR (300 MHz, DMSO-d6): δ 8.62 (s, 1H), 7.91-7.86 (dd, J=2.8 Hz, J=8.4 Hz, 1H), 7.78-7.71 (m, 1H), 7.67-7.63 (m, 1H), 7.20 (t, J=6.3 Hz, 1H), 4.28 (d, J=12.3 Hz, 1H), 4.13 (d, J=13.2 Hz, 1H), 3.18-3.10 (m, 1H), 3.01-2.86 (m, 3H), 2.59-2.54 (m, 1H), 1.90-1.62 (m, 4H), 1.34-4.12 (m, 1H), 0.92-0.89 (m, 4H); MS (MM) m/z 365.1 [M+H]⁺; HPLC purity: >99 (% of AUC).

pp. Synthesis of 4-(3-(cyclopropanesulfonamidomethyl)piperidin-1-yl)-6-fluoroquinazoline-7-carboxamide (59)

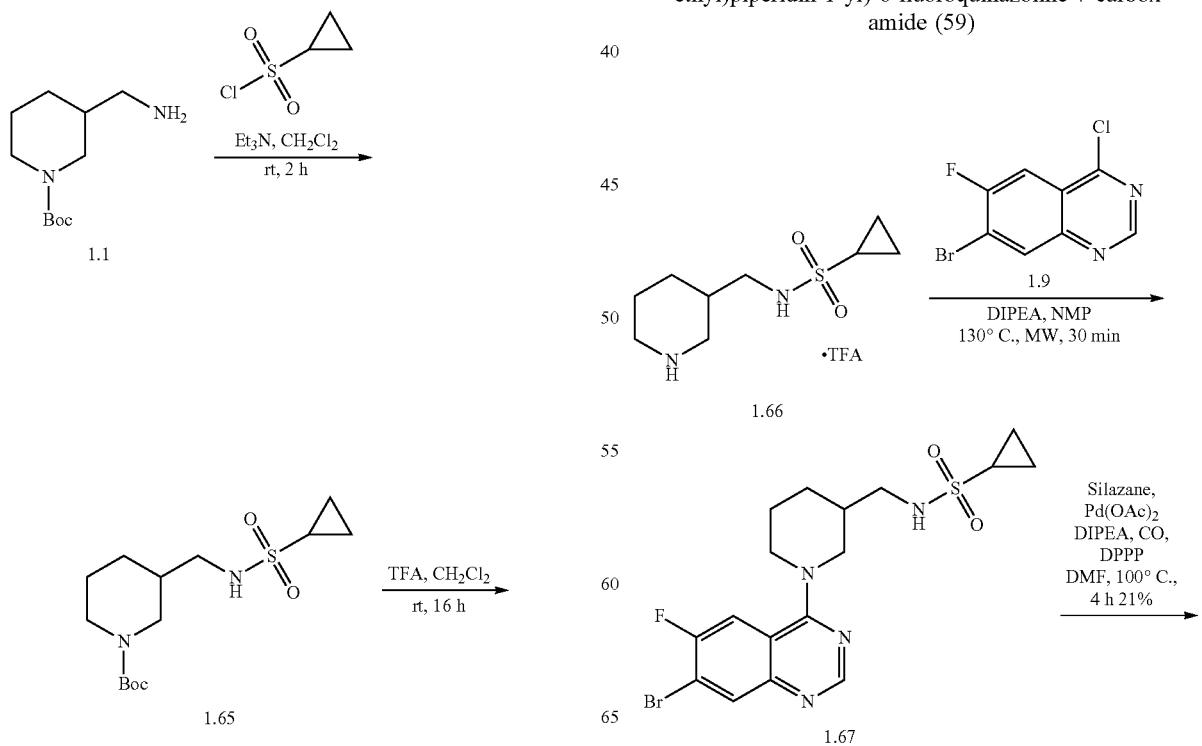

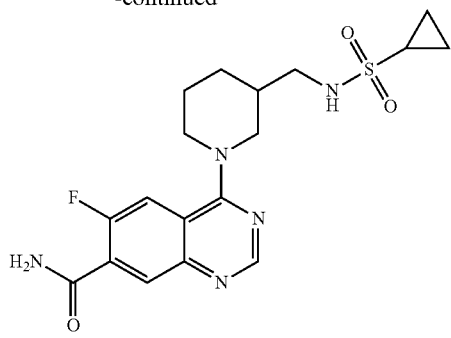

59 i. Preparation of N-((1-(7-bromo-6-fluoroquinazolin-4-yl)piperidin-3-yl)methyl)-cyclopropanesulfonamide (1.67)

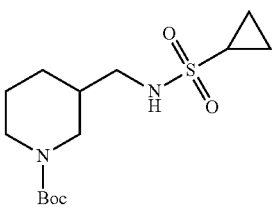

1.65

Same procedure described for 57.

ii. Preparation of 4-(3-(cyclopropanesulfonamidomethyl)piperidin-1-yl)-6-fluoroquinazoline-7-carboxamide (59)

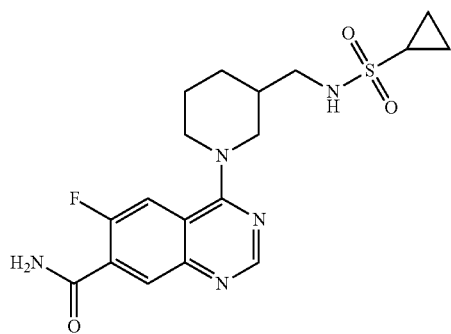

59

To a stirred solution of 1.67 (80 mg, 0.13 mmol) in DMF (5 mL) taken in a steel bomb was added silazane (0.08 mL, 0.40 mmol) and DIPEA (0.06 mL, 0.40 mmol). Argon gas was purged and the reaction was degassed for about 5 min. added Pd(OAc) (3 mg, 0.013 mmol), DPPP (10 mg). CO was filled up to 250 Psi, stirred at 100° C. for 4 h. Upon complete consumption of starting material, the reaction mixture was poured into water (20 mL), extracted with EtOAc (2×20 mL). The organic extracts were washed with water (2×20 mL), brine (20 mL), dried over anhydrous Na$_2$SO$_4$ and concentrated under reduced pressure. The residue was purified by silica gel column chromatography (gradient elution 80-90% of EtOAc in hexanes) to afford 59 (15 mg, 21%) as an off-white solid. $^1$H NMR (400 MHz, DMSO-d6): δ 8.63 (s, 1H), 8.07 (s, 1H), 7.98 (d, J=6.8 Hz, 1H), 7.83 (s, 1H), 7.71 (d, J=11.2 Hz, 1H), 7.19 (t, J=5.6 Hz, 1H), 4.31 (d, J=14 Hz, 1H), 4.17 (d, J=12.4 Hz, 1H), 3.20-3.15 (m, 1H), 2.98-2.91 (m, 3H), 1.89-1.79 (m, 4H), 1.72-1.66 (m, 1H), 1.33-1.29 (m, 1H), 0.92-0.88 (m, 4H); MS (MM) m/z 406.1 [M+H]$^+$; HPLC purity >96 (% of AUC).

qq. Synthesis of N-((1-(6-fluoroquinazolin-4-yl)piperidin-3-yl)methyl)morpholine-4-sulfonamide (60)

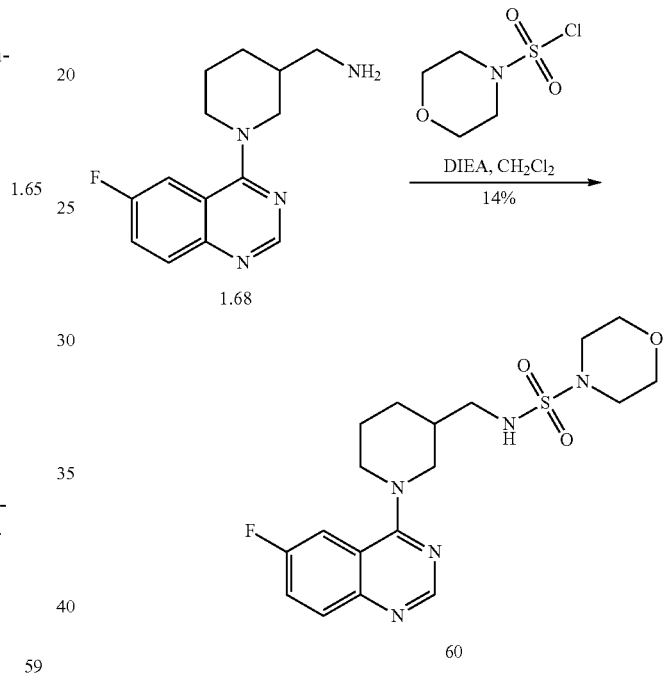

60 i. Preparation of (1-(6-fluoroquinazolin-4-yl)piperidin-3-yl)methanamine (1.68)

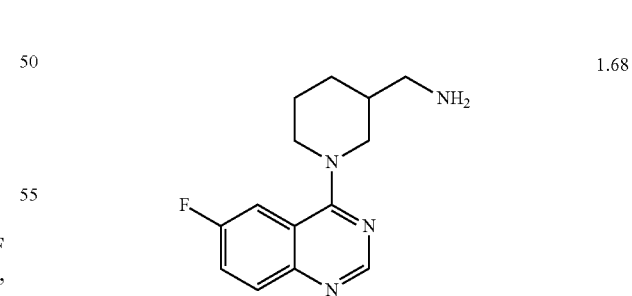

1.68

The amine 1.68 was prepared in two steps according to the same procedure described for compounds 1-14 above. 1H NMR (400 MHz, DMSO-d6) δ 8.70 (s, 1H), 7.95-7.78 (m, 4H), 7.76 (dd, J=9.7, 2.7 Hz, 1H), 4.34 (d, J=11.1 Hz, 1H), 4.24 (d, J=13.1 Hz, 1H), 3.34 (tt, J=11.0, 2.9 Hz, 1H), 3.24-3.12 (m, 3H), 2.82 (dh, J=25.3, 6.5 Hz, 1H), 1.96-1.78 (m, 2H), 1.65 (s, 1H), 1.45-1.30 (m, 1H); FABMS (M+H)

calculated for C$_{14}$H$_7$FN$_4$.H was 261.1510 found 261.1507; HPLC purity=100 (% of AUC), t$_R$=0.79 minutes.

ii. Preparation of N-((1-(6-fluoroquinazolin-4-yl)piperidin-3-yl)methyl)morpholine-4-sulfonamide (60)

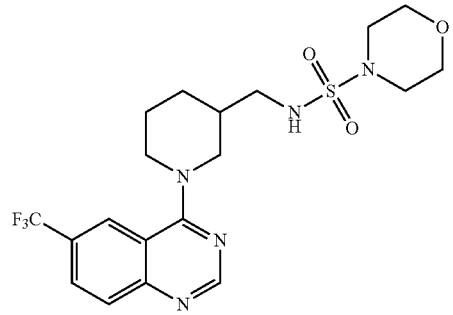

Compound 60 was synthesized in 14% yield according the same procedure described for 1.2. 1H NMR (400 MHz, DMSO-d6) δ 8.60 (s, 1H), 7.87 (dd, J=9.2, 5.6 Hz, 1H), 7.73 (ddd, J=9.2, 8.3, 2.8 Hz, 1H), 7.63 (dd, J=9.8, 2.8 Hz, 1H), 7.44 (t, J=5.8 Hz, 1H), 4.25 (d, J=12.9 Hz, 1H), 4.11 (d, J=13.2 Hz, 1H), 3.61-3.54 (m, 4H), 3.13 (ddd, J=13.9, 11.4, 2.8 Hz, 1H), 3.01-2.93 (m, 4H), 2.96-2.78 (m, 2H), 1.85 (d, J=12.7 Hz, 3H), 1.77 (s, 1H), 1.65 (d, J=12.4 Hz, 1H), 1.30-1.11 (m, 1H).FABMS (M+H) calculated for C$_{18}$H$_{24}$FN$_5$O$_3$S.H was 410.1657 found 410.1653; HPLC purity >95 (% of AUC), t$_R$=4.12 minutes.

iii. Preparation 4-(3-(methylsulfonamidomethyl)piperidin-1-yl)-6-(trifluoromethyl)quinazoline-1-oxide (61) AND N-((1-(2-hydroxy-6-(trifluoromethyl)quinazolin-4-yl)piperidin-3-yl)methyl)methanesulfonamide (62)

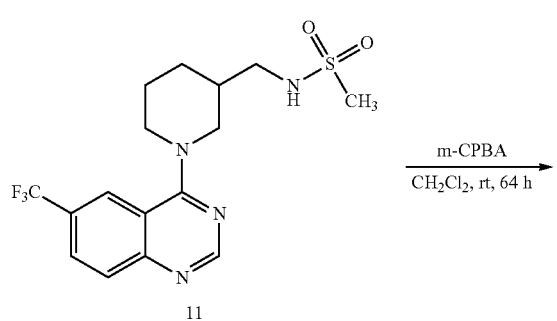

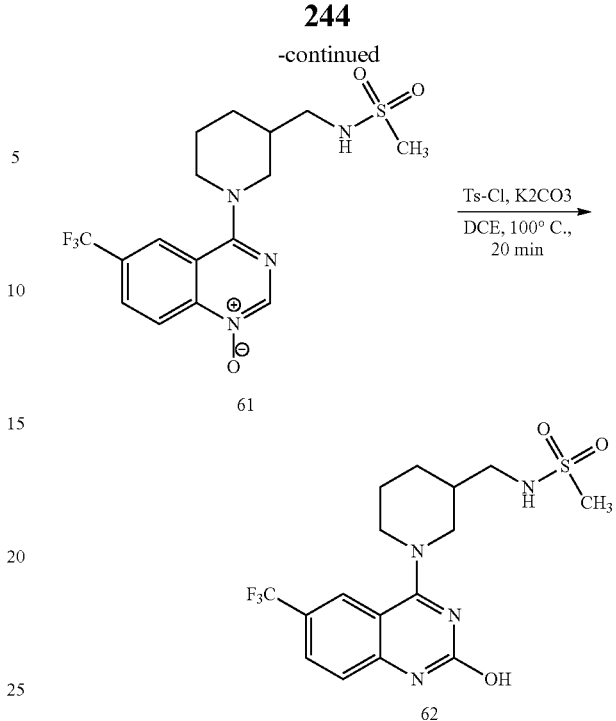

rr. Synthesis of 61

To a solution of compound 11 (200 mg, 0.515 mmol) in CH$_2$Cl$_2$ (10 ml), at rt under N$_2$ atmosphere, was added m-CPBA (410 mg, 1.545 mmol) and and the reaction mixture was stirred at rt for 64 hr. The reaction mixture was diluted with CH$_2$Cl$_2$ (20 mL) and the organic layer was washed with sat.NaHCO$_3$ solution (10 mL) and sat.NaSO$_3$ solution (10 mL). The organic layer was dried over anhydrous Na$_2$SO$_4$, filtered and concentrated under vacuum to obtain the crude product. The product was purified by silica-gel chromatography (15-20% CH$_3$OH:CH$_2$Cl$_2$). Fractions containing the product were combined and concentrated under vacuum. The obtained solids were washed with MTBE and filtered, dried under vacuum to obtain 61 (60 mg, 0.148 mmol, 29%) as a light yellow solid. $^1$H NMR (400 MHz, DMSO-d$_6$) δ: 8.87 (s, 1H), 8.59 (d, J=8.8 Hz, 1H), 8.28-8.25 (m, 2H), 7.10 (t, J=6.0 Hz, 1H), 4.19-4.16 (m, 1H), 4.04-4.01 (m, 1H), 3.30-3.24 (m, 1H), 3.03-2.88 (m, 6H), 1.89-1.83 (m, 3H), 1.79-1.68 (m, 1H), 1.34-1.26 (m, 1H). LCMS (ESI): m/z=405 [M+H]$^+$. HPLC: >99% (AUC).

ss. Synthesis of 62

To a solution of 61 (150 mg, 0.371 mmol) in DCE (10 ml), at rt under N$_2$ atmosphere was added Tosylchloride (141 mg, 0.742 mmol) and K$_2$CO$_3$ (103 mg, 0.742 mmol) and the mixture was heated at 100° C. for 20 min under microwave condition. Concentrated the reaction mixture under vacuum and the product was purified by silica-gel chromatography (10-12% CH$_3$OH:CH$_2$Cl$_2$). Fractions containing the product were combined and concentrated under vacuum. The obtained solids were washed with MTBE and filtered, dried under vacuum to obtain 62 (63 mg, 0.156 mmol, 42%) as an off white solid. $^1$H NMR (400 MHz, DMSO-d$_6$) δ: 11.25 (s, 1H), 7.90-7.88 (m, 2H), 7.35 (d, J=8.8 Hz, 1H), 7.10 (t, J=6.0 Hz, 1H), 4.25-4.22 (m, 1H), 4.11-4.08 (m, 1H), 3.23-3.18 (m, 1H), 2.97-2.82 (m, 6H), 1.87-1.77 (m, 3H), 1.63-1.57 (m, 1H), 1.34-1.29 (m, 1H). LCMS (ESI): m/z=405 [M+H]$^+$. HPLC: >99% (AUC).

iv. Preparation of N-((1-(7-hydroxy-6-(trifluoromethyl)quinazolin-4-yl)piperidin-3-yl)methyl)methanesulfonamide (63)

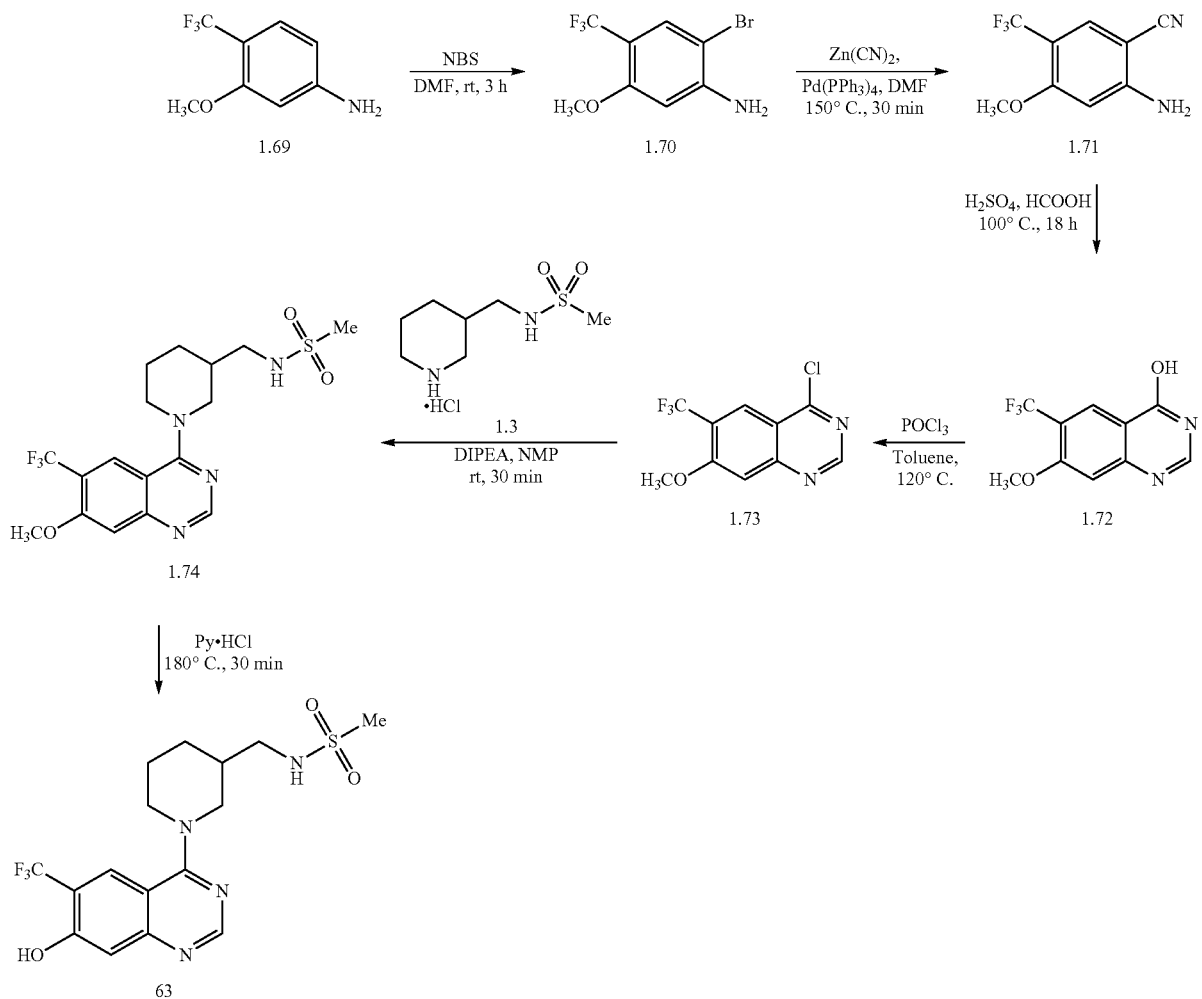

tt. Preparation of 1.70

To a stirred solution of 1.69 (500 mg, 2.62 mmol) in DMF (10 ml) was added NBS (466 mg, 2.62 mmol) at rt and was stirred at same temperature for 3 h under argon. After 3 h; diluted the reaction mixture with water (50 mL) and the aqueous layer was extracted with EtOAc (100 mL). The organic layer was washed with water (3×100 mL), dried over anhydrous $Na_2SO_4$, filtered and concentrated under vacuum to give 1.70 (600 mg, 2.22 mmol, 85%) as an light brown solid. $^1$H NMR (400 MHz, $CDCl_3$) δ: 7.55 (s, 1H), 6.32 (s, 1H), 4.38 (brs, 2H), 3.82 (s, 3H).

uu. Preparation of 1.71

To a stirred solution of 1.70 (700 mg, 2.59 mmol) in DMF (10 ml) was added Zinc cyanide (457 mg, 3.89 mmol) and the mixture was purged with argon for 5 mins; then added $Pd(PPh_3)_4$ (300 mg, 0.259 mmol) and the mixture was irradiated under microwave condition at 150° C. for 30 min. After 30 mins; cooled the reaction mixture to rt and was diluted with EtOAc (150 mL) and filtered through celite bed. The filtrate was washed with $H_2O$ (3×150 mL), dried over anhydrous $Na_2SO_4$, filtered and concentrated under vacuum. The crude compound was purified by combiflash chromatography eluting with 25% EtOAc in Hexane to give 1.71 (500 mg, 2.31 mmol, 89%, AMRI lot #AMR100625-36-1) as an off white solid. $^1$H NMR (400 MHz, $CDCl_3$) δ: 7.58 (s, 1H), 6.24 (s, 1H), 4.74 (brs, 2H), 3.88 (s, 3H).

vv. Preparation of 1.72

Formic acid (2.5 mL, 28.2 mmol) and sulfuric acid (2.5 mL, 20.28 mmol) was added to 1.71 (500 mg, 2.31 mmol) at rt and the mixture was stirred at 100° C. for 18 hr. After 18 hr; cooled the reaction mixture to rt and the reaction mixture was slowly added to the crushed ice with stirring. The aqueous layer was basified with aq. $NH_3$ solution and the aqueous layer was extracted with EtOAc (2×100 mL). The combined organic layer was dried over anhydrous $Na_2SO_4$, filtered and concentrated under vacuum to give 1.72 (350 mg, 1.43 mmol, 62.0%) as an off white solid. $^1$H NMR (400 MHz, DMSO-d$_6$) δ: 12.42 (s, 1H), 8.25 (s, 1H), 8.21 (s, 1H), 7.36 (s, 1H), 4.02 (s, 3H).

ww. Preparation of 1.73

To the stirred suspension of 1.72 (100 mg, 0.410 mmol) in POCl$_3$ (0.382 ml, 4.10 mmol) was added N,N-Dimethylaniline (0.123 ml, 1.024 mmol) at rt and was stirred at 120° C. for 4 hr under argon. After 4 hr, cooled the reaction mixture to rt and the reaction mixture was concentrated under vacuum. The crude residue was dissolved in CH$_2$Cl$_2$ (50 mL) and the organic layer was washed with water (50 mL). The organic layer was dried over anhydrous Na$_2$SO$_4$ and filtered and concentrated under vacuum. The crude residue was purified by combiflash chromatography eluting with 10% EtOAc in Hexane to give 1.73 (50 mg, 0.190 mmol, 46.5%) as an off white solid. $^1$H NMR (400 MHz, CDCl$_3$) δ: 9.02 (s, 1H), 8.51 (s, 1H), 7.47 (s, 1H), 4.09 (s, 3H).

xx. Preparation of 1.74

To a stirred solution of 1.73 (250 mg, 0.952 mmol) in NMP (10 mL) were added 6 (261 mg, 1.142 mmol) and DIPEA (0.499 ml, 2.86 mmol) at rt and was stirred at rt for 30 min under argon. After 30 min; diluted the reaction mixture with water (50 mL) and extracted with EtOAc (50 mL). The organic layer was washed with water (3×100 mL) and dried over anhydrous Na$_2$SO$_4$, filtered and concentrated under vacuum to afford 1.74 (300 mg, 0.717 mmol, 75%) as a color less gummy solid. $^1$H NMR (400 MHz, DMSO-d$_6$) δ: 8.59 (s, 1H), 8.11 (s, 1H), 7.38 (s, 1H), 7.09 (t, J=6.0 Hz, 1H), 4.36-4.33 (m, 1H), 4.19-4.15 (m, 1H), 4.02 (s, 3H), 3.30-3.22 (m, 1H), 2.99-2.85 (m, 6H), 1.89-1.79 (m, 3H), 1.68-1.59 (m, 1H), 1.35-1.27 (m, 1H).

yy. Preparation of 63

Mixture of 1.74 (200 mg, 0.478 mmol) and pyridine hydrochloride (552 mg, 4.78 mmol) was heated at 180° C. for 30 min under microwave. After 30 min; cooled the reaction mixture and diluted with EtOAc (50 mL) and saturated NaHCO$_3$ solution (10 mL). Separated the organic layer and the aqueous layer was extracted with EtOAc (50 mL), the combined organic layer was dried over anhydrous NaSO$_4$, filtered and concentrated under vacuum. The crude residue was purified by mass triggered HPLC to give 63 (31 mg, 0.077 mmol, 16.04%) as an off white solid. $^1$H NMR (400 MHz, DMSO-d$_6$) δ: 11.69 (brs, 1H), 8.49 (s, 1H), 8.05 (s, 1H), 7.14-7.08 (m, 2H), 4.31-4.28 (m, 1H), 4.15-4.11 (m, 1H), 3.24-3.18 (m, 1H), 2.97-2.85 (m, 6H), 1.90-1.76 (m, 3H), 1.67-1.58 (m, 1H), 1.35-1.26 (m, 1H). LCMS (ESI): m/z=405 [M+H]$^+$; HPLC: >99% (AUC).

v. Preparation of N-((1-(8-hydroxy-6-(trifluoromethyl)quinazolin-4-yl)piperidin-3-yl)methyl)methanesulfonamide (64) AND N-((1-(5-hydroxy-6-(trifluoromethyl)quinazolin-4-yl)piperidin-3-yl)methyl)methanesulfonamide (65)

Same procedure described for 63.

3. Characterization of Inhibitors of TXNIP Transcription

A list of compounds evaluated for their ability to inhibit TXNIP expression is shown in Table 1 below.

TABLE 1

| No. | Structure | TXNIP % Inhibition at 1.5 μM | TXNIP % Inhibition at 12.5 μM | CC$_{50}$/72 h (μM) |
|---|---|---|---|---|
| 1 | 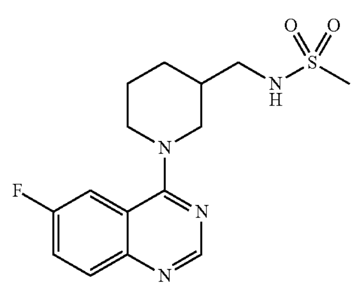 [SMILES: CS(=O)(=O)NCC1CCCN(c2ncnc3ccc(F)cc23)C1] | 44 | 54 | >100 |
| 2 | 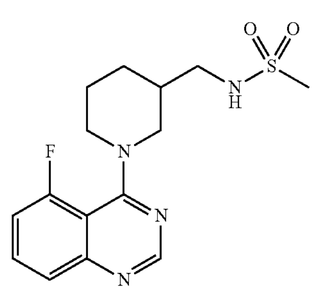 [SMILES: CS(=O)(=O)NCC1CCCN(c2ncnc3cccc(F)c23)C1] | 13 | 61 | >100 |

TABLE 1-continued

| No. | Structure | TXNIP % Inhibition at 1.5 μM | TXNIP % Inhibition at 12.5 μM | CC$_{50}$/72 h (μM) |
|---|---|---|---|---|
| 3 | 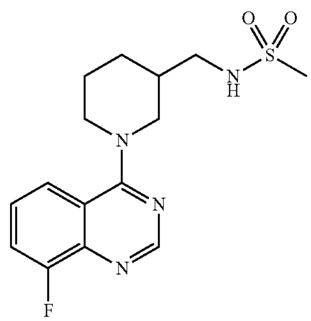 [SMILES: CS(=O)(=O)NCC1CCCN(c2ncnc3c(F)cccc23)C1] | 4 | 59 | >100 |
| 4 | 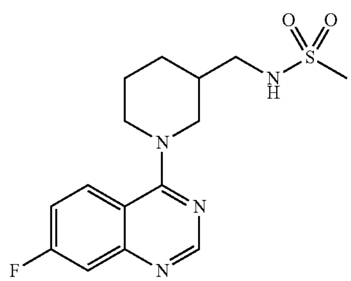 [SMILES: CS(=O)(=O)NCC1CCCN(c2ncnc3cc(F)ccc23)C1] | 24 | 16 | >100 |
| 5 | 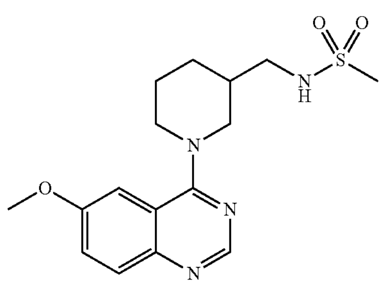 | 30 | 58 | >100 |
| 6 | 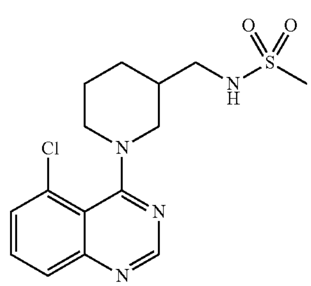 [SMILES: CS(=O)(=O)NCC1CCCN(c2ncnc3cccc(Cl)c23)C1] | 29 | 43 | >100 |
| 7 | 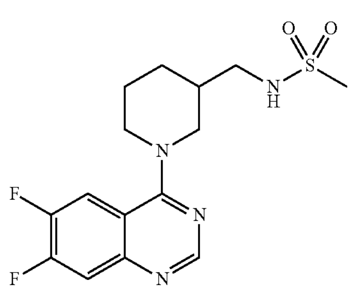 [SMILES: CS(=O)(=O)NCC1CCCN(c2ncnc3cc(F)c(F)cc23)C1] | 40 | 54 | >100 |

TABLE 1-continued

| No. | Structure | TXNIP % Inhibition at 1.5 μM | TXNIP % Inhibition at 12.5 μM | CC$_{50}$/72 h (μM) |
|---|---|---|---|---|
| 8 | 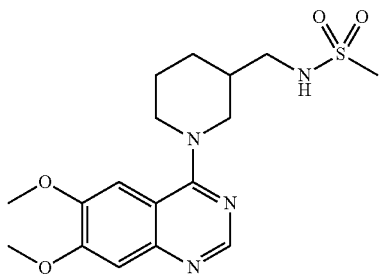 | 0 | 7 | >100 |
| 9 | 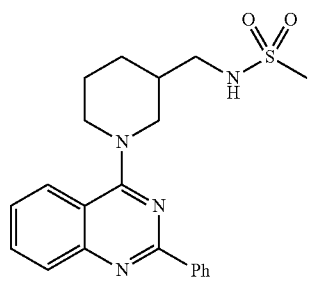 [SMILES: CS(=O)(=O)NCC1CCCN(c2nc(-c3ccccc3)nc3ccccc23)C1] | 0 | 10 | 71 |
| 10 | 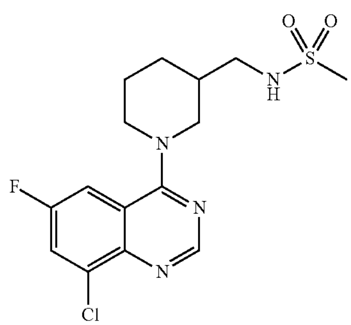 [SMILES: CS(=O)(=O)NCC1CCCN(c2ncnc3c(Cl)cc(F)cc23)C1] | 23 | 51 | >100 |
| 11 | 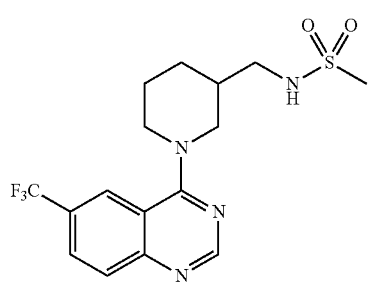 [SMILES: CS(=O)(=O)NCC1CCCN(c2ncnc3ccc(C(F)(F)F)cc23)C1] | 45 | 53 | 56 |
| 11a | 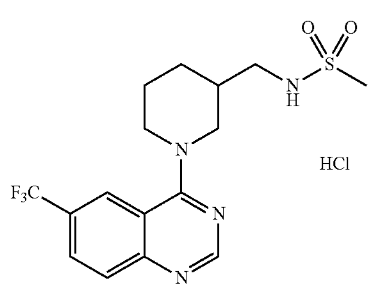 [SMILES: CS(=O)(=O)NCC1CCCN(c2ncnc3ccc(C(F)(F)F)cc23)C1 ; Cl] | 35 | 57 | >100 |

TABLE 1-continued

| No. | Structure | TXNIP % Inhibition at 1.5 μM | TXNIP % Inhibition at 12.5 μM | CC$_{50}$/72 h (μM) |
|---|---|---|---|---|
| 12 | 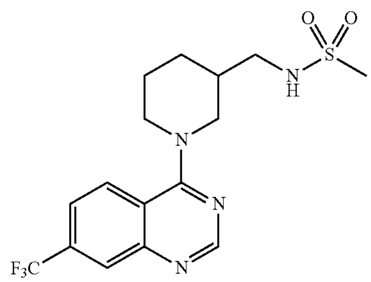 [SMILES: CS(=O)(=O)NCC1CCCN(c2ncnc3cc(C(F)(F)F)ccc23)C1] | 0 | 13 | >100 |
| 13 | 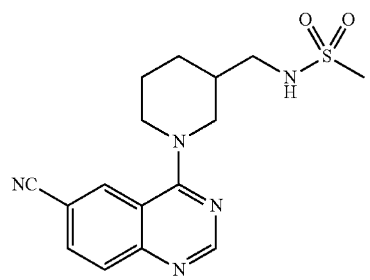 [SMILES: CS(=O)(=O)NCC1CCCN(c2ncnc3ccc(C#N)cc23)C1] | 41 | 1 | 42 |
| 14 | 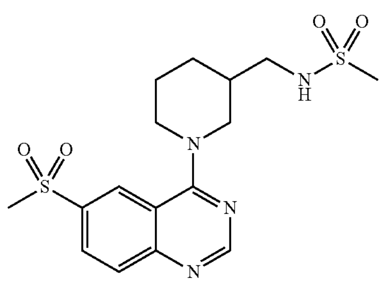 | 0 | 24 | >100 |
| 15 | 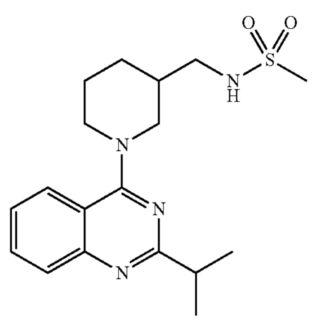 [SMILES: CC(C)c1nc(N2CCCC(CNS(C)(=O)=O)C2)c2ccccc2n1] | 0 | 20 | 73 |
| 16 | 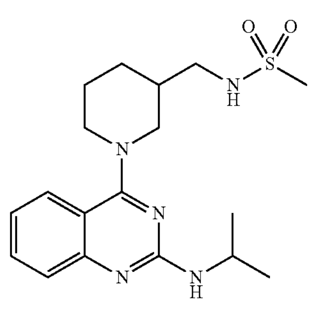 [SMILES: CC(C)Nc1nc(N2CCCC(CNS(C)(=O)=O)C2)c2ccccc2n1] | 0 | 33 | >100 |

TABLE 1-continued
| No. | Structure | TXNIP % Inhibition at 1.5 μM | TXNIP % Inhibition at 12.5 μM | CC$_{50}$/72 h (μM) |
|---|---|---|---|---|
| 17 | 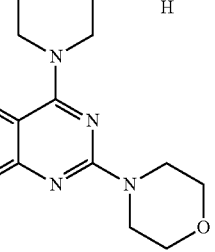 | 0 | 15 | >100 |
| 18 | 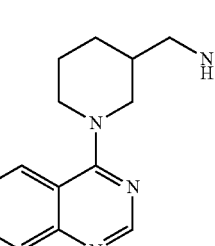 | 10 | 10 | >100 |
| 19 | 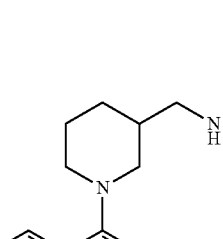 | 0 | 5 | >100 |
| 20 | 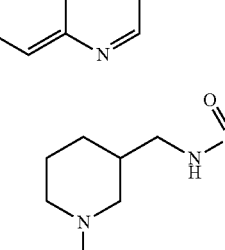 | 19 | 30 | >100 |
| 21 | 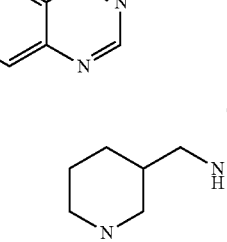 | 0 | 12 | >100 |

TABLE 1-continued

| No. | Structure | TXNIP % Inhibition at 1.5 µM | TXNIP % Inhibition at 12.5 µM | CC$_{50}$/72 h (µM) |
| --- | --- | --- | --- | --- |
| 22 | 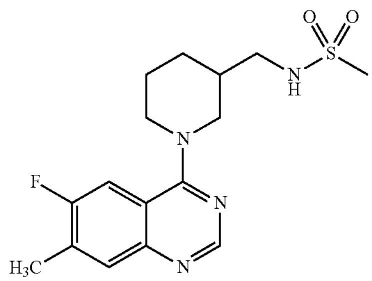 [SMILES: Cc1cc2ncnc(N3CCCC(CNS(C)(=O)=O)C3)c2cc1F] | 15 | 34 | >100 |
| 23 | 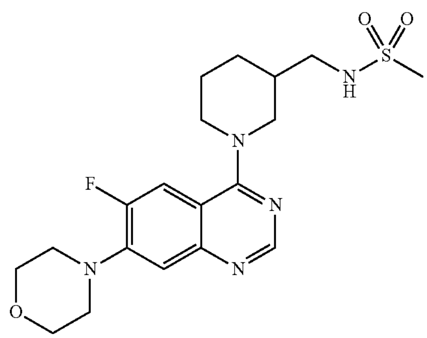 [SMILES: CS(=O)(=O)NCC1CCCN(c2ncnc3cc(N4CCOCC4)c(F)cc23)C1] | 0 | 23 | >100 |
| 24 | 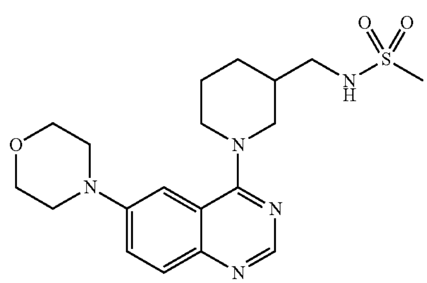 [SMILES: CS(=O)(=O)NCC1CCCN(c2ncnc3ccc(N4CCOCC4)cc23)C1] | 20 | 20 | >100 |
| 25 | 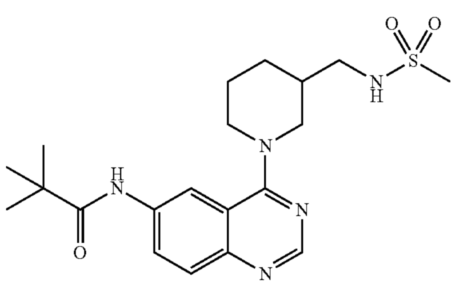 [SMILES: CC(C)(C)C(=O)Nc1ccc2ncnc(N3CCCC(CNS(C)(=O)=O)C3)c2c1] | 28 | 51 | >100 |
| 26 | 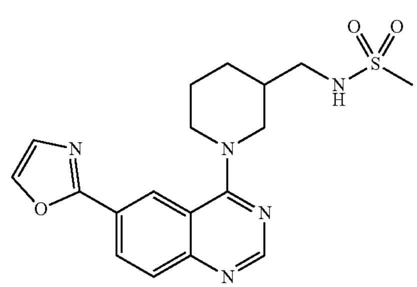 [SMILES: CS(=O)(=O)NCC1CCCN(c2ncnc3ccc(-c4ncco4)cc23)C1] | 2 | 28 | >100 |

TABLE 1-continued

| No. | Structure | TXNIP % Inhibition at 1.5 μM | TXNIP % Inhibition at 12.5 μM | CC$_{50}$/72 h (μM) |
| --- | --- | --- | --- | --- |
| 27 | 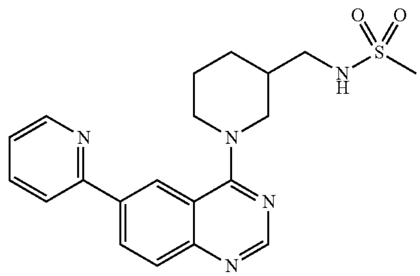 [SMILES: CS(=O)(=O)NCC1CCCN(c2ncnc3ccc(-c4ccccn4)cc23)C1] | 9 | 4 | 70 |
| 28 | 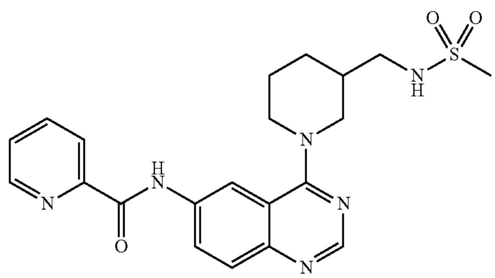 [SMILES: CS(=O)(=O)NCC1CCCN(c2ncnc3ccc(NC(=O)c4ccccn4)cc23)C1] | 4 | 5 | >100 |
| 29 | 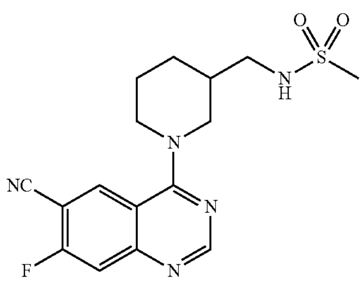 [SMILES: CS(=O)(=O)NCC1CCCN(c2ncnc3cc(F)c(C#N)cc23)C1] | 39 | 66 | >100 |
| 29a | HCl | 35 | 55 | >100 |
| 30 | 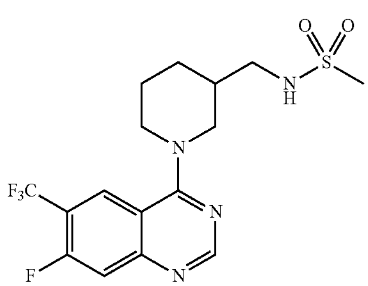 [SMILES: CS(=O)(=O)NCC1CCCN(c2ncnc3cc(F)c(C(F)(F)F)cc23)C1] | 9 | 33 | >100 |

TABLE 1-continued

| No. | Structure | TXNIP % Inhibition at 1.5 μM | TXNIP % Inhibition at 12.5 μM | CC$_{50}$/72 h (μM) |
|---|---|---|---|---|
| 31 | 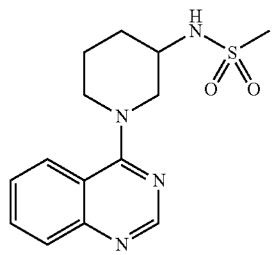 [SMILES: CS(=O)(=O)NC1CCCN(c2ncnc3ccccc23)C1] | 17 | 82 | 67 |
| 32 | 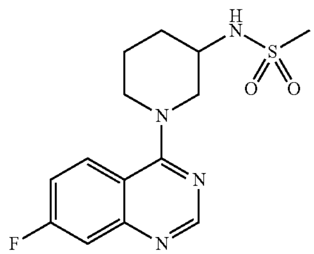 [SMILES: CS(=O)(=O)NC1CCCN(c2ncnc3cc(F)ccc23)C1] | 21 | 62 | 65 |
| 33 | 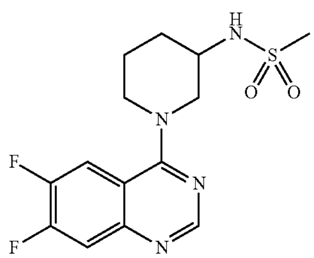 [SMILES: CS(=O)(=O)NC1CCCN(c2ncnc3cc(F)c(F)cc23)C1] | 29 | 68 | 68 |
| 34 | 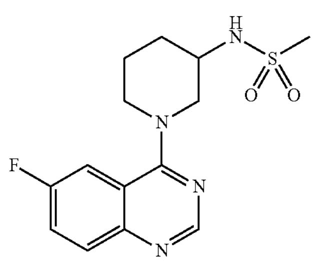 [SMILES: CS(=O)(=O)NC1CCCN(c2ncnc3ccc(F)cc23)C1] | 56 | 61 | 33 |
| 35 | 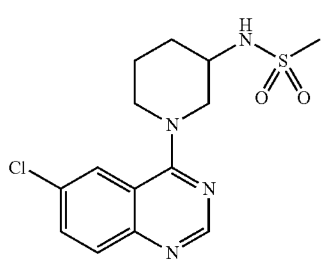 [SMILES: CS(=O)(=O)NC1CCCN(c2ncnc3ccc(Cl)cc23)C1] | 38 | 64 | 41 |
| 36 | 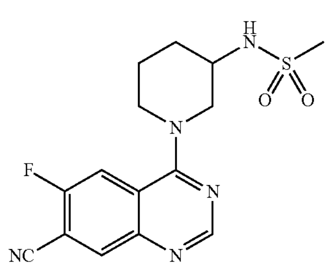 [SMILES: CS(=O)(=O)NC1CCCN(c2ncnc3cc(C#N)c(F)cc23)C1] | 0 | 34 | 35 |

TABLE 1-continued

| No. | Structure | TXNIP % Inhibition at 1.5 μM | TXNIP % Inhibition at 12.5 μM | CC$_{50}$/72 h (μM) |
|---|---|---|---|---|
| 37 | 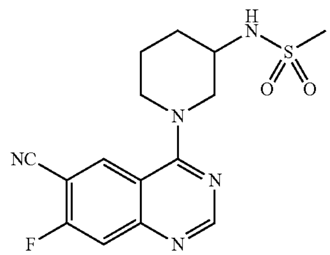 [SMILES: CS(=O)(=O)NC1CCCN(c2ncnc3cc(F)c(C#N)cc23)C1] | 0 | 24 | >100 |
| 38 | 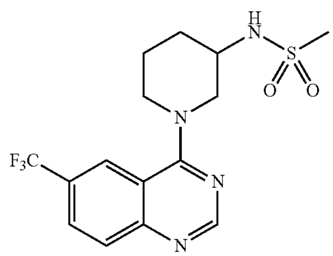 [SMILES: CS(=O)(=O)NC1CCCN(c2ncnc3ccc(C(F)(F)F)cc23)C1] | 34 | 60 | >100 |
| 39 | 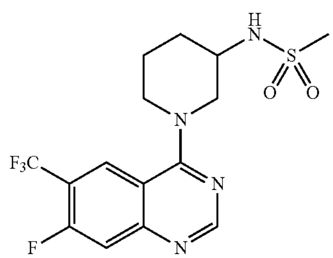 [SMILES: CS(=O)(=O)NC1CCCN(c2ncnc3cc(F)c(C(F)(F)F)cc23)C1] | 7 | 28 | >100 |
| 40 | 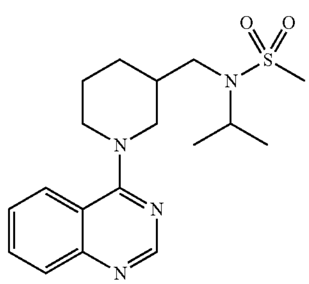 [SMILES: CC(C)N(CC1CCCN(c2ncnc3ccccc23)C1)S(C)(=O)=O] | 14 | 46 | 70 |
| 41 | 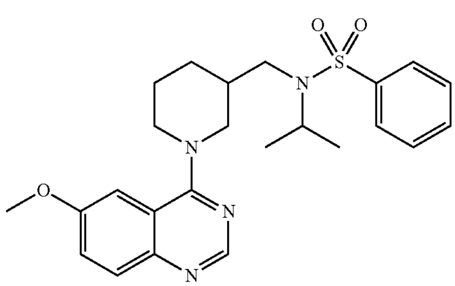 [SMILES: COc1ccc2ncnc(N3CCCC(CN(C(C)C)S(=O)(=O)c4ccccc4)C3)c2c1] | 36 | 65 | 7 |

| No. | Structure | TXNIP % Inhibition at 1.5 μM | TXNIP % Inhibition at 12.5 μM | CC$_{50}$/72 h (μM) |
|---|---|---|---|---|
| 42 | 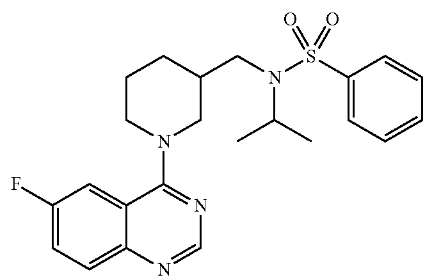 [SMILES: CC(C)N(CC1CCCN(c2ncnc3ccc(F)cc23)C1)S(=O)(=O)c1ccccc1] | 32 | 30 | 4 |
| 43 | 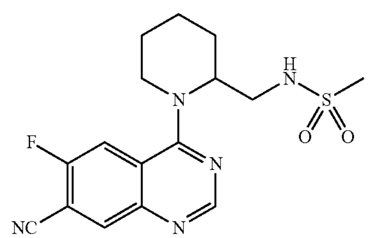 [SMILES: CS(=O)(=O)NCC1CCCCN1c1ncnc2cc(C#N)c(F)cc12] | 0 | 16 | >100 |
| 44 | 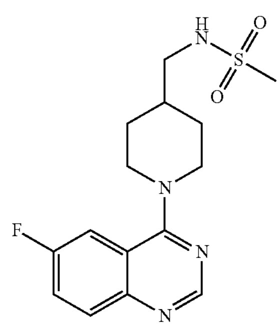 [SMILES: CS(=O)(=O)NCC1CCN(c2ncnc3ccc(F)cc23)CC1] | 4 | 22 | >100 |
| 45 | 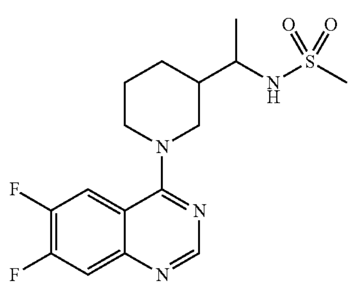 [SMILES: CC(NS(C)(=O)=O)C1CCCN(c2ncnc3cc(F)c(F)cc23)C1] | 22 | 44 | >100 |
| 46 | 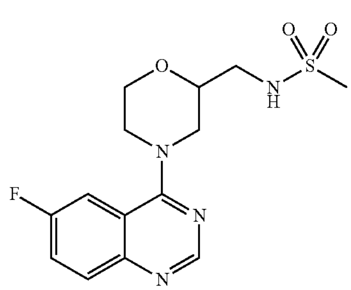 [SMILES: CS(=O)(=O)NCC1CN(c2ncnc3ccc(F)cc23)CCO1] | 0 | 55 | >100 |

TABLE 1-continued

| No. | Structure | TXNIP % Inhibition at 1.5 µM | TXNIP % Inhibition at 12.5 µM | CC$_{50}$/72 h (µM) |
|---|---|---|---|---|
| 47 | 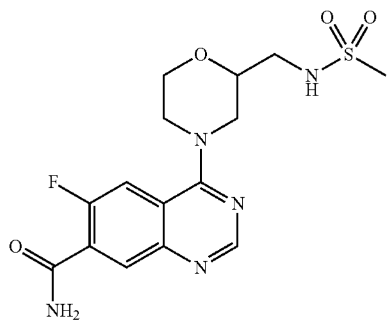 [SMILES: CS(=O)(=O)NCC1CN(c2ncnc3cc(C(N)=O)c(F)cc23)CCO1] | 5 | 7 | >100 |
| 48 | 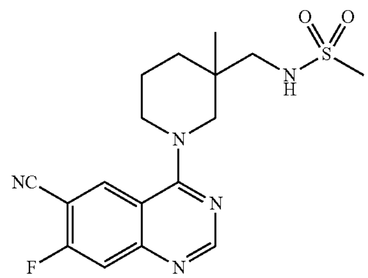 [SMILES: CC1(CNS(C)(=O)=O)CCCN(c2ncnc3cc(F)c(C#N)cc23)C1] | 3 | 26 | >100 |
| 49 | 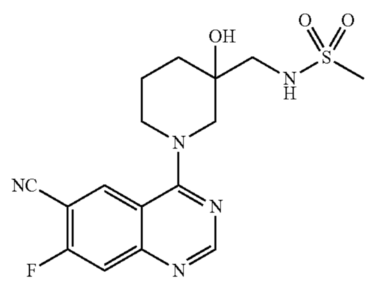 [SMILES: CS(=O)(=O)NCC1(O)CCCN(c2ncnc3cc(F)c(C#N)cc23)C1] | 2 | 2 | >100 |
| 50 | 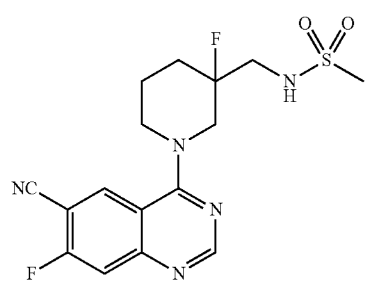 [SMILES: CS(=O)(=O)NCC1(F)CCCN(c2ncnc3cc(F)c(C#N)cc23)C1] | 2 | 18 | >100 |
| 51 | 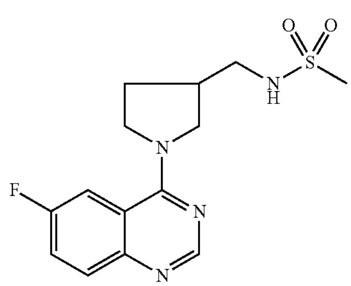 [SMILES: CS(=O)(=O)NCC1CCN(c2ncnc3ccc(F)cc23)C1] | 18 | 20 | >100 |

TABLE 1-continued

| No. | Structure | TXNIP % Inhibition at 1.5 μM | TXNIP % Inhibition at 12.5 μM | CC$_{50}$/72 h (μM) |
|---|---|---|---|---|
| 52 | 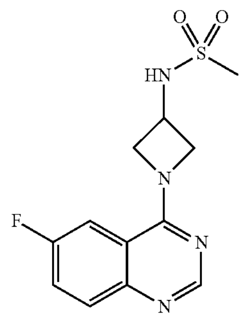 [SMILES: CS(=O)(=O)NC1CN(c2ncnc3ccc(F)cc23)C1] | 4 | 5 | >100 |
| 53 | 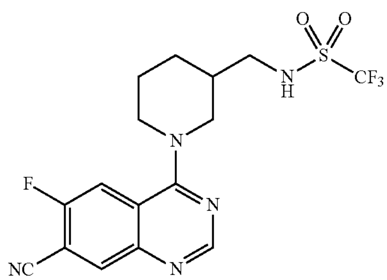 [SMILES: N#Cc1cc2ncnc(N3CCCC(CNS(=O)(=O)C(F)(F)F)C3)c2cc1F] | 7 | 24 | >100 |
| 54 | 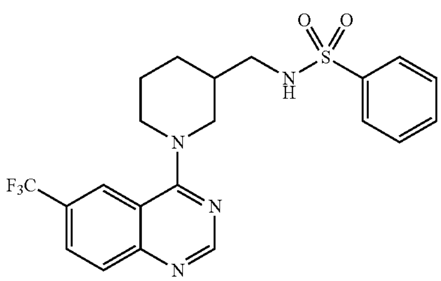 [SMILES: O=S(=O)(NCC1CCCN(c2ncnc3ccc(C(F)(F)F)cc23)C1)c1ccccc1] | 19 | 53 | 17 |
| 55 | 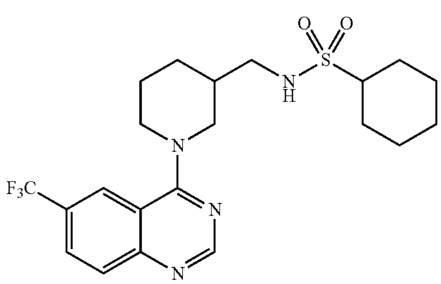 [SMILES: O=S(=O)(NCC1CCCN(c2ncnc3ccc(C(F)(F)F)cc23)C1)C1CCCCC1] | 29 | 41 | 7 |
| 56 | 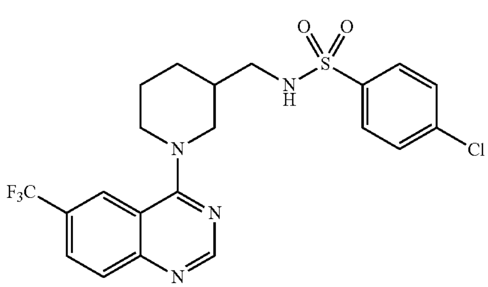 [SMILES: O=S(=O)(NCC1CCCN(c2ncnc3ccc(C(F)(F)F)cc23)C1)c1ccc(Cl)cc1] | 19 | 30 | 17 |

TABLE 1-continued
| No. | Structure | TXNIP % Inhibition at 1.5 μM | TXNIP % Inhibition at 12.5 μM | CC$_{50}$/72 h (μM) |
|---|---|---|---|---|
| 57 | 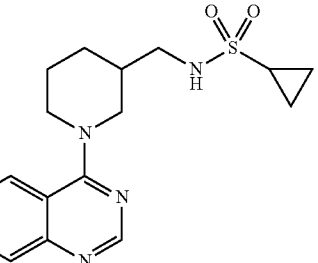 | 33 | 67 | 43 |
| 58 | 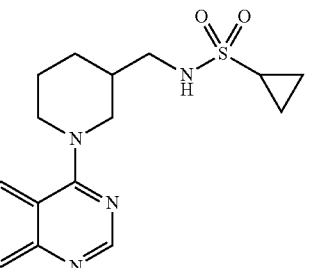 | 15 | 65 | 57 |
| 59 | 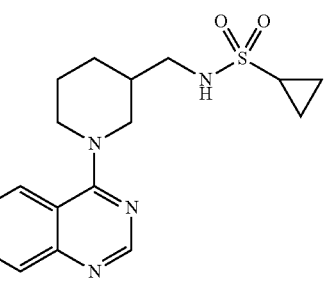 | 5 | 5 | >100 |
| 60 | 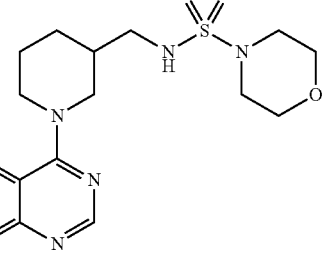 | 32 | 56 | 16 |
| 61 | 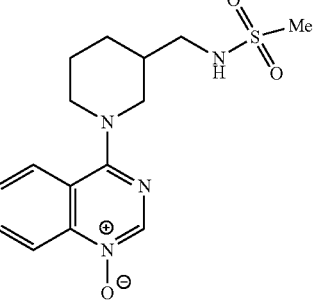 | 2 | 25 | >100 |

TABLE 1-continued

| No. | Structure | TXNIP % Inhibition at 1.5 μM | TXNIP % Inhibition at 12.5 μM | CC$_{50}$/72 h (μM) |
|---|---|---|---|---|
| 62 | 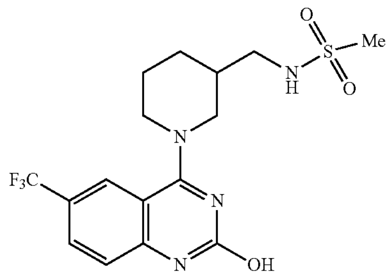 [SMILES: CS(=O)(=O)NCC1CCCN(c2nc(O)nc3ccc(C(F)(F)F)cc23)C1] | 20 | 20 | >100 |
| 63 | 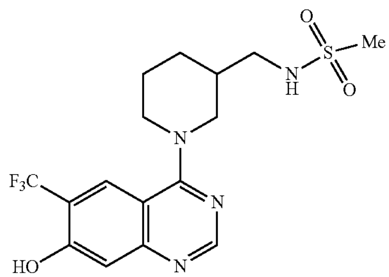 [SMILES: CS(=O)(=O)NCC1CCCN(c2ncnc3cc(O)c(C(F)(F)F)cc23)C1] | 10 | 5 | >100 |

REFERENCES

Kenneth L and Thomas S. Analysis of relative gene expression data using real-time quantitative PCR and the $2^{-\Delta\Delta C_T}$ method. *Methods* 2001; 25: 402-408.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for treating diabetes or a diabetes related disorder associated with elevated TXNIP or elevated glucagon in a mammal, the method comprising the step of administering to the mammal a therapeutically effective amount of at least one compound having a structure represented by a formula selected from:

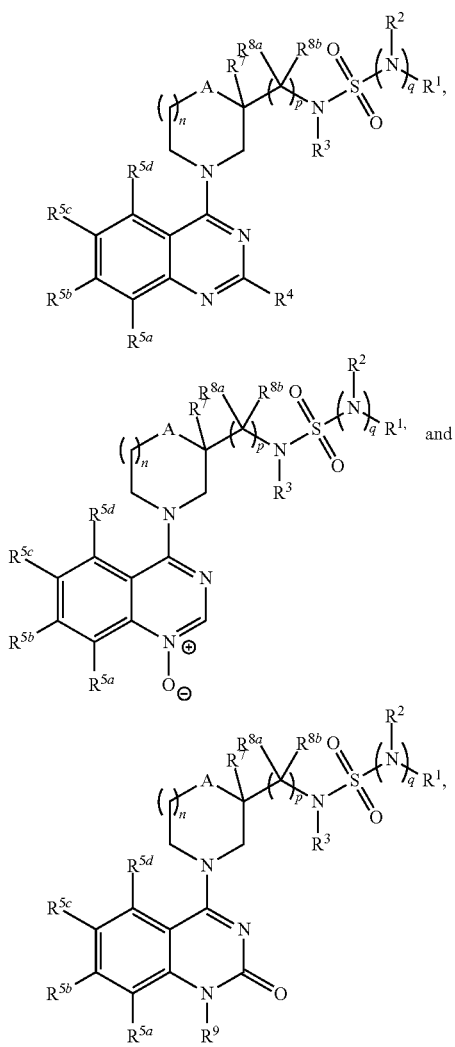

wherein n is 0, 1, or 2;

wherein p is 0, 1, 2, 3, or 4;

wherein q is 0 or 1;

wherein $R^1$ is —$NH_2$, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)$CO_2H$, or $Cy^1$;

wherein $Cy^1$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino;

wherein $R^2$ is hydrogen or C1-C4 alkyl, or wherein each of $R^1$ and $R^2$ are covalently bonded together and, together with the intermediate atoms, comprise a 3- to 6-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino;

wherein $R^3$ is hydrogen or C1-C4 alkyl, or wherein each of $R^1$ and $R^3$ are covalently bonded together and, together with the intermediate atoms, comprise a 5- to 7-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino;

wherein $R^4$ is hydrogen, halogen, —$NH_2$, —OH, C1-C4 alkyl, C1-C4 alkoxy, C1-C4 alkylamino, (C1-C4)(C1-C4) dialkylamino, or $Cy^2$;

wherein $Cy^2$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino;

wherein each of $R^{5a}$, $R^{5b}$, $R^{5c}$, and $R^{5d}$ is independently hydrogen, halogen, —$NH_2$, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —$CO_2$(C1-C4 alkyl), —$CO_2H$, —$CO_2NH_2$, —NHC(O)$Cy^3$, —NHC(O)(C1-C4 alkyl), or $Cy^3$;

wherein $Cy^3$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino;

wherein A is O, NR$^{6a}$, or CHR$^{6b}$;
wherein R$^{6a}$ is hydrogen or C1-C4 alkyl; and
wherein R$^{6b}$ is hydrogen, C1-C4 alkyl, C1-C4 haloalkyl, C1-C4 alkoxy, C1-C4 alkylamino, (C1-C4)(C1-C4) dialkylamino, or —CO$_2$H;
wherein R$^7$ is hydrogen, halogen, —OH, C1-C4 alkyl, C1-C4 haloalkyl, or C1-C4 alkoxy;
wherein each occurrence of R$^{8a}$ and R$^{8b}$, when present, is independently hydrogen, C1-C4 alkyl, C1-C4 haloalkyl, phenyl, or —CO$_2$H;
or wherein p is 1 and each of R$^{8a}$ and R$^{8b}$ together comprise =O; and
wherein R$^9$ is hydrogen, C1-C4 alkyl, or Cy$^4$,
wherein Cy$^4$, when present, is C3-C6 cycloalkyl, C2-C5 heterocycloalkyl, or aryl, and is substituted with 0, 1, 2, or 3 groups independently selected from halogen, —NH$_2$, —OH, C1-C4 alkyl, C1-C4 haloalkyl, C1-C4 alkoxy, C1-C4 alkylamino, and (C1-C4)(C1-C4) dialkylamino,
or a pharmaceutically acceptable salt thereof.

2. The method of claim 1, wherein the compound has a structure represented by a formula:

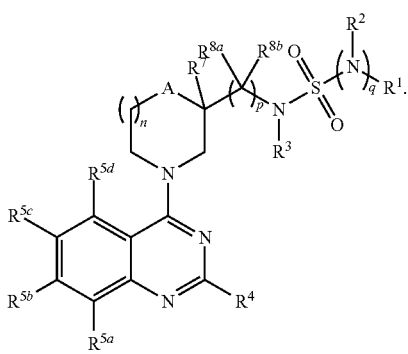

3. The method of claim 2, wherein p is 0 or 1; R$^1$ is —NH$_2$, —OH, C1-C4 alkyl, C1-C4 haloalkyl, C1-C4 alkoxy, C1-C4 alkylamino, (C1-C4)(C1-C4) dialkylamino, or Cy$^1$; each of R$^{5a}$, R$^{5b}$, R$^{5c}$, and R$^{5d}$ is independently hydrogen, halogen, —NH$_2$, —CN, —OH, C1-C4 alkyl, C1-C4 haloalkyl, C1-C4 alkoxy, C1-C4 alkylamino, (C1-C4)(C1-C4) dialkylamino, —CO$_2$(C1-C4 alkyl), —CO$_2$H, —CO$_2$NH$_2$, —NHC(O)Cy$^3$, —NHC(O)(C1-C4 alkyl), or Cy$^3$; and R$^{8a}$ is hydrogen and R$^{8b}$ is hydrogen, C1-C4 alkyl, or C1-C4 haloalkyl.

4. The method of claim 1, wherein the compound has a structure represented by a formula selected from:

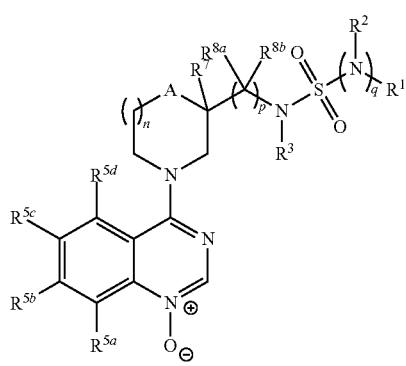

and

5. The method of claim 1, wherein p is 1.

6. A method for inhibiting TXNIP expression or lowering glucagon levels in a mammal, the method comprising the step of administering to the mammal an effective amount of at least one compound having a structure represented by a formula selected from:

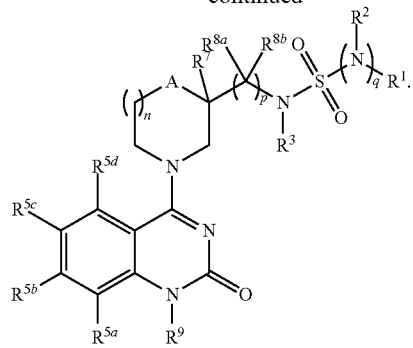

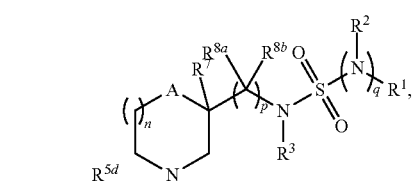

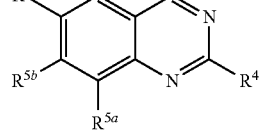

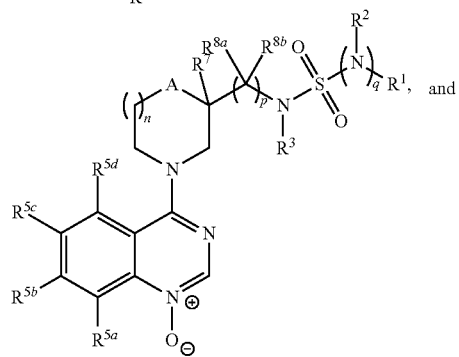

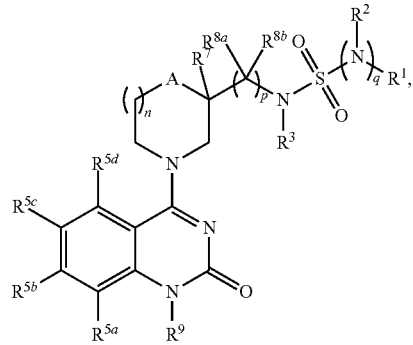

wherein n is 0, 1, or 2;
wherein p is 0, 1, 2, 3, or 4;
wherein q is 0 or 1;

wherein R¹ is —NH₂, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)CO₂H, or Cy¹;

wherein Cy¹, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein R² is hydrogen or C1-C4 alkyl, or wherein each of R¹ and R² are covalently bonded together and, together with the intermediate atoms, comprise a 3- to 6-membered heterocycloalkyl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein R³ is hydrogen or C1-C4 alkyl, or wherein each of R¹ and R³ are covalently bonded together and, together with the intermediate atoms, comprise a 5- to 7-membered heterocycloalkyl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein R⁴ is hydrogen, halogen, —NH₂, —OH, C1-C4 alkyl, C1-C4 alkoxy, C1-C4 alkylamino, (C1-C4)(C1-C4) dialkylamino, or Cy²;

wherein Cy², when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein each of $R^{5a}$, $R^{5b}$, $R^{5c}$, and $R^{5d}$ is independently hydrogen, halogen, —NH₂, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —CO₂(C1-C4 alkyl), —CO₂H, —CO₂NH₂, —NHC(O)Cy³, —NHC(O)(C1-C4 alkyl), or Cy³;

wherein Cy³, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein A is O, $NR^{6a}$, or $CHR^{6b}$;

wherein $R^{6a}$ is hydrogen or C1-C4 alkyl; and wherein $R^{6b}$ is hydrogen, C1-C4 alkyl, C1-C4 haloalkyl, C1-C4 alkoxy, C1-C4 alkylamino, (C1-C4)(C1-C4) dialkylamino, or —CO₂H;

wherein R⁷ is hydrogen, halogen, —OH, C1-C4 alkyl, C1-C4 haloalkyl, or C1-C4 alkoxy;

wherein each occurrence of $R^{8a}$ and $R^{8b}$, when present, is independently hydrogen, C1-C4 alkyl, C1-C4 haloalkyl, phenyl, or —CO₂H;

or wherein p is 1 and each of $R^{8a}$ and $R^{8b}$ together comprise =O; and wherein R⁹ is hydrogen, C1-C4 alkyl, or Cy⁴, wherein Cy⁴, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino, or a pharmaceutically acceptable salt thereof.

7. The method of claim 6, wherein the compound has a structure represented by a formula:

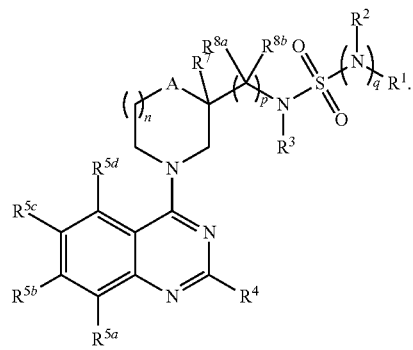

8. The method of claim 7, wherein p is 0 or 1; R¹ is —NH₂, —OH, C1-C4 alkyl, C1-C4 haloalkyl, C1-C4 alkoxy, C1-C4 alkylamino, (C1-C4)(C1-C4) dialkylamino, or Cy¹; each of $R^{5a}$, $R^{5b}$, $R^{5c}$, and $R^{5d}$ is independently hydrogen, halogen, —NH₂, —CN, —OH, C1-C4 alkyl, C1-C4 haloalkyl, C1-C4 alkoxy, C1-C4 alkylamino, (C1-C4)(C1-C4) dialkylamino, —CO₂(C1-C4 alkyl), —CO₂H, —CO₂NH₂, —NHC(O)Cy³, —NHC(O)(C1-C4 alkyl), or Cy³; and $R^{8a}$ is hydrogen and $R^{8b}$ is hydrogen, C1-C4 alkyl, or C1-C4 haloalkyl.

9. The method of claim 6, wherein the compound has a structure represented by a formula selected from:

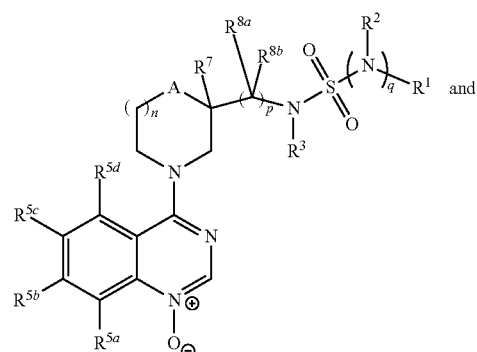
and

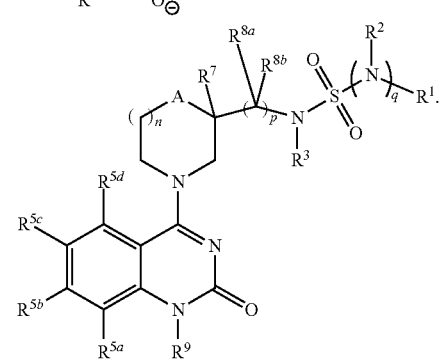

10. A pharmaceutical composition comprising a pharmaceutically acceptable carrier and a therapeutically effective amount of at least one compound having a structure represented by a formula:

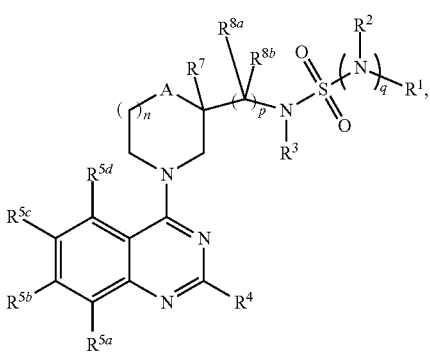

wherein n is 0, 1, or 2;
wherein p is 1, 2, 3, or 4;
wherein q is 0 or 1;
wherein $R^1$ is —$NH_2$, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)$CO_2H$, or $Cy^1$;
wherein $Cy^1$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino;
wherein $R^2$ is hydrogen or C1-C4 alkyl, or wherein each of $R^1$ and $R^2$ are covalently bonded together and, together with the intermediate atoms, comprise a 3- to 6-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino;
wherein $R^3$ is hydrogen or C1-C4 alkyl, or wherein each of $R^1$ and $R^3$ are covalently bonded together and, together with the intermediate atoms, comprise a 5- to 7-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino;
wherein $R^4$ is hydrogen, halogen, —$NH_2$, —OH, C1-C4 alkyl, C1-C4 alkoxy, C1-C4 alkylamino, (C1-C4)(C1-C4) dialkylamino, or $Cy^2$;
wherein $Cy^2$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino;
wherein each of $R^{5a}$, $R^{5b}$, $R^{5c}$, and $R^{5d}$ is independently hydrogen, halogen, —$NH_2$, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —$CO_2$(C1-C4 alkyl), —$CO_2H$, —$CO_2NH_2$, —NHC(O)$Cy^3$, —NHC(O)(C1-C4 alkyl), or $Cy^3$;
wherein $Cy^3$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino;

wherein A is O, $NR^{6a}$, or $CHR^{6b}$;
wherein $R^{6a}$ is hydrogen or C1-C4 alkyl; and
wherein $R^{6b}$ is hydrogen, C1-C4 alkyl, C1-C4 haloalkyl, C1-C4 alkoxy, C1-C4 alkylamino, (C1-C4)(C1-C4) dialkylamino, or —$CO_2H$;
wherein $R^7$ is hydrogen, halogen, —OH, C1-C4 alkyl, C1-C4 haloalkyl, or C1-C4 alkoxy;
wherein each occurrence of $R^{8a}$ and $R^{8b}$, when present, is independently hydrogen, C1-C4 alkyl, C1-C4 haloalkyl, phenyl, or —$CO_2H$;
or wherein p is 1 and each of $R^{8a}$ and $R^{8b}$ together comprise =O; and
wherein $R^9$ is hydrogen, C1-C4 alkyl, or $Cy^4$,
wherein $Cy^4$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino,
or a pharmaceutically acceptable salt thereof.

11. The pharmaceutical composition of claim 10, wherein p is 1; $R^1$ is —$NH_2$, —OH, C1-C4 alkyl, C1-C4 haloalkyl, C1-C4 alkoxy, C1-C4 alkylamino, (C1-C4)(C1-C4) dialkylamino, or $Cy^1$; each of $R^{5a}$, $R^{5b}$, $R^{5c}$, and $R^{5d}$ is independently hydrogen, halogen, —$NH_2$, —CN, —OH, C1-C4 alkyl, C1-C4 haloalkyl, C1-C4 alkoxy, C1-C4 alkylamino, (C1-C4)(C1-C4) dialkylamino, —$CO_2$(C1-C4 alkyl), —$CO_2H$, —$CO_2NH_2$, —NHC(O)$Cy^3$, —NHC(O)(C1-C4 alkyl), or $Cy^3$; and $R^{8a}$ is hydrogen and $R^{8b}$ is hydrogen, C1-C4 alkyl, or C1-C4 haloalkyl.

12. The pharmaceutical composition of claim 10, wherein n is 1.

13. The pharmaceutical composition of claim 10, wherein $R^{5c}$ is hydrogen, halogen, —$NH_2$, —OH, C1-C4 alkyl, C1-C4 alkoxy, C1-C4 alkylamino, or (C1-C4)(C1-C4) dialkylamino.

14. The pharmaceutical composition of claim 10, wherein $Cy^3$, when present, is C3-C6 cycloalkyl or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino.

15. A pharmaceutical composition comprising a pharmaceutically acceptable carrier and a therapeutically effective amount of at least one compound having a structure represented by a formula:

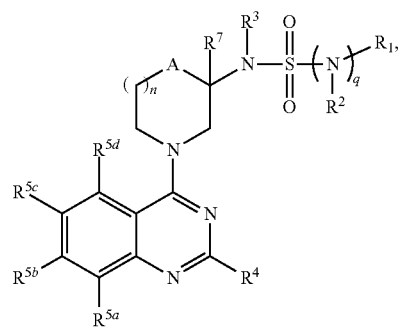

wherein n is 0, 1, or 2;
wherein q is 0 or 1;
wherein $R^1$ is —$NH_2$, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)$CO_2H$, or $Cy^1$;

wherein Cy¹, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein R² is hydrogen or C1-C4 alkyl, or wherein each of R¹ and R² are covalently bonded together and, together with the intermediate atoms, comprise a 3- to 6-membered heterocycloalkyl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein R³ is hydrogen or C1-C4 alkyl, or wherein each of R¹ and R³ are covalently bonded together and, together with the intermediate atoms, comprise a 5- to 7-membered heterocycloalkyl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein R⁴ is hydrogen, halogen, —NH₂, —OH, C1-C4 alkyl, C1-C4 alkoxy, C1-C4 alkylamino, (C1-C4)(C1-C4) dialkylamino, or Cy²;

wherein Cy², when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein each of R⁵ᵃ, R⁵ᵇ, and R⁵ᵈ is independently hydrogen, halogen, —NH₂, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —CO₂(C1-C4 alkyl), —CO₂H, —CO₂NH₂, —NHC(O)Cy³, —NHC(O)(C1-C4 alkyl), or Cy³;

wherein Cy³, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein R⁵ᶜ is hydrogen, halogen, —NH₂, —OH, —CN, C1-C4 alkyl, C1-C4 haloalkyl, C1-C4 alkoxy, C1-C4 haloalkoxy, C1-C4 alkylamino, (C1-C4)(C1-C4) dialkylamino, —CO₂(C1-C4 alkyl), —CO₂H, —CO₂NH₂, —NHC(O)Cy³, —NHC(O)(C1-C4 alkyl), or aryl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein A is O, NR⁶ᵃ, or CHR⁶ᵇ;

wherein R⁶ᵃ is hydrogen or C1-C4 alkyl;

wherein R⁶ᵇ is hydrogen, C1-C4 alkyl, C1-C4 haloalkyl, C1-C4 alkoxy, C1-C4 alkylamino, (C1-C4)(C1-C4) dialkylamino, or —CO₂H; and wherein R⁷ is hydrogen, halogen, —OH, C1-C4 alkyl, C1-C4 haloalkyl, or C1-C4 alkoxy;

provided that when R⁵ᵇ is morpholinyl and R¹ is thiophenyl or thiazolyl, then q is 1 and at least one of R⁵ᵃ, R⁵ᶜ, and R⁵ᵈ is not hydrogen, or a pharmaceutically acceptable salt thereof.

16. The pharmaceutical composition of claim 15, wherein R¹ is —NH₂, —OH, C1-C4 alkyl, C1-C4 haloalkyl, C1-C4 alkoxy, C1-C4 alkylamino, (C1-C4)(C1-C4) dialkylamino, or Cy¹; each of R⁵ᵃ, R⁵ᵇ, and R⁵ᵈ is independently hydrogen, halogen, —NH₂, —CN, —OH, C1-C4 alkyl, C1-C4 haloalkyl, C1-C4 alkoxy, C1-C4 alkylamino, (C1-C4)(C1-C4) dialkylamino, —CO₂(C1-C4 alkyl), —CO₂H, —CO₂NH₂, —NHC(O)Cy³, —NHC(O)(C1-C4 alkyl), or Cy³; and R⁵ᶜ is hydrogen, halogen, —NH₂, —OH, —CN, C1-C4 alkyl, C1-C4 haloalkyl, C1-C4 alkoxy, C1-C4 haloalkoxy, C1-C4 alkylamino, (C1-C4)(C1-C4) dialkylamino, —CO₂(C1-C4 alkyl), —CO₂H, —CO₂NH₂, —NHC(O)Cy³, —NHC(O)(C1-C4 alkyl), or aryl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino.

17. The pharmaceutical composition of claim 15, wherein n is 1.

18. The pharmaceutical composition of claim 15, wherein R⁵ᶜ is hydrogen, halogen, —NH₂, —OH, C1-C4 alkyl, C1-C4 alkoxy, C1-C4 alkylamino, or (C1-C4)(C1-C4) dialkylamino.

19. The pharmaceutical composition of claim 15, wherein each of R⁵ᵃ, R⁵ᵇ, R⁵ᶜ, and R⁵ᵈ is independently hydrogen, halogen, —NH₂, —OH, C1-C4 alkyl, C1-C4 alkoxy, C1-C4 alkylamino, or (C1-C4)(C1-C4) dialkylamino.

20. A pharmaceutical composition comprising a pharmaceutically acceptable carrier and a therapeutically effective amount of at least one compound having a structure represented by a formula selected from:

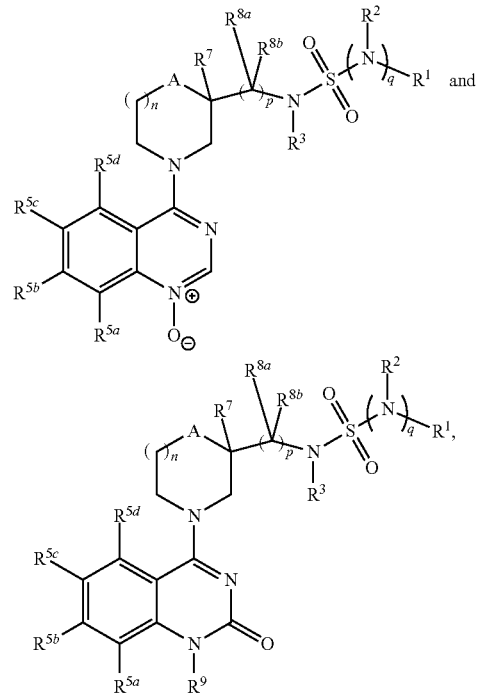

wherein n is 0, 1, or 2;
wherein p is 0, 1, 2, 3, or 4;
wherein q is 0 or 1;
wherein R¹ is —NH₂, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)CO₂H, or Cy¹;
wherein Cy¹, when present, is C3-C6 cycloalkyl, C2-C5 heterocycloalkyl, or aryl, and is substituted with 0, 1, 2, or 3 groups independently selected from halogen,

285

—NH₂, —OH, C1-C4 alkyl, C1-C4 haloalkyl, C1-C4 alkoxy, C1-C4 alkylamino, and (C1-C4)(C1-C4) dialkylamino;

wherein R² is hydrogen or C1-C4 alkyl, or wherein each of R¹ and R² are covalently bonded together and, together with the intermediate atoms, comprise a 3- to 6-membered heterocycloalkyl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein R³ is hydrogen or C1-C4 alkyl, or wherein each of R¹ and R³ are covalently bonded together and, together with the intermediate atoms, comprise a 5- to 7-membered heterocycloalkyl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein R⁴ is hydrogen, halogen, —NH₂, —OH, C1-C4 alkyl, C1-C4 alkoxy, C1-C4 alkylamino, (C1-C4)(C1-C4) dialkylamino, or Cy²;

wherein Cy², when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein each of $R^{5a}$, $R^{5b}$, $R^{5c}$, and $R^{5d}$ is independently hydrogen, halogen, —NH₂, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —CO₂(C1-C4 alkyl), —CO₂H, —CO₂NH₂, —NHC(O)Cy³, —NHC(O)(C1-C4 alkyl), or Cy³;

wherein Cy³, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein A is O, $NR^{6a}$, or $CHR^{6b}$;

wherein $R^{6a}$ is hydrogen or C1-C4 alkyl; and wherein $R^{6b}$ is hydrogen, C1-C4 alkyl, C1-C4 haloalkyl, C1-C4 alkoxy, C1-C4 alkylamino, (C1-C4)(C1-C4) dialkylamino, or —CO₂H;

wherein R⁷ is hydrogen, halogen, —OH, C1-C4 alkyl, C1-C4 haloalkyl, or C1-C4 alkoxy;

wherein each occurrence of $R^{8a}$ and $R^{8b}$, when present, is independently hydrogen, C1-C4 alkyl, C1-C4 haloalkyl, phenyl, or —CO₂H;

or wherein p is 1 and each of $R^{8a}$ and $R^{8b}$ together comprise =O; and wherein R⁹ is hydrogen, C1-C4 alkyl, or Cy⁴, wherein Cy⁴, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino, or a pharmaceutically acceptable salt thereof.

286

21. A compound having a structure represented by a formula:

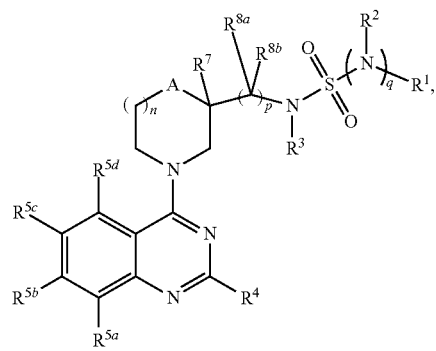

wherein n is 0, 1, or 2;
wherein p is 1, 2, 3, or 4;
wherein q is 0 or 1;
wherein R¹ is —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)CO₂H, or Cy¹;

wherein Cy¹, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein R² is hydrogen or C1-C4 alkyl, or wherein each of R¹ and R² are covalently bonded together and, together with the intermediate atoms, comprise a 3- to 6-membered heterocycloalkyl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein R³ is hydrogen or C1-C4 alkyl, or wherein each of R¹ and R³ are covalently bonded together and, together with the intermediate atoms, comprise a 5- to 7-membered heterocycloalkyl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein R⁴ is hydrogen, halogen, —NH₂, —OH, C1-C4 alkyl, C1-C4 alkoxy, C1-C4 alkylamino, (C1-C4)(C1-C4) dialkylamino, or Cy²;

wherein Cy², when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein each of $R^{5a}$, $R^{5b}$, $R^{5c}$, and $R^{5d}$ is independently hydrogen, halogen, —NH₂, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —CO₂(C1-C4 alkyl), —CO₂H, —CO₂NH₂, —NHC(O)Cy³, —NHC(O)(C1-C4 alkyl), or Cy³;

wherein Cy³, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein A is O, NR$^{6a}$, or CHR$^{6b}$;

wherein R$^{6a}$ is hydrogen or C1-C4 alkyl;

wherein R$^{6b}$ is hydrogen, C1-C4 alkyl, C1-C4 haloalkyl, C1-C4 alkoxy, C1-C4 alkylamino, (C1-C4)(C1-C4) dialkylamino, or —CO₂H;

wherein R$^7$ is hydrogen, halogen, —OH, C1-C4 alkyl, C1-C4 haloalkyl, or C1-C4 alkoxy; and wherein each occurrence of R$^{8a}$ and R$^{8b}$, when present, is independently hydrogen, C1-C4 alkyl, C1-C4 haloalkyl, phenyl, or —CO₂H;

or wherein p is 1 and each of R$^{8a}$ and R$^{8b}$ together comprise =O;

provided that when R$^1$ is methyl and each of R$^3$ and R$^4$ is hydrogen then each of R$^{5a}$, R$^{5b}$, R$^{5c}$, and R$^{5d}$ is independently hydrogen, fluorine, —NH₂, —OH, C1-C4 alkyl, C1-C4 alkoxy, C1-C4 alkylamino, (C1-C4)(C1-C4) dialkylamino, or Cy$^3$, and provided that when n is 1, p is 1, q is 0, A is CHR$^{6b}$, and R$^1$ is methyl, then at least two of R$^4$, R$^{5a}$, R$^{5b}$, R$^{5c}$, and R$^{5d}$ are not hydrogen, or a pharmaceutically acceptable salt thereof.

22. The compound of claim 21, wherein p is 1; R$^1$ is —OH, C1-C4 alkyl, C1-C4 haloalkyl, C1-C4 alkoxy, C1-C4 alkylamino, (C1-C4)(C1-C4) dialkylamino, or Cy$^1$; each of R$^{5a}$, R$^{5b}$, R$^{5c}$, and R$^{5d}$ is independently hydrogen, halogen, —NH₂, —CN, —OH, C1-C4 alkyl, C1-C4 haloalkyl, C1-C4 alkoxy, C1-C4 alkylamino, (C1-C4)(C1-C4) dialkylamino, —CO₂(C1-C4 alkyl), —CO₂H, —CO₂NH₂, —NHC(O)Cy$^3$, —NHC(O)(C1-C4 alkyl), or Cy$^3$; and R$^{8a}$ is hydrogen and R$^{8b}$ is hydrogen, C1-C4 alkyl, or C1-C4 haloalkyl.

23. The compound of claim 21, wherein R$^{5c}$ is fluorine.

24. The compound of claim 21, wherein R$^1$ is methyl, each of R$^3$ and R$^4$ is hydrogen, and each of R$^{5a}$, R$^{5b}$, R$^{5c}$, and R$^{5d}$ is independently hydrogen, —NH₂, —OH, C1-C4 alkyl, C1-C4 alkoxy, C1-C4 alkylamino, (C1-C4)(C1-C4) dialkylamino, or Cy$^3$.

25. The compound of claim 21, wherein R$^1$ is methyl, each of R$^3$ and R$^4$ is hydrogen, and R$^{5b}$ is fluorine.

26. The compound of claim 21, wherein R$^{5c}$ is hydrogen, halogen, —NH₂, —OH, C1-C4 alkyl, C1-C4 alkoxy, C1-C4 alkylamino, or (C1-C4)(C1-C4) dialkylamino.

27. The compound of claim 21, wherein Cy$^3$, when present, is C3-C6 cycloalkyl or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino.

28. A compound having a structure represented by a formula:

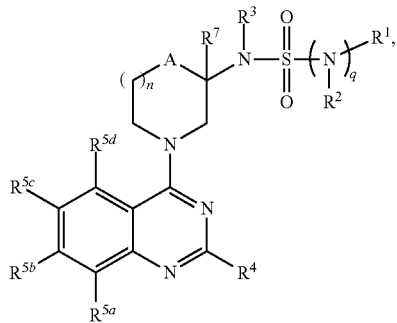

wherein n is 0, 1, or 2;

wherein q is 0 or 1;

wherein R$^1$ is —NH₂, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)CO₂H, or Cy$^1$;

wherein Cy$^1$, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein R$^2$ is hydrogen or C1-C4 alkyl, or wherein each of R$^1$ and R$^2$ are covalently bonded together and, together with the intermediate atoms, comprise a 3- to 6-membered heterocycloalkyl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein R$^3$ is hydrogen or C1-C4 alkyl, or wherein each of R$^1$ and R$^3$ are covalently bonded together and, together with the intermediate atoms, comprise a 5- to 7-membered heterocycloalkyl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein R$^4$ is hydrogen, halogen, —NH₂, —OH, C1-C4 alkyl, C1-C4 alkoxy, C1-C4 alkylamino, (C1-C4)(C1-C4) dialkylamino, or Cy$^2$;

wherein Cy$^2$, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein each of R$^{5a}$, R$^{5b}$, and R$^{5d}$ is independently hydrogen, halogen, —NH₂, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —CO₂(C1-C4 alkyl), —CO₂H, —CO₂NH₂, —NHC(O)Cy$^3$, —NHC(O)(C1-C4 alkyl), or Cy$^3$;

wherein Cy$^3$, when present, is C3-C6 cycloalkyl, C2-C5 heterocycloalkyl, or aryl, and is substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein R$^{5c}$ is hydrogen, halogen, —CN, —NH₂, —OH, C1-C4 alkyl, C1-C4 haloalkyl, C1-C4 alkoxy, C1-C4 haloalkoxy, C1-C4 alkylamino, (C1-C4)(C1-C4) dialkylamino, —CO₂(C1-C4 alkyl), —CO₂H, —CO₂NH₂, —NHC(O)Cy$^3$, —NHC(O)(C1-C4 alkyl), or aryl substituted with 0, 1, 2, or 3 groups independently selected from halogen, —NH₂, —OH, C1-C4 alkyl, C1-C4 haloalkyl, C1-C4 alkoxy, C1-C4 alkylamino, and (C1-C4)(C1-C4) dialkylamino;

wherein A is O, NR$^{6a}$, or CHR$^{6b}$;

wherein R$^{6a}$ is hydrogen or C1-C4 alkyl;

wherein R$^{6b}$ is hydrogen, C1-C4 alkyl, C1-C4 haloalkyl, C1-C4 alkoxy, C1-C4 alkylamino, (C1-C4)(C1-C4) dialkylamino, or —CO₂H; and wherein R$^7$ is hydrogen, halogen, —OH, C1-C4 alkyl, C1-C4 haloalkyl, or C1-C4 alkoxy;

provided that when $R^{5b}$ is morpholinyl and $R^1$ is thiophenyl or thiazolyl, then q is 1 and at least one of $R^{5a}$, $R^{5c}$, and $R^{5d}$ is not hydrogen;

provided that when q is 0 then $Cy^1$ is not aryl; and provided that at least one of $R^{5a}$, $R^{5b}$, $R^{5c}$, and $R^{5d}$ is not hydrogen, or a pharmaceutically acceptable salt thereof.

29. The compound of claim 28, wherein $R^1$ is —$NH_2$, —OH, C1-C4 alkyl, C1-C4 haloalkyl, C1-C4 alkoxy, C1-C4 alkylamino, (C1-C4)(C1-C4) dialkylamino, or $Cy^1$; each of $R^{5a}$, $R^{5b}$, and $R^{5d}$ is independently hydrogen, halogen, —$NH_2$, —CN, —OH, C1-C4 alkyl, C1-C4 haloalkyl, C1-C4 alkoxy, C1-C4 alkylamino, (C1-C4)(C1-C4) dialkylamino, —$CO_2$(C1-C4 alkyl), —$CO_2H$, —$CO_2NH_2$, —NHC(O)$Cy^3$, —NHC(O)(C1-C4 alkyl), or $Cy^3$; and $R^{5c}$ is hydrogen, halogen, —$NH_2$, —OH, —CN, C1-C4 alkyl, C1-C4 haloalkyl, C1-C4 alkoxy, C1-C4 haloalkoxy, C1-C4 alkylamino, (C1-C4)(C1-C4) dialkylamino, —$CO_2$(C1-C4 alkyl), —$CO_2H$, —$CO_2NH_2$, —NHC(O)$Cy^3$, —NHC(O)(C1-C4 alkyl), or aryl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino.

30. The compound of claim 28, wherein n is 1.

31. The compound of claim 28, wherein $R^{5c}$ is hydrogen, halogen, —$NH_2$, —OH, —C1-C4 alkoxy, C1-C4 alkylamino, or (C1-C4)(C1-C4) dialkylamino.

32. The compound of claim 28, wherein each of $R^{5a}$, $R^{5b}$, $R^{5c}$, and $R^{5d}$ is independently hydrogen, halogen, —$NH_2$, —OH, C1-C4 alkyl, C1-C4 alkoxy, C1-C4 alkylamino, or (C1-C4)(C1-C4) dialkylamino.

33. A compound having a structure represented by a formula selected from:

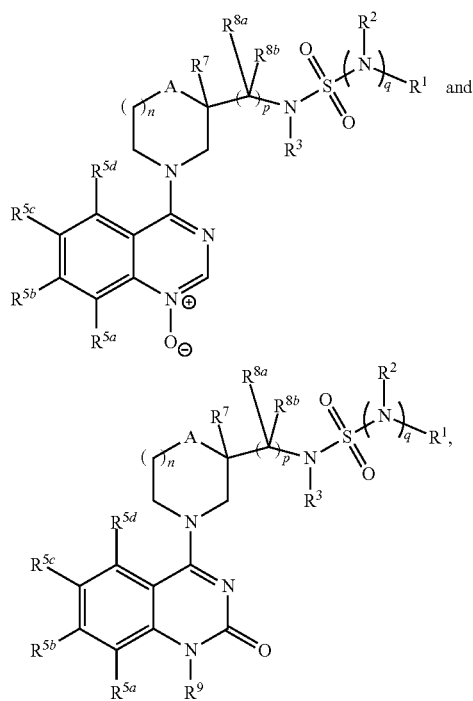

wherein n is 0, 1, or 2;
wherein p is 0, 1, 2, 3, or 4;
wherein q is 0 or 1;

wherein $R^1$ is —$NH_2$, —OH, C1-C4 alkyl, C1-C4 haloalkyl, C1-C4 alkoxy, C1-C4 hydroxyalkyl, C1-C4 alkylamino, (C1-C4)(C1-C4) dialkylamino, —(C1-C4 alkyl)(C1-C4 alkoxy), —(C1-C4 alkyl)$CO_2H$, or $Cy^1$;

wherein $Cy^1$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino;

wherein $R^2$ is hydrogen or C1-C4 alkyl, or wherein each of $R^1$ and $R^2$ are covalently bonded together and, together with the intermediate atoms, comprise a 3- to 6-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino;

wherein $R^3$ is hydrogen or C1-C4 alkyl, or wherein each of $R^1$ and $R^3$ are covalently bonded together and, together with the intermediate atoms, comprise a 5- to 7-membered heterocycloalkyl substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino;

wherein $R^4$ is hydrogen, halogen, —$NH_2$, —OH, C1-C4 alkyl, C1-C4 alkoxy, C1-C4 alkylamino, (C1-C4)(C1-C4) dialkylamino, or $Cy^2$;

wherein $Cy^2$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino;

wherein each of $R^{5a}$, $R^{5b}$, $R^{5c}$, and $R^{5d}$ is independently hydrogen, halogen, —$NH_2$, —CN, —OH, C1-C4 alkyl, C1-C4 haloalkyl, C1-C4 alkoxy, C1-C4 haloalkoxy, C1-C4 alkylamino, (C1-C4)(C1-C4) dialkylamino, —$CO_2$(C1-C4 alkyl), —$CO_2H$, —$CO_2NH_2$, —NHC(O)$Cy^3$, —NHC(O)(C1-C4 alkyl), or $Cy^3$;

wherein $Cy^3$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino;

wherein A is O, $NR^{6a}$, or $CHR^{6b}$;

wherein $R^{6a}$ is hydrogen or C1-C4 alkyl; and wherein $R^{6b}$ is hydrogen, C1-C4 alkyl, C1-C4 haloalkyl, C1-C4 alkoxy, C1-C4 alkylamino, (C1-C4)(C1-C4) dialkylamino, or —$CO_2H$;

wherein $R^7$ is hydrogen, halogen, —OH, C1-C4 alkyl, C1-C4 haloalkyl, or C1-C4 alkoxy;

wherein each occurrence of $R^{8a}$ and $R^{8b}$, when present, is independently hydrogen, C1-C4 alkyl, C1-C4 haloalkyl, phenyl, or —$CO_2H$;

or wherein p is 1 and each of $R^{8a}$ and $R^{8b}$ together comprise =O; and wherein $R^9$ is hydrogen, C1-C4 alkyl, or $Cy^4$, wherein $Cy^4$, when present, is C3-C6 cycloalkyl, C2-C5 heterocycloalkyl, or aryl, and is substituted with 0, 1, 2, or 3 groups independently selected from halogen, —$NH_2$, —OH, C1-C4 alkyl, C1-C4 haloalkyl, C1-C4 alkoxy, C1-C4 alkylamino, and (C1-C4)(C1-C4) dialkylamino, or a pharmaceutically acceptable salt thereof.

34. A method for treating diabetes or a diabetes related disorder associated with elevated TXNIP or elevated glucagon in a mammal, comprising administering to the mammal a therapeutically effective amount of a pharmaceutical composition of claim 10.

35. A method of lowering hepatic glucose production in a mammal in need thereof, comprising administering to the mammal a therapeutically effective amount of at a pharmaceutical composition of claim 10.

36. The method of claim 35, wherein the mammal has diabetes or a diabetes related disorder.

37. A method for treating hyperlipidemia in a mammal, comprising administering to the mammal a therapeutically effective amount of a pharmaceutical composition of claim 10.

38. A method for treating fatty liver disease in a mammal, comprising administering to the mammal a therapeutically effective amount of a pharmaceutical composition of claim 10.

39. The method of claim 38, wherein the fatty liver disease is nonalcoholic fatty liver disease.

\* \* \* \* \*

UNITED STATES PATENT AND TRADEMARK OFFICE
CERTIFICATE OF CORRECTION

PATENT NO. : 11,103,508 B2
APPLICATION NO. : 16/470074
DATED : August 31, 2021
INVENTOR(S) : Corinne E. Augelli-Szafran et al.

It is certified that error appears in the above-identified patent and that said Letters Patent is hereby corrected as shown below:

In the Claims

Column 282, Lines 47-60, please delete:

" 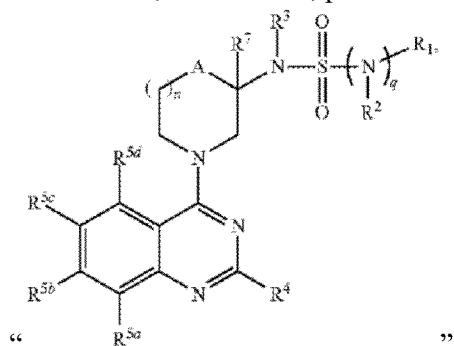 "

And insert:

-- 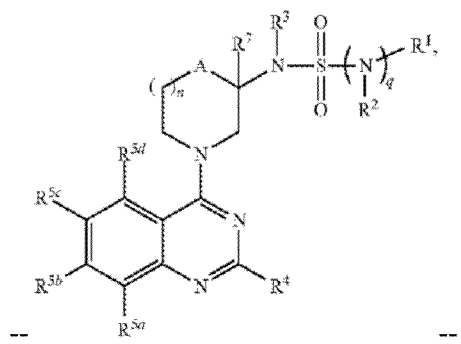 --

Column 291, Line 8, please delete:
"mammal a therapeutically effective amount of at a pharma-"

Signed and Sealed this
Thirteenth Day of September, 2022

Katherine Kelly Vidal
*Director of the United States Patent and Trademark Office*

And insert:

-- mammal a therapeutically effective amount of a pharma- --